(12) United States Patent
Petersen et al.

(10) Patent No.: US 11,999,958 B2
(45) Date of Patent: Jun. 4, 2024

(54) **METHODS OF GENE EDITING AND TRANSFORMING *CANNABIS***

(71) Applicant: Wisconsin Alumni Research Foundation, Madison, WI (US)

(72) Inventors: Michael W. Petersen, Merrimac, WI (US); Edward James Williams, Madison, WI (US); Robert Harnish, Middleton, WI (US); Heidi Flewelling Kaeppler, Oregon, WI (US); Brian Martinell, Mt. Horeb, WI (US); Ray Collier, Middleton, WI (US); Frank McFarland, Madison, WI (US); Shawn Michael Kaeppler, Oregon, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/930,936

(22) Filed: Jul. 16, 2020

(65) Prior Publication Data
US 2021/0071186 A1    Mar. 11, 2021

Related U.S. Application Data

(60) Provisional application No. 62/982,522, filed on Feb. 27, 2020, provisional application No. 62/906,210, filed on Sep. 26, 2019, provisional application No. 62/875,311, filed on Jul. 17, 2019.

(51) Int. Cl.
| | | |
|---|---|---|
| *C12N 15/82* | (2006.01) | |
| *A01H 4/00* | (2006.01) | |
| *A01H 6/28* | (2018.01) | |
| *C07K 14/415* | (2006.01) | |

(52) U.S. Cl.
CPC ......... *C12N 15/8201* (2013.01); *A01H 4/005* (2013.01); *A01H 6/28* (2018.05); *C07K 14/415* (2013.01)

(58) Field of Classification Search
CPC .... A01H 6/28; C12N 15/102; C12N 15/8201; C12N 15/8213; C12N 15/8218; C12N 2310/20; C12N 15/63; C12N 15/8205
See application file for complete search history.

(56) References Cited

U.S. PATENT DOCUMENTS

| | | |
|---|---|---|
| 8,884,100 B2 | 11/2014 | Page |
| 2012/0311744 A1* | 12/2012 | Sirkowski .......... C12N 15/8212 435/8 |
| 2018/0258439 A1* | 9/2018 | Boudko ................... A61P 25/00 |
| 2019/0208723 A1 | 7/2019 | Petersen |
| 2020/0396918 A1 | 12/2020 | Martinell |

FOREIGN PATENT DOCUMENTS

WO   WO-2019006466 A1 *  1/2019  ............ A01G 22/15

OTHER PUBLICATIONS

Slusarkiewicz-Jarzina, A. U. R. E. L. I. A., Aleksandra Ponitka, and Zygmunt Kaczmarek. "Influence of cultivar, explant source and plant growth regulator on callus induction and plant regeneration of *Cannabis sativa* L." Acta Biol. Crac. Ser. Bot 47 (2005): 145-151 . (Year: 2005).*
Tian, Nini, et al. "Overexpression of BraLTP2, a lipid transfer protein of *Brassica napus*, results in increased trichome density and altered concentration of secondary metabolites." International journal of molecular sciences 19.6 (2018): 1733. (Year: 2018).*
Andre, Christelle M., Jean-Francois Hausman, and Gea Guerriero. "*Cannabis sativa*: the plant of the thousand and one molecules." Frontiers in plant science 7 (2016): 19. (Year: 2016).*
Slusarkiewicz-Jarzina, A. U. R. E. L. I. A., Aleksandra Ponitka, and Zygmunt Kaczmarek. "Influence of cultivar, explant source and plant growth regulator on callus induction and plant regeneration of *Cannabis sativa* L." Acta Biol. Crac. Ser. Bot 47.2005 (2005): 145-151. (Year: 2005).*
Lata, H, et al. (2016) In vitro mass propagation of *Cannabis sativa* L.: A protocol refinement using novel aromatic cytokinin metatopolin and the assessment of eco-physiological, biochemical and genetic fidelity of micropropagated plants. J Appl Res Med Aromat Plants 3:18-26. (Year: 2016).*
Cearley JA, et al: Regeneration of *Solanum tuberosum* cv. Katahdin from leaf explants in vitro. Am Potato J 74: 125-129 (1997).
Chen, Y., et al. "High throughput Agrobacterium tumefaciens-mediated germline transformation of mechanically isolated meristem explants of cotton (*Gossypium hirsutum* L.)." Plant cell reports 33.1 (2014): 153-164.
Christou P (1992) Genetic transformation of crop plants using microprojectile bombardment. The Plant Journal 2 (3);275-281.
Farag S, et al. (2015) Cannabinoids production by hairy root cultures of *Cannabis sativa* L. Am J Plant Sci 6:1874-1884.
Feeney M, et al. (2003) Tissue culture and Agrobacterium mediated transformation of hemp (*Cannabis sativa* L.). In vitro Cell Dev-Pl 39 (6):578-585.
Feeney M., et al. (2006) Hemp (*Cannabis sativa* L.). In: Wang K. (eds) Agrobacterium Protocols vol. 2. Methods In Molecular Biology, vol. 344. Humana Press.
Flanagan, B. Monsanto Creates First Genetically Modified Strain of Marijuana. Webpage. Apr. 9, 2015. Accessed online at https://web.archive.org/web/20150414034831/https://worldnewsdailyreport.com/monsanto-creates-first-genetically-modified-strain-of-marijuana/.
Hiei et al. "Improved frequency of transformation in rice and maize by treatment of immature embryos with centrifugation and heat prior to infection with Agrobacterium tumefaciens," Plant Cell, Tissue, and Organ Culture, 2006, 87(3):233-243.

(Continued)

*Primary Examiner* — Weihua Fan
(74) *Attorney, Agent, or Firm* — Quarles & Brady, LLP

(57) ABSTRACT

Disclosed herein are methods for the production of *Cannabis* meristem explants from dry seeds. Also described are methods of transforming and gene editing using the *Cannabis* meristem explants disclosed herein.

11 Claims, 83 Drawing Sheets
(80 of 83 Drawing Sheet(s) Filed in Color)
Specification includes a Sequence Listing.

(56) References Cited

OTHER PUBLICATIONS

Huang et al. "Creating completely both male and female sterile plants by specifically ablating microspore and megaspore mother cells," Frontiers in Plant Science, 2016, 7(30).
Kapila et al. "An Agrobacterium-mediated transient gene expression system for intact leaves," Plant Science, 1997, 122(1):101-108.
Khanna, et al. "Centrifugation assisted Agrobacterium tumefaciens-mediated transformation (CAAT) of embryogenic cell suspensions of banana (*Musa* spp. Cavendish AAA and Lady finger AAA)," Molecular Breeding, 2004, 14:239-252.
Komari T, et al. (2006) Binary vectors and super-binary vectors. In: KanWang (ed.), and Methods in Molecular Biology, vol. 343: Agrobacterium Protocols, vol. 1, Second Edition. Humana Press Inc., Totowa, NJ, pp. 15-41.
Lata, H, et al. (2016) In vitro mass propagation of *Cannabis sativa* L .: A protocol refinement using novel aromatic cytokinin meta-topolin and the assessment of eco-physiological, biochemical and genetic fidelity of micropropagated plants. J Appl Res Med Aromat Plants 3:18-26.
Laverty et al., "A physical and genetic map of Cannabis sativa identifies extensive rearrangements at the THC/CBD acid synthase loci," Genome Research, 2018, 29:146-156.
Luo et al., "Complete biosynthesis of cannabinoids and their unnatural analogues in yeast," Nature, 2019, 567.
McCabe D, et al. (1988) Stable transformation of soybean (*Glycine max*) by particle acceleration. Bio/Technology 6:923-926.
Miller, N. New UW-Madison project to support Wisconsin hemp growers. Webpage. Published Apr. 25, 2019. Available online at https://news.wisc.edu/new-uw-madison-project-to-support-wisconsin-hemp-growers/.
Schiller, M. Trait Biosciences Announces Successful Stable Transformation of a Hemp Plant. Cannabis Business Times. Jun. 12, 2019. Available online at https://www.cannabisbusinesstimes.com/article/trait-biosciences-transformation-hemp-plant/.
Schrammeijer B, et al. (1990). Meristem transformation of sunflower via Agrobacterium. Plant Cell Reports 9 (2):55-60.
Sirikantaramas, S., et al. "The gene controlling marijuana psychoactivity molecular cloning and heterologous expression of ?1-tetrahydrocannabinolic acid synthase from *Cannabis sativa* L." Journal of Biological Chemistry 279.38 (2004): 39767-39774.
Slusarkiewicz-Jarzina A, et al (2005) Influence of cultivar, explant source and plant growth regulator on callus induction and plant regeneration of *Cannabis sativa* L. Acta Biol Craco Series Bot 47(2):145-151.
Tian et al., "Overexpression fo BraLTP2, a lipid transfer protein of *Brassica napus*, results in increased trichom density and altered concentration of secondary metabolites," Int. J. Mol. Sci., 2018, 19:1733.
Trick et al. "SAAT: sonication-assisted Agrobacterium-mediated transformation," Transgenic Research, 1997, 6 (5):329-336.
Wahby I, et al. (2004) Assessment of Agrobacterium-mediated genetic transformation in hemp (*Cannabis sativa* L.). Congress International de Biochimie, Marrakech, Morocco, pp. 565-568.
Wahby I, et al. (2013) Agrobacterium infection of hemp (*Cannabis sativa* L.): establishment of hairy root cultures. J Plant Interact 8:312-320.
Wrobel, T., et al. "The application of plant in vitro cultures in cannabinoid production." Biotechnology letters 40.3 (2018): 445-454.
Ye, X., et al. "Enhanced production of single copy backbone-free transgenic plants in multiple crop species using binary vectors with a pRi replication origin in Agrobacterium tumefaciens." Transgenic research 20.4 (2011): 773-786.
Zager, J. J., et al. "Gene networks underlying cannabinoid and terpenoid accumulation in cannabis." Plant physiology 180.4 (2019): 1877-1897.

\* cited by examiner

Cannabis seed and meristem explants

*Cannabis* meristem explants on B5 medium; post 4 day co-culture after inoculation with Ar18r12v / Dicot Binary 19

Transient GUS expression in *Cannabis* meristem explants transformed with Ar18r12v / Dicot Binary 19

Transient GUS expression in *Cannabis* meristem explants transformed with Ar18r12v / Dicot Binary 19 (explants de-stained in 70% EtOH)

Non-inoculated Cannabis seed sanitized in 20% Clorox on B5 media (left)
Non-inoculated meristem explants on B5 media (right)
* POC of viability of Cannabis seeds, meristem explants for transformation Spectinomycin sensitive (bleaching) phenotype visible in inoculated Cannabis meristem explants on 150 mg/L spectinomycin B5
* POC of use of aadA / spectinomycin resistance as a selectable marker in Cannabis
* Imaged 12April2019

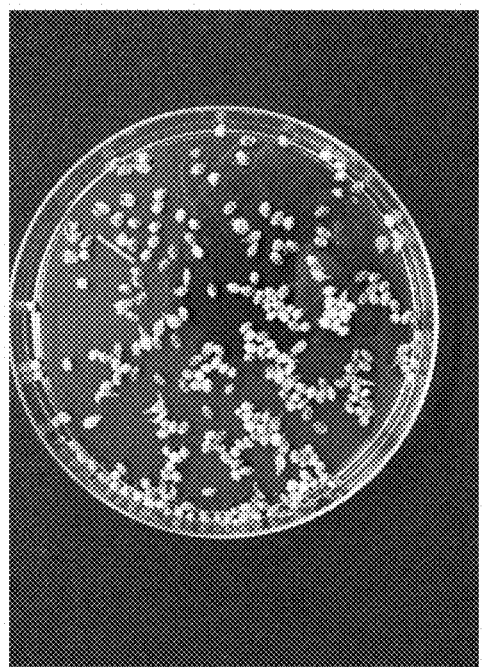
FIG. 14

FIG. 24
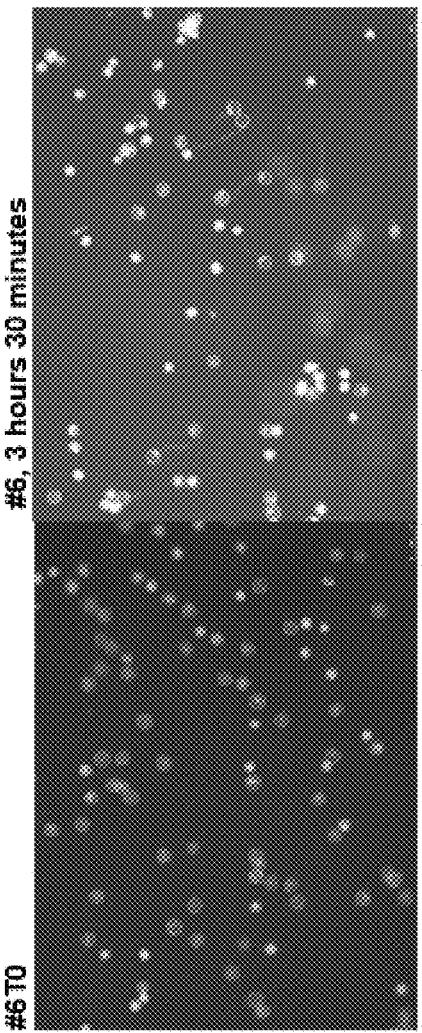
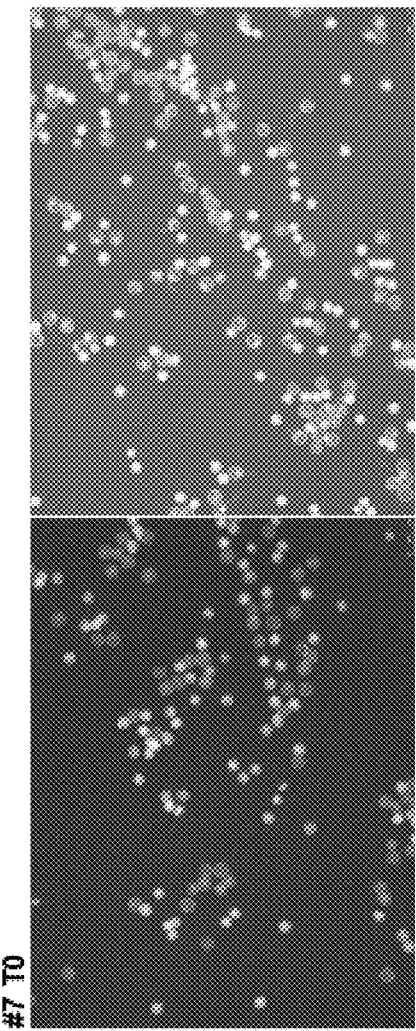

FIG. 26

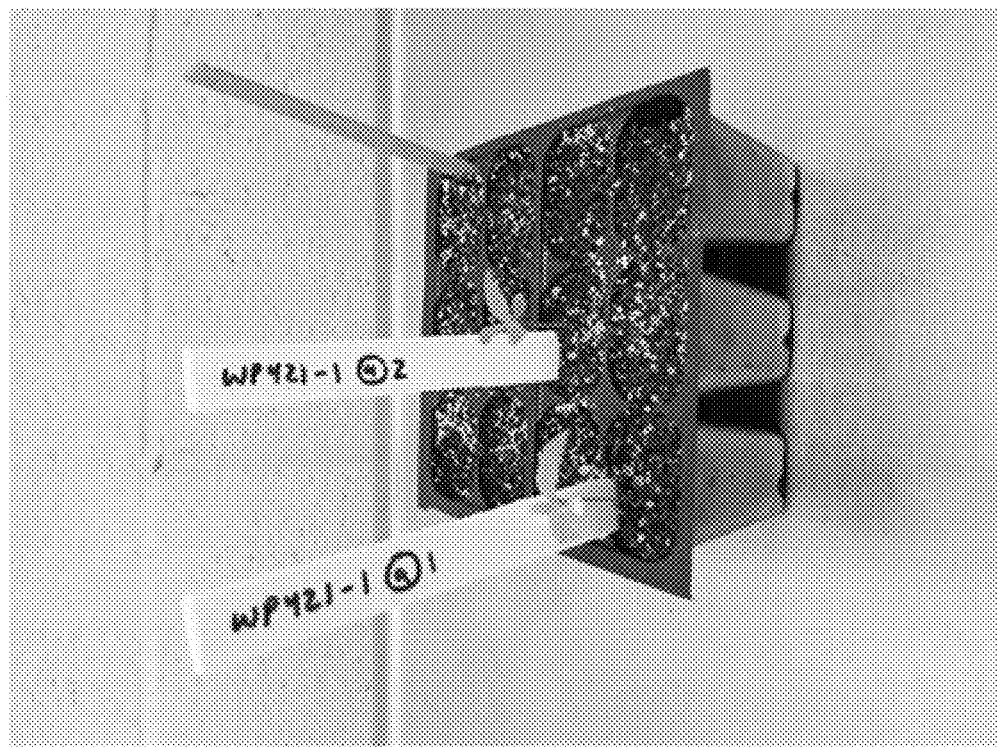
FIG. 40

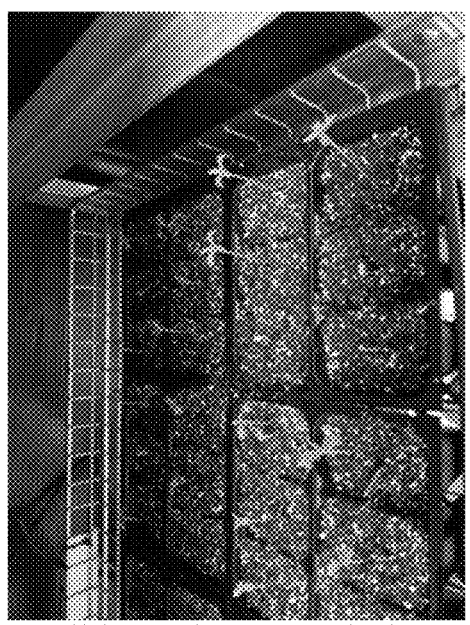
FIG. 45

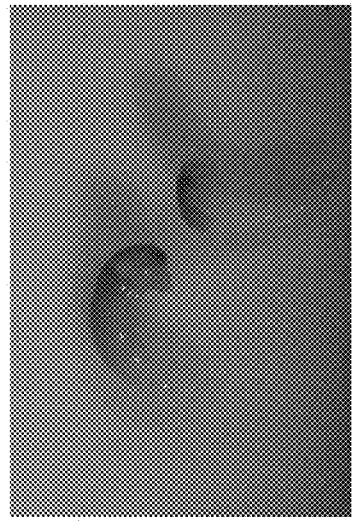
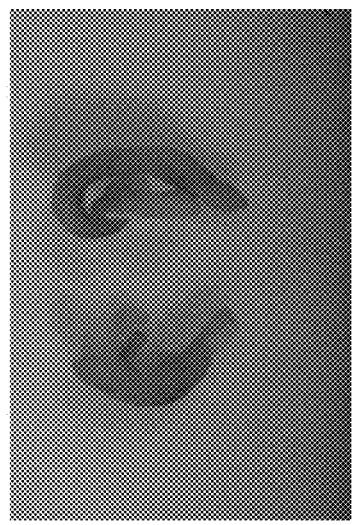
FIG. 60

BraLTP2 Original sequence: Type IIS recognition sequences: BsaI, BbsI, BsmBI ATGGCGACAGGTTCTCGTGTTCTGATCGGTCTAGCAATGATCCTATAATCTCAGGAGAACTGCTAGTCCAGGCAAGGA
ACGTGCCAAGGAGACATAGAGGGTCTGATGAGAGAATGTGCGGTCTACGTCCAGGTCCAGGCCAAAGGTAAACCATC
CGCAGCGGTGTGTGCAAAGTCGTCAAGAGATCAGACATCCCCTGCGCATGTGGCCGTATCACACCCTCGGTTCAAAAATGAT
AGACATGAATAAGGTTGTCTTGTCACTTCCTTTGTGGGAGGCCTCGCTCATGGTACCAAGTGTGGAAGCTACATTGTG
CCATGA

BraLTP2 CDS1 STOP Part for synthesis: Type IIS recognition sequences: BsaI, BbsI, BsmBI; START; STOP; XXXX = motif liberated by BsaI digestion during Golden Gate Level 1 assembly of Transcriptional Unit.

GGTCTCAAATGGCGACAGGTTCTCGTGTTCTGATCGGTCTAGCAATGATCCTATAATCTCAGGAGAACTGCTAGTCCAGG
GCAAGGAACGTGCCAAGGAGACATAGAGGGTCTGATGAGAGAATGTGCGGTCTACGTCCAGGTCCAGGCCAAAGGTA
AACCCATCCGCAGCGGTGTGTGCAAAGTCGTCAAGAGATCAGACATCCCCTGCGCATGTGGCCGTATCACACCCTCGGTTCAAA
AAATGATAGACATGAATAAGGTTGTCTTGTCACTTCCTTTGTGGGAGGCCTCGCTCATGGTACCAAGTGTGGAAGCTA
CATTGTGCCATGAGCTTAGAGACC

BraLTP2 CDS1 ns Part for synthesis: Type IIS recognition sequences: BsaI, BbsI, BsmBI; START; STOP; XXXX = replaces STOP motif liberated by BsaI digestion during Golden Gate Level 1 assembly of Transcriptional Unit; ;  (and produces a Serine-Serine linker)

GGTCTCAAATGGCGACAGGTTCTCGTGTTCTGATCGGTCTAGCAATGATCCTATAATCTCAGGAGAACTGCTAGTCCAGG
GCAAGGAACGTGCCAAGGAGACATAGAGGGTCTGATGAGAGAATGTGCGGTCTACGTCCAGGTCCAGGCCAAAGGTA
AACCCATCCGCAGCGGTGTGTGCAAAGTCGTCAAGAGATCAGACATCCCCTGCGTATCACACCCTCGGTTCAAA
AAATGATAGACATGAATAAGGTTGTCTTGTCACTTCCTTTGTGGGAGGCCTCGCTCATGGTACCAAGTGTGGAAGCTA
CATTGTGCCATTCGAGAGACC

FIG. 67

CsPT1 Original sequence: Type IIS recognition sequences: BsaI, ▮▮▮, ▮▮▮▮
ATGGGACTCTCATCAGTTTGTACCTTTTCATTTCAAACTAATTACCATACTTTATTAAATCCTCACAATAATAATCCCAAAACCTCATTATTA
TGTTATCGACACCCCAAAACACCAATTAAATACTCTTACAATAATTTTCCCTCTAAACATTGCTCCACCAAGAGTTTTCATCTACAAAACAA
ATGCTCAGAATCATTATCAATCGCAAAAAATTCCATTAGGGCAGCTACTACAAATCAAACTGAGCCTCCAGAATCTGATAATCATTCAGTA
GCAACTAAAATTTTAAACTTTGGGAAGGCATGTTGGAAACTTCAAAGACCATATACAATCATAGCATTTACTTCATGCGCTTGTGGATTGT
TTGGGAAAGAGTTGTTGCATAACACAAATTTAATAAGTTGGTCTCTGATGTTCAAGGCATTCTTTTTTTTGGTGGCTGTATTATGCATTGCT
TCTTTTACAACTACCATCAATCAGATTTACGATCTTCACATTGACAGAATAAACAAGCCTGATCTACCACTAGCTTCAGGGGAAATATCAG
TAAACACAGCTTGGATTATGAGCATAATTGTGGCACTGTTTGGATTGATAATAACTATAAAAATGAAGGGTGGACCACTCTATATATTTG
GCTACTGTTTTGGTATTTTTGGTGGGATTGTCTATTCTGTTCCACCATTTAGATGGAAGCAAAATCCTTCCACTGCATTTCTTCTCAATTTCC
TGGCCCATATTATTACAAATTTCACATTTTATTATGCCAGCAGAGCAGCTCTTGGCCTACCATTTGAGTTGAGGCCTTCTTTTACTTTCCTGC
TAGCATTTATGAAATCAATGGGTTCAGCTTTGGCTTTAATCAAAGATGCTTCAGACGTTGAAGGCGACACTAAATTTGGCATATCAACCTT
GGCAAGTAAATATGGTTCCAGAAACTTGACATTATTTTGTTCTGGAATTGTTCTCCTATCCTATGTGGCTGCTATACTTGCTGGGATTATCT
GGCCCCAGGCTTTCAACAGTAACGTAATGTTACTTTCTCATGCAATCTTAGCATTTTGGTTAATCCTCCAGACTCGAGATTTTGCGTTAACA
AATTACGACCCGGAAGCAGGCAGAAGATTTTACGAGTTCATGTGGAAGCTTTATTATGCTGAATATTTAGTATATGTTTTCATATAA CsPT1 CDS1 STOP Part for synthesis: Type IIS recognition sequences: BsaI, ▮▮▮, ▮▮▮▮, ▮▮▮▮, STOP, XXXX = motif liberated by BsaI digestion during Golden Gate Level 1 assembly of Transcriptional Unit.
GGTCTCAA▮▮GGACTCTCATCAGTTTGTACCTTTTCATTTCAAACTAATTACCATACTTTATTAAATCCTCACAATAATAATCCCAAAACCT
CATTATTATGTTATCGACACCCCAAAACACCAATTAAATACTCTTACAATAATTTTCCCTCTAAACATTGCTCCACCAAGAGTTTTCATCTAC
AAAACAAATGCTCAGAATCATTATCAATCGCAAAAAATTCCATTAGGGCAGCTACTACAAATCAAACTGAGCCTCCAGAATCTGATAATC
ATTCAGTAGCAACTAAAATTTTAAACTTTGGGAAGGCATGTTGGAAACTTCAAAGACCATATACAATCATAGCATTTACTTCATGCGCTTG
TGGATTGTTTGGGAAAGAGTTGTTGCATAACACAAATTTAATAAGTTGGTCTCTGATGTTCAAGGCATTCTTTTTTTTGGTGGCTGTATTA
TGCATTGCTTCTTTTACAACTACCATCAATCAGATTTACGATCTTCACATTGACAGAATAAACAAGCCTGATCTACCACTAGCTTCAGGGG
AAATATCAGTAAACACAGCTTGGATTATGAGCATAATTGTGGCACTGTTTGGATTGATAATAACTATAAAAATGAAGGGTGGACCACTCT
ATATATTTGGCTACTGTTTTGGTATTTTTGGTGGGATTGTCTATTCTGTTCCACCATTTAGATGGAAGCAAAATCCTTCCACTGCATTTCTTC
TCAATTTCCTGGCCCATATTATTACAAATTTCACATTTTATTATGCCAGCAGAGCAGCTCTTGGCCTACCATTTGAGTTGAGGCCTTCTTTTA
CTTTCCTGCTAGCATTTATGAAATCAATGGGTTCAGCTTTGGCTTTAATCAAAGATGCTTCAGACGTTGAAGGCGACACTAAATTTGGCAT
ATCAACCTTGGCAAGTAAATATGGTTCCAGAAACTTGACATTATTTTGTTCTGGAATTGTTCTCCTATCCTATGTGGCTGCTATACTTGCTG
GGATTATCTGGCCCCAGGCTTTCAACAGTAACGTAATGTTACTTTCTCATGCAATCTTAGCATTTTGGTTAATCCTCCAGACTCGAGATTTT
GCGTTAACAAATTACGACCCGGAAGCAGGCAGAAGATTTTACGAGTTCATGTGGAAGCTTTATTATGCTGAATATTTAGTATATGTTTTCA
TA▮▮▮GCTTAGAGACC CsPT1 CDS1 ns Part for synthesis: Type IIS recognition sequences: BsaI, ▮▮▮, ▮▮▮▮, ▮▮▮▮, STOP, XXXX = motif liberated by BsaI digestion during Golden Gate Level 1 assembly of Transcriptional Unit; ▮▮ replaces STOP (and produces a Serine-Serine linker)
GGTCTCAA▮▮GGACTCTCATCAGTTTGTACCTTTTCATTTCAAACTAATTACCATACTTTATTAAATCCTCACAATAATAATCCCAAAACCT
CATTATTATGTTATCGACACCCCAAAACACCAATTAAATACTCTTACAATAATTTTCCCTCTAAACATTGCTCCACCAAGAGTTTTCATCTAC
AAAACAAATGCTCAGAATCATTATCAATCGCAAAAAATTCCATTAGGGCAGCTACTACAAATCAAACTGAGCCTCCAGAATCTGATAATC
ATTCAGTAGCAACTAAAATTTTAAACTTTGGGAAGGCATGTTGGAAACTTCAAAGACCATATACAATCATAGCATTTACTTCATGCGCTTG
TGGATTGTTTGGGAAAGAGTTGTTGCATAACACAAATTTAATAAGTTGGTCTCTGATGTTCAAGGCATTCTTTTTTTTGGTGGCTGTATTA
TGCATTGCTTCTTTTACAACTACCATCAATCAGATTTACGATCTTCACATTGACAGAATAAACAAGCCTGATCTACCACTAGCTTCAGGGG
AAATATCAGTAAACACAGCTTGGATTATGAGCATAATTGTGGCACTGTTTGGATTGATAATAACTATAAAAATGAAGGGTGGACCACTCT
ATATATTTGGCTACTGTTTTGGTATTTTTGGTGGGATTGTCTATTCTGTTCCACCATTTAGATGGAAGCAAAATCCTTCCACTGCATTTCTTC
TCAATTTCCTGGCCCATATTATTACAAATTTCACATTTTATTATGCCAGCAGAGCAGCTCTTGGCCTACCATTTGAGTTGAGGCCTTCTTTTA
CTTTCCTGCTAGCATTTATGAAATCAATGGGTTCAGCTTTGGCTTTAATCAAAGATGCTTCAGACGTTGAAGGCGACACTAAATTTGGCAT
ATCAACCTTGGCAAGTAAATATGGTTCCAGAAACTTGACATTATTTTGTTCTGGAATTGTTCTCCTATCCTATGTGGCTGCTATACTTGCTG
GGATTATCTGGCCCCAGGCTTTCAACAGTAACGTAATGTTACTTTCTCATGCAATCTTAGCATTTTGGTTAATCCTCCAGACTCGAGATTTT
GCGTTAACAAATTACGACCCGGAAGCAGGCAGAAGATTTTACGAGTTCATGTGGAAGCTTTATTATGCTGAATATTTAGTATATGTTTTCA
TA▮▮TTCGAGAGACC

FIG. 70

Reference CsEPSPS sequence:
LOC115705599:  TGACGAAGTTCAACTTCTTGGAAATGTGGAAAAGCAATGCGTCACTCACAGCTGC (SEQ ID NO:55)
LOC115705595:  TGACGAAGTTCAACTTCTTGGAAATGTGGAAAAGCAATGCGTCACTCACAGCTGC (SEQ ID NO:55)

nick
                                               ↓
TTGACGAAGTTCAACTTCTTGGAAATGTGGAAAAGCAATGCGTCACTCACAGCTGC (SEQ ID NO:55)

XXX = spacer; XXX = PAM; X = editing position +1

* double-nucleotide mutation: CsEPSPS_9CtoT and 20CtoT (mutation from C to T at position 9 and from C to T at position 20)

pegRNA: CAACTTCTTGGAAATG-scaffold-TGAGTGAACGCATTGCTATTCCAGCATTTCCAAGGA (SEQ ID NO:56)
                                         RT          +        PBS CsEPSPS-gRNA1 as oligos:
TGAAGACTTGCAACTTCTTGGAAATGTGTTTAAGTCTTTCT (Forward)   (SEQ ID NO:41)

AGAAGACTTAAACACATTTCCAAGAAGTTGCAAAGTCTTCA (Reverse)   (SEQ ID NO:42)

CsEPSPS-Ext1 Part for synthesis: (PBS+RT flanked by BspMI sites):
ACCTGCTATAGTGCTGAGTGAACGCATTGCTATTCCAGCATTTCCAAGGAAACATATAGCAGGT (SEQ ID NO:43)

FIG. 71

Reference CsEPSPS sequence:

LOC115705599: <u>TTGGAGAACACTTGAGGA</u>AGGACGATTACTGCGTGATCACTCCACCAGAGAA (SEQ ID NO:57)

LOC115705595: <u>TTGGAGCAACAGTTGAGGCA</u>AGGACGATTACTGCGTGATCACTCCACCAGAGAA (SEQ ID NO:57)

 nick

<u>TTGGAGCAACAGTTGA</u>_<u>GA</u>AGGACGATTACTGCGTGATCACTCCACCAGAGAA (SEQ ID NO:57)

XXX = spacer; XXX = PAM; 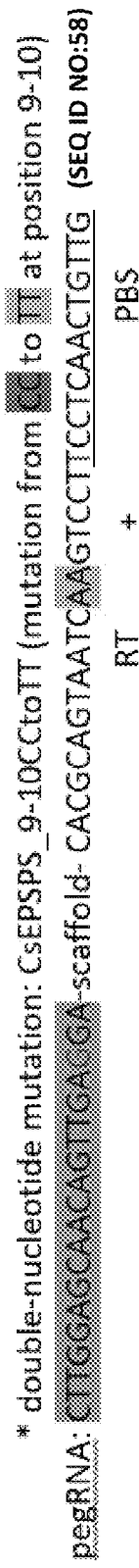 = editing position +1

* double-nucleotide mutation: CsEPSPS_9-10CCtoTT (mutation from ██ to ██ at position 9-10)

pegRNA: <u>TTGGAGCAACAGTTGA</u>_<u>GA</u>-scaffold-CACGCAGTAATCA<u>AGTCCTTCCTCAACTGTTG</u> (SEQ ID NO:58)

RT   +   PBS

CsEPSPS-gRNA2 as oligos:

<u>T</u><u>GAAGACTT</u>TGCA<u>TTGGAGCAACAGTTGAGGCA</u><u>GTTTAAGTCTTC</u>T (Forward) (SEQ ID NO:44)

AGAAGACTTAAAC<u>TGCCTCAACTGTTGCTCCAA</u>TGCAA<u>AGTCTTC</u>A (Reverse) (SEQ ID NO:45)

CsEPSPS-Ext2 Part for synthesis: (PBS+RT flanked by BspMI sites):

ACCTGCTATAGTGCCACGCAGTAATCAAGTCCTTCCTCAACTGTTGAACATATAGCAGGT (SEQ ID NO:46)

SEQUENCE LISTING

```
<160> NUMBER OF SEQ ID NOS: 61

<210> SEQ ID NO 1
<211> LENGTH: 1638
<212> TYPE: DNA
<213> ORGANISM: Cannabis sativa

<400> SEQUENCE: 1
```

```
atgaattgct cagcatttc cttttggttt gtttgcaaaa taatattttt ctttctctca      60
ttccatatcc aaatttcaat agctaatcct cgagaaaact tccttaaatg cttctcaaaa     120
catattccca acaatgtagc aaatccaaaa ctcgtataca ctcaacacga ccaattgtat     180
atgtctatcc tgaattcgac aatacaaaat cttagattca tctctgatac aaccccaaaa     240
ccactcgtta ttgtcactcc ttcaaataac tcccatatcc aagcaactat tttatgctct     300
aagaaagttg gcttgcagat tcgaactcga agcggtggcc atgatgctga gggtatgtcc     360
tacatatctc aagtcccatt tgttgtagta gacttgagaa acatgcattc gatcaaaata     420
gatgttcata gccaaactgc gtgggttgaa gccggagcta cccttggaga agtttattat     480
tggatcaatg agaagaatga gaatcttagt tttcctggtg ggtattgccc tactgttggc     540
gtaggtggac actttagtgg aggaggctat ggagcattga tgcgaaatta tggccttgcg     600
gctgataata ttattgatgc acacttagtc aatgttgatg gaaaagttct agatcgaaaa     660
tccatgggag aagatctgtt tgggctata cgtggtggtg gaggagaaaa ctttggaatc     720
attgcagcat ggaaaatcaa actggttgat gtcccatcaa agtctactat attcagtgtt     780
aaaaagaaca tggagataca tgggcttgtc aagttattta caaatggca aaatattgct     840 tacaagtatg acaaagattt agtactcatg actcacttca taacaaagaa tattacagat     900
aatcatggga gaataagac tacagtacat ggttacttct cttcaatttt tcatggtgga     960
gtggatagtc tagtcgactt gatgaacaag agctttcctg agttgggtat taaaaaaact    1020
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agttagacta tgttaagaaa ccaattccag aaactgcaat ggtcaaaatt    1200
ttggaaaaat tatatgaaga agatgtagga gctgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacgact ccttatgtgt cccaaaatcc aagattggcg    1440
tatctcaatt atagggacct tgatttagga aaaactaatc atgcgagtcc taataattac    1500
acacaagcac gtatttgggg tgaaaagtat tttggtaaaa attttaacag gttagttaag    1560
gtgaaaacta agttgatcc caataatttt tttagaaacg aacaaagtat cccacctctt    1620
ccaccgcatc atcattaa                                                  1638
```

<210> SEQ ID NO 2  
<211> LENGTH: 1638  
<212> TYPE: DNA  
<213> ORGANISM: Cannabis sativa

<400> SEQUENCE: 2

```
atgaattgct cagcatttc cttttggttt gtttgcaaaa taatattttt ctttctctca      60
ttccatatcc aaatttcaat agctaatcct cgagaaaact tccttaaatg cttctcaaaa     120
catattccca acaatgtagc aaatccaaaa ctcgtataca ctcaacacga ccaattgtat     180
atgtctatcc tgaattcgac aatacaaaat cttagattca tctctgatac aaccccaaaa     240
ccactcgtta ttgtcactcc ttcaaataac tcccatatcc aagcaactat tttatgctct     300
aagaaagttg gcttgcagat tcgaactcga agcggtggcc atgatgctga gggtatgtcc     360
tacatatctc aagtcccatt tgttgtagta gacttgagaa acatgcattc gatcaaaata     420
```

```
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg gaaagttcct agatcgaaaa    660
tccatgggag aagatctgtt tgggctata cgtggtggtg gaggagaaaa ctttggaatc     720
attgcagcat ggaaaatcaa actggttgct gtcccatcaa agtctactat attcagtgtt    780
aaaaagaaca tggagataca tgggcttgtc aagttattta caaatggca aaatattgct     840
tacaagtatg acaaagattt agtactcatg actcacttca taacaaagaa tattacagat    900
aatcatggga agaataagac tacagtacat ggttacttct cttcaatttt tcatggtgga    960
gtggatagtc tagtcgactt gatgaacaag agctttcgtg agttgggtat taaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta gttagacta tgttaagaaa ccaattccag aaactgcaat ggtcaaaatt    1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa ttttacgact ccttatgtgt cccaaaatcc aagattggcg   1440
tatctcaatt atagggacct tgatttagga aaaactaatc atgcgagtcc taataattac   1500
acacaagcac gtatttgggg tgaaaagtat tttggtaaaa attttaacag gttagttaag   1560
gtgaaaacta agttgatcc caataatttt tttagaaacg aacaaagtat cccacctctt    1620
mcaccgcatc atcattaa                                                 1638

<210> SEQ ID NO 3
<211> LENGTH: 1635
<212> TYPE: DNA
<213> ORGANISM: Cannabis sativa

<400> SEQUENCE: 3
atgaattgct cagcattttc cttttggttt gtttgcaaaa taatattttt ctttctctca     60
ttccatatcc aaatttcaat agctaatcct cgagaaaact tccttaaatg cttctcaaaa    120
catattccca acaatgtagc aaatccaaaa ctcgtataca ctcaacacga ccaattgtat    180
atgtctatcc tgaattcgac aatacaaaat cttagattca tctctgatac aaccccaaaa    240
ccactcgtta ttgtcactcc ttcaaataac tcccatatcc aagcaactat tttatgctct    300
aagaaagttg gcttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata ttattgatgc acacttagtc aatgttgatg gaaagttcct agatcgaaaa    660
tccatgggag aagatctgtt tgggctata cgtggtggtg gaggagaaaa ctttggaatc     720
attgcagcat ggaaaatcaa actggttgct gtcccatcaa agtctactat attcagtgtt    780
aaaaagaaca tggagataca tgggcttgtc aagttattta caaatggca aaatattgct     840
tacaagtatg acaaagattt agtactcatg actcacttca taacaaagaa tattacagat    900
```

```
aatcatggga agaataagac tacagtacat ggttacttct cttcaatttt tcatggtgga    960
gtggatagtc tagtcgactt gatgaacaag agctttcctg agttgggtat aaaaaaaact   1020
gattgcaaag aatttagctg gattgataca accatcttct acagtggtgt tgtaaatttt   1080
aacactgcta attttaaaaa ggaaattttg cttgatagat cagctgggaa gaagacggct   1140
ttctcaatta agttagacta tgttaagaaa ccaattccag aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
tatgaacttt ggtacactgc ttcctgggag aagcaagaag ataatgaaaa gcatataaac   1380
tgggttcgaa gtgtttataa ttttacgact ccttatgtgt cccaaaatcc aagattggcg   1440
tatctcaatt atagggacct tgatttagga aaaactaatc atgcgagtcc taataattac   1500
acacaagcac gtatttgggg tgaaaagtat tttggtaaaa attttaacag gttagttaag   1560
gtgaaaacta agttgatcc caataatttt tttagaaacg aacaaagtat cccacctctt   1620
ccaccgcatc atcat                                                    1635

<210> SEQ ID NO 4
<211> LENGTH: 1638
<212> TYPE: DNA
<213> ORGANISM: Cannabis sativa

<400> SEQUENCE: 4
atgaattgct cagcattttc cttttggttt gtttgcaaaa taatattttt ctttctctca     60
ttccatatcc aaatttcaat agctaatcct cgagaaaact tccttaaatg cttctcaaaa    120
catattccca acaatgtagc aaatccaaaa ctcgtataca ctcaacacga ccaattgtat    180
atgtctatcc tgaattcgac aatacaaaat cttagattca tctctgatac aaccccaaaa    240
ccactcgtta ttgtcactcc ttcaaataac tcccatatcc aagcaactat tttatgctct    300
aagaaagttg gcttgcagat tcgaactcga agcggtggcc atgatgctga gggtatgtcc    360
tacatatctc aagtcccatt tgttgtagta gacttgagaa acatgcattc gatcaaaata    420
gatgttcata gccaaactgc gtgggttgaa gccggagcta cccttggaga agtttattat    480
tggatcaatg agaagaatga gaatcttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttcct agatcgaaaa    660
tccatgggag aagatctgtt tgggctata cgtggtggtg gaggagaaaa ctttggaatc    720
attgcagcat ggaaaatcaa actggttgct gtcccatcaa agtctactat attcagtgtt    780
aaaaagaaca tggagataca tgggcttgtc aagttattta caaatggca aaatattgct    840
tacaagtatg acaaagattt agtactcatg actcacttca taacaaagaa tattacagat    900
aatcatggga agaataagac tacagtacat ggttacttct cttcaatttt tcatggtgga    960
gtggatagtc tagtcgactt gatgaacaag agctttcgtg agttgggtat aaaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ccaattccag aaactgcaat ggtcaaaatt   1200
ttggaaaaat tatatgaaga agatgtagga gctgggatgt atgtgttgta cccttacggt   1260
ggtataatgg aggagatttc agaatcagca attccattcc ctcatcgagc tggaataatg   1320
```

| | |
|---|---|
| tatgaactttt ggtacactgc ttcctgggag aagcaagaag ataatgaaaa gcatataaac | 1380 |
| tgggttcgaa gtgtttataa ttttacgact ccttatgtgt cccaaaatcc aagattggcg | 1440 |
| tatctcaatt atagggacct tgatttagga aaaactaatc atgcgagtcc taataattac | 1500 |
| acacaagcac gtatttgggg tgaaaagtat tttggtaaaa attttaacag gttagttaag | 1560 |
| gtgaaaacta aagttgatcc caataatttt tttagaaacg aacaaagtat cccacctctt | 1620 |
| ccaccgcatc atcattaa | 1638 |

<210> SEQ ID NO 5
<211> LENGTH: 1638
<212> TYPE: DNA
<213> ORGANISM: Cannabis sativa

<400> SEQUENCE: 5

| | |
|---|---|
| atgaattgct cagcattctc cttttggttt gtttgcaaaa taatattttt ctttctctca | 60 |
| ttcaatatcc aaatttcaat agctaatcct caagaaaact tccttaaatg cttctcggaa | 120 |
| tatattccta acaatccagc aaatccaaaa ttcatataca ctcaacacga ccaattgtat | 180 |
| atgtctgtcc tgaattcgac aatacaaaat cttagattca cctctgatac aaccccaaaa | 240 |
| ccactcgtta ttgtcactcc ttcaaatgtc tcccatatcc aggccagtat tctctgctcc | 300 |
| aagaaagttg gtttgcagat tcgaactcga agcggtggcc atgatgctga gggtttgtcc | 360 |
| tacatatctc aagtcccatt tgctatagta gacttgagaa acatgcatac ggtcaaagta | 420 |
| gatattcata gccaaactgc gtgggttgaa gccggagcta cccttggaga agtttattat | 480 |
| tggatcaatg agatgaatga gaattttagt tttcctggtg ggtattgccc tactgttggc | 540 |
| gtaggtggac actttagtgg aggaggctat ggagcattga tgcgaaatta tggccttgcg | 600 |
| gctgataata tcattgatgc acacttagtc aatgttgatg aaaagttct agatcgaaaa | 660 |
| tccatgggag aagatctatt tggggctata cgtggtggag gaggagaaaa ctttggaatc | 720 |
| attgcagcat ggaaaatcaa acttgttgtt gtcccatcaa aggctactat attcagtgtt | 780 |
| aaaaagaaca tggagataca tgggcttgtc aagttatttta acaaatggca aaatattgct | 840 |
| tacaagtatg acaaagattt aatgctcacg actcacttca gaactaggaa tattacagat | 900 |
| aatcatggga agaataagac tacagtacat ggttacttct cttccatttt tcttggtgga | 960 |
| gtggatagtc tagttgactt gatgaacaag agctttcctg agttgggtat taaaaaaact | 1020 |
| gattgcaaag aattgagctg gattgataca accatcttct acagtggtgt tgtaaattac | 1080 |
| aacactgcta atttttaaaaa ggaaattttg cttgatagat cagctgggaa gaagacggct | 1140 |
| ttctcaatta agtttagacta tgttaagaaa ctaatacctg aaactgcaat ggtcaaaatt | 1200 |
| ttggaaaaat tatatgaaga gaggtaggga gttgggatgt atgtgttgta cccttacggt | 1260 |
| ggtataatgg atgagatttc agaatcagca attccattcc ctcatcgagc tggaataatg | 1320 |
| tatgaactttt ggtacactgc tacctgggag aagcaagaag ataacgaaaa gcatataaac | 1380 |
| tgggttcgaa gtgtttataa tttcacaact ccttatgtgt cccaaaatcc aagattggcg | 1440 |
| tatctcaatt atagggacct tgatttagga aaaactaatc ctgagagtcc taataattac | 1500 |
| acacaagcac gtatttgggg tgaaaagtat tttggtaaaa attttaacag gttagttaag | 1560 |
| gtgaaaacca aagctgatcc caataatttt tttagaaacg aacaaagtat cccacctctt | 1620 |
| ccaccgcgtc atcattaa | 1638 |

<210> SEQ ID NO 6
<211> LENGTH: 545

<212> TYPE: PRT
<213> ORGANISM: Cannabis sativa

<400> SEQUENCE: 6

```
Met Asn Cys Ser Ala Phe Ser Phe Trp Phe Val Cys Lys Ile Ile Phe
1               5                   10                  15

Phe Phe Leu Ser Phe His Ile Gln Ile Ser Ile Ala Asn Pro Arg Glu
                20                  25                  30

Asn Phe Leu Lys Cys Phe Ser Lys His Ile Pro Asn Asn Val Ala Asn
            35                  40                  45

Pro Lys Leu Val Tyr Thr Gln His Asp Gln Leu Tyr Met Ser Ile Leu
        50                  55                  60

Asn Ser Thr Ile Gln Asn Leu Arg Phe Ile Ser Asp Thr Thr Pro Lys
65                  70                  75                  80

Pro Leu Val Ile Val Thr Pro Ser Asn Asn Ser His Ile Gln Ala Thr
                85                  90                  95

Ile Leu Cys Ser Lys Lys Val Gly Leu Gln Ile Arg Thr Arg Ser Gly
            100                 105                 110

Gly His Asp Ala Glu Gly Met Ser Tyr Ile Ser Gln Val Pro Phe Val
        115                 120                 125

Val Val Asp Leu Arg Asn Met His Ser Ile Lys Ile Asp Val His Ser
130                 135                 140

Gln Thr Ala Trp Val Glu Ala Gly Ala Thr Leu Gly Glu Val Tyr Tyr
145                 150                 155                 160

Trp Ile Asn Glu Lys Asn Glu Asn Leu Ser Phe Pro Gly Gly Tyr Cys
                165                 170                 175

Pro Thr Val Gly Val Gly His Phe Ser Gly Gly Gly Tyr Gly Ala
            180                 185                 190

Leu Met Arg Asn Tyr Gly Leu Ala Ala Asp Asn Ile Ile Asp Ala His
        195                 200                 205

Leu Val Asn Val Asp Gly Lys Val Leu Asp Arg Lys Ser Met Gly Glu
210                 215                 220

Asp Leu Phe Trp Ala Ile Arg Gly Gly Gly Gly Glu Asn Phe Gly Ile
225                 230                 235                 240

Ile Ala Ala Trp Lys Ile Lys Leu Val Asp Val Pro Ser Lys Ser Thr
                245                 250                 255

Ile Phe Ser Val Lys Lys Asn Met Glu Ile His Gly Leu Val Lys Leu
            260                 265                 270

Phe Asn Lys Trp Gln Asn Ile Ala Tyr Lys Tyr Asp Lys Asp Leu Val
        275                 280                 285

Leu Met Thr His Phe Ile Thr Lys Asn Ile Thr Asp Asn His Gly Lys
        290                 295                 300

Asn Lys Thr Thr Val His Gly Tyr Phe Ser Ser Ile Phe His Gly Gly
305                 310                 315                 320

Val Asp Ser Leu Val Asp Leu Met Asn Lys Ser Phe Pro Glu Leu Gly
                325                 330                 335

Ile Lys Lys Thr Asp Cys Lys Glu Phe Ser Trp Ile Asp Thr Thr Ile
            340                 345                 350

Phe Tyr Ser Gly Val Val Asn Phe Asn Thr Ala Asn Phe Lys Lys Glu
        355                 360                 365

Ile Leu Leu Asp Arg Ser Ala Gly Lys Lys Thr Ala Phe Ser Ile Lys
        370                 375                 380

Leu Asp Tyr Val Lys Lys Pro Ile Pro Glu Thr Ala Met Val Lys Ile
385                 390                 395                 400
```

```
Leu Glu Lys Leu Tyr Glu Glu Asp Val Gly Ala Gly Met Tyr Val Leu
                405                 410                 415
Tyr Pro Tyr Gly Gly Ile Met Glu Glu Ile Ser Glu Ser Ala Ile Pro
            420                 425                 430
Phe Pro His Arg Ala Gly Ile Met Tyr Glu Leu Trp Tyr Thr Ala Ser
        435                 440                 445
Trp Glu Lys Gln Glu Asp Asn Glu Lys His Ile Asn Trp Val Arg Ser
    450                 455                 460
Val Tyr Asn Phe Thr Thr Pro Tyr Val Ser Gln Asn Pro Arg Leu Ala
465                 470                 475                 480
Tyr Leu Asn Tyr Arg Asp Leu Asp Leu Gly Lys Thr Asn His Ala Ser
                485                 490                 495
Pro Asn Asn Tyr Thr Gln Ala Arg Ile Trp Gly Glu Lys Tyr Phe Gly
            500                 505                 510
Lys Asn Phe Asn Arg Leu Val Lys Val Lys Thr Lys Val Asp Pro Asn
        515                 520                 525
Asn Phe Phe Arg Asn Glu Gln Ser Ile Pro Pro Leu Pro Pro His His
    530                 535                 540
His
545

<210> SEQ ID NO 7
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 7
tgcagcatgg aaaatcaaac                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 8
cccttacggt ggtataatgg                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 9
tagctattga aatttggata                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 10
tagagcataa aatagttgct                                                    20
```

<210> SEQ ID NO 11
<211> LENGTH: 1635
<212> TYPE: DNA
<213> ORGANISM: Cannabis sativa

<400> SEQUENCE: 11

| | | | | | |
|---|---|---|---|---|---|
| atgaagtgct | caacattctc | cttttggttt | gtttgcaaga | taatattttt | cttttctca | 60 |
| ttcaatatcc | aaacttccat | tgctaatcct | cgagaaaact | tccttaaatg | cttctcgcaa | 120 |
| tatattccca | ataatgcaac | aaatctaaaa | ctcgtataca | ctcaaaacaa | cccattgtat | 180 |
| atgtctgtcc | taaattcgac | aatacacaat | cttagattca | gctctgacac | aaccccaaaa | 240 |
| ccacttgtta | tcgtcactcc | ttcacatgtc | tctcatatcc | aaggcactat | tctatgctcc | 300 |
| aagaaagttg | gcttgcagat | tcgaactcga | agtggtggtc | atgattctga | gggcatgtcc | 360 |
| tacatatctc | aagtcccatt | tgttatagta | gacttgagaa | acatgcgttc | aatcaaaata | 420 |
| gatgttcata | gccaaactgc | atgggttgaa | gccggagcta | cccttggaga | agtttattat | 480 |
| tgggttaatg | agaaaaatga | gagtcttagt | ttggctgctg | gtattgccc | tactgtttgc | 540 |
| gcaggtggac | actttggtgg | aggaggctat | ggaccattga | tgagaagcta | tggcctcgcg | 600 |
| gctgataata | tcattgatgc | acacttagtc | aacgttcatg | aaaagtgct | agatcgaaaa | 660 |
| tctatggggg | aagatctctt | tgggctttta | cgtggtggtg | gagcagaaag | cttcggaatc | 720 |
| attgtagcat | ggaaaattag | actggttgct | gtcccaaagt | ctactatgtt | tagtgttaaa | 780 |
| aagatcatgg | agatacatga | gcttgtcaag | ttagttaaca | aatggcaaaa | tattgcttac | 840 |
| aagtatgaca | agattttatt | actcatgact | cacttcataa | ctaggaacat | tacagataat | 900 |
| caagggaaga | ataagacagc | aatacacact | tacttctctt | cagttttcct | tggtggagtg | 960 |
| gatagtctag | tcgacttgat | gaacaagagt | tttcctgagt | tgggtattaa | aaaaacggat | 1020 |
| tgcagacaat | tgagctggat | tgatactatc | atcttctata | gtggtgttgt | aaattacgac | 1080 |
| actgataatt | ttaacaagga | aattttgctt | gatagatccg | ctgggcagaa | cggtgctttc | 1140 |
| aagattaagt | tagactacgt | taagaaacca | attccagaat | ctgtatttgt | ccaaattttg | 1200 |
| gaaaaattat | atgaagaaga | tataggagct | gggatgtatg | cgttgtaccc | ttacggtggt | 1260 |
| ataatggatg | agatttctga | atcagcaatt | ccattccctc | atcgagctgg | aatcttgtat | 1320 |
| gagttatggt | acatatgtag | ctgggagaag | caagaagata | cgaaaagca | tctaaactgg | 1380 |
| attagaaata | tttataactt | catgactcct | tatgtgtccc | aaaatccaag | attggcatat | 1440 |
| ctcaattata | gagaccttga | tataggaata | aatgatccca | agaatccaaa | taattacaca | 1500 |
| caagcacgta | tttggggtga | aagtattttt | ggtaaaaatt | ttgacaggct | agtaaaagtg | 1560 |
| aaaaccctgg | ttgatcccaa | taatttttt | agaaacgaac | aaagcatccc | acctcttcca | 1620 |
| cggcatcgtc | attaa | | | | | 1635 |

<210> SEQ ID NO 12
<211> LENGTH: 544
<212> TYPE: PRT
<213> ORGANISM: Cannabis sativa

<400> SEQUENCE: 12

Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn

```
                35                  40                  45
Leu Lys Leu Val Tyr Thr Gln Asn Asn Pro Leu Tyr Met Ser Val Leu
 50                  55                  60

Asn Ser Thr Ile His Asn Leu Arg Phe Ser Ser Asp Thr Thr Pro Lys
 65                  70                  75                  80

Pro Leu Val Ile Val Thr Pro Ser His Val Ser His Ile Gln Gly Thr
                 85                  90                  95

Ile Leu Cys Ser Lys Lys Val Gly Leu Gln Ile Arg Thr Arg Ser Gly
                100                 105                 110

Gly His Asp Ser Glu Gly Met Ser Tyr Ile Ser Gln Val Pro Phe Val
                115                 120                 125

Ile Val Asp Leu Arg Asn Met Arg Ser Ile Lys Ile Asp Val His Ser
                130                 135                 140

Gln Thr Ala Trp Val Glu Ala Gly Ala Thr Leu Gly Glu Val Tyr Tyr
145                 150                 155                 160

Trp Val Asn Glu Lys Asn Glu Ser Leu Ser Leu Ala Ala Gly Tyr Cys
                165                 170                 175

Pro Thr Val Cys Ala Gly Gly His Phe Gly Gly Gly Tyr Gly Pro
                180                 185                 190

Leu Met Arg Ser Tyr Gly Leu Ala Ala Asp Asn Ile Ile Asp Ala His
                195                 200                 205

Leu Val Asn Val His Gly Lys Val Leu Asp Arg Lys Ser Met Gly Glu
                210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
                260                 265                 270

Asn Lys Trp Gln Asn Ile Ala Tyr Lys Tyr Asp Lys Asp Leu Leu Leu
                275                 280                 285

Met Thr His Phe Ile Thr Arg Asn Ile Thr Asp Asn Gln Gly Lys Asn
290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Ile Phe
                340                 345                 350

Tyr Ser Gly Val Val Asn Tyr Asp Thr Asp Asn Phe Asn Lys Glu Ile
                355                 360                 365

Leu Leu Asp Arg Ser Ala Gly Gln Asn Gly Ala Phe Lys Ile Lys Leu
                370                 375                 380

Asp Tyr Val Lys Lys Pro Ile Pro Glu Ser Val Phe Val Gln Ile Leu
385                 390                 395                 400

Glu Lys Leu Tyr Glu Glu Asp Ile Gly Ala Gly Met Tyr Ala Leu Tyr
                405                 410                 415

Pro Tyr Gly Gly Ile Met Asp Glu Ile Ser Glu Ser Ala Ile Pro Phe
                420                 425                 430

Pro His Arg Ala Gly Ile Leu Tyr Glu Leu Trp Tyr Ile Cys Ser Trp
                435                 440                 445

Glu Lys Gln Glu Asp Asn Glu Lys His Leu Asn Trp Ile Arg Asn Ile
                450                 455                 460
```

Tyr Asn Phe Met Thr Pro Tyr Val Ser Gln Asn Pro Arg Leu Ala Tyr
465                 470                 475                 480

Leu Asn Tyr Arg Asp Leu Asp Ile Gly Ile Asn Asp Pro Lys Asn Pro
            485                 490                 495

Asn Asn Tyr Thr Gln Ala Arg Ile Trp Gly Glu Lys Tyr Phe Gly Lys
        500                 505                 510

Asn Phe Asp Arg Leu Val Lys Val Lys Thr Leu Val Asp Pro Asn Asn
    515                 520                 525

Phe Phe Arg Asn Glu Gln Ser Ile Pro Pro Leu Pro Arg His Arg His
530                 535                 540

<210> SEQ ID NO 13
<211> LENGTH: 1635
<212> TYPE: DNA
<213> ORGANISM: Cannabis sativa

<400> SEQUENCE: 13

| | |
|---|---|
| atgaagtgct caacattctc cttttggttt gtttgcaaga taatattttt ctttttctca | 60 |
| ttcaatatcc aaacttccat tgctaatcct cgagaaaact tccttaaatg cttctcgcaa | 120 |
| tatattccca ataatgcaac aaatctaaaa ctcgtataca ctcaaaacaa cccattgtat | 180 |
| atgtctgtcc taaattcgac aatacacaat cttagattca cctctgacac aaccccaaaa | 240 |
| ccacttgtta tcgtcactcc ttcacatgtc tctcatatcc aaggcactat tctatgctcc | 300 |
| aagaaagttg gcttgcagat tcgaactcga agtggtggtc atgattctga gggcatgtcc | 360 |
| tacatatctc aagtcccatt tgttatagta gacttgagaa acatgcgttc aatcaaaata | 420 |
| gatgttcata gccaaactgc atgggttgaa gccggagcta cccttggaga gtttattat | 480 |
| tgggttaatg agaaaaatga gaatcttagt ttggcggctg gtattgccc tactgtttgc | 540 |
| gcaggtggac actttggtgg aggaggctat ggaccattga tgagaaacta ggcctcgcg | 600 |
| gctgataata tcattgatgc acacttagtc aacgttcatg aaaagtgct agatcgaaaa | 660 |
| tctatggggg aagatctctt tgggcttta cgtggtggtg gagcagaaag cttcggaatc | 720 |
| attgtagcat ggaaaattag actggttgct gtcccaaagt ctactatgtt tagtgttaaa | 780 |
| aagatcatgg agatacatga gcttgtcaag ttagttaaca aatggcaaaa tattgcttac | 840 |
| aagtatgaca agattttatt actcatgact cacttcataa ctaggaacat tacagataat | 900 |
| caagggaaga ataagacagc aatacacact tacttctctt cagttttcct tggtggagtg | 960 |
| gatagtctag tcgacttgat gaacaagagt tttcctgagt tgggtattaa aaaaacggat | 1020 |
| tgcagacaat tgagctggat tgatactatc atcttctata gtggtgttgt aaattacgac | 1080 |
| actgataatt ttaacaagga aattttgctt gatagatccg ctgggcagaa cggtgctttc | 1140 |
| aagattaagt tagactacgt taagaaacca attccagaat ctgtatttgt ccaaattttg | 1200 |
| gaaaaattat atgaagaaga tataggagct gggatgtatg cgttgtaccc ttacggtggt | 1260 |
| ataatggatg agatttcaga atcagcaatt ccattccctc atcgagctgg aatcttgtat | 1320 |
| gagttatggt acatatgtag ttgggagaag caagaagata cgaaaagca tctaaactgg | 1380 |
| attagaaata tttataactt catgactcct tatgtgtcca aaaatccaag attggcatat | 1440 |
| ctcaattata gagaccttga tataggaata atgatccca agaatccaaa taattacaca | 1500 |
| caagcacgta tttggggtga gaagtatttt ggtaaaaatt ttgacaggct agtaaaagtg | 1560 |
| aaaaccctgg ttgatcccaa taacttttt agaaacgaac aaagcatccc acctcttcca | 1620 |
| cggcatcgtc attaa | 1635 |

<210> SEQ ID NO 14
<211> LENGTH: 544
<212> TYPE: PRT
<213> ORGANISM: Cannabis sativa

<400> SEQUENCE: 14

```
Met Lys Cys Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Thr Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Ser Gly
            100                 105                 110

Gly His Asp Ser Glu Gly Met Ser Tyr Ile Ser Gln Val Pro Phe Val
        115                 120                 125

Ile Val Asp Leu Arg Asn Met Arg Ser Ile Lys Ile Asp Val His Ser
    130                 135                 140

Gln Thr Ala Trp Val Glu Ala Gly Ala Thr Leu Gly Glu Val Tyr Tyr
145                 150                 155                 160

Trp Val Asn Glu Lys Asn Glu Asn Leu Ser Leu Ala Ala Gly Tyr Cys
                165                 170                 175

Pro Thr Val Cys Ala Gly Gly His Phe Gly Gly Gly Tyr Gly Pro
            180                 185                 190

Leu Met Arg Asn Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
                245                 250                 255

Phe Ser Val Lys Lys Ile Met Glu Ile His Glu Leu Val Lys Leu Val
            260                 265                 270

Asn Lys Trp Gln Asn Ile Ala Tyr Lys Tyr Asp Lys Asp Leu Leu Leu
        275                 280                 285

Met Thr His Phe Ile Thr Arg Asn Ile Thr Asp Asn Gln Gly Lys Asn
    290                 295                 300

Lys Thr Ala Ile His Thr Tyr Phe Ser Ser Val Phe Leu Gly Gly Val
305                 310                 315                 320

Asp Ser Leu Val Asp Leu Met Asn Lys Ser Phe Pro Glu Leu Gly Ile
                325                 330                 335

Lys Lys Thr Asp Cys Arg Gln Leu Ser Trp Ile Asp Thr Ile Ile Phe
            340                 345                 350

Tyr Ser Gly Val Val Asn Tyr Asp Thr Asp Asn Phe Asn Lys Glu Ile
        355                 360                 365

Leu Leu Asp Arg Ser Ala Gly Gln Asn Gly Ala Phe Lys Ile Lys Leu
```

| | | | | | | | | | | |
|---|---|---|---|---|---|---|---|---|---|---|
| | | 370 | | | 375 | | | 380 | | |
| Asp | Tyr | Val | Lys | Lys | Pro | Ile | Pro | Glu | Ser | Val | Phe | Val | Gln | Ile | Leu |
| 385 | | | | 390 | | | | 395 | | | | 400 | | | |
| Glu | Lys | Leu | Tyr | Glu | Glu | Asp | Ile | Gly | Ala | Gly | Met | Tyr | Ala | Leu | Tyr |
| | | | | 405 | | | | 410 | | | | 415 | | | |
| Pro | Tyr | Gly | Gly | Ile | Met | Asp | Glu | Ile | Ser | Glu | Ser | Ala | Ile | Pro | Phe |
| | | | 420 | | | | | 425 | | | | 430 | | | |
| Pro | His | Arg | Ala | Gly | Ile | Leu | Tyr | Glu | Leu | Trp | Tyr | Ile | Cys | Ser | Trp |
| | | | 435 | | | | 440 | | | | 445 | | | | |
| Glu | Lys | Gln | Glu | Asp | Asn | Glu | Lys | His | Leu | Asn | Trp | Ile | Arg | Asn | Ile |
| 450 | | | | | 455 | | | | | | | 460 | | | |
| Tyr | Asn | Phe | Met | Thr | Pro | Tyr | Val | Ser | Lys | Asn | Pro | Arg | Leu | Ala | Tyr |
| 465 | | | | | 470 | | | | 475 | | | | | 480 | |
| Leu | Asn | Tyr | Arg | Asp | Leu | Asp | Ile | Gly | Ile | Asn | Asp | Pro | Lys | Asn | Pro |
| | | | | 485 | | | | | 490 | | | | 495 | | |
| Asn | Asn | Tyr | Thr | Gln | Ala | Arg | Ile | Trp | Gly | Glu | Lys | Tyr | Phe | Gly | Lys |
| | | | 500 | | | | | 505 | | | | | 510 | | |
| Asn | Phe | Asp | Arg | Leu | Val | Lys | Val | Lys | Thr | Leu | Val | Asp | Pro | Asn | Asn |
| | | | 515 | | | | 520 | | | | | 525 | | | |
| Phe | Phe | Arg | Asn | Glu | Gln | Ser | Ile | Pro | Pro | Leu | Pro | Arg | His | Arg | His |
| | 530 | | | | | 535 | | | | | 540 | | | | |

```
<210> SEQ ID NO 15
<211> LENGTH: 1635
<212> TYPE: DNA
<213> ORGANISM: Cannabis sativa
<220> FEATURE:
<221> NAME/KEY: misc_feature
<222> LOCATION: (333)..(441)
<223> OTHER INFORMATION: n is a, c, g, or t

<400> SEQUENCE: 15
```

| | | | | | |
|---|---|---|---|---|---|
| atgaagtact | caacattctc | cttttggttt | gtttgcaaga | taatattttt | cttttctca | 60 |
| ttcaatatcc | aaacttccat | tgctaatcct | cgagaaaact | tccttaaatg | cttctcgcaa | 120 |
| tatattccca | ataatgcaac | aaatctaaaa | ctcgtataca | ctcaaaacaa | cccattgtat | 180 |
| atgtctgtcc | taaattcgac | aatacacaat | cttagattca | gctctgacac | aaccccaaaa | 240 |
| ccacttgtta | tcgtcactcc | ttcacatgtc | tctcatatcc | aaggcactat | tctatgctcc | 300 |
| aagaaagttg | gcttgcagat | tcgaactcga | agnnnnnnnn | nnnnnnnnnn | nnnnnnnnnn | 360 |
| nnnnnnnnnn | nnnnnnnnnn | nnnnnnnnnn | nnnnnnnnnn | nnnnnnnnnn | nnnnnnnnnn | 420 |
| nnnnnnnnnn | nnnnnnnnnn | ntgggttgaa | gccggagcta | cccttggaga | agtttattat | 480 |
| tgggttaatg | agaaaaatga | gagtcttagt | ttggctgctg | ggtattgccc | tactgtttgc | 540 |
| gcaggtggac | actttggtgg | aggaggctat | ggaccattga | tgagaagcta | tggcctcgcg | 600 |
| gctgataata | tcattgatgc | acacttagtc | aacgttcatg | gaaagtgct | agatcgaaaa | 660 |
| tctatggggg | aagatctctt | ttgggcttta | cgtggtggtg | gagcagaaag | cttcggaatc | 720 |
| attgtagcat | ggaaaattag | actggttgct | gtcccaaagt | ctactatgtt | tagtgttaaa | 780 |
| aagatcatgg | agatacatga | gcttgtcaag | ttagttaaca | aatggcaaaa | tattgcttac | 840 |
| aagtatgaca | agatttatt | actcatgact | cacttcataa | ctaggaacat | tacagataat | 900 |
| caagggaaga | ataagacagc | aatacacact | tacttctctt | cagttttcct | tggtggagtg | 960 |
| gatagtctag | tcgacttgat | gaacaagagt | tttcctgagt | tgggtattaa | aaaacggat | 1020 |
| tgcagacaat | tgagctggat | tgatactatc | atcttctata | gtggtgttgt | aaattacgac | 1080 |

```
actgataatt ttaacaagga aattttgctt gatagatccg ctgggcagaa cggtgctttc    1140
aagattaagt tagactacgt taagaaacca attccagaat ctgtatttgt ccaaattttg    1200
gaaaaattat atgaagaaga tataggagct gggatgtatg cgttgtaccc ttacggtggt    1260
ataatggatg agatttctga atcagcaatt ccattccctc atcgagctgg aatcttgtat    1320
gagttatggt acatatgtag ctgggagaag caagaagata acgaaaagca tctaaactgg    1380
attagaaata tttataactt catgactcct tatgtgtccc aaaatccaag attggcatat    1440
ctcaattata gagaccttga tataggaata aatgatccca agaatccaaa taattacaca    1500
caagcacgta tttggggtga gaagtatttt ggtaaaaatt ttgacaggct agtaaaagtg    1560
aaaaccctgg ttgatcccaa taatttttt agaaacgaac aaagcatccc acctcttcca    1620
cggcatcatc attaa                                                    1635

<210> SEQ ID NO 16
<211> LENGTH: 544
<212> TYPE: PRT
<213> ORGANISM: Cannabis sativa
<220> FEATURE:
<221> NAME/KEY: misc_feature
<222> LOCATION: (111)..(147)
<223> OTHER INFORMATION: Xaa can be any naturally occurring amino acid

<400> SEQUENCE: 16

Met Lys Tyr Ser Thr Phe Ser Phe Trp Phe Val Cys Lys Ile Ile Phe
1               5                   10                  15

Phe Phe Phe Ser Phe Asn Ile Gln Thr Ser Ile Ala Asn Pro Arg Glu
            20                  25                  30

Asn Phe Leu Lys Cys Phe Ser Gln Tyr Ile Pro Asn Asn Ala Thr Asn
        35                  40                  45

Leu Lys Leu Val Tyr Thr Gln Asn Asn Pro Leu Tyr Met Ser Val Leu
    50                  55                  60

Asn Ser Thr Ile His Asn Leu Arg Phe Ser Ser Asp Thr Thr Pro Lys
65                  70                  75                  80

Pro Leu Val Ile Val Thr Pro Ser His Val Ser His Ile Gln Gly Thr
                85                  90                  95

Ile Leu Cys Ser Lys Lys Val Gly Leu Gln Ile Arg Thr Arg Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Trp Val Glu Ala Gly Ala Thr Leu Gly Glu Val Tyr Tyr
145                 150                 155                 160

Trp Val Asn Glu Lys Asn Glu Ser Leu Ser Leu Ala Ala Gly Tyr Cys
                165                 170                 175

Pro Thr Val Cys Ala Gly Gly His Phe Gly Gly Gly Tyr Gly Pro
            180                 185                 190

Leu Met Arg Ser Tyr Gly Leu Ala Ala Asp Asn Ile Ile Asp Ala His
        195                 200                 205

Leu Val Asn Val His Gly Lys Val Leu Asp Arg Lys Ser Met Gly Glu
    210                 215                 220

Asp Leu Phe Trp Ala Leu Arg Gly Gly Gly Ala Glu Ser Phe Gly Ile
225                 230                 235                 240

Ile Val Ala Trp Lys Ile Arg Leu Val Ala Val Pro Lys Ser Thr Met
```

-continued

```
                    245                 250                 255
Phe Ser Val Lys Lys Ile Met Glu Ile His Glu Leu Val Lys Leu Val
            260                 265                 270
Asn Lys Trp Gln Asn Ile Ala Tyr Lys Tyr Asp Lys Asp Leu Leu Leu
        275                 280                 285
Met Thr His Phe Ile Thr Arg Asn Ile Thr Asp Asn Gln Gly Lys Asn
    290                 295                 300
Lys Thr Ala Ile His Thr Tyr Phe Ser Val Phe Leu Gly Val
305                 310                 315                 320
Asp Ser Leu Val Asp Leu Met Asn Lys Ser Phe Pro Glu Leu Gly Ile
                325                 330                 335
Lys Lys Thr Asp Cys Arg Gln Leu Ser Trp Ile Asp Thr Ile Ile Phe
            340                 345                 350
Tyr Ser Gly Val Val Asn Tyr Asp Thr Asp Asn Phe Asn Lys Glu Ile
        355                 360                 365
Leu Leu Asp Arg Ser Ala Gly Gln Asn Gly Ala Phe Lys Ile Lys Leu
    370                 375                 380
Asp Tyr Val Lys Lys Pro Ile Pro Glu Ser Val Phe Val Gln Ile Leu
385                 390                 395                 400
Glu Lys Leu Tyr Glu Glu Asp Ile Gly Ala Gly Met Tyr Ala Leu Tyr
                405                 410                 415
Pro Tyr Gly Gly Ile Met Asp Glu Ile Ser Glu Ser Ala Ile Pro Phe
            420                 425                 430
Pro His Arg Ala Gly Ile Leu Tyr Glu Leu Trp Tyr Ile Cys Ser Trp
        435                 440                 445
Glu Lys Gln Glu Asp Asn Glu Lys His Leu Asn Trp Ile Arg Asn Ile
    450                 455                 460
Tyr Asn Phe Met Thr Pro Tyr Val Ser Gln Asn Pro Arg Leu Ala Tyr
465                 470                 475                 480
Leu Asn Tyr Arg Asp Leu Asp Ile Gly Ile Asn Asp Pro Lys Asn Pro
                485                 490                 495
Asn Asn Tyr Thr Gln Ala Arg Ile Trp Gly Glu Lys Tyr Phe Gly Lys
            500                 505                 510
Asn Phe Asp Arg Leu Val Lys Val Lys Thr Leu Val Asp Pro Asn Asn
        515                 520                 525
Phe Phe Arg Asn Glu Gln Ser Ile Pro Pro Leu Pro Arg His His His
    530                 535                 540
```

<210> SEQ ID NO 17
<211> LENGTH: 1634
<212> TYPE: DNA
<213> ORGANISM: Cannabis sativa

<400> SEQUENCE: 17

```
atgaagtgct caacattccc cttttggttt gtttgcaaga taatattttt ctttctctca    60
ttcaatatcc aaacttcaat tgctaatcct cgagaaaact tccttaaatg cttctcgcaa   120
tatattccca ccaatgtaac aaatctaaaa cttacaccca aacaaccaa ttgtatatgc    180
ctgtccaaaa ttcaacaata cacaatctta gattcacctc taacacaacc caaaactac    240
ttgttatcgt cactccttca tatgtctctc atatccaagg cactattcta tgtccaagaa   300
aattggtttg caaattcgaa ctcgaagcgg tggtcatgat tctgaagaca tgtcctacat   360
atctcaagtc ccatttgtta tagtagactt gagaaacatg cattcaatca acatagatgt   420
tcatagccaa atcgcaaggg ttgaagccgg agctacccct ggagaagttt attattgggt   480
```

| | |
|---|---|
| taatgagaaa aatgagaatc ttagtttggc tgctgggtat tgccctactg ttagcgcagc | 540 |
| tggacactttt ggtggaggag gatatggacc attgatgcaa aattatggcc tcgcggctga | 600 |
| taatatcgtt gatgcacact tagtcaacgt tgatgcaaaa gtgctagatc gaaaatctat | 660 |
| gggggaagat ctcttttggg ctatacgtgg tggtggagga gaaagcttcg gaatcattgt | 720 |
| agcatggaaa attagactgg ttgctgtccc aacaaagtct actatgttta gtgttaaaaa | 780 |
| gatcatggag atacatgagc ttgtcaagtg agttaacaaa tggcaaaata ttgcttacaa | 840 |
| gtatgacaaa gatttattac tcatgactca cttcataact aggaatatta caaataatca | 900 |
| tgggaagaat aagacaacaa tacacactta cttctcttca gttttccttg gtggagtgga | 960 |
| tagtctagtc gacttgatga ataagagttt tcctgagttg ggtattaaaa aaacagattg | 1020 |
| caaacaattg agctagattg atattatcat cttttatagc ggtgttgtaa attacggcac | 1080 |
| tgataatttt aataaggaaa ttttgcttga tagatcagct gggcagaacg gttctttaaa | 1140 |
| gattaagtta gactacgtta agaaaccaat tccagaatct gcgtttgtca aaattttgga | 1200 |
| aaaattatat gaagaagatg aaggagttgg gatgtatgcg ttgtacccctt acggtggtat | 1260 |
| aatggatgag atttcagaat cagcaattcc attccctcat tgagctggaa tcatgtatga | 1320 |
| attatggtac atatgtagct gggagaagca cgaagataac gaaaaagcat ctaaactgga | 1380 |
| ttcgaaatgt ttatagcttc attactcctt atgtgtccta aaatccaaga ttggcatatc | 1440 |
| tcaattatag agaccttgat actggaataa atgatcccaa gagtccaaat aattacacac | 1500 |
| aagaaagtat ttgggggtgag aagtattttg gtaaaaattt tgacagggta gtaaaagtga | 1560 |
| aaaccctggt tgatcccaat aatttttta gaaatgaaca aagcatccca cctcttccac | 1620 |
| ggcatcgtca ttaa | 1634 |

```
<210> SEQ ID NO 18
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 18
gctagatcga aaatctatgg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 19
aaagcatccc acctcttcca                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 20
tttaggacag acatatacaa                                              20

<210> SEQ ID NO 21
```

```
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 21
gaaagcaccg ttctgcccag                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 22
catttaagga agttttctcg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 23
aaatgggact tgagatatgt                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 24
cccttggaga agtttattat                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 25
gtacccttac ggtggtataa                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 26
attccagctc gatgagggaa                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic- guide RNA

<400> SEQUENCE: 27
```

```
tacacacaag cacgtatttg                                                  20
```

<210> SEQ ID NO 28
<211> LENGTH: 109
<212> TYPE: PRT
<213> ORGANISM: Brassica napus

<400> SEQUENCE: 28

```
Met Ala Thr Gly Ser Arg Val Leu Ile Gly Leu Ala Met Ile Leu Ile
1               5                   10                  15

Ile Ser Gly Glu Leu Leu Val Pro Gly Gln Gly Thr Cys Gln Gly Asp
            20                  25                  30

Ile Glu Gly Leu Met Arg Glu Cys Ala Val Tyr Val Gln Arg Pro Gly
        35                  40                  45

Pro Lys Val Asn Pro Ser Ala Ala Cys Cys Lys Val Val Lys Arg Ser
    50                  55                  60

Asp Ile Pro Cys Ala Cys Gly Arg Ile Thr Pro Ser Val Gln Lys Met
65                  70                  75                  80

Ile Asp Met Asn Lys Val Val Leu Val Thr Ser Phe Cys Gly Arg Pro
                85                  90                  95

Leu Ala His Gly Thr Lys Cys Gly Ser Tyr Ile Val Pro
            100                 105
```

<210> SEQ ID NO 29
<211> LENGTH: 330
<212> TYPE: DNA
<213> ORGANISM: Brassica napus

<400> SEQUENCE: 29

```
atggcgacag gttctcgtgt tctgatcggt ctagcaatga tcctcataat ctcaggagaa    60
ctgctagttc cagggcaagg aacgtgccaa ggagacatag agggtctgat gagagaatgt   120
gcggtctacg tccagcgtcc aggcccaaag gtaaacccat ccgcagcgtg ttgcaaagtc   180
gtcaagagat cagacatccc ctgcgcatgt ggccgtatca caccctcggt tcaaaaaatg   240
atagacatga ataaggttgt tcttgtcact tccttttgtg ggaggcctct cgctcatggt   300
accaagtgtg gaagctacat tgtgccatga                                    330
```

<210> SEQ ID NO 30
<211> LENGTH: 395
<212> TYPE: PRT
<213> ORGANISM: Cannabis sativa

<400> SEQUENCE: 30

```
Met Gly Leu Ser Ser Val Cys Thr Phe Ser Phe Gln Thr Asn Tyr His
1               5                   10                  15

Thr Leu Leu Asn Pro His Asn Asn Pro Lys Thr Ser Leu Leu Cys
            20                  25                  30

Tyr Arg His Pro Lys Thr Pro Ile Lys Tyr Ser Tyr Asn Asn Phe Pro
        35                  40                  45

Ser Lys His Cys Ser Thr Lys Ser Phe His Leu Gln Asn Lys Cys Ser
    50                  55                  60

Glu Ser Leu Ser Ile Ala Lys Asn Ser Ile Arg Ala Ala Thr Thr Asn
65                  70                  75                  80

Gln Thr Glu Pro Pro Glu Ser Asp Asn His Ser Val Ala Thr Lys Ile
                85                  90                  95

Leu Asn Phe Gly Lys Ala Cys Trp Lys Leu Gln Arg Pro Tyr Thr Ile
```

|  | 100 |  | 105 |  | 110 |  |
|---|---|---|---|---|---|---|
| Ile Ala Phe Thr Ser Cys Ala Cys Gly Leu Phe Gly Lys Glu Leu Leu
    115                 120                 125

His Asn Thr Asn Leu Ile Ser Trp Ser Leu Met Phe Lys Ala Phe Phe
    130                 135                 140

Phe Leu Val Ala Val Leu Cys Ile Ala Ser Phe Thr Thr Thr Ile Asn
145                 150                 155                 160

Gln Ile Tyr Asp Leu His Ile Asp Arg Ile Asn Lys Pro Asp Leu Pro
                    165                 170                 175

Leu Ala Ser Gly Glu Ile Ser Val Asn Thr Ala Trp Ile Met Ser Ile
                    180                 185                 190

Ile Val Ala Leu Phe Gly Leu Ile Ile Thr Lys Met Lys Gly Gly
                    195                 200                 205

Pro Leu Tyr Ile Phe Gly Tyr Cys Phe Gly Ile Phe Gly Gly Ile Val
    210                 215                 220

Tyr Ser Val Pro Pro Phe Arg Trp Lys Gln Asn Pro Ser Thr Ala Phe
225                 230                 235                 240

Leu Leu Asn Phe Leu Ala His Ile Ile Thr Asn Phe Thr Phe Tyr Tyr
                    245                 250                 255

Ala Ser Arg Ala Ala Leu Gly Leu Pro Phe Glu Leu Arg Pro Ser Phe
                    260                 265                 270

Thr Phe Leu Leu Ala Phe Met Lys Ser Met Gly Ser Ala Leu Ala Leu
                    275                 280                 285

Ile Lys Asp Ala Ser Asp Val Glu Gly Asp Thr Lys Phe Gly Ile Ser
    290                 295                 300

Thr Leu Ala Ser Lys Tyr Gly Ser Arg Asn Leu Thr Leu Phe Cys Ser
305                 310                 315                 320

Gly Ile Val Leu Leu Ser Tyr Val Ala Ala Ile Leu Ala Gly Ile Ile
                    325                 330                 335

Trp Pro Gln Ala Phe Asn Ser Asn Val Met Leu Leu Ser His Ala Ile
                    340                 345                 350

Leu Ala Phe Trp Leu Ile Leu Gln Thr Arg Asp Phe Ala Leu Thr Asn
                    355                 360                 365

Tyr Asp Pro Glu Ala Gly Arg Arg Phe Tyr Glu Phe Met Trp Lys Leu
                    370                 375                 380

Tyr Tyr Ala Glu Tyr Leu Val Tyr Val Phe Ile
385                 390                 395 |

<210> SEQ ID NO 31
<211> LENGTH: 1188
<212> TYPE: DNA
<213> ORGANISM: Cannabis sativa

<400> SEQUENCE: 31

```
atgggactct catcagtttg tacctttttca tttcaaacta attaccatac tttattaaat      60
cctcacaata ataatcccaa aacctcatta ttatgttatc gacaccccaa aacaccaatt     120
aaatactctt acaataattt tccctctaaa cattgctcca ccaagagttt tcatctacaa     180
aacaaatgct cagaatcatt atcaatcgca aaaaattcca ttagggcagc tactacaaat     240
caaactgagc ctccagaatc tgataatcat tcagtagcaa ctaaaatttt aaactttggg     300
aaggcatgtt ggaaacttca aagaccatat acaatcatag catttacttc atgcgcttgt     360
ggattgtttg gaaagagtt gttgcataac acaaatttaa taagtggtc tctgatgttc     420
aaggcattct ttttttttggt ggctgtatta tgcattgctt cttttacaac taccatcaat     480
```

```
cagatttacg atcttcacat tgacagaata acaagcctg atctaccact agcttcaggg      540
gaaatatcag taaacacagc ttggattatg agcataattg tggcactgtt tggattgata      600
ataactataa aaatgaaggg tggaccactc tatatatttg gctactgttt tggtattttt      660
ggtgggattg tctattctgt tccaccattt agatggaagc aaaatccttc cactgcattt      720
cttctcaatt tcctggccca tattattaca aatttcacat tttattatgc cagcagagca      780
gctcttggcc taccatttga gttgaggcct tcttttactt tcctgctagc atttatgaaa      840
tcaatgggtt cagctttggc tttaatcaaa gatgcttcag acgttgaagg cgacactaaa      900
tttggcatat caaccttggc aagtaaatat ggttccagaa acttgacatt attttgttct      960
ggaattgttc tcctatccta tgtggctgct atacttgctg ggattatctg cccccaggct     1020
ttcaacagta acgtaatgtt actttctcat gcaatcttag cattttggtt aatcctccag     1080
actcgagatt ttgcgttaac aaattacgac ccggaagcag gcagaagatt ttacgagttc     1140
atgtggaagc tttattatgc tgaatattta gtatatgttt tcatataa                   1188
```

<210> SEQ ID NO 32
<211> LENGTH: 370
<212> TYPE: PRT
<213> ORGANISM: Cannabis sativa

<400> SEQUENCE: 32

```
Met Gly Ser Thr Gly Ile Glu Thr Gln Met Thr Pro Thr Gln Ile Ser
1               5                   10                  15

Asp Glu Glu Ala Asn Leu Phe Ala Met Gln Leu Ala Ser Ala Ser Val
            20                  25                  30

Leu Pro Met Val Leu Lys Ala Ala Leu Glu Leu Asp Leu Leu Glu Ile
        35                  40                  45

Ile Ala Lys Ala Gly Pro Gly Ala Phe Leu Ser Pro Ser Asp Ile Ala
    50                  55                  60

Gln Gln Leu Pro Thr Gln Asn Pro Asp Ala Pro Val Met Leu Asp Arg
65                  70                  75                  80

Met Leu Arg Leu Leu Ala Ser Tyr Asn Val Val Thr Tyr Ser Leu Arg
                85                  90                  95

Glu Arg Glu Thr Ala Glu Glu Glu Gly Lys Val Glu Arg Leu Tyr Gly
            100                 105                 110

Leu Ala Pro Val Ser Lys Tyr Leu Thr Lys Asn Glu Asp Gly Val Ser
        115                 120                 125

Ile Ala Pro Leu Cys Leu Met Asn Gln Asp Lys Val Leu Met Glu Ser
    130                 135                 140

Trp Tyr His Leu Lys Asp Ala Val Leu Asp Gly Gly Ile Pro Phe Asn
145                 150                 155                 160

Lys Ala Tyr Gly Met Thr Ala Phe Glu Tyr His Gly Thr Asp Gln Arg
                165                 170                 175

Phe Asn Lys Ile Phe Asn Arg Gly Met Ser Asp His Ser Thr Ile Thr
            180                 185                 190

Met Lys Lys Ile Leu Glu Thr Tyr Lys Gly Phe Glu Gly Leu Asn Ser
        195                 200                 205

Ile Val Asp Val Gly Gly Gly Thr Gly Ala Val Val Asn Met Ile Val
    210                 215                 220

Ser Lys Tyr Pro Thr Ile Lys Gly Ile Asn Phe Asp Leu Pro His Val
225                 230                 235                 240

Ile Glu Asp Ala Pro Pro Leu Thr Gly Val Glu His Val Gly Gly Asp
```

245                 250                 255
Met Phe Val Ser Val Pro Lys Gly Asp Ala Ile Phe Met Lys Trp Ile
            260                 265                 270

Cys His Asp Trp Ser Asp Glu His Cys Leu Lys Phe Leu Lys Asn Cys
        275                 280                 285

His Ala Ala Leu Pro Glu His Gly Lys Val Ile Val Ala Glu Cys Ile
    290                 295                 300

Leu Pro Val Ala Pro Asp Ser Ser Leu Ala Thr Lys Ser Thr Val His
305                 310                 315                 320

Ile Asp Val Ile Met Leu Ala His Asn Pro Gly Gly Lys Glu Arg Thr
                325                 330                 335

Glu Lys Glu Phe Glu Ala Leu Ala Lys Gly Ala Gly Phe Lys Gly Phe
            340                 345                 350

Lys Val His Cys Asn Ala Phe Asn Thr His Ile Met Glu Phe Leu Lys
        355                 360                 365

Thr Ile
    370

<210> SEQ ID NO 33
<211> LENGTH: 1113
<212> TYPE: DNA
<213> ORGANISM: Cannabis sativa

<400> SEQUENCE: 33

| | | |
|---|---|---|
| atgggttcaa caggaataga gacccaaatg accccaaccc aaatatccga cgaagaagcc | 60 |
| aacctcttcg ccatgcaatt agccagtgcc tcagtcttac ccatggttct caaagcagct | 120 |
| ttagagctcg acctcttgga gatcatagcc aaggccggtc caggcgcgtt tctctcacct | 180 |
| tccgacatag ctcaacagct tccgactcag aacccagacg ccccggtgat gctggaccgg | 240 |
| atgctgagac tgttggctag ctacaacgtg gtgacgtact cgctgcgtga cgtgagacg | 300 |
| gcggaagagg aagggaaggt ggagaggctt tatgggttgg ctccggtgag taaatatctg | 360 |
| acgaagaatg aagatggagt ctccattgct cctctttgtc tcatgaacca ggataaggtt | 420 |
| cttatggaga gttggtatca cttaaaagat gcagtacttg atggaggaat acctttcaac | 480 |
| aaggcatatg gaatgacagc atttgaatat catggaaccg atcaaaggtt caataaaatc | 540 |
| tttaatagag aatgtccga ccactcgact attaccatga aaaaaatcct cgaaacttac | 600 |
| aagggtttcg agggtcttaa ctcgattgtt gatgttggtg gtggtactgg agctgttgtt | 660 |
| aacatgatcg tctctaagta ccctactatt aagggtatta acttcgattt gcctcatgtc | 720 |
| atcgaagatg caccctccatt gaccggtgta gagcatgttg gaggagacat gtttgtaagt | 780 |
| gtaccaaaag gagatgcaat tttcatgaag tggatttgcc atgattggag cgatgaacac | 840 |
| tgcttgaaat tcttgaagaa ctgccacgct gcactgcccg aacacggaaa agtgatcgtg | 900 |
| gcggagtgca ttcttccggt ggcaccggac tcgagcttg ccacaaagag tacggtccac | 960 |
| attgatgtga tcatgttggc ccataaccct ggtggcaaag agaaacaga gaaagagttt | 1020 |
| gaggcattgg ctaagggagc tggctttaaa ggcttcaaag tccattgcaa tgctttcaat | 1080 |
| acccatatca tggaatttct caagaccatt taa | 1113 |

<210> SEQ ID NO 34
<211> LENGTH: 400
<212> TYPE: PRT
<213> ORGANISM: Cannabis sativa

<400> SEQUENCE: 34

```
Met Val Phe Ser Ser Val Cys Ser Phe Pro Ser Ser Leu Gly Thr Asn
1               5                   10                  15

Phe Lys Leu Val Pro Arg Ser Asn Phe Lys Ala Ser Ser His Tyr
            20                  25                  30

His Glu Ile Asn Asn Phe Ile Asn Asn Lys Pro Ile Lys Phe Ser Tyr
            35                  40                  45

Phe Ser Ser Arg Leu Tyr Cys Ser Ala Lys Pro Ile Val His Arg Glu
50                  55                  60

Asn Lys Phe Thr Lys Ser Phe Ser Leu Ser His Leu Gln Arg Lys Ser
65                  70                  75                  80

Ser Ile Lys Ala His Gly Glu Ile Glu Ala Asp Gly Ser Asn Gly Thr
                85                  90                  95

Ser Glu Phe Asn Val Met Lys Ser Gly Asn Ala Ile Trp Arg Phe Val
                100                 105                 110

Arg Pro Tyr Ala Ala Lys Gly Val Leu Phe Asn Ser Ala Ala Met Phe
            115                 120                 125

Ala Lys Glu Leu Val Gly Asn Leu Asn Leu Phe Ser Trp Pro Leu Met
130                 135                 140

Phe Lys Ile Leu Ser Phe Thr Leu Val Ile Leu Cys Ile Phe Val Ser
145                 150                 155                 160

Thr Ser Gly Ile Asn Gln Ile Tyr Asp Leu Asp Ile Asp Arg Leu Asn
                165                 170                 175

Lys Pro Asn Leu Pro Val Ala Ser Gly Glu Ile Ser Val Glu Leu Ala
            180                 185                 190

Trp Leu Leu Thr Ile Val Cys Thr Ile Ser Gly Leu Thr Leu Thr Ile
            195                 200                 205

Ile Thr Asn Ser Gly Pro Phe Phe Pro Phe Leu Tyr Ser Ala Ser Ile
210                 215                 220

Phe Phe Gly Phe Leu Tyr Ser Ala Pro Pro Phe Arg Trp Lys Lys Asn
225                 230                 235                 240

Pro Phe Thr Ala Cys Phe Cys Asn Val Met Leu Tyr Val Gly Thr Ser
                245                 250                 255

Val Gly Val Tyr Tyr Ala Cys Lys Ala Ser Leu Gly Leu Pro Ala Asn
            260                 265                 270

Trp Ser Pro Ala Phe Cys Leu Leu Phe Trp Phe Ile Ser Leu Leu Ser
            275                 280                 285

Ile Pro Ile Ser Ile Ala Lys Asp Leu Ser Asp Ile Glu Gly Asp Arg
290                 295                 300

Lys Phe Gly Ile Ile Thr Phe Ser Thr Lys Phe Gly Ala Lys Pro Ile
305                 310                 315                 320

Ala Tyr Ile Cys His Gly Leu Met Leu Leu Asn Tyr Val Ser Val Met
                325                 330                 335

Ala Ala Ala Ile Ile Trp Pro Gln Phe Phe Asn Ser Ser Val Ile Leu
            340                 345                 350

Leu Ser His Ala Phe Met Ala Ile Trp Val Leu Tyr Gln Ala Trp Ile
            355                 360                 365

Leu Glu Lys Ser Asn Tyr Ala Thr Glu Thr Cys Gln Lys Tyr Tyr Ile
370                 375                 380

Phe Leu Trp Ile Ile Phe Ser Leu Glu His Ala Phe Tyr Leu Phe Met
385                 390                 395                 400

<210> SEQ ID NO 35
<211> LENGTH: 1203
```

<212> TYPE: DNA
<213> ORGANISM: Cannabis sativa

<400> SEQUENCE: 35

```
atggtgttct catcagtttg tagttttcca tcctcccttg gaactaattt taaattagtt      60
cctcgtagta attttaaggc atcatcttct cattatcatg aaataaataa ttttattaat     120
aataaaccaa ttaaattctc atattttct tcaagactat attgctctgc caaaccaatt     180
gtacacagag aaaacaaatt cacaaaatca ttttcactca gccacctcca aaggaaaagc     240
tccataaagg cacatggtga aattgaagct gatgggagta atggcacatc tgaatttaat     300
gtaatgaaaa gtgaaacgc aatttggaga tttgtaaggc catatgcagc caagggagta     360
ttgtttaact ctgctgctat gtttgcaaaa gagttggtgg ggaacctaaa tctatttagt     420
tggcctttga tgtttaagat actctctttt acattggtta ttttatgcat ttttgtaagt     480
acaagtggca tcaatcaaat ttatgatctc gacatcgaca ggttaaacaa acctaatttg     540
ccagtagcat caggagaaat ttcagttgaa ttggcatggt tgttgactat agtttgtaca     600
ataagtggcc tcacattaac aattataacg aactcagggc cattcttccc ttttctctac     660
tctgctagta tctttttttgg ctttctctat tctgctcctc cattcagatg gaagaagaat     720
ccttttacag catgtttctg taatgttatg ttgtatgttg gcacaagcgt tggtgtctat     780
tatgcttgta aggctagtct cgggcttcca gccaactgga gccctgcttt tgtttgctc     840
ttttggttta tttcattgtt gagtataccc atctccattg caaagatct ttcagacata     900
gaaggtgacc gcaagtttgg aatcataacc ttctcaacta aatttggagc aaaacccata     960
gcatatattt gtcatggact catgcttctg aattacgtga gtgttatggc tgcagctatt    1020
atttggccac agttttttcaa cagtagcgta atattgcttt ctcatgcatt catggcaatt    1080
tgggtattat atcaggcttg gatattggag aaatcaaatt acgccacgga gacgtgccaa    1140
aaatactata tattcctttg gataattttt tctcttgaac atgccttcta tttgttcatg    1200
tag                                                                  1203
```

<210> SEQ ID NO 36
<211> LENGTH: 523
<212> TYPE: PRT
<213> ORGANISM: Cannabis sativa

<400> SEQUENCE: 36

```
Met Ala Gln Val Ser Lys Ile Cys Ser Asn Gly Ala Gln Thr Ile Leu
1               5                   10                  15

Thr Leu Pro Asn Ile Ser Lys Ser His Thr Pro Arg Ser Leu Asn Ser
            20                  25                  30

Val Ser Leu Arg Ser Pro Phe Leu Gly Ser Ser Asn Ser Leu Ser Leu
        35                  40                  45

Lys Ile Gly Thr Glu Phe Gly Gly Cys Ser Thr Val Gly Lys Ala Met
    50                  55                  60

Ala Gly Pro Val Met Ala Ser Ala Val Thr Ala Glu Lys Pro Ser Lys
65                  70                  75                  80

Val Pro Glu Ile Val Leu Gln Pro Ile Lys Asp Ile Ser Gly Thr Val
                85                  90                  95

Lys Leu Pro Gly Ser Lys Ser Leu Ser Asn Arg Ile Leu Leu Leu Ala
            100                 105                 110

Ala Leu Ser Glu Gly Thr Thr Val Val Asp Asn Leu Leu Asp Ser Asp
        115                 120                 125
```

```
Asp Ile His Tyr Met Leu Gly Ala Leu Glu Thr Leu Gly Leu Arg Val
    130                 135                 140

Glu Ala Asp Lys Glu Ser Lys Arg Ala Ile Val Glu Gly Cys Ala Gly
145                 150                 155                 160

Gln Phe Pro Ala Gly Lys Glu Ser Val Asp Glu Val Gln Leu Phe Leu
                165                 170                 175

Gly Asn Ala Gly Thr Ala Met Arg Pro Leu Thr Ala Ala Val Thr Val
                180                 185                 190

Ala Gly Gly Asn Ala Ser Tyr Val Leu Asp Gly Val Pro Arg Met Arg
            195                 200                 205

Glu Arg Pro Ile Gly Asp Leu Val Thr Gly Leu Lys Gln Leu Gly Ala
210                 215                 220

Asp Val Asp Cys Phe His Gly Thr Asp Cys Pro Pro Val Arg Val Leu
225                 230                 235                 240

Gly Lys Gly Gly Leu Pro Gly Gly Lys Val Lys Leu Ser Gly Ser Ile
                245                 250                 255

Ser Ser Gln Tyr Leu Thr Ala Leu Leu Met Ala Ala Pro Leu Ala Leu
            260                 265                 270

Gly Asp Val Glu Ile Glu Ile Ile Asp Lys Leu Ile Ser Val Pro Tyr
        275                 280                 285

Val Asp Met Thr Leu Lys Leu Met Ala Arg Phe Gly Val Thr Val Glu
290                 295                 300

His Ser Asp Ser Trp Asp Arg Phe Leu Val Lys Gly Gly Gln Lys Tyr
305                 310                 315                 320

Lys Ser Pro Gly Asn Ala Tyr Val Glu Gly Asp Ala Ser Ser Ala Ser
                325                 330                 335

Tyr Phe Leu Ala Gly Ala Ala Val Thr Gly Gly Thr Val Thr Val Glu
            340                 345                 350

Gly Cys Gly Thr Ser Ser Leu Gln Gly Asp Val Lys Phe Ala Glu Val
        355                 360                 365

Leu Glu Lys Met Gly Ala Lys Val Ser Trp Thr Glu Asn Ser Val Thr
370                 375                 380

Val Thr Gly Pro Pro Arg Asp Ser Val Lys Ser Lys His Leu Lys Ala
385                 390                 395                 400

Ile Asp Val Asn Met Asn Lys Met Pro Asp Val Ala Met Thr Leu Ala
                405                 410                 415

Val Val Ala Leu Phe Ala Asp Gly Pro Thr Ala Ile Arg Asp Val Ala
            420                 425                 430

Ser Trp Arg Val Lys Glu Thr Glu Arg Met Ile Ala Ile Cys Thr Glu
435                 440                 445

Leu Arg Lys Leu Gly Ala Thr Val Glu Glu Gly Pro Asp Tyr Cys Val
450                 455                 460

Ile Thr Pro Pro Glu Lys Leu Asn Ile Thr Ala Ile Asp Thr Tyr Asp
465                 470                 475                 480

Asp His Arg Met Ala Met Ala Phe Ser Leu Ala Ala Cys Ser Asp Val
                485                 490                 495

Pro Val Thr Ile Lys Asp Pro Gly Cys Thr Arg Lys Thr Phe Pro Asp
                500                 505                 510

Tyr Phe Glu Val Leu Glu Arg Phe Thr Lys His
            515                 520

<210> SEQ ID NO 37
<211> LENGTH: 523
<212> TYPE: PRT
```

<213> ORGANISM: Artificial Sequence
<220> FEATURE:
<223> OTHER INFORMATION: Synthetic- engineered protein

<400> SEQUENCE: 37

Met Ala Gln Val Ser Lys Ile Cys Ser Asn Gly Ala Gln Thr Ile Leu
1               5                   10                  15

Thr Leu Pro Asn Ile Ser Lys Ser His Thr Pro Arg Ser Leu Asn Ser
            20                  25                  30

Val Ser Leu Arg Ser Pro Phe Leu Gly Ser Ser Asn Ser Leu Ser Leu
        35                  40                  45

Lys Ile Gly Thr Glu Phe Gly Gly Cys Ser Thr Val Gly Lys Ala Met
    50                  55                  60

Ala Gly Pro Val Met Ala Ser Ala Val Thr Ala Glu Lys Pro Ser Lys
65                  70                  75                  80

Val Pro Glu Ile Val Leu Gln Pro Ile Lys Asp Ile Ser Gly Thr Val
                85                  90                  95

Lys Leu Pro Gly Ser Lys Ser Leu Ser Asn Arg Ile Leu Leu Leu Ala
            100                 105                 110

Ala Leu Ser Glu Gly Thr Thr Val Val Asp Asn Leu Leu Asp Ser Asp
        115                 120                 125

Asp Ile His Tyr Met Leu Gly Ala Leu Glu Thr Leu Gly Leu Arg Val
    130                 135                 140

Glu Ala Asp Lys Glu Ser Lys Arg Ala Ile Val Glu Gly Cys Ala Gly
145                 150                 155                 160

Gln Phe Pro Ala Gly Lys Glu Ser Val Asp Glu Val Gln Leu Phe Leu
                165                 170                 175

Gly Asn Ala Gly Ile Ala Met Arg Ser Leu Thr Ala Ala Val Thr Val
            180                 185                 190

Ala Gly Gly Asn Ala Ser Tyr Val Leu Asp Gly Val Pro Arg Met Arg
        195                 200                 205

Glu Arg Pro Ile Gly Asp Leu Val Thr Gly Leu Lys Gln Leu Gly Ala
    210                 215                 220

Asp Val Asp Cys Phe His Gly Thr Asp Cys Pro Pro Val Arg Val Leu
225                 230                 235                 240

Gly Lys Gly Gly Leu Pro Gly Gly Lys Val Lys Leu Ser Gly Ser Ile
                245                 250                 255

Ser Ser Gln Tyr Leu Thr Ala Leu Leu Met Ala Ala Pro Leu Ala Leu
            260                 265                 270

Gly Asp Val Glu Ile Glu Ile Ile Asp Lys Leu Ile Ser Val Pro Tyr
        275                 280                 285

Val Asp Met Thr Leu Lys Leu Met Ala Arg Phe Gly Val Thr Val Glu
    290                 295                 300

His Ser Asp Ser Trp Asp Arg Phe Leu Val Lys Gly Gly Gln Lys Tyr
305                 310                 315                 320

Lys Ser Pro Gly Asn Ala Tyr Val Glu Gly Asp Ala Ser Ser Ala Ser
                325                 330                 335

Tyr Phe Leu Ala Gly Ala Ala Val Thr Gly Gly Thr Val Thr Val Glu
            340                 345                 350

Gly Cys Gly Thr Ser Ser Leu Gln Gly Asp Val Lys Phe Ala Glu Val
        355                 360                 365

Leu Glu Lys Met Gly Ala Lys Val Ser Trp Thr Glu Asn Ser Val Thr
    370                 375                 380

Val Thr Gly Pro Pro Arg Asp Ser Val Lys Ser Lys His Leu Lys Ala

```
                385             390             395             400
        Ile Asp Val Asn Met Asn Lys Met Pro Asp Val Ala Met Thr Leu Ala
                        405                 410                 415

Val Val Ala Leu Phe Ala Asp Gly Pro Thr Ala Ile Arg Asp Val Ala
                        420                 425                 430

Ser Trp Arg Val Lys Glu Thr Glu Arg Met Ile Ala Ile Cys Thr Glu
                        435                 440                 445

Leu Arg Lys Leu Gly Ala Thr Val Glu Glu Leu Asp Tyr Cys Val
                    450                 455                 460

Ile Thr Pro Pro Glu Lys Leu Asn Ile Thr Ala Ile Asp Thr Tyr Asp
        465                 470                 475                 480

Asp His Arg Met Ala Met Ala Phe Ser Leu Ala Ala Cys Ser Asp Val
                        485                 490                 495

Pro Val Thr Ile Lys Asp Pro Gly Cys Thr Arg Lys Thr Phe Pro Asp
                        500                 505                 510

Tyr Phe Glu Val Leu Glu Arg Phe Thr Lys His
                        515                 520
```

<210> SEQ ID NO 38
<211> LENGTH: 1572
<212> TYPE: DNA
<213> ORGANISM: Cannabis sativa

<400> SEQUENCE: 38

```
atggcccaag tgagcaaaat ctgtagcaat ggagctcaaa ctatccttac tctcccaaat      60
atatctaagt ctcatacacc aagatcccta aattcagttt cgttgagatc accgtttttg     120
ggttcatcta actctttgag tttgaagatt ggaactgaat tgggggttg ttctacggtt      180
ggtaaagcta tggctggtcc agtcatggct tcagctgtca cagcggagaa gccttcaaag     240
gtaccggaga ttgtgttgca gcccattaaa gatatctctg cactgtcaa gttgccgggt      300
tccaagtcac tatcgaatcg gattctactc ctggctgctc tttctgaggg acaactgtt      360
gtggacaact tgttagatag tgatgacatt cactacatgc ttggtgcctt ggaaaccctt     420
ggtcttcgtg ttgaagcaga caaggaaagc aaacgagcaa ttgtgaagg ttgtgcgggt      480
cagtttcctg caggtaaaga atctgttgac gaagttcaac ttttccttgg aaatgctgga     540
acagcaatgc gtccactcac agctgcggtg actgttgctg gtggaaatgc tagctacgta     600
cttgatggtg ttcctcgaat gagagaaaga ccaattggag atttggtgac tggtcttaag     660
cagcttggtg cagatgttga ttgttttcat ggtacggatt gtcccctgt tcgtgtgctt      720
ggaaaaggag gccttcctgg gggcaaggtg aaactttctg gatcaattag cagtcaatat     780
ttgacagcct tgcttatggc agctcccttg gctcttggag atgttgaaat cgagataatt     840
gataaattga tctcggttcc ctatgttgat atgactttga gttgatggc acgttttggg     900
gttactgttg aacacagtga tagctgggat cgattttag ttaaaggagg tcaaaagtac      960
aaatctcctg gaaacgctta tgttgaaggt gatgcttcaa gtgctagtta cttcctagct    1020
ggtgctgcag tcactggtgg tacagtcacc gtagaaggtt gtgggactag tagtttacag    1080
ggagacgtaa aatttgctga agttcttgag aaaatgggtg ctaaagttag ctggacagag    1140
aacagtgtca cggtcactgg accaccacga gattctgtaa aaagtaaaca cttgaaagcc    1200
attgatgtca acatgaacaa aatgcctgat gttgccatga ctcttgctgt agttgctctt    1260
tttgctgatg gccccactgc tataagagat gtggcaagtt ggagagtcaa ggagacagag    1320
agaatgattg ccatctgcac tgaactcaga aagcttggag caacagttga ggaaggaccc    1380
```

-continued

| gattactgcg tgatcactcc accagagaaa ctaaatatca cagcaataga cacatacgac | 1440 |
| gaccacagga tggctatggc gttctctctt gcagcttgtt cagatgtgcc agttaccatt | 1500 |
| aaggatcctg gttgcacccg aaaaactttc ccagattact ttgaagtcct tgagagattt | 1560 |
| acaaagcact ga | 1572 |

<210> SEQ ID NO 39
<211> LENGTH: 1572
<212> TYPE: DNA
<213> ORGANISM: Artificial Sequence
<220> FEATURE:
<223> OTHER INFORMATION: Synthetic- engineered gene

<400> SEQUENCE: 39

| atggcccaag tgagcaaaat ctgtagcaat ggagctcaaa ctatccttac tctcccaaat | 60 |
| atatctaagt ctcatacacc aagatcccta aattcagttt cgttgagatc accgttttttg | 120 |
| ggttcatcta actctttgag tttgaagatt ggaactgaat ttgggggttg ttctacggtt | 180 |
| ggtaaagcta tggctggtcc agtcatggct tcagctgtca cagcggagaa gccttcaaag | 240 |
| gtaccggaga ttgtgttgca gcccattaaa gatatctctg gcactgtcaa gttgccgggt | 300 |
| tccaagtcac tatcgaatcg gattctactc ctggctgctc tttctgaggg acaactgtt | 360 |
| gtggacaact tgttagatag tgatgacatt cactacatgc ttggtgcctt ggaaacccctt | 420 |
| ggtcttcgtg ttgaagcaga caaggaaagc aaacgagcaa ttgtggaagg ttgtgcgggt | 480 |
| cagtttcctg caggtaaaga atctgttgac gaagttcaac ttttccttgg aaatgctgga | 540 |
| atagcaatgc gttcactcac agctgcggtg actgttgctg gtggaaatgc tagctacgta | 600 |
| cttgatggtg ttcctcgaat gagagaaaga ccaattggag atttggtgac tggtcttaag | 660 |
| cagcttggtg cagatgttga ttgttttcat ggtacggatt gtccccctgt tcgtgtgctt | 720 |
| ggaaaaggag gccttcctgg gggcaaggtg aaactttctg gatcaattag cagtcaatat | 780 |
| ttgacagcct tgcttatggc agctcccttg gctcttggag atgttgaaat cgagataatt | 840 |
| gataaattga tctcggttcc ctatgttgat atgactttga agttgatggc acgttttggg | 900 |
| gttactgttg aacacagtga tagctgggat cgatttttag ttaaaggagg tcaaaagtac | 960 |
| aaatctcctg gaaacgctta tgttgaaggt gatgcttcaa gtgctagtta cttcctagct | 1020 |
| ggtgctgcag tcactggtgg tacagtcacc gtagaaggtt gtgggactag tagtttacag | 1080 |
| ggagacgtaa aatttgctga agttcttgag aaaatgggtg ctaaagttag ctggacagag | 1140 |
| aacagtgtca cggtcactgg accaccacga gattctgtaa aaagtaaaca cttgaaagcc | 1200 |
| attgatgtca acatgaacaa aatgcctgat gttgccatga ctcttgctgt agttgctctt | 1260 |
| tttgctgatg gccccactgc tataagagat gtggcaagtt ggagagtcaa ggagacagag | 1320 |
| agaatgattg ccatctgcac tgaactcaga aagcttggag caacagttga ggaaggactt | 1380 |
| gattactgcg tgatcactcc accagagaaa ctaaatatca cagcaataga cacatacgac | 1440 |
| gaccacagga tggctatggc gttctctctt gcagcttgtt cagatgtgcc agttaccatt | 1500 |
| aaggatcctg gttgcacccg aaaaactttc ccagattact ttgaagtcct tgagagattt | 1560 |
| acaaagcact ga | 1572 |

<210> SEQ ID NO 40
<211> LENGTH: 4196
<212> TYPE: DNA
<213> ORGANISM: Cannabis sativa

<400> SEQUENCE: 40

```
ggttggtaag ccctcctacc ctctttgaaa attgaaagag agtcaatgtc gacctacagc    60
agcagcatcc attaacgtta ccattgccac caaaaatcca acctttattt gtatagagag   120
aatcagagaa ggtttgggtt tcagagagag agagaagaag aacaaaaaaa tggcccaagt   180
gagcaaaatc tgtagcaatg gagctcaaac tatccttact ctcccaaata tatctaagtc   240
tcatacacca agatccctaa attcagtttc gttgagatca ccgttttgg gttcatctaa    300
ctctttgagt ttgaagattg gaactgaatt tgggggttgt tctacggttg gtaaagctat   360
ggctggtcca gtcatggctt cagctgtcac agcggagaag ccttcaaagg taccggagat   420
tgtgttgcag cccattaaag atatctctgg cactgtcaag ttgccgggtt ccaagtcact   480
atcgaatcgg attctactcc tggctgctct ttctgaggta tatttcattt tttttaaaac   540
gtcaaacatg tattttttgtc gaggaagttt tctgtatata caaagataag agagtaaaaa 600
tatgaacat caataccaaa atgaaccaaa actaggctaa gctatcaaat catgtcatgg    660
tatgccatac tctactttcc tatctcaagc tccacagcta taaaatacta tatcgtaatt   720
attttgtcaa ctgctttcat attccttgta atttccctca ttcccactaa aactagttcc   780
aatggattgt gtggctggaa actgtagtta gttacattag ctagatctga accatgatca   840
gcatcgactg cccaactggt aaaccatgta attgcatgga attcttcctt tgttatccac   900
aaatttgaaa agtattttg aggtatacaa agattgtgct ttttatgagc aattttcttt   960
tagttttatg ttaagagttt gtagcgatgg gatgtttttt ttctagaaaa tggacagtaa  1020
agcttagcat ttttactttta ttggtgtaaa tgaatagtgt tcattgaagc tgaactcatg  1080
cccttaattg ggaggaaaat tgagagaaat ggagtaaagt aatatgatat tttggttaaa  1140
ttcgtaagaa tatgatggaa ataaaaaatg caactcaact gggttactga agttatattt  1200
ctggtctcag ttgtgctttt acaactttag tctagagctc cacgctgcgg agagattcgg  1260
agtccttaca gttatttttg ataatgattt atgagaattt cataactcta cgcttttgtt  1320
acattatata tgaggtgttt cgttggtgca ttgtctcacc tgaactccct aaatttaga   1380
atgtgggatt tagaatgaag ttatactatt agtgtttgag tcatctagaa tttgtagctg  1440
ctcattctcc atatactctt tctctatttc ctccccatat tttggcgcta ctacttatct  1500
ttacagttca tgttatttc atgtacttga gttttttgcc ctataaaata ttttgagcgg   1560
tgggaagtaa ctgtttttt tgttataatt atccagggga caactgttgt ggacaacttg   1620
ttagatagtg atgacattca ctacatgctt ggtgccttgg aaacccttgg tcttcgtgtt  1680
gaagcagaca aggaaagcaa acgagcaatt gtggaaggtt gtgcgggtca gtttcctgca  1740
ggtaaagaat ctgttgacga agttcaactt ttccttggaa atgctggaac agcaatgcgt  1800
ccactcacag ctgcggtgac tgttgctggt ggaaatgcta ggtttgtctt cattgcaatt  1860
gcttttgaat ataaagtact tctaatgcag tgaatttatg ctcttgtttt tcttactggc  1920
cgagtagctc ttcatttta ggtaaagaaa gtcacttttg ctaacaacat caccatttat   1980
acttccctct ttactttgat gtggttatgc tagaaattac atgttggaaa tgaactagca  2040
catatcataa attattttgt atgctgttat tacatttttct cagtaacctc ttaacttcta  2100
tatctcagct acgtacttga tggtgttcct cgaatgagag aaagaccaat tggagatttg  2160
gtgactggtc ttaagcagct tggtgcagat gttgattgtt ttcatggtac ggattgtccc  2220
cctgttcgtg tgcttggaaa aggaggcctt cctgggggca aggtgaggct tgcattgctt  2280
cttcttattc ttttttggcca taaaacatca ttgtaatagt ggttttatgt tatgaaatcc  2340
```

-continued

```
attgactggt ttattttag gttgttgttt tgcttttaaa taaaaacaat attgtcaaat      2400
gatgcataag tagtgattac atctacatca tttaatttat tatcttaaat gatgacaaac      2460
ttcatcattt tgactcagaa ttatgtaata ttacccttg caggtgaaac tttctggatc      2520
aattagcagt caatatttga cagccttgct tatggcagct cccttggctc ttggagatgt      2580
tgaaatcgag ataattgata aattgatctc ggttccctat gttgatatga ctttgaagtt      2640
gatggcacgt tttgggtta ctgttgaaca cagtgatagc tgggatcgat ttttagttaa      2700
aggaggtcaa aagtacaagt aggtttcttc tgaatatagt tgatagtatt gttacattac      2760
atctggttat gtcaaagagt aataaattga aaaataaaaa tctgtcagat ctcctggaaa      2820
cgcttatgtt gaaggtgatg cttcaagtgc tagttacttc ctagctggtg ctgcagtcac      2880
tggtggtaca gtcaccgtag aaggttgtgg gactagtagt ttacaggtat tttgcttaga      2940
ccttgaaatc tcttattctt gtacttgtgt ttacatagaa tctaagatta agtgtattta      3000
catacattaa ctggtgttta ataaagggag acgtaaaatt tgctgaagtt cttgagaaaa      3060
tgggtgctaa agttagctgg acagagaaca gtgtcacggt cactggacca ccacgagatt      3120
ctgtaaaag taaacacttg aaagccattg atgtcaacat gaacaaaatg cctgatgttg      3180
ccatgactct tgctgtagtt gctctttttg ctgatggccc cactgctata agagatggta      3240
tgttttcct taaatttgtg agatggtaaa atggggcagt cggttgggt tggggtagat      3300
tatcggttct cgtctgccat aataaaaaat aatctgctca tttgcaataa atttcacaga      3360
cacaaaaatg aaaaccaata aaatattatt ttgtttagag gattaaatac tcatttcttg      3420
ccttcctaa ttcccagtgg caagttggag agtcaaggag acagagagaa tgattgccat      3480
ctgcactgaa ctcagaaagg ttagttttta tgctgtttta tgtacttgtt atgtcatgcg      3540
ccttggaatg taatggctga tagctatctg ttcttatggg aacaaacatt tcagcttgga      3600
gcaacagttg aggaaggacc cgattactgc gtgatcactc caccagagaa actaaatatc      3660
acagcaatag acacatacga cgaccacagg atggctatga cgttctctct tgcagcttgt      3720
tcagatgtgc cagttaccat taaggatcct ggttgcaccc gaaaaacttt cccagattac      3780
tttgaagtcc ttgagagatt tacaaagcac tgaatgagta tttattaact ggatagagaa      3840
caatagcatc ggctactgtc attacaacta aagcagttgg gaggcaggca atccttttca      3900
attatcatgt gtttgatttt ggtcgactgt attgcaagtt gagcttctca ttattattaa      3960
gactgtaatc gtagttattt gttgtaactt ctgcaaaccc ttcatgttat tttttcaccc      4020
ttctaataag ccagtggggc aaattctata tctgctatat gagcttgagt gtagagagaa      4080
cttttgtcaa tgtataggtt tctagcagaa gcaccatccc taatatgctt tattataaga      4140
gttgctgtga tcgtgtagtg ttattttatt gaaagtaacc gacgcatctc atatta         4196
```

<210> SEQ ID NO 41
<211> LENGTH: 46
<212> TYPE: DNA
<213> ORGANISM: Artificial Sequence
<220> FEATURE:
<223> OTHER INFORMATION: Synthetic- prime editing guide RNA

<400> SEQUENCE: 41

```
tgaagacttt gcacaacttt tccttggaaa tgcgtttaag tcttct                      46
```

<210> SEQ ID NO 42
<211> LENGTH: 46
<212> TYPE: DNA

```
<213> ORGANISM: Artificial Sequence
<220> FEATURE:
<223> OTHER INFORMATION: Synthetic- prime editing guide RNA

<400> SEQUENCE: 42
agaagactta aacgcatttc caaggaaaag ttgtgcaaag tcttca                      46

<210> SEQ ID NO 43
<211> LENGTH: 64
<212> TYPE: DNA
<213> ORGANISM: Artificial Sequence
<220> FEATURE:
<223> OTHER INFORMATION: Synthetic- engineered gene

<400> SEQUENCE: 43
acctgctata gtgctgagtg aacgcattgc tattccagca tttccaagga aacatatagc      60
aggt                                                                   64

<210> SEQ ID NO 44
<211> LENGTH: 46
<212> TYPE: DNA
<213> ORGANISM: Artificial Sequence
<220> FEATURE:
<223> OTHER INFORMATION: Synthetic- prime editing guide RNA

<400> SEQUENCE: 44
tgaagacttt gcacttggag caacagttga ggagtttaag tcttct                      46

<210> SEQ ID NO 45
<211> LENGTH: 46
<212> TYPE: DNA
<213> ORGANISM: Artificial Sequence
<220> FEATURE:
<223> OTHER INFORMATION: Synthetic- prime editing guide RNA

<400> SEQUENCE: 45
agaagactta aactcctcaa ctgttgctcc aagtgcaaag tcttca                      46

<210> SEQ ID NO 46
<211> LENGTH: 60
<212> TYPE: DNA
<213> ORGANISM: Artificial Sequence
<220> FEATURE:
<223> OTHER INFORMATION: Synthetic- engineered gene

<400> SEQUENCE: 46
acctgctata gtgccacgca gtaatcaagt ccttcctcaa ctgttgaaca tatagcaggt      60

<210> SEQ ID NO 47
<211> LENGTH: 349
<212> TYPE: DNA
<213> ORGANISM: Artificial Sequence
<220> FEATURE:
<223> OTHER INFORMATION: Synthetic- engineered gene

<400> SEQUENCE: 47
ggtctcaaat ggcgacaggt tctcgtgttc tgatcggtct agcaatgatc ctcataatct      60
caggagaact gctagttcca gggcaaggaa cgtgccaagg agacatagag ggtctgatga     120
gagaatgtgc ggtctacgtc cagcgtccag gcccaaaggt aaacccatcc gcagcgtgtt     180
gcaaagtcgt caagagatca gacatcccct gcgcatgtgg ccgtatcaca ccctcggttc     240
aaaaaatgat agacatgaat aaggttgttc ttgtcacttc cttttgtggg aggcctctcg     300
ctcatggtac caagtgtgga agctacattg tgccatgagc ttagagacc                 349
```

<210> SEQ ID NO 48
<211> LENGTH: 348
<212> TYPE: DNA
<213> ORGANISM: Artificial Sequence
<220> FEATURE:
<223> OTHER INFORMATION: Synthetic- engineered gene

<400> SEQUENCE: 48

| ggtctcaaat | ggcgacaggt | tctcgtgttc | tgatcggtct | agcaatgatc | ctcataatct | 60 |
| caggagaact | gctagttcca | gggcaaggaa | cgtgccaagg | agacatagag | ggtctgatga | 120 |
| gagaatgtgc | ggtctacgtc | cagcgtccag | gcccaaaggt | aaacccatcc | gcagcgtgtt | 180 |
| gcaaagtcgt | caagagatca | gacatcccct | gcgcatgtgg | ccgtatcaca | ccctcggttc | 240 |
| aaaaaatgat | agacatgaat | aaggttgttc | ttgtcacttc | cttttgtggg | aggcctctcg | 300 |
| ctcatggtac | caagtgtgga | agctacattg | tgccaagttc | gagagacc | | 348 |

<210> SEQ ID NO 49
<211> LENGTH: 1207
<212> TYPE: DNA
<213> ORGANISM: Artificial Sequence
<220> FEATURE:
<223> OTHER INFORMATION: Synthetic- engineered gene

<400> SEQUENCE: 49

| ggtctcaaat | gggactctca | tcagtttgta | ccttttcatt | tcaaactaat | taccatactt | 60 |
| tattaaatcc | tcacaataat | aatcccaaaa | cctcattatt | atgttatcga | caccccaaaa | 120 |
| caccaattaa | atactcttac | aataattttc | cctctaaaca | ttgctccacc | aagagttttc | 180 |
| atctacaaaa | caaatgctca | gaatcattat | caatcgcaaa | aaattccatt | agggcagcta | 240 |
| ctacaaatca | aactgagcct | ccagaatctg | ataatcattc | agtagcaact | aaaatttttaa | 300 |
| actttgggaa | ggcatgttgg | aaacttcaaa | gaccatatac | aatcatagca | tttacttcat | 360 |
| gcgcttgtgg | attgtttggg | aaagagttgt | tgcataacac | aaatttaata | agttggtcac | 420 |
| tgatgttcaa | ggcattcttt | tttttggtgg | ctgtattatg | cattgcttct | tttacaacta | 480 |
| ccatcaatca | gatttacgat | cttcacattg | acagaataaa | caagcctgat | ctaccactag | 540 |
| cttcagggga | aatatcagta | aacacagctt | ggattatgag | cataattgtg | gcactgtttg | 600 |
| gattgataat | aactataaaa | atgaagggtg | gaccactcta | tatatttggc | tactgttttg | 660 |
| gtatttttgg | tgggattgtc | tattctgttc | caccatttag | atggaagcaa | aatccttcca | 720 |
| ctgcatttct | tctcaatttc | ctggcccata | ttattacaaa | tttcacattt | tattatgcca | 780 |
| gcagagcagc | tcttggccta | ccatttgagt | tgaggccttc | ttttactttc | ctgctagcat | 840 |
| ttatgaaatc | aatgggttca | gctttggctt | taatcaaaga | tgcttcagac | gttgaaggcg | 900 |
| acactaaatt | tggcatatca | accttggcaa | gtaaatatgg | ttccagaaac | ttgacattat | 960 |
| tttgttctgg | aattgttctc | ctatcctatg | tggctgctat | acttgctggg | attatctggc | 1020 |
| cccaggcttt | caacagtaac | gtaatgttac | tttctcatgc | aatcttagca | ttttggttaa | 1080 |
| tcctccagac | tcgagatttt | gcgttaacaa | attacgaccc | ggaagcaggc | agaagatttt | 1140 |
| acgagttcat | gtggaagctt | tattatgctg | aatatttagt | atatgttttc | atataagctt | 1200 |
| agagacc | | | | | | 1207 |

<210> SEQ ID NO 50
<211> LENGTH: 1206
<212> TYPE: DNA

<213> ORGANISM: Artificial Sequence
<220> FEATURE:
<223> OTHER INFORMATION: Synthetic- engineered gene

<400> SEQUENCE: 50

```
ggtctcaaat gggactctca tcagtttgta cctttcatt tcaaactaat taccatactt      60
tattaaatcc tcacaataat aatcccaaaa cctcattatt atgttatcga caccccaaaa    120
caccaattaa atactcttac aataatttc cctctaaaca ttgctccacc aagagtttc     180
atctacaaaa caaatgctca gaatcattat caatcgcaaa aaattccatt agggcagcta    240
ctacaaatca aactgagcct ccagaatctg ataatcattc agtagcaact aaaatttaa    300
actttgggaa ggcatgttgg aaacttcaaa gaccatatac aatcatagca tttacttcat    360
gcgcttgtgg attgtttggg aaagagttgt tgcataacac aaatttaata agttggtcac    420
tgatgttcaa ggcattcttt tttttggtgg ctgtattatg cattgcttct tttacaacta    480
ccatcaatca gatttacgat cttcacattg acagaataaa caagcctgat ctaccactag    540
cttcagggga aatatcagta aacacagctt ggattatgag cataattgtg gcactgtttg    600
gattgataat aactataaaa atgaaggggtg gaccactcta tatatttggc tactgttttg    660
gtattttgg tgggattgtc tattctgttc caccatttag atggaagcaa aatccttcca    720
ctgcatttct tctcaatttc ctggcccata ttattacaaa tttcacattt tattatgcca    780
gcagagcagc tcttggccta ccatttgagt tgaggccttc tttactttc ctgctagcat    840
ttatgaaatc aatgggttca gctttggctt taatcaaaga tgcttcagac gttgaaggcg    900
acactaaatt tggcatatca accttggcaa gtaaatatgg ttccagaaac ttgacattat    960
tttgttctgg aattgttctc ctatcctatg tggctgctat acttgctggg attatctggc   1020
cccaggcttt caacagtaac gtaatgttac tttctcatgc aatcttagca ttttggttaa   1080
tcctccagac tcgagatttt gcgttaacaa attacgaccc ggaagcaggc agaagatttt   1140
acgagttcat gtggaagctt tattatgctg aatattagt atatgtttc ataagttcga   1200
gagacc                                                              1206
```

<210> SEQ ID NO 51
<211> LENGTH: 1132
<212> TYPE: DNA
<213> ORGANISM: Artificial Sequence
<220> FEATURE:
<223> OTHER INFORMATION: Synthetic- engineered gene

<400> SEQUENCE: 51

```
ggtctcaaat gggttcaaca ggaatagaaa cccaaatgac cccaacccaa atatccgacg      60
aagaagccaa cctcttcgcc atgcaattag ccagtgcctc agtcttaccc atggttctca    120
aagcagcttt agagctcgac ctcttggaga tcatagccaa ggccggtcca ggcgcgtttc    180
tctcaccttc cgacatagct caacagcttc cgactcagaa cccagacgcc ccggtgatgc    240
tggaccggat gctgagactg ttggctagct acaacgtggt gacgtactcg ctgcgtgagc    300
gtgaaacggc ggaagaggaa gggaaggtgg agaggcttta tgggttggct ccggtgagta    360
aatatctgac gaagaatgaa gatggagtct ccattgctcc tctttgtctc atgaaccagg    420
ataaggttct tatggagagt tggtatcact taaagatgc agtacttgat ggaggaatac    480
ctttcaacaa ggcatatgga atgacagcat ttgaatatca tggaaccgat caaaggttca    540
ataaaatctt taatagagga atgtccgacc actcgactat taccatgaaa aaaatcctcg    600
aaacttacaa gggtttcgag ggtcttaact cgattgttga tgttggtggt ggtactggag    660
```

```
ctgttgttaa catgatcgtt tctaagtacc ctactattaa gggtattaac ttcgatttgc    720
ctcatgtcat cgaagatgca cctccattga ccggtgtaga gcatgttgga ggagacatgt    780
ttgtaagtgt accaaaagga gatgcaattt tcatgaagtg gatttgccat gattggagcg    840
atgaacactg cttgaaattc ttgaagaact gccacgctgc actgcccgaa cacggaaaag    900
tgatcgtggc ggagtgcatt cttccggtgg caccggactc gagccttgcc acaaagagta    960
cggtccacat tgatgtgatc atgttggccc ataaccctgg tggcaaagag agaacagaga   1020
aagagtttga ggcattggct aagggagctg gctttaaagg cttcaaagtc cattgcaatg   1080 cttttcaatac ccatatcatg gaatttctca agaccattta agcttagaga cc          1132
```

```
<210> SEQ ID NO 52
<211> LENGTH: 1131
<212> TYPE: DNA
<213> ORGANISM: Artificial Sequence
<220> FEATURE:
<223> OTHER INFORMATION: Synthetic- engineered gene

<400> SEQUENCE: 52
ggtctcaaat gggttcaaca ggaatagaaa cccaaatgac cccaacccaa atatccgacg     60
aagaagccaa cctcttcgcc atgcaattag ccagtgcctc agtcttaccc atggttctca    120
aagcagcttt agagctcgac ctcttggaga tcatagccaa ggccggtcca ggcgcgtttc    180
tctcaccttc cgacatagct caacagcttc cgactcagaa cccagacgcc ccggtgatgc    240
tggaccggat gctgagactg ttggctagct acaacgtggt gacgtactcg ctgcgtgagc    300
gtgaaacggc ggaagaggaa gggaaggtgg agaggcttta tgggttggct ccggtgagta    360
aatatctgac gaagaatgaa gatggagtct ccattgctcc tctttgtctc atgaaccagg    420
ataaggttct tatggagagt tggtatcact taaaagatgc agtacttgat ggaggaatac    480
ctttcaacaa ggcatatgga atgacagcat ttgaatatca tggaaccgat caaaggttca    540
ataaaatctt taatagagga atgtccgacc actcgactat taccatgaaa aaaatcctcg    600
aaacttacaa gggtttcgag ggtcttaact cgattgttga tgttggtggt ggtactggag    660
ctgttgttaa catgatcgtt tctaagtacc ctactattaa gggtattaac ttcgatttgc    720
ctcatgtcat cgaagatgca cctccattga ccggtgtaga gcatgttgga ggagacatgt    780
ttgtaagtgt accaaaagga gatgcaattt tcatgaagtg gatttgccat gattggagcg    840
atgaacactg cttgaaattc ttgaagaact gccacgctgc actgcccgaa cacggaaaag    900
tgatcgtggc ggagtgcatt cttccggtgg caccggactc gagccttgcc acaaagagta    960
cggtccacat tgatgtgatc atgttggccc ataaccctgg tggcaaagag agaacagaga   1020
aagagtttga ggcattggct aagggagctg gctttaaagg cttcaaagtc cattgcaatg   1080 cttttcaatac ccatatcatg gaatttctca agaccattag ttcgagagac c           1131
```

```
<210> SEQ ID NO 53
<211> LENGTH: 1222
<212> TYPE: DNA
<213> ORGANISM: Artificial Sequence
<220> FEATURE:
<223> OTHER INFORMATION: Synthetic- engineered gene

<400> SEQUENCE: 53
ggtctcaaat ggtgttctca tcagtttgta gttttccatc ctcccttgga actaatttta     60
aattagttcc tcgtagtaat tttaaggcat catcttctca ttatcatgaa ataaataatt    120
```

-continued

| | |
|---|---|
| ttattaataa taaaccaatt aaattctcat attttcttc aagactatat tgctctgcca | 180 |
| aaccaattgt acacagagaa aacaaattca caaaatcatt ttcactcagc cacctccaaa | 240 |
| ggaaaagctc cataaaggca catggtgaaa ttgaagctga tgggagtaat ggcacatctg | 300 |
| aatttaatgt aatgaaaagt ggaaacgcaa tttggagatt tgtaaggcca tatgcagcca | 360 |
| agggagtatt gtttaactct gctgctatgt ttgcaaaaga gttggtgggg aacctaaatc | 420 |
| tatttagttg gcctttgatg tttaagatac tctcttttac attggttatt ttatgcattt | 480 |
| ttgtaagtac aagtggcatc aatcaaattt atgatctcga catcgacagg ttaaacaaac | 540 |
| ctaatttgcc agtagcatca ggagaaattt cagttgaatt ggcatggttg ttgactatag | 600 |
| tttgtacaat aagtggcctc acattaacaa ttataacgaa ctcagggcca ttcttccctt | 660 |
| ttctctactc tgctagtatc ttttttggct ttctctattc tgctcctcca ttcagatgga | 720 |
| agaagaatcc ttttacagca tgtttctgta atgttatgtt gtatgttggc acaagcgttg | 780 |
| gtgtctatta tgcttgtaag gctagtctcg ggcttccagc caactggagc cctgcttttt | 840 |
| gtttgctctt ttggtttatt tcattgttga gtatacccat ctccattgca aaagatcttt | 900 |
| cagacataga aggtgaccgc aagtttggaa tcataacctt ctcaactaaa tttggagcaa | 960 |
| aacccatagc atatatttgt catggactca tgcttctgaa ttacgtgagt gttatggctg | 1020 |
| cagctattat ttggccacag ttttcaaca gtagcgtaat attgctttct catgcattca | 1080 |
| tggcaatttg gtattatat caggcttgga tattggagaa atcaaattac gccacggaaa | 1140 |
| cgtgccaaaa atactatata ttcctttgga taattttttc tcttgaacat gccttctatt | 1200 |
| tgttcatgta ggcttagaga cc | 1222 |

<210> SEQ ID NO 54
<211> LENGTH: 1221
<212> TYPE: DNA
<213> ORGANISM: Artificial Sequence
<220> FEATURE:
<223> OTHER INFORMATION: Synthetic- engineered gene

<400> SEQUENCE: 54

| | |
|---|---|
| ggtctcaaat ggtgttctca tcagtttgta gttttccatc ctcccttgga actaattta | 60 |
| aattagttcc tcgtagtaat tttaaggcat catcttctca ttatcatgaa ataaataatt | 120 |
| ttattaataa taaaccaatt aaattctcat attttcttc aagactatat tgctctgcca | 180 |
| aaccaattgt acacagagaa aacaaattca caaaatcatt ttcactcagc cacctccaaa | 240 |
| ggaaaagctc cataaaggca catggtgaaa ttgaagctga tgggagtaat ggcacatctg | 300 |
| aatttaatgt aatgaaaagt ggaaacgcaa tttggagatt tgtaaggcca tatgcagcca | 360 |
| agggagtatt gtttaactct gctgctatgt ttgcaaaaga gttggtgggg aacctaaatc | 420 |
| tatttagttg gcctttgatg tttaagatac tctcttttac attggttatt ttatgcattt | 480 |
| ttgtaagtac aagtggcatc aatcaaattt atgatctcga catcgacagg ttaaacaaac | 540 |
| ctaatttgcc agtagcatca ggagaaattt cagttgaatt ggcatggttg ttgactatag | 600 |
| tttgtacaat aagtggcctc acattaacaa ttataacgaa ctcagggcca ttcttccctt | 660 |
| ttctctactc tgctagtatc ttttttggct ttctctattc tgctcctcca ttcagatgga | 720 |
| agaagaatcc ttttacagca tgtttctgta atgttatgtt gtatgttggc acaagcgttg | 780 |
| gtgtctatta tgcttgtaag gctagtctcg ggcttccagc caactggagc cctgcttttt | 840 |
| gtttgctctt ttggtttatt tcattgttga gtatacccat ctccattgca aaagatcttt | 900 |
| cagacataga aggtgaccgc aagtttggaa tcataacctt ctcaactaaa tttggagcaa | 960 |

```
aacccatagc atatatttgt catggactca tgcttctgaa ttacgtgagt gttatggctg    1020
cagctattat ttggccacag tttttcaaca gtagcgtaat attgctttct catgcattca    1080
tggcaatttg ggtattatat caggcttgga tattggagaa atcaaattac gccacggaaa    1140
cgtgccaaaa atactatata ttcctttgga taatttttc tcttgaacat gccttctatt     1200
tgttcatgag ttcgagagac c                                              1221
```

<210> SEQ ID NO 55
<211> LENGTH: 61
<212> TYPE: DNA
<213> ORGANISM: Cannabis sativa

<400> SEQUENCE: 55

```
ttgacgaagt tcaacttttc cttggaaatg ctggaacagc aatgcgtcca ctcacagctg    60
c                                                                    61
```

<210> SEQ ID NO 56
<211> LENGTH: 57
<212> TYPE: DNA
<213> ORGANISM: Artificial Sequence
<220> FEATURE:
<223> OTHER INFORMATION: Synthetic- engineered gene
<220> FEATURE:
<221> NAME/KEY: misc_feature
<222> LOCATION: (21)..(21)
<223> OTHER INFORMATION: N represents any nucleotide

<400> SEQUENCE: 56

```
caacttttcc ttggaaatgc ntgagtgaac gcattgctat tccagcattt ccaagga       57
```

<210> SEQ ID NO 57
<211> LENGTH: 56
<212> TYPE: DNA
<213> ORGANISM: Cannabis sativa

<400> SEQUENCE: 57

```
cttggagcaa cagttgagga aggacccgat tactgcgtga tcactccacc agagaa        56
```

<210> SEQ ID NO 58
<211> LENGTH: 53
<212> TYPE: DNA
<213> ORGANISM: Artificial Sequence
<220> FEATURE:
<223> OTHER INFORMATION: Synthetic- engineered gene
<220> FEATURE:
<221> NAME/KEY: misc_feature
<222> LOCATION: (21)..(21)
<223> OTHER INFORMATION: N represents any nucleotide

<400> SEQUENCE: 58

```
cttggagcaa cagttgagga ncacgcagta atcaagtcct tcctcaactg ttg           53
```

<210> SEQ ID NO 59
<211> LENGTH: 1638
<212> TYPE: DNA
<213> ORGANISM: Artificial Sequence
<220> FEATURE:
<223> OTHER INFORMATION: In silico- consensus sequence

<400> SEQUENCE: 59

```
atgaattgct cagcattttc cttttggttt gtttgcaaaa taatattttt ctttctctca    60
ttccatatcc aaatttcaat agctaatcct cgagaaaact tccttaaatg cttctcaaaa    120
```

| | |
|---|---|
| catattccca acaatgtagc aaatccaaaa ctcgtataca ctcaacacga ccaattgtat | 180 |
| atgtctatcc tgaattcgac aatacaaaat cttagattca tctctgatac aaccccaaaa | 240 |
| ccactcgtta ttgtcactcc ttcaaataac tcccatatcc aagcaactat tttatgctct | 300 |
| aagaaagttg gcttgcagat tcgaactcga agcggtggcc atgatgctga gggtatgtcc | 360 |
| tacatatctc aagtcccatt tgttgtagta gacttgagaa acatgcattc gatcaaaata | 420 |
| gatgttcata gccaaactgc gtgggttgaa gccggagcta cccttggaga agtttattat | 480 |
| tggatcaatg agaagaatga gaatcttagt tttcctggtg ggtattgccc tactgttggc | 540 |
| gtaggtggac actttagtgg aggaggctat ggagcattga tgcgaaatta tggccttgcg | 600 |
| gctgataata ttattgatgc acacttagtc aatgttgatg gaaaagttct agatcgaaaa | 660 |
| tccatgggag aagatctgtt tgggctata cgtggtggtg gaggagaaaa ctttggaatc | 720 |
| attgcagcat ggaaaatcaa actggttgct gtcccatcaa agtctactat attcagtgtt | 780 |
| aaaaagaaca tggagataca tgggcttgtc aagttattta caaatggca aaatattgct | 840 |
| tacaagtatg acaagatttt agtactcatg actcacttca taacaaagaa tattacagat | 900 |
| aatcatggga agaataagac tacagtacat ggttacttct cttcaatttt tcatggtgga | 960 |
| gtggatagtc tagtcgactt gatgaacaag agctttcctg agttgggtat taaaaaaact | 1020 |
| gattgcaaag aatttagctg gattgataca accatcttct acagtggtgt tgtaaatttt | 1080 |
| aacactgcta attttaaaaa ggaaattttg cttgatagat cagctgggaa gagacggct | 1140 |
| ttctcaatta agttagacta tgttaagaaa ccaattccag aaactgcaat ggtcaaaatt | 1200 |
| ttggaaaaat tatatgaaga agatgtagga gctgggatgt atgtgttgta cccttacggt | 1260 |
| ggtataatgg aggagatttc agaatcagca attccattcc ctcatcgagc tggaataatg | 1320 |
| tatgaacttt ggtacactgc ttcctgggag aagcaagaag ataatgaaaa gcatataaac | 1380 |
| tgggttcgaa gtgtttataa ttttacgact ccttatgtgt cccaaaatcc aagattggcg | 1440 |
| tatctcaatt atagggacct tgatttagga aaaactaatc atgcgagtcc taataattac | 1500 |
| acacaagcac gtatttgggg tgaaaagtat tttggtaaaa attttaacag gttagttaag | 1560 |
| gtgaaaacta agttgatccc caataatttt tttagaaacg aacaaagtat cccacctctt | 1620 |
| ccaccgcatc atcattaa | 1638 |

<210> SEQ ID NO 60
<211> LENGTH: 1737
<212> TYPE: DNA
<213> ORGANISM: Arabidopsis thaliana

<400> SEQUENCE: 60

| | |
|---|---|
| atgaaggaga tcgcgatgag gaattcaaag cgcaagcctg agccgacgcc gttcgccggg | 60 |
| aagaagctcc ggtcgacgcg attacgccgg aagagagcac agatctctcc cgttcttgtt | 120 |
| caatcacctc tctggagcaa acaaatcgga gtctctgctg cttctgtcga ttcctgctcc | 180 |
| gatttgctag ctgatgacaa cgtttcctgt ggttcgagca gagtcgagaa gagctcgaat | 240 |
| ccgaagaaga ctctaattga agaggtagaa gtttctaaac ctggttataa tgtgaaggag | 300 |
| acgattggtg attcgaaatt tcgaaggatt acgaggtctt actctaagct acacaaggag | 360 |
| aaggagggag atgagatcga agtaagcgaa tcgtcttgtg ttgattcgaa ttctggtgct | 420 |
| ggattaagga gattgaatgt gaagggaaat aaaattaacg acaacgatga gatctctttc | 480 |
| tcacgatccg atgtgacctt cgccggacat gtctccaaca gccggagttt gaatttcgaa | 540 |
| tcggagaata aggagagcga cgtcgtttct gtcatatctg gagttgagta ctgttccaag | 600 |

```
ttcgggagcg ttaccggagg agctgataac gaagaaattg aaatctccaa gccgagcagc      660
ttcgtggaag ctgattcctc tcttggatcg gccaaggaat tgaagccgga gcttgagata      720
gtcggatgcg tctctgatct cgcttgctct gagaaattct cggaagaggt ttcggattct      780
ctcgatgatg agtcatctga gcaacgttca gagatatatt cacagtattc cgacttcgat      840
tactcggatt acactccgtc catcttcttc gactctggca gcgaattctc tgagaaatct      900
tcctctgatt ctcctatttc acattctcgc tctctgtacc tccagttcaa ggaacagttc      960
tgtagatcca cgattcccaa cgatttggga tcttcttgcg aggaagaaat tcactctgaa     1020
ttgctaaggt ttgatgatga ggaggtggaa gagagctatc taaggctgag ggaaagagaa     1080
agaagtcatg catatatgcg ggactgtgct aaggcatact gctccaggat ggacaatact     1140
ggtctcatcc ctcgtctacg ctccatcatg gttcaatgga ttgtaaagca atgttctgac     1200
atggggcttc agcaagagac attgtttcta ggagttggtc tgttggatcg attcctgagc     1260
aaaggatcat tcaaaagcga aaggactcta atactagtcg ggattgcgag tcttactctg     1320
gccaccagaa ttgaagaaaa tcaaccttac aacagcatcc ggaaaaggaa cttcaccatt     1380
cagaacctaa gatatagccg gcatgaagtg gtggcaatgg agtggctggt tcaagaagtc     1440
ctcaacttca aatgcttcac acccacaatc ttcaacttct gtggttccta cttaaaagct     1500
gctcgagcca atccgaagt tgaaaggaaa gccaaatcct tggctgttac ctcactatcc     1560
gaccaaactc aactctgttt ttggccctca actgtagcag ctgcactcgt ggttctcgcc     1620
tgcatcgaac acaacaaaat ctctgcatac caacgagtca taaggtcca tgttagaaca     1680 acagataacg agttgcctga atgcgttaag agtctggact ggttgcttgg gcagtaa       1737
```

<210> SEQ ID NO 61
<211> LENGTH: 832
<212> TYPE: DNA
<213> ORGANISM: Bacillus amyloliquefaciens

<400> SEQUENCE: 61

```
ctggaaaacg tcacattgct tccgcatatc gggtcagcaa cggctaaaat ccgcttgaat       60
atgttcacac aagccgctca aaacatgatt gacgccgtat acggaagaac gccgaaaaac      120
cttactaagg aatttcaata agaagaaaaa tcccggttgg ttcagccggg gtttattttt      180
cgctagataa aaagtactat ttttaaattc tttctattcc tttctttcgt tgctgataca      240
atgaaaagga atcagcttca catgatgaaa atgggaggta ttgctttgaa aaaacgatta      300
tcgtggattt ccgtttgttt actggtgctt gtctccgcgg cggggatgct gttttcaaca      360
gctgccaaaa cggaaacatc ttctcacaag gcacacacag aagcacaggt tatcaacacg      420
tttgacgggg ttgcggatta tcttcagaca tatcataagc tacctgataa ttacattaca      480
aaatcagaag cacaagccct cggctgggtg gcatcaaaag gaaccttgc agacgtcgct       540 ccggggaaaa gcatcggcgg agacatcttc tcaaacaggg aaggcaaact cccgggcaaa      600
agcggacgaa catggcgtga agcggatatt aactatacat caggcttcag aaattcagac      660
cggattcttt actcaagcga ctggctgatt tacaaaacaa cggaccatta tcagaccttt      720
acaaaaatca gataacgaaa aaaacggctt ccctgcggag gccgtttttt tcagctttac      780
ataaagtgtg taataaattt ttcttcaaac tctgatcggt caatttcact tt              832
```

METHODS OF GENE EDITING AND TRANSFORMING *CANNABIS*

CROSS-REFERENCE TO RELATED APPLICATIONS

This application claims priority to U.S. Provisional Application No. 62/875,311, filed Jul. 17, 2019, U.S. Provisional Application No. 62/906,210, filed Sep. 26, 2019, and U.S. Provisional Application No. 62/982,522, filed Feb. 27, 2020, each of which is incorporated herein by reference in their entirety.

STATEMENT REGARDING FEDERALLY SPONSORED RESEARCH

Not Applicable.

SEQUENCE LISTING

A Sequence Listing accompanies this application and is submitted as an ASCII text file of the sequence listing named "960296_04047_ST25.txt" which is 95.4 KB in size and was created on Nov. 23, 2020. The sequence listing is electronically submitted via EFS-Web on Nov. 23, 2020 and is incorporated herein by reference in its entirety.

BACKGROUND

A key hurdle in the transformation of plants is the responsiveness of cells in tissue culture to produce embryogenic cells that go on to form clonal, intact and fertile plants. Many species and varieties of plants are recalcitrant to this type of regeneration, including *Cannabis sativa* and *Cannabis indica*. Therefore, a need in the art exists for improved *Cannabis* transformation and gene editing methods.

SUMMARY OF THE INVENTION

In a first aspect, provided herein is a method of preparing an explant, the method comprising the steps of, rehydrating a dry *Cannabis* seed in a hydration medium, and excising meristematic tissue from the rehydrated *Cannabis* seed to form an explant. In some embodiments, the hydration medium comprises one or more priming agents. In some embodiments, the seed is a *Cannabis sativa* seed.

In some embodiments, the explant preparation method additionally comprises the step of surface sterilizing the *Cannabis* seed prior to rehydration. In some embodiments, the seed is surface sterilized using bleach.

In some embodiments, the explant preparation method additionally comprises the step of drying the explant. In some embodiments, the dried explant is capable of being stored for at least 10 days. In some embodiments, the explant is dried in the presence of one or more transformation supplements. In some embodiments, the transformation supplement is selected from the group consisting of a small molecule, a nucleic acid, a polypeptide, a protein, an antibody, a transcription factor, a biological macromolecule, a nanoparticle, and a liposome.

In some embodiments, the explant preparation method additionally comprise the step of transforming the explant with a heterologous nucleic acid of interest. In some embodiments, the explant is transformed using *Agrobacterium* mediated transformation or particle bombardment.

In a second aspect, provided herein is a *Cannabis* explant generated by the explant preparation methods described herein.

In a third aspect, provided herein is a dried *Cannabis* explant generated by the methods described herein.

In a forth aspect, provided herein is a method of transforming *Cannabis* with a heterologous nucleic acid, the method comprising the steps of rehydrating a dry *Cannabis* seed in a hydration medium, excising meristematic tissue from the rehydrated *Cannabis* seed to form a *Cannabis* explant, incubating the *Cannabis* explant in a pretreatment medium, inoculating the *Cannabis* explant with *Agrobacterium* spp. comprising the heterologous nucleic acid, co-culturing the *Cannabis* explant in a co-culture medium for between about 1 day and about 6 days, and culturing the *Cannabis* explant on a selection medium to select for transformed *Cannabis* explants.

In some embodiments, the method of transforming *Cannabis* additionally comprises the step of force treating the *Cannabis* explant prior to or following inoculation. In some embodiments, the force treatment is selected from the group consisting of sonication, vortexing, centrifugation, heat-shock, and addition of chemicals.

In some embodiments, the *Cannabis* transformation method additionally comprises the step of surface sterilizing the *Cannabis* seed prior to rehydration.

In some embodiments, the heterologous nucleic acid modulates the expression or activity of an endogenous *Cannabis* gene selected from the group consisting of tetrahydrocannabinolic acid synthase (THCA synthase), cannabidiolic acid synthase (CBDA synthase), O-methyltransferase (CsOMT21), lipid transfer protein 2 (LTP2), prenyltransferase 3 (CsPT3), and prenyltransferase 1 (CsPT1). In some embodiments, the heterologous nucleic acid encodes a polypeptide at least 90% identical to SEQ ID NO:28. In some embodiments, the heterologous nucleic acid encodes a guide RNA that targets *Cannabis sativa* THCA synthase gene, *Cannabis sativa* CBDA synthase gene, or *Cannabis sativa* EPSP synthase gene In some embodiments, the *Cannabis* seed is a *Cannabis sativa* seed. In some embodiments, the *Cannabis* seed is a seed from a *Cannabis* plant with less than 0.3 percent THC based on dry weight.

In a fifth aspect, provided herein is a transformed *Cannabis* explant produced by the methods described herein.

In a sixth aspect, provided herein is a *Cannabis* plant grown from the *Cannabis* explant generated by the methods described herein.

In a seventh aspect, provided herein is a method of producing a transformed *Cannabis* seed, the method comprising contacting a female *Cannabis* flower with an *Agrobacterium* spp. culture, wherein the *Agrobacterium* comprises a heterologous nucleic acid and pollinating the contacted female *Cannabis* flower with male pollen from a suitable donor plant, whereby a transformed *Cannabis* seed is produced. In some embodiments, the *Agrobacterium* spp. culture comprises sucrose and a wetting agent. In some embodiments, the *Agrobacterium* comprises a vector comprising the heterologous nucleic acid.

In an eighth aspect, provided herein is a method of transforming a *Cannabis* plant, the method comprising growing a sanitized and imbibed *Cannabis* seed on a non-selective culture medium suitable for supporting the growth and survival of the *Cannabis* seed until a *Cannabis* explant is formed, inoculating the *Cannabis* explant with a heterologous nucleic acid, co-culturing the *Cannabis* explant in a co-culture medium for between about 1 day and about 6 days, and culturing the *Cannabis* explant on a selection medium to select for transformed *Cannabis* explants. In some embodiments, the explant is selected from the group consisting of a leaf explant, a node explant, an internode explant, a petiole explant, a hypocotyl explant, and a bud explant. In some embodiments, the *Cannabis* explant is inoculated using particle bombardment, high velocity microprojection, microinjection, electroporation, direct DNA uptake, cell-penetrating peptides, silica carbide fibers, nanoparticles, and bacterially-mediated transformation. In some embodiments, *Agrobacterium* spp. is used to inoculate the *Cannabis* explant.

In some embodiments, the method additionally comprises the step of force treating the *Cannabis* explant prior to or following inoculation. In some embodiments, the force treatment is selected from the group consisting of sonication, vortexing, centrifugation, heat-shock, and addition of chemicals.

In some embodiments, the heterologous nucleic acid modulates the expression or activity of an endogenous *Cannabis* gene selected from the group consisting of tetrahydrocannabinolic acid synthase (THCA synthase), cannabidiolic acid synthase (CBDA synthase), O-methyltransferase (CsOMT21), lipid transfer protein 2 (LTP2), prenyltransferase 3 (CsPT3), and prenyltransferase 1 (CsPT1). In some embodiments, the heterologous nucleic acid encodes a polypeptide at least 90% identical to SEQ ID NO:28. In some embodiments, the heterologous nucleic acid encodes a guide RNA that targets *Cannabis sativa* THCA synthase gene, *Cannabis sativa* CBDA synthase gene, or *Cannabis sativa* EPSP synthase gene.

In some embodiments, the *Cannabis* seed is a *Cannabis sativa* seed.

BRIEF DESCRIPTION OF DRAWINGS

The patent or patent application file contains at least one drawing in color. Copies of this patent or patent application publication with color drawings will be provided by the Office upon request and payment of the necessary fee.

FIG. 14 shows sanitized *Cannabis* seeds and axenic plantlets on B5 medium after about 6 weeks.

FIG. 24 shows pollen germination results.

FIG. 26 shows the phenotype of plant WP421-1 on the day of transfer from tissue culture to the greenhouse (right) and after approximately 4 weeks in the greenhouse (left).

FIG. 40 shows T1 seedlings of WP421-1 and RFP expression in T1 seedling WP421-1@2 "Carly."

FIG. 45 shows stable RFP expression (tdTomato) in T1 seedlings of WP421-1 (germinated in flats).

FIG. 56 shows GUS expression in vascular tissue in petiole sections (and corresponding leaf) of *Cannabis* T0 particle gun event WP001181-1a.

FIG. 60 shows transient GUS expression in *Cannabis* (Abacus variety) meristem explants mechanically excised by crushing under a rolling pin, then stored for 2 months at −20 C (left image seed crushed wet and crushed material then dried; right image seed dried first then crushed.

FIG. 66 shows embodiments of a cloning strategy for BraLTP2. From top to bottom, the sequences shown are: SEQ ID NO:29, SEQ ID NO:47, and SEQ ID NO:48.

FIG. 67 shows embodiments of a cloning strategy for CsPT1. From top to bottom, the sequences shown are: SEQ ID NO:31, SEQ ID NO:49, and SEQ ID NO:50.

FIG. 70 shows an embodiment of the CsEPSPS prime editing mutation strategy as described herein.

FIG. 71 shows an embodiment of the CsEPSPS prime editing mutation strategy as described herein.

INCORPORATION BY REFERENCE

Figure 1:
FIG. 1 shows stable RFP expression in *Cannabis* plantlet from meristem transformation experiments outlined in Example 1.

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present disclosure describes methods for preparation and transformation of meristem explants from *Cannabis*. The meristem explant preparation methods described herein allow for pretreatment of the tissues for higher explant transformation and longer explant storage following excision.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

Provided herein are methods for preparing an explant suitable for transformation from a *Cannabis* seed. Also provided herein are methods of transforming and gene editing *Cannabis* meristem explant tissue. The explants generated by the methods described herein exhibit higher transformation efficiency with a broader capacity to customize the transformation process via pretreatment of the meristematic tissue used to generate the explants. The methods described herein allow for high scale production of storable explants for more effect transformation methods. As described in further detail below, the protocols described herein allow for targeted pretreatment of the meristematic tissues used in explant preparation at various stages and with various factors to improve explant storage and transformation efficiency.

As used herein, "embryo" refers to part of a seed, consisting of precursor tissues (meristematic tissues) for the leaves, stem, and root, as well as one or more cotyledons. Once the embryo begins to grow (germinate), it becomes a seedling plant.

As used herein, "meristem" or "meristematic tissue" refers to the portion of a seed that consists of undifferentiated cells, the meristematic cells, which differentiate to produce multiple plant structures including stem, roots, leaves, germline tissues and seeds. The meristematic cells are the targets for transformation to obtain transgenic plants.

As used herein, "explant" refers to the target material for transformation.

As used herein, "germline transformation" refers to the transformation of a gene of interest into cells that give rise to pollen or ovule thus into seed.

In a first aspect, provided herein is a method for preparing an explant from the meristematic tissue of a seed, where the method generally comprises the steps of drying the seed, surface sterilizing the seed, imbibing the seed until sufficiently hydrated, excising meristematic tissue from the hydrated seed to generate an explant, and optionally drying the excised meristematic tissue to generate the storable explant for transformation. The explants generated by the methods described herein are suitable for use in any transformation method known in the art.

The methods described herein also include one or more priming steps in which one or more priming agents are added to either the hydration medium during imbibing of the seed or to the explant as it is drying to generate a value added explant. As used herein, the term "value added explant" refers to an explant prepared by the methods described herein when a priming factor has been included in the hydration medium or a transformation supplement is included during drying of the explant.

The method includes a first step of drying a seed or acquiring a dried seed from which the explant will be generated. Preferably, a dry seed for use in the methods of the present invention will have a moisture content of between 1% and 25%. Ideally seeds are grown and harvested to achieve a viable embryo and are grown and harvested and cleaned to achieve blemish-free identity preserved seeds free of plant diseases and microbes that could interfere with sterile tissue culture. It may be desirable to treat the plants with fungicides and/or natural or synthetic plant regulators to improve embryo viability, embryo storage quality, seed coat intactness, seed vigor, percent germination cell response in tissue culture and transformation.

Seeds from which explants are to be prepared may be harvested from any *Cannabis* cultivar of interest. In some embodiments, the seed is from *Cannabis sativa*. In some embodiments, the seed is from *Cannabis indica*. In some embodiments, the seed is from a *Cannabis* variety developed from cross breeding of *Cannabis sativa* and *Cannabis indica*. In some embodiments, the seed is from a *Cannabis sativa* L. plant with less than 0.3 percent tetrahydrocannabinol (THC) based on the dry weight. In some embodiments, the *Cannabis sativa* cultivar is selected from the group consisting of Elektra x Chardonnay, Honey Gold 3WS (also referred to in the art at 3W1), Abacus, and Fiber Hemp.

In some embodiments of the present invention, the dry seed is surface sterilized. Any means known in the art for surface sterilization can be used. Suitable methods for surface sterilization may include, but are not limited to, exposure of the seed surface to radiation, UV light, oxidizing gasses, heat, plasma, disinfecting solvents and agents. In some embodiments, the seed is surface sterilized with a chemical agent such as sodium hypochlorite. In some embodiments, the seed is surface sterilized with an antibacterial or antifungal agent. In some embodiments, the seed is surface sterilized with ethanol (e.g., 20%, 30%, 40%, 50%, 60%, 70%, 80%, 90%, or 100% ethanol). In some embodiments, the seed is surface sterilized with Clorox™ bleach.

The dry seed, which in some embodiments has undergone surface sterilization, is imbibed under conditions that support hydration of the seed. The dry seed is hydrated in a hydration medium and for a time sufficient for the seed to reach a moisture content of between 30% and 70%. In some embodiments, the seed is hydrated for at least 12 hours. In some embodiments, the seed is hydrated between 2 and 24 hours.

The hydration medium used for hydration of the seed maybe any suitable sterile hydration medium known in the art that supports survival of the meristematic tissue in the seed. In some embodiments, the hydration medium is a modified sterile water and includes antibiotics or antifungals. In some embodiments, the hydration medium is a tissue culture medium that includes natural or synthetic plant growth regulators, plant tissue culture nutrients, a carbon source or a non-nutritive osmoregulator. In one embodiment, the hydration medium is bean germination medium, which includes the components outlined in Table 1 of Example 1.

In some embodiments of the invention, the hydration medium may optionally include one or more priming factors for pretreatment of the meristematic tissue. As used herein, "priming factor" or "priming agent" references to any molecule or substance included in the hydration medium which promotes survival and storage of the prepared explant or that promotes or increases the transformation efficiency of the prepared explant. Priming factors for use in the hydration medium of the present invention may include, but are not limited to, small molecules, biological molecules such as nucleic acids, polypeptides, proteins, antibodies, transcription factors, and macromolecules or complexes thereof, nanoparticles, liposomes, and cell-penetrating peptides. In some embodiments, the priming factor is a plant growth factor including, but not limited to, thidiazuron (TDZ), 6-benzylaminopurine (BAP), polyethylene glycol (PEG), 2,4-dichlorophenoxyacetic acid (2,4-D), Paczol™, gibberellic acid (GA3), indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, dicamba, polyvinylpyrrolidone (PVP), polyvinylpolypyrrolidone (PVPP), salicylic acid, proline, betaine, ethylene, brassinosteroids, nitrates, and gibberellins.

Following hydration of the seed, meristematic tissue is excised to form an explant. Excision of the meristematic tissue may be performed by any means known in the art in which the seed coat and cotyledons are removed from the seed. Suitable methods for the excision of the meristematic tissue may include, but are not limited to manual processing, wet milling using a series of rollers and spray nozzles, adjustable grinding plates, rods, knives, wheels and other mechanical or machine based excision methods. These may be composed of, but are not limited to, ceramics, metals, and synthetic polymers. Induced pressure, injected gasses, vacuum and turbulence are also suitable methods. Hydrated explants may be stored in suitable storage medium for up to 7 days. Suitable storage medium for the hydrated explants may be any medium that supports survival and competence of the explant tissue. In some embodiments, the explants are stored with an excess of liquid to explants by volume. In some embodiments, the storage medium is liquid medium including MS salts.

In some embodiments, the meristematic tissue is excised from a dry seed to form an explant without first imbibing the seed. A dry seed suitable for dry excision will typically have a moisture content of between 1% and 25%. Excision of the meristematic tissue from the dry seed may be performed by any means known in the art in which the seed coat and cotyledons are removed from the seed. Suitable methods for the excision of the meristematic tissue may include, but are not limited to manual processing, wet milling using a series of rollers and spray nozzles, adjustable grinding plates, rods, knives, wheels and other mechanical or machine based excision methods. These may be composed of, but are not limited to, ceramics, metals, and synthetic polymers. Induced pressure, injected gasses, vacuum and turbulence are also suitable methods.

Following excision, the explant may be dried. Desiccation of the explant may be performed by any means known in the art such that the moisture content of the dry explant is between 1% and 25%. Suitable methods for desiccating the explant may include, but are not limited to, drying in the presence of air with and without an added dehumidifying agent. In some embodiments, the explants are dried in a laminar flow hood. In some embodiments, the explants are dried on the surface of filter paper in a laminar flow hood for about 26 hours. In some embodiments, the explants are dried in a dehumidifier. In some embodiments, the explants are dried at a temperature between 0° C. and 35° C. for at least 5 hours (e.g., at least 5, 7, 9, 12, 15, 18, 24, 30, 36, 42, 48, 72, 96 or 120 hours) and up to 2 weeks (e.g., up to 1, 2, 3, 4, 5, 6, 7, 8, 9, 10, 11, 12, 13, or 14 days). In some embodiments, it may be beneficial to control rates of drying by tightly controlling temperature, humidity, air flow, and time.

During desiccation of the explant, one or more transformation supplements may be added. As used herein, "transformation supplement" refers to any molecule or substance added to the explant during desiccation, which promotes survival and storage of the prepared explant or that promotes or increases the transformation efficiency of the prepared explant. Transformation supplements for use during desiccation of the explant of the present invention may include small molecules, biological molecules such as nucleic acids, polypeptides, proteins, antibodies, transcription factors, and macromolecules or complexes thereof, nanoparticles, liposomes, *Agrobacterium, Rhizobium*, and cell-penetrating peptides. In some embodiments, the transformation supplement is a plant growth factor, cell protectant agent including, or other agent including, but not limited to, thidiazuron (TDZ), 6-benzylaminopurine (BAP), polyethylene glycol (PEG), alginates and alginate complexes, starches, celluloses, synthetic polymers, gums, waxes, proline, betaine, polyvinylpyrrolidone (PVP), polyvinylpolypyrrolidone (PVPP), salicylic acid, calcium sources, silicone sources, colchicine, 2,4-dichlorophenoxyacetic acid (2,4-D), Paczol™, gibberellic acid (GA3), gibberellin (GA) pathway inhibitors, indole-3-acetic acid (IAA), indole-3-butyric acid (IBA), 1-naphthalaneacetic acid (NAA), forchlorfenuron (CPPU), spectinomycin, streptomycin, glyphosate, glufosinate, bialophos, hygromycin, amikacin, tobramycin, imazapyr, lyophilized agrobacterium, lyophilized rhizobium, and potassium hydroxide (KOH). In some embodiments, the transformation supplement is an agent, which promotes multiplication of the meristematic tissue, such as, but not limited to, TDZ, BAP, zeatin, kinetin, and CPPU. In some embodiments, explants are mechanically wounded prior to drying and storage. This can be achieved with exposure to ultrasound energy (e.g., sonication), liquid nitrogen, centrifugation, pressure, and chemical (ex. KOH, PEG, acids, bases), enzymes, abrasives, water jets, lasers, needles, or blades.

The dried explants are suitable for storage in a variety of conditions. Dried explants may be stored at temperatures ranging from about −200° C. to 50° C. (i.e., about −190° C. to 40° C., about −170° C. to 30° C., about −150° C. to 20° C., about −130° C. to 10° C., and about −102° C. to 0° C.) for a period of time of at least 7 days (i.e., at least 10 days, at least 30 days, at least 50 days, at least 60 days, at least 75 days, at least 90 days, and at least 120 days). Storable dried explants can also be banked to create libraries of germplasms from a variety of cultivars of agronomic significance. In general, lower temperature storage under dry conditions or controlled humidity will allow for prolonged storage of the dried Cannabis explants.

Explants generated by the methods described herein can be transformed with a heterologous gene or nucleic acid of interest by any means known in the art. Various methods have been developed for transferring genes or nucleic acids into plant tissue including particle bombardment, high velocity microprojection, microinjection, electroporation, direct DNA uptake, silica carbide fibers, cell-penetrating peptides, nanoparticles, viral vectors, and bacterially-mediated transformation. Bacteria known to mediate plant cell transformation include a number of species of the Rhizobiaceae, including, but not limited to, *Agrobacterium* spp., *Sinorhizobium* spp., *Mesorhizobium* spp., *Rhizobium* spp., *Ochrobacterium* spp., and *Bradyrhizobium* spp. In some embodiments, the explant is transformed using *Agrobacterium* spp. In some embodiments, the explant is transformed using *Agrobacterium* strain Ar18r12v. In some embodiments, the explant is transformed using particle bombardment using gold microcarriers. Suitable viral vectors are known and described in the art and may include, but are not limited to, tomato yellow leaf curl virus (TYLCV), tobacco yellow dwarf virus (TobYDV), tomato golden mosaic virus (TGMV), bean pod mottle virus (BPMV). Suitable methods of plant transformation are described in the art, such as, for example, by McCabe et al. (McCabe, D. E., Swain, W. F., Martinell, B. J., Christou, P. (1988) *Nature Biotechnology* 6(8), 923-926), Chen et al. (Chen, Y., Rivlin, A. Lange, A., Ye, X., Vaghchhipawala, Z., Eisinger, E., Dersch, E., Paris, M., Martinell, B., Wan, Y. (2014) *Plant Cell Reports* 33(1), 153-164), Ye et al. (Ye, X., Williams, E. J., Shen, J., Johnson, S., Lowe, B., Radke, S., Strickland, S. Esser, J. A., Petersen, M. W., and Gilbertson, L. A. (2011) *Transgenic Research* 20(4), 773-7860), and *Plant Transformation Technologies* (Edited by C. Neal Stewart, Alisher Touraev, Vitaly Citovsky and Tzvi Tzfira ©2011 Blackwell Publishing Ltd. ISBN: 978-0-813-82195-5.)

Prior to inoculation, dried explants to be transformed may be rehydrated using suitable tissue culture medium. In some embodiments, the rehydration medium is Soy INO medium, VAE rehydration medium, or a solid medium such as Basal MS or Gamborg's B5 medium. In some embodiments, the rehydration step is combined with the pretreatment step described below.

Embryos may be pretreated prior to inoculation and transformation. In some embodiments, the embryos are pretreated with a polyethylene glycol (PEG) solution. In some embodiments, the PEG solution includes about 20% PEG4000. In some embodiments, the embryos are pretreated in the PEG-ethanol solution for between about 1 minute and about 3 hours (e.g. 1 min., 2 min., 5 min., 15 min., 30 min., 45 min., 1 hr., 1.5 hr., 2 hr., 2.5 hr., or 3 hr.). In some embodiments, salts may be added to the PEG solution. In some embodiments, the PEG solution includes one or more fungicides (e.g., Captan, Bravo, etc.). In some embodiments, the PEG solution includes Murashige and Skoog (MS) salts. In some embodiments, the pretreatment step includes sonication, vortexing, centrifugation, heat-shock, or addition of chemicals (e.g., TDZ, glyphosate, or metolachlor).

In some embodiments, the explant transformation is supplemented with force treatments. Force treatments may include, but are not limited to, sonication, vortexing, centrifugation, increased pressure, vacuum infiltration, heat-shock, dessication or addition of chemicals (e.g., TDZ, glyphosate, or metolachlor). Force treatments may be applied prior to or during transformation. For example, prior to or concurrently with inoculation with *Agrobacterium* or particle bombardment treatment. In some embodiments, explants are sonicated for about 20 seconds at about 45 kHz. Force treatment transformation methods are described in the art. See, for example, Khanna, et al. ("Centrifugation assisted *Agrobacterium tumefaciens*-mediated transformation (CAAT) of embryogenic cell suspensions of banana (Musa spp. Cavendish AAA and Lady finger AAA)," Molecular Breeding, 2004, 14:239-252), Kapila et al. ("An *Agrobacterium*-mediated transient gene expression system for intact leaves," Plant Science, 1997, 122(1):101-108), Trick et al. ("SAAT: sonication-assisted *Agrobacterium*-mediated transformation," Transgenic Research, 1997, 6(5): 329-336), and Hiei et al. ("Improved frequency of transformation in rice and maize by treatment of immature embryos with centrifugation and heat prior to infection with *Agrobacterium tumefaciens*," Plant Cell, Tissue, and Organ Culture, 2006, 87(3):233-243).

Following inoculation, the explants are co-cultured for between about 1 day and about 6 days in any suitable co-culture medium that supports the growth and survival of the inoculated explant. In some embodiments, the co-culture medium is WCIC INO medium, which includes the components outlined in Table 2 of Example 1.

Following transformation, the explants or transformed tissue is regenerated using a suitable regeneration medium that supports the growth and survival of at least the positively transformed explants or transformed tissues. Suitable regeneration medium are known and described in the art. For example, the regeneration medium may be B5 medium, WPM based medium, MS salts based medium, ½×MS salts based medium, or similar medium with or without supplementation. The regeneration medium may additionally comprise nystatin, TBZ, meta-topolin (mT), napthylacetic acid (NAA) and GA3. In some embodiments, the regeneration medium includes a selection agent to select for positive transformants. Examples of suitable selection agents include, but are not limited to, RFP, GUS, aadA1a, spectinomycin, streptomycin, and imazapyr.

The heterologous gene or nucleic acid of interest may be any gene or nucleic acid that may confer a particular desirable trait or phenotype in the transformed plant. Examples of suitable genes of agronomic interest envisioned by the present invention would include but are not limited to genes for disease, insect, or pest tolerance, herbicide tolerance, genes for quality improvements such as yield, nutritional enhancements, environmental or stress tolerances, or any desirable changes in plant physiology, growth, development, morphology or plant product(s) including starch production, modified oils production, high oil production, modified fatty acid content, high protein production, fruit ripening, enhanced animal and human nutrition, and biopolymers production. Also environmental stress resistance, pharmaceutical peptides and secretable peptides, improved processing traits, industrial enzyme production, improved flavor, nitrogen fixation, hybrid seed production, and fiber production. Any of these or other genetic elements, methods, and transgenes may be used with the invention as will be appreciated by those of skill in the art in view of the instant disclosure. The heterologous gene or nucleic acid of interest may also be a sequence that can affect a phenotype of interest by encoding an RNA molecule that causes the targeted inhibition of expression on an endogenous gene via gene silencing technologies.

In some embodiments, the heterologous nucleic acid of interest modulates the expression or function of the endogenous *Cannabis* tetrahydrocannabinolic acid synthase (THCA synthase) gene. A heterologous nucleic acid is introduced into the *Cannabis* explant to knockout or silence the THCA synthase gene. *Cannabis* plants grown from the transformed *Cannabis* explant are characterized by a tetrahydrocannabinol (THC) low or THC free phenotype. The sequence and activity of the THCA synthase gene is known and described in the art. See, for example, Laverty et al. (Laverty et al., "A physical and genetic map of *Cannabis sativa* identifies extensive rearrangements at the THC/CBD acid synthase loci," Genome Research, 2018, 29:146-156).

Figure 64:
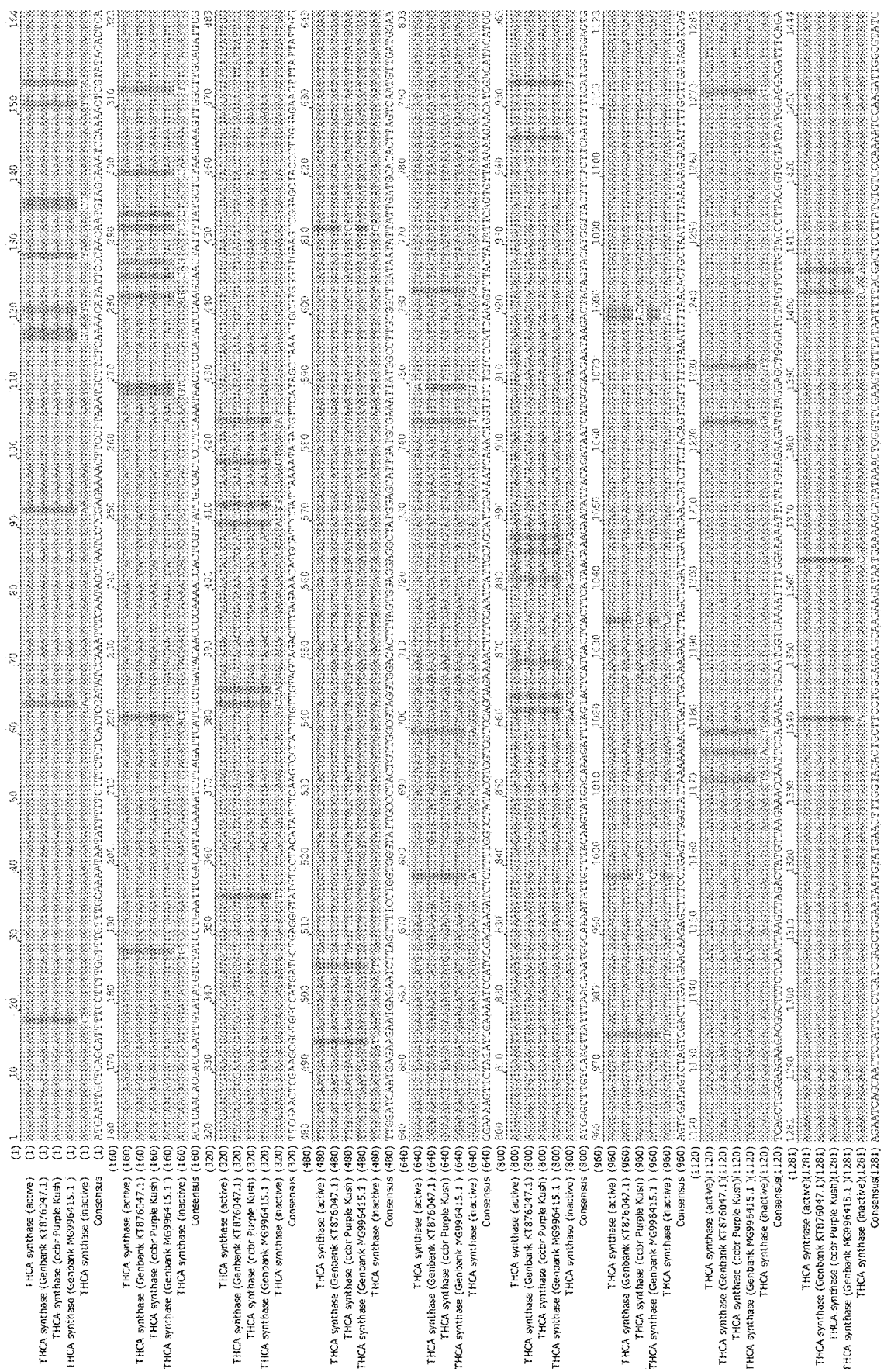
FIG. 64 shows a sequence alignment of various THCA synthase cDNA sequences. From top to bottom, the sequences shown are: SEQ ID NO:1, SEQ ID NO:3, SEQ ID NO:4, SEQ ID NO:2, SEQ ID NO:5, and SEQ ID NO:59.

Provided below are five cDNA sequences (SEQ ID NOs: 1-5) of THCA genes from various *Cannabis sativa* strains. Single nucleotide polymorphs (SNPs) between the active THCA synthase of SEQ ID NO:1 and each of SEQ ID NOs:2-5 are indicated in each of the respective sequences and a full sequence alignment is shown in FIG. 64.

*Cannabis sativa* cultivar Skunk #1 tetrahydrocannabinolic acid synthase (THCA1) gene cDNA (SEQ ID NO:1), Genbank: KJ469378.1

```
ATGAATTGCTCAGCATTTTCCTTTTGGTTTGTTTGCAAAATAATATT
TTTCTTTCTCTCATTCCATATCCAAATTTCAATAGCTAATCCTCGAG
AAAACTTCCTTAAATGCTTCTCAAAACATATTCCCAACAATGTAGCA
AATCCAAAACTCGTATACACTCAACACGACCAATTGTATATGTCTAT
CCTGAATTCGACAATACAAAATCTTAGATTCATCTCTGATACAACCC
CAAAACCACTCGTTATTGTCACTCCTTCAAATAACTCCCATATCCAA
GCAACTATTTTATGCTCTAAGAAAGTTGGCTTGCAGATTCGAACTCG
AAGCGGTGGCCATGATGCTGAGGGTATGTCCTACATATCTCAAGTCC
CATTTGTTGTAGTAGACTTGAGAAACATGCATTCGATCAAAATAGAT
GTTCATAGCCAAACTGCGTGGGTTGAAGCCGGAGCTACCCTTGGAGA
AGTTTATTATTGGATCAATGAGAAGAATGAGAATCTTAGTTTTCCTG
GTGGGTATTGCCCTACTGTTGGCGTAGGTGGACACTTTAGTGGAGGA
GGCTATGGAGCATTGATGCGAAATTATGCCTTGCGGCTGATAATAT
TATTGATGCACACTTAGTCAATGTTGATGGAAAAGTTCTAGATCGAA
AATCCATGGGAGAAGATCTGTTTTGGGCTATACGTGGTGGTGGAGGA
GAAAACTTTGGAATCATTGCAGCATGGAAAATCAAACTGGTTGATGT
CCCATCAAAGTCTACTATATTCAGTGTTAAAAAGAACATGGAGATAC
ATGGGCTTGTCAAGTTATTTAACAAATGGCAAAATATTGCTTACAAG
TATGACAAAGATTTAGTACTCATGACTCACTTCATAACAAAGAATAT
TACAGATAATCATGGGAAGAATAAGACTACAGTACATGGTTACTTCT
CTTCAATTTTTCATGGTGGAGTGGATAGTCTAGTCGACTTGATGAAC
AAGAGCTTTCCTGAGTTGGGTATTAAAAAAACTGATTGCAAAGAATT
TAGCTGGATTGATACAACCATCTTCTACAGTGGTGTTGTAAATTTTA
ACACTGCTAATTTTAAAAAGGAAATTTTGCTTGATAGATCAGCTGGG
AAGAAGACGGCTTTCTCAATTAAGTTAGACTATGTTAAGAAACCAAT
TCCAGAAACTGCAATGGTCAAAATTTTGGAAAAATTATATGAAGAAG
ATGTAGGAGCTGGGATGTATGTGTTGTACCCTTACGGTGGTATAATG
GAGGAGATTTCAGAATCAGCAATTCCATTCCCTCATCGAGCTGGAAT
AATGTATGAACTTTGGTACACTGCTTCCTGGGAGAAGCAAGAAGATA
ATGAAAAGCATATAAACTGGGTTCGAAGTGTTTATAATTTTACGACT
CCTTATGTGTCCCAAAATCCAAGATTGGCGTATCTCAATTATAGGGA
CCTTGATTTAGGAAAAACTAATCATGCGAGTCCTAATAATTACACAC
AAGCACGTATTTGGGGTGAAAAGTATTTTGGTAAAAATTTTAACAGG
TTAGTTAAGGTGAAAACTAAAGTTGATCCCAATAATTTTTTTAGAAA
CGAACAAAGTATCCCACCTCTTCCACCGCATCATCATTAA
```

*Cannabis sativa* isolate 60D2 tetrahydrocannabinolic acid synthase (THCA) gene (SEQ ID NO:2), GenBank: MG996415.1, single nucleotide polymorph (SNP) relative to SEQ ID NO:1 shown in bold underline.

```
atgaattgctcagcattttccttttggtttgtttgcaaaataatatt
tttctttctctcattccatatccaaatttcaatagctaatcctcgag
aaaacttccttaaatgcttctcaaaacatattcccaacaatgtagca
aatccaaaactcgtatacactcaacacgaccaattgtatatgtctat
cctgaattcgacaatacaaaatcttagattcatctctgatacaaccc
caaaaccactcgttattgtcactccttcaaataactcccatatccaa
gcaactattttatgctctaagaaagttggcttgcagattcgaactcg
aagcggtggccatgatgctgagggtatgtcctacatatctcaagtcc
catttgttgtagtagacttgagaaacatgcattcgatcaaaatagat
gttcatagccaaactgcgtgggttgaagccggagctaccccttggaga
agtttattattggatcaatgagaagaatgagaatcttagttttcctg
gtgggtattgccctactgttggcgtaggtggacactttagtggagga
ggctatggagcattgatgcgaaattatggccttgcggctgataatat
tattgatgcacacttagtcaatgttgatggaaaagttctagatcgaa
aatccatgggagaagatctgtttgggctatacgtggtggtggagga
gaaaactttggaatcattgcagcatggaaaatcaaactggttgctgt
cccatcaaagtctactatattcagtgttaaaaagaacatggagatac
atgggcttgtcaagttatttaacaaatggcaaaatattgcttacaag
tatgacaaagatttagtactcatgactcacttcataacaaagaatat
tacagataatcatgggaagaataagactacagtacatggttacttct
cttcaattttcatggtggagtggatagtctagtcgacttgatgaac
aagagctttcgtgagttgggtattaaaaaaactgattgcaaagaatt
tagctggattgatacaaccatcttctacagtggtgttgtaaatttta
acactgctaatttaaaaaggaaattttgcttgatagatcagctggg
aagaagacggctttctcaattaagttagactatgttaagaaaccaat
tccagaaactgcaatggtcaaaattttggaaaaattatatgaagaag
atgtaggagctgggatgtatgtgttgtaccttacggtggtataatg
gaggagatttcagaatcagcaattccattccctcatcgagctggaat
aatgtatgaactttggtacactgcttcctgggagaagcaagaagata
atgaaaagcatataaactgggttcgaagtgtttataattttacgact
ccttatgtgtcccaaaatccaagattggcgtatctcaattatagggga
ccttgatttaggaaaaactaatcatgcgagtcctaataattacacac
aagcacgtatttggggtgaaaagtattttggtaaaaattttaacagg
ttagttaaggtgaaaactaaagttgatcccaataatttttttagaaa
cgaacaaagtatcccacctcttmcaccgcatcatcattaa
```

*Cannabis sativa* clone ABC67 THCA synthase gene (SEQ ID NO:3), GenBank: KT876047.1, SNPs relative to SEQ ID NO: shown in bold underline.

```
atgaattgctcagcattttccttttggtttgtttgcaaaataatatt
tttctttctctcattccatatccaaatttcaatagctaatcctcgag
aaaacttccttaaatgcttctcaaaacatattcccaacaatgtagca
aatccaaaactcgtatacactcaacacgaccaattgtatatgtctat
cctgaattcgacaatacaaaatcttagattcatctctgatacaaccc
caaaaccactcgttattgtcactccttcaaataactcccatatccaa
gcaactattttatgctctaagaaagttggcttgcagattcgaactcg
aagcggtggccatgatgctgagggtatgtcctacatatctcaagtcc
catttgttgtagtagacttgagaaacatgcattcgatcaaaatagat
gttcatagccaaactgcgtgggttgaagccggagctaccccttggaga
agtttattattggatcaatgagaagaatgagaatcttagttttcctg
gtgggtattgccctactgttggcgtaggtggacactttagtggagga
ggctatggagcattgatgcgaaattatggccttgcggctgataatat
tattgatgcacacttagtcaatgttgatggaaaagttctagatcgaa
aatccatgggagaagatctgtttgggctatacgtggtggtggagga
gaaaactttggaatcattgcagcatggaaaatcaaactggttgctgt
cccatcaaagtctactatattcagtgttaaaaagaacatggagatac
atgggcttgtcaagttatttaacaaatggcaaaatattgcttacaag
tatgacaaagatttagtactcatgactcacttcataacaaagaatat
tacagataatcatgggaagaataagactacagtacatggttacttct
cttcaattttcatggtggagtggatagtctagtcgacttgatgaac
aagagctttcctgagttgggtattaaaaaaactgattgcaaagaatt
tagctggattgatacaaccatcttctacagtggtgttgtaaatttta
acactgctaatttaaaaaggaaattttgcttgatagatcagctggg
aagaagacggctttctcaattaagttagactatgttaagaaaccaat
tccagaaactgcaatggtcaaaattttggaaaaattatatgaagaag
atgtaggagctgggatgtatgtgttgtaccttacggtggtataatg
gaggagatttcagaatcagcaattccattccctcatcgagctggaat
aatgtatgaactttggtacactgcttcctgggagaagcaagaagata
atgaaaagcatataaactgggttcgaagtgtttataattttacgact
ccttatgtgtcccaaaatccaagattggcgtatctcaattatagggga
ccttgatttaggaaaaactaatcatgcgagtcctaataattacacac
aagcacgtatttggggtgaaaagtattttggtaaaaattttaacagg
ttagttaaggtgaaaactaaagttgatcccaataatttttttagaaa
cgaacaaagtatcccacctcttccaccgcatcatcat
```

THCA synthase *Cannabis sativa* Purple Kush (SEQ ID NO:4), SNPs relative to SEQ ID NO:1 shown in bold underline.

```
ATGAATTGCTCAGCATTTTCCTTTTGGTTTGTTTGCAAAATAATAT
TTTTCTTTCTCTCATTCCATATCCAAATTTCAATAGCTAATCCTCG
```

-continued

AGAAAACTTCCTTAAATGCTTCTCAAAACATATTCCCAACAATGTA

GCAAATCCAAAACTCGTATACACTCAACACGACCAATTGTATATGT

CTATCCTGAATTCGACAATACAAAATCTTAGATTCATCTCTGATAC

AACCCCAAAACCACTCGTTATTGTCACTCCTTCAAATAACTCCCAT

ATCCAAGCAACTATTTTATGCTCTAAGAAAGTTGGCTTGCAGATTC

GAACTCGAAGCGGTGGCCATGATGCTGAGGGTATGTCCTACATATC

TCAAGTCCCATTTGTTGTAGTAGACTTGAGAAACATGCATTCGATC

AAAATAGATGTTCATAGCCAAACTGCGTGGGTTGAAGCCGGAGCTA

CCCTTGGAGAAGTTTATTATTGGATCAATGAGAAGAATGAGAATCT

TAGTTTTCCTGGTGGGTATTGCCCTACTGTTGGCGTAGGTGGACAC

TTTAGTGGAGGAGGCTATGGAGCATTGATGCGAAATTATGGCCTTG

CGGCTGATAATATCATTGATGCACACTTAGTCAATGTTGATGGAAA

AGTTCTAGATCGAAAATCCATGGGAGAAGATCTGTTTTGGGCTATA

CGTGGTGGTGGAGGAGAAAACTTTGGAATCATTGCAGCATGGAAAA

TCAAACTGGTTGCTGTCCCATCAAAGTCTACTATATTCAGTGTTAA

AAAGAACATGGAGATACATGGGCTTGTCAAGTTATTTAACAAATGG

CAAAATATTGCTTACAAGTATGACAAAGATTTAGTACTCATGACTC

ACTTCATAACAAAGAATATTACAGATAATCATGGGAAGAATAAGAC

TACAGTACATGGTTACTTCTCTTCAATTTTTCATGGTGGAGTGGAT

AGTCTAGTCGACTTGATGAACAAGAGCTTTCGTGAGTTGGGTATTA

AAAAAACTGATTGCAAAGAATTGAGCTGGATTGATACAACCATCTT

CTACAGTGGTGTTGTAAATTACAACACTGCTAATTTTAAAAAGGAA

ATTTTGCTTGATAGATCAGCTGGGAAGAAGACGGCTTTCTCAATTA

AGTTAGACTATGTTAAGAAACCAATTCCAGAAACTGCAATGGTCAA

AATTTTGGAAAAATTATATGAAGAAGATGTAGGAGCTGGGATGTAT

GTGTTGTACCCTTACGGTGGTATAATGGAGGAGATTTCAGAATCAG

CAATTCCATTCCCTCATCGAGCTGGAATAATGTATGAACTTTGGTA

CACTGCTTCCTGGGAGAAGCAAGAAGATAATGAAAAGCATATAAAC

TGGGTTCGAAGTGTTTATAATTTTACGACTCCTTATGTGTCCCAAA

ATCCAAGATTGGCGTATCTCAATTATAGGGACCTTGATTTAGGAAA

AACTAATCATGCGAGTCCTAATAATTACACACAAGCACGTATTTGG

GGTGAAAAGTATTTTGGTAAAAATTTTAACAGGTTAGTTAAGGTGA

AAACTAAAGTTGATCCCAATAATTTTTTAGAAACGAACAAAGTAT

CCCACCTCTTCCACCGCATCATCATTAA

Inactive THCA synthase gene (SEQ ID NO:5), SNPs relative to SEQ ID NO:1 shown in bold underline.

ATGAATTGCTCAGCATTCTCCTTTTGGTTTGTTTGCAAAATAATATT

TTTCTTTCTCTCATTCAATATCCAAATTTCAATAGCTAATCCTCAAG

AAAACTTCCTTAAATGCTTCTCGGAATATATTCCTAACAATCCAGCA

AATCCAAAATTCATATACACTCAACACGACCAATTGTATATGTCTGT

CCTGAATTCGACAATACAAAATCTTAGATTCACCTCTGATACAACCC

CAAAACCACTCGTTATTGTCACTCCTTCAAATGTCTCCCATATCCAG

GCCAGTATTCTCTGCTCCAAGAAAGTTGGTTTGCAGATTCGAACTCG

AAGCGGTGGCCATGATGCTGAGGGTTTGTCCTACATATCTCAAGTCC

CATTTGCTATAGTAGACTTGAGAAACATGCATACGGTCAAAGTAGAT

ATTCATAGCCAAACTGCGTGGGTTGAAGCCGGAGCTACCCTTGGAGA

AGTTTATTATTGGATCAATGAGATGAATGAGAATTTTAGTTTTCCTG

GTGGGTATTGCCCTACTGTTGGCGTAGGTGGACACTTTAGTGGAGGA

GGCTATGGAGCATTGATGCGAAATTATGGCCTTGCGGCTGATAATAT

CATTGATGCACACTTAGTCAATGTTGATGGAAAAGTTCTAGATCGAA

AATCCATGGGAGAAGATCTATTTTGGGCTATACGTGGTGGAGGAGGA

GAAAACTTTGGAATCATTGCAGCATGGAAAATCAAACTTGTTGTTGT

CCCATCAAAGGCTACTATATTCAGTGTTAAAAAGAACATGGAGATAC

ATGGGCTTGTCAAGTTATTTAACAAATGGCAAAATATTGCTTACAAG

TATGACAAAGATTTAATGCTCACGACTCACTTCAGAACTAGGAATAT

TACAGATAATCATGGGAAGAATAAGACTACAGTACATGGTTACTTCT

CTTCCATTTTTCTTGGTGGAGTGGATAGTCTAGTTGACTTGATGAAC

AAGAGCTTTCCTGAGTTGGGTATTAAAAAAACTGATTGCAAAGAATT

GAGCTGGATTGATACAACCATCTTCTACAGTGGTGTTGTAAATTACA

ACACTGCTAATTTTAAAAAGGAAATTTTGCTTGATAGATCAGCTGGG

AAGAAGACGGCTTTCTCAATTAAGTTAGACTATGTTAAGAAACTAAT

ACCTGAAACTGCAATGGTCAAAATTTTGGAAAAATTATATGAAGAAG

AGGTAGGAGTTGGGATGTATGTGTTGTACCCTTACGGTGGTATAATG

GATGAGATTTCAGAATCAGCAATTCCATTCCCTCATCGAGCTGGAAT

AATGTATGAACTTTGGTACACTGCTACCTGGGAAGCAAGAAGATA

ACGAAAGCATATAAACTGGGTTCGAAGTGTTTATAATTTCACAACT

CCTTATGTGTCCCAAAATCCAAGATTGGCGTATCTCAATTATAGGGA

CCTTGATTTAGGAAAAACTAATCCTGAGAGTCCTAATAATTACACAC

AAGCACGTATTTGGGGTGAAAAGTATTTTGGTAAAAATTTTAACAGG

TTAGTTAAGGTGAAAACCAAAGCTGATCCCAATAATTTTTTTAGAAA

CGAACAAAGTATCCCACCTCTTCCACCGCGTCATCATTAA

THCA synthase polypeptide sequence (SEQ ID NO:6)

MNCSAFSFWFVCKIIFFFLSHITQISIANPRENFLKCFSKHIPNNVA

NPKLVYTQHDQLYMSILNSTIQNLRFISDTTPKPLVIVTPSNNSHIQ

ATILCSKKVGLQIRTRSGGHDAEGMSYISQVPFVVVDLRNMHSIKID

VHSQTAWVEAGATLGEVYYVVINEKNENLSFPGGYCPTVGVGGHFSG

GGYGALMRNYGLAADNIIDAHLVNVDGKVLDRKSMGEDLFWAIRGGG

GENFGIIAAWKIKLVDVPSKSTIFSVKKNMEIHGLVKLFNKWQNIAY

KYDKDLVLMTHFITKNITDNHGKNKTTVHGYFSSIFHGGVDSLVDLM

NKSFPELGIKKTDCKEFSWIDTTIFYSGVVNFNTANFKKEILLDRSA

-continued

GKKTAFSIKLDYVKKPIPETAMVKILEKLYEEDVGAGMYVLYPYGGI

MEEISESAIPFPHRAGIMYELWYTASWEKQEDNEKHINVVVRSVYNF

TTPYVSQNPRLAYLNYRDLDLGKTNHASPNNYTQARIWGEKYFGKNF

NRLVKVKTKVDPNNFFRNEQSIPPLPPHHH

In some embodiments, the THCA synthase gene may be knocked out using Clustered Randomly Interspersed Short Palindromic Repeats (CRISPR)/Cas mediated gene editing. To knockout the THCA synthase gene using CRISPR/Cas mediated gene editing, one or more guide RNAs are designed that target the THCA synthase gene or a region adjacent there to and proximal to a Protospacer Adjacent Motif (PAM) site. Upon introduction to a *Cannabis* cell, the guide RNAs target a nuclease to induce a double strand break at the designated cut site. The cell will then undergo non-homologous end joining (NHEJ) to repair the cut site. Due to the nature of NHEJ, one or more insertions or deletions (indels) are introduced at the cut site, thereby silencing the target THCA synthase gene. In some embodiments, a homology directed repair (HDR) template oligonucleotide may be used to direct the repair at the cut site to introduce a mutation of interest. The mutation of interest may be an insertion of a stop codon, a frameshift mutation, or a nonsense mutation that disrupts expression of the THCA synthase gene. In some embodiments, the HDR oligonucleotide encodes a sequence comprising one or more of the THCA synthase gene SNPs recited herein. In some embodiments, the guide RNAs direct cleavage of the THCA gene such that all or a portion of the THCA gene is removed.

In some embodiments, the nuclease is a Cas nuclease. Suitable Cas nucleases are known and described in the art including, but not limited to, a Cas9 nuclease.

In some embodiments, the guide RNA targeting the THCA gene is selected from SEQ ID NO:7 (TGCAGCATGGAAAATCAAAC, forward gRNA gRF743), SEQ ID NO:8 (CCCTTACGGTGGTATAATGG, forward gRNA gRF1271), SEQ ID NO:9 (TAGCTATTGAAATTTGGATA, reverse gRNA gRR63), SEQ ID NO:10 (TAGAGCATAAAATAGTTGCT, reverse gRNA gRR279), or combinations thereof. As used herein, the guide RNA (gRNA) nomenclature (e.g., gRF743) refers to the template direction of the gRNA, either forward (F) or reverse (R), and nucleotide position at which the 20 base pair (bp) gRNA ends. For example, gRF743 is a forward gRNA that aligns with the THCA synthase gene and ends at nucleotide 743. Other nomenclature schemes and identification methods will be known to a skilled artisan. In some embodiments, the guide RNA sequences are cloned into a vector for introduction to the cell. In some embodiments, the vector also encodes a Cas nuclease (e.g., Cas9 nuclease). In some embodiments, one or more vectors encoding the guide RNA and the Cas nuclease are introduced into the cell in the presence of an HDR oligonucleotide. Cells positive for transformation and the desired CRISPR/Cas mediated editing results may be screened and selected for using standard molecular biology and sequencing techniques known in the art.

In some embodiments, the heterologous nucleic acid of interest modulates the expression or function of the endogenous *Cannabis* cannabidiolic-acid synthase (CBDA synthase) gene. A heterologous nucleic acid is introduced into the *Cannabis* explant to knockout or silence the CBDA synthase gene. *Cannabis* plants grown from the transformed *Cannabis* explant are characterized by a tetrahydrocannabinol (THC) low or THC free phenotype. The sequence and activity of the CBDA synthase gene is known and described in the art. See, for example, Laverty et al. (Laverty et al., "A physical and genetic map of *Cannabis sativa* identifies extensive rearrangements at the THC/CBD acid synthase loci," Genome Research, 2018, 29:146-156).

Figure 65:
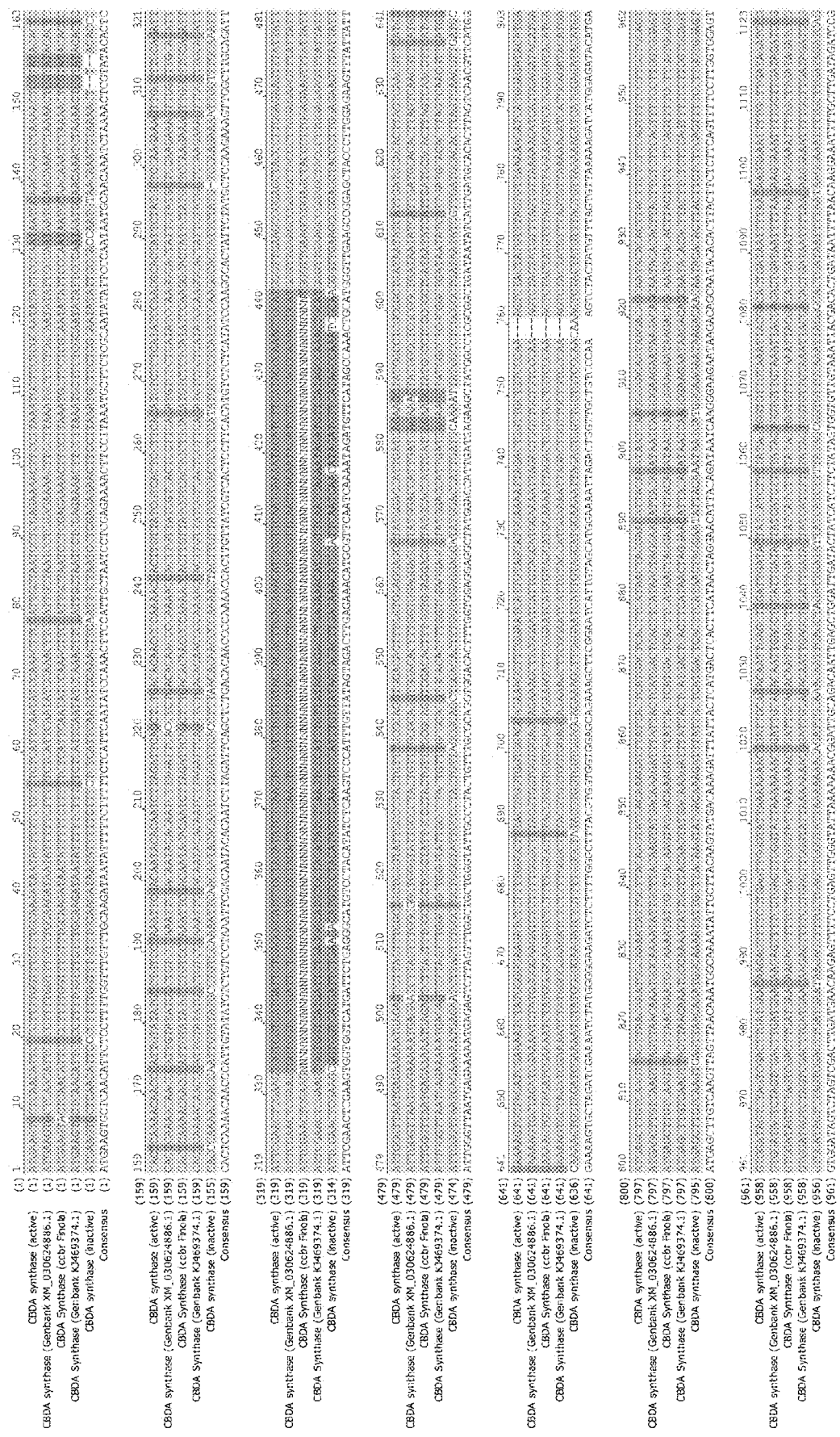
FIG. 65 shows a sequence alignment of various CBDA synthase cDNA sequences. From top to bottom, the sequences shown are: SEQ ID NO:11, SEQ ID NO:13, SEQ ID NO:15, SEQ ID NO:11, SEQ ID NO:17, and SEQ ID NO:11.
Figure 65:
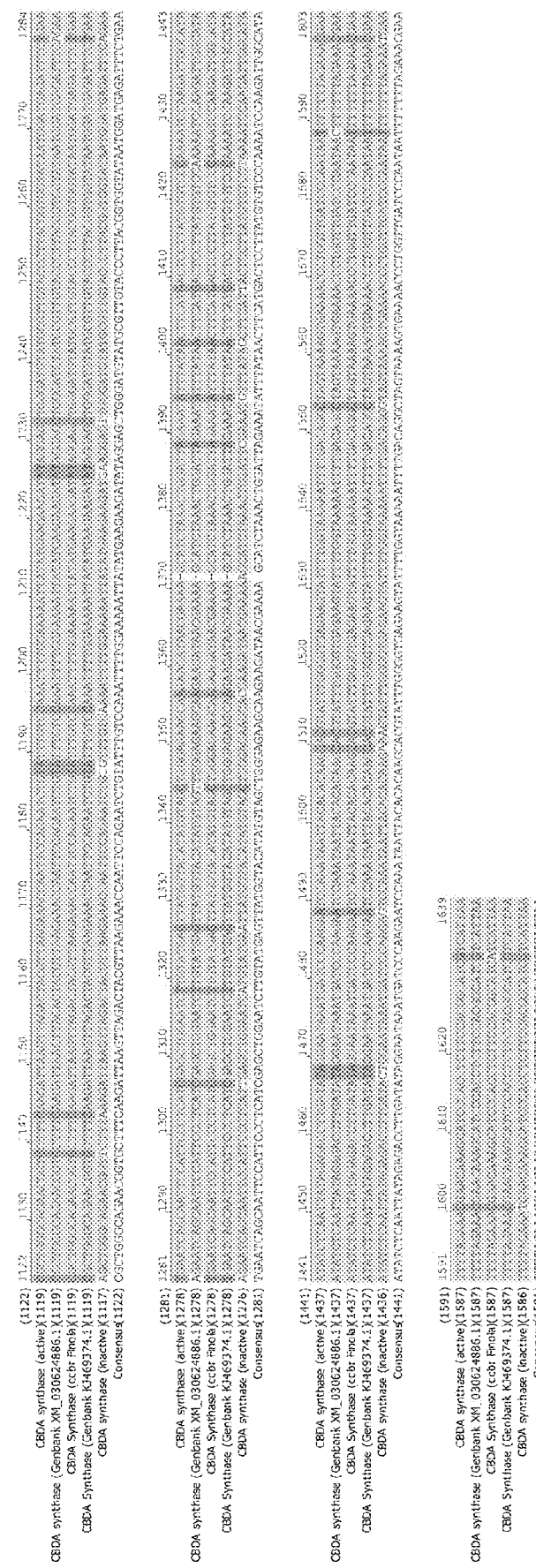

Provided below are four cDNA or reverse complement sequences (SEQ ID NOs:11, 13, 15, and 17) of CBDA genes from various *Cannabis sativa* strains. Single nucleotide polymorphs (SNPs) between the active CBDA synthase of SEQ ID NO:11 and each of SEQ ID NOs:13 and 15 are indicated in each of the respective sequences and a full sequence alignment is shown in FIG. 65. Additionally, mutations in the CBDA synthase sequences of SEQ ID NOs:14 and 16 are shown relative to SEQ ID NO:12.

*Cannabis sativa* cultivar Carmen cannabidiolic acid synthase (CBDA1) gene (SEQ ID NO:11), GenBank: KJ469374.1 atgaagtgctcaacattctccttttggtttgtttgcaagataatatt tttcttttctcattcaatatccaaacttccattgctaatcctcgag aaaacttccttaaatgcttctcgcaatatattcccaataatgcaaca aatctaaaactcgtatacactcaaaacaacccattgtatatgtctgt cctaaattcgacaatacacaatcttagattcagctctgacacaaccc caaaaccacttgttatcgtcactccttcacatgtctctcatatccaa ggcactattctatgctccaagaaagttggcttgcagattcgaactcg aagtggtggtcatgattctgagggcatgtcctacatatctcaagtcc catttgttatagtagacttgagaaacatgcgttcaatcaaaatagat gttcatagccaaactgcatgggttgaagccggagctacccttggaga agtttattattgggttaatgagaaaaatgagagtcttagtttggctg ctgggtattgccctactgtttgcgcaggtggacactttggtggagga ggctatggaccattgatgagaagctatggcctcgcggctgataatat cattgatgcacacttagtcaacgttcatggaaaagtgctagatcgaa aatctatggggaagatctcttttgggctttacgtggtggtggagca gaaagcttcggaatcattgtagcatggaaaattagactggttgctgt cccaaagtctactatgtttagtgttaaaaagatcatggagatacatg agcttgtcaagttagttaacaaatggcaaaatattgcttacaagtat gacaaagatttattactcatgactcacttcataactaggaacattac agataatcaagggaagaataagacagcaatacacacttacttctctt cagttttccttggtggagtggatagtctagtcgacttgatgaacaag agttttcctgagttgggtattaaaaaaacggattgcagacaattgag ctggattgatactatcatcttctatagtggtgttgtaaattacgaca ctgataattttaacaaggaaattttgcttgatagatccgctgggcag aacggtgctttcaagattaagttagactacgttaagaaaccaattcc agaatctgtatttgtccaaattttggaaaaattatatgaagaagata taggagctgggatgtatgcgttgtacccttacggtggtataatggat gagatttctgaatcagcaattccattccctcatcgagctggaatctt gtatgagttatggtacatatgtagctgggagaagcaagaagataacg -continued

```
aaaagcatctaaactggattagaaatatttataacttcatgactcct
tatgtgtcccaaaatccaagattggcatatctcaattatagagacct
tgatataggaataaatgatcccaagaatccaaataattacacacaag
cacgtatttggggtgagaagtattttggtaaaaattttgacaggcta
gtaaaagtgaaaaccctggttgatcccaataatttttttagaaacga
acaaagcatcccacctcttccacggcatcgtcattaa
```

*Cannabis sativa* CBDA synthase (SEQ ID NO:12)

```
MKCSTFSFWFVCKIIFFFFSFNIQTSIANPRENFLKCFSQYIPNNAT
NLKLVYTQNNPLYMSVLNSTIHNLRFSSDTTPKPLVIVTPSHVSHIQ
GTILCSKKVGLQIRTRSGGHDSEGMSYISQVPFVIVDLRNMRSIKID
VHSQTAWVEAGATLGEVYYWVNEKNESLSLAAGYCPTVCAGGHFGGG
GYGPLMRSYGLAADNIIDAHLVNVHGKVLDRKSMGEDLFWALRGGGA
ESFGIIVAWKIRLVAVPKSTMFSVKKIMEIHELVKLVNKWQNIAYKY
DKDLLLMTHFITRNITDNQGKNKTAIHTYFSSVFLGGVDSLVDLMNK
SFPELGIKKTDCRQLSWIDTIIFYSGVVNYDTDNFNKEILLDRSAGQ
NGAFKIKLDYVKKPIPESVFVQILEKLYEEDIGAGMYALYPYGGIMD
EISESAIPFPHRAGILYELWYICSWEKQEDNEKHLNVVIRNIYNFMT
PYVSQNPRLAYLNYRDLDIGINDPKNPNNYTQARIWGEKYFGKNFDR
LVKVKTLVDPNNFFRNEQSIPPLPREIRH
```

*Cannabis sativa* cannabidiolic acid synthase (LOC115697762) (SEQ ID NO:13), GenBank: XM_030624886.1, SNPs relative to SEQ ID NO:11 shown in bold underline.

```
ATGAAGTGCTCAACATTCTCCTTTTGGTTTGTTTGCAAGATAATATT
TTTCTTTTTCTCATTCAATATCCAAACTTCCATTGCTAATCCTCGAG
AAAACTTCCTTAAATGCTTCTCGCAATATATTCCCAATAATGCAACA
AATCTAAAACTCGTATACACTCAAAACAACCCATTGTATATGTCTGT
CCTAAATTCGACAATACACAATCTTAGATTCACCTCTGACACAACCC
CAAAACCACTTGTTATCGTCACTCCTTCACATGTCTCTCATATCCAA
GGCACTATTCTATGCTCCAAGAAAGTTGGCTTGCAGATTCGAACTCG
AAGTGGTGGTCATGATTCTGAGGGCATGTCCTACATATCTCAAGTCC
CATTTGTTATAGTAGACTTGAGAAACATGCGTTCAATCAAAATAGAT
GTTCATAGCCAAACTGCATGGGTTGAAGCCGGAGCTACCCTTGGAGA
AGTTTATTATTGGGTTAATGAGAAAAATGAGAATCTTAGTTTGGCGG
CTGGGTATTGCCCTACTGTTTGCGCAGGTGGACACTTTGGTGGAGGA
GGCTATGGACCATTGATGAGAACTATGGCCTCGCGGCTGATAATAT
CATTGATGCACACTTAGTCAACGTTCATGGAAAGTGCTAGATCGAA
AATCTATGGGGAAGATCTCTTTTGGGCTTTACGTGGTGGTGGAGCA
GAAAGCTTCGGAATCATTGTAGCATGGAAAATTAGACTGGTTGCTGT
CCCAAAGTCTACTATGTTTAGTGTTAAAAAGATCATGGAGATACATG
```

```
AGCTTGTCAAGTTAGTTAACAAATGGCAAAATATTGCTTACAAGTAT
GACAAAGATTTATTACTCATGACTCACTTCATAACTAGGAACATTAC
AGATAATCAAGGGAAGAATAAGACAGCAATACACACTTACTTCTCTT
CAGTTTTCCTTGGTGGAGTGGATAGTCTAGTCGACTTGATGAACAAG
AGTTTTCCTGAGTTGGGTATTAAAAAAACGGATTGCAGACAATTGAG
CTGGATTGATACTATCATCTTCTATAGTGGTGTTGTAAATTACGACA
CTGATAATTTTAACAAGGAAATTTTGCTTGATAGATCCGCTGGGCAG
AACGGTGCTTTCAAGATTAAGTTAGACTACGTTAAGAAACCAATTCC
AGAATCTGTATTTGTCCAAATTTTGGAAAAATTATATGAAGAAGATA
TAGGAGCTGGGATGTATGCGTTGTACCCTTACGGTGGTATAATGGAT
GAGATTTCAGAATCAGCAATTCCATTCCCTCATCGAGCTGGAATCTT
GTATGAGTTATGGTACATATGTAGTTGGGAGAAGCAAGAAGATAACG
AAAAGCATCTAAACTGGATTAGAAATATTTATAACTTCATGACTCCT
TATGTGTCCAAAAATCCAAGATTGGCATATCTCAATTATAGAGACCT
TGATATAGGAATAAATGATCCCAAGAATCCAAATAATTACACACAAG
CACGTATTTGGGGTGAGAAGTATTTTGGTAAAAATTTTGACAGGCTA
GTAAAAGTGAAAACCCTGGTTGATCCCAATAACTTTTTTAGAAACGA
ACAAAGCATCCCACCTCTTCCACGGCATCGTCATTAA
```

CBDA synthase protein sequence corresponding to SEQ ID NO:13 (SEQ ID NO:14), mutations relative to SEQ ID NO:12 shown in bold underline.

```
MKCSTFSFWFVCKIIFFFFSFNIQTSIANPRENFLKCFSQYIPNNATN
LKLVYTQNNPLYMSVLNSTIHNLRFTSDTTPKPLVIVTPSHVSHIQGT
ILCSKKVGLQIRTRSGGEIDSEGMSYISQVPFVIVDLRNMRSIKIDVH
SQTAWVEAGATLGEVYYVVVNEKNENLSLAAGYCPTVCAGGEIFGGGG
YGPLMRNYGLAADNIIDAHLVNVHGKVLDRKSMGEDLFWALRGGGAES
FGIIVAWKIRLVAVPKSTMFSVKKIMEIHELVKLVNKWQNIAYKYDKD
LLLMTHFITRNITDNQGKNKTAIHTYFSSVFLGGVDSLVDLMNKSFPE
LGIKKTDCRQLSWIDTIIFYSGVVNYDTDNFNKEILLDRSAGQNGAFK
IKLDYVKKPIPESVFVQILEKLYEEDIGAGMYALYPYGGIMDEISESA
IPFPHRAGILYELWYICSWEKQEDNEKHLNVVIRNIYNFMTPYVSKNP
RLAYLNYRDLDIGINDPKNPNNYTQARIWGEKYFGKNFDRLVKVKTLV
DPNNFFRNEQSIPPLPREIRH
```

*Cannabis sativa* Finola CBDA synthase gene reverse complement (SEQ ID NO:15), SNPs relative to both SEQ ID NOs:11 and 13 shown in bold underline, SNPs relative to SEQ ID NO:13 shown in bold italics.

```
ATGAAGTACTCAACATTCTCCTTTTGGTTTGTTTGCAAGATAATATT
TTTCTTTTTCTCATTCAATATCCAAACTTCCATTGCTAATCCTCGAG
AAAACTTCCTTAAATGCTTCTCGCAATATATTCCCAATAATGCAACA
AATCTAAAACTCGTATACACTCAAAACAACCCATTGTATATGTCTGT
```

CCTAAATTCGACAATACACAATCTTAGATTCAGCTCTGACACAACC

CCAAAACCACTTGTTATCGTCACTCCTTCACATGTCTCTCATATCCA

AGGCACTATTCTATGCTCCAAGAAAGTTGGCTTGCAGATTCGAACTC

GAAGNNNNNNNNNNNNNNNNNNNNNNNNNNNNNNNNNNNNNNNNNNNN

NNNNNNNNNNNNNNNNNNNNNNNNNNNNNNNNNNNNNNNNNNNNNNNN

NNNNNNNNNNNNNNNNNNNNNTGGGTTGAAGCCGGAGCTACCCTTGGAG

AAGTTTATTATTGGGTTAATGAGAAAAATGAGAGTCTTAGTTTGGC*T*

GCTGGGTATTGCCCTACTGTTTGCGCAGGTGGACACTTTGGTGGAGG

AGGCTATGGACCATTGATGAGAAG*C*TATGGCCTCGCGGCTGATAATA

TCATTGATGCACACTTAGTCAACGTTCATGGAAAAGTGCTAGATCGAA

AATCTATGGGGAAGATCTCTTTTGGGCTTTACGTGGTGGTGGAGCAG

AAAGCTTCGGAATCATTGTAGCATGGAAAATTAGACTGGTTGCTGTCC

CAAAGTCTACTATGTTTAGTGTTAAAAAGATCATGGAGATACATGAGC

TTGTCAAGTTAGTTAACAAATGGCAAAATATTGCTTACAAGTATGACA

AAGATTTATTACTCATGACTCACTTCATAACTAGGAACATTACAGATA

ATCAAGGGAAGAATAAGACAGCAATACACACTTACTTCTCTTCAGTTT

TCCTTGGTGGAGTGGATAGTCTAGTCGACTTGATGAACAAGAGTTTTC

CTGAGTTGGGTATTAAAAAAACGGATTGCAGACAATTGAGCTGGATTG

ATACTATCATCTTCTATAGTGGTGTTGTAAATTACGACACTGATAATT

TTAACAAGGAAATTTTGCTTGATAGATCCGCTGGGCAGAACGGTGCTT

TCAAGATTAAGTTAGACTACGTTAAGAAACCAATTCCAGAATCTGTAT

TTGTCCAAATTTTGGAAAAATTATATGAAGAAGATATAGGAGCTGGGA

TGTATGCGTTGTACCCTTACGGTGGTATAATGGATGAGATTT*C*T

GAATCAGCAATTCCATTCCCTCATCGAGCTGGAATCTTGTATGAGTTA

TGGTACATATGTAGCTGGGAGAAGCAAGAAGATAACGAAAAGCATCTA

AACTGGATTAGAAATATTTATAACTTCATGACTCCTTATGTGTCCCAA

AATCCAAGATTGGCATATCTCAATTATAGAGACCTTGATATAGGAATA

AATGATCCCAAGAATCCAAATAATTACACACAAGCACGTATTTGGGGT

GAGAAGTATTTTGGTAAAAATTTTGACAGGCTAGTAAAAGTGAAAACC

CTGGTTGATCCCAATAA*T*TTTTTTAGAAACGAACAAAGCATCCCACCT

CTTCCACGGCATCATCATTAA

CBDA synthase protein sequence corresponding to SEQ ID NO:15 (SEQ ID NO:16), mutations relative to both SEQ ID NOs:12 and 14 shown in bold underline, mutations relative to SEQ ID NO:14 shown in bold italics.

MKYSTFSFWFVCKIIFFFFSFNIQTSIANPRENFLKCFSQYIPNNATN

LKLVYTQNNPLYMSVLNSTIHNLRFSSDTTPKPLVIVTPSHVSHIQGT

ILCSKKVGLQIRTRXXXXXXXXXXXXXXXXXXXXXXXXXXXXXXXXXX

XXXWVEAGATLGEVYYVVVNEKNE*S*LSLAAGYCPTVCAGGHFGGGGY

GPLMR*S*YGLAADNIIDAHLVNVHGKVLDRKSMGEDLFWALRGGGAESF

GIIVAWKIRLVAVPKSTMFSVKKIMEIHELVKLVNKWQNIAYKYDKDL

LLMTHFITRNITDNQGKNKTAIHTYFSSVFLGGVDSLVDLMNKSFPEL

GIKKTDCRQLSWIDTIIFYSGVVNYDTDNFNKEILLDRSAGQNGAFKI

KLDYVKKPIPESVFVQILEKLYEEDIGAGMYALYPYGGIMDEISESAI

PFPHRAGILYELWYICSWEKQEDNEKHLNVVIRNIYNFMTPYVSQNPR

LAYLNYRDLDIGINDPKNPNNYTQARIWGEKYFGKNFDRLVKVKTLVD

PNNFFRNEQSIPPLPRHHH

Inactive CBDA synthase (SEQ ID NO:17)

ATGAAGTGCTCAACATTCCCCTTTTGGTTTGTTTGCAAGATAATATTT

TTCTTTCTCTCATTCAATATCCAAACTTCAATTGCTAATCCTCGAGAA

AACTTCCTTAAATGCTTCTCGCAATATATTCCCACCAATGTAACAAAT

CTAAAACTTACACCCAAAACAACCAATTGTATATGCCTGTCCAAAATT

CAACAATACACAATCTTAGATTCACCTCTAACACAACCCCAAAACTAC

TTGTTATCGTCACTCCTTCATATGTCTCTCATATCCAAGGCACTATTC

TATGTCCAAGAAAATTGGTTTGCAAATTCGAACTCGAAGCGGTGGTCA

TGATTCTGAAGACATGTCCTACATATCTCAAGTCCCATTTGTTATAGT

AGACTTGAGAAACATGCATTCAATCAACATAGATGTTCATAGCCAAAT

CGCAAGGGTTGAAGCCGGAGCTACCCTTGGAGAAGTTTATTATTGGGT

TAATGAGAAAAATGAGAATCTTAGTTTGGCTGCTGGGTATTGCCCTAC

TGTTAGCGCAGCTGGACACTTTGGTGGAGGAGGATATGGACCATTGAT

GCAAAATTATGGCCTCGCGGCTGATAATATCGTTGATGCACACTTAGT

CAACGTTGATGCAAAAGTGCTAGATCGAAAATCTATGGGGAAGATCT

CTTTTGGGCTATACGTGGTGGTGGAGGAGAAAGCTTCGGAATCATTGT

AGCATGGAAAATTAGACTGGTTGCTGTCCCAACAAAGTCTACTATGTT

TAGTGTTAAAAAGATCATGGAGATACATGAGCTTGTCAAGTGAGTTAA

CAAATGGCAAAATATTGCTTACAAGTATGACAAAGATTTATTACTCAT

GACTCACTTCATAACTAGGAATATTACAAATAATCATGGGAAGAATAA

GACAACAATACACACTTACTTCTCTTCAGTTTTCCTTGGTGGAGTGGA

TAGTCTAGTCGACTTGATGAATAAGAGTTTTCCTGAGTTGGGTATTAA

AAAAACAGATTGCAAACAATTGAGCTAGATTGATATTATCATCTTTTA

TAGCGGTGTTGTAAATTACGGCACTGATAATTTTAATAAGGAAATTTT

GCTTGATAGATCAGCTGGGCAGAACGGTTCTTTAAAGATTAAGTTAGA

CTACGTTAAGAAACCAATTCCAGAATCTGCGTTTGTCAAAATTTTGGA

AAAATTATATGAAGAAGATGAAGGAGTTGGGATGTATGCGTTGTACCC

TTACGGTGGTATAATGGATGAGATTTCAGAATCAGCAATTCCATTCCC

TCATTGAGCTGGAATCATGTATGAATTATGGTACATATGTAGCTGGGA

GAAGCACGAAGATAACGAAAAGCATCTAAACTGGATTCGAAATGTTT

ATAGCTTCATTACTCCTTATGTGTCCTAAAATCCAAGATTGGCATATC

TCAATTATAGAGACCTTGATACTGGAATAAATGATCCCAAGAGTCCAA

ATAATTACACACAAGAAAGTATTTGGGGTGAGAAGTATTTTGGTAAAA

```
-continued
ATTTTGACAGGGTAGTAAAAGTGAAAACCCTGGTTGATCCCAATAATT

TTTTTAGAAATGAACAAAGCATCCCACCTCTTCCACGGCATCGTCATT

AA
```

In some embodiments, the CBDA synthase gene may be knocked out using CRISPR/Cas mediated gene editing. To knockout the CBDA synthase gene using CRISPR/Cas mediated gene editing, one or more guide RNAs are designed that target the CBDA synthase gene or a region adjacent there to and proximal to a PAM site. Upon introduction to a *Cannabis* cell, the guide RNAs target a nuclease to induce a double strand break at the designated cut site. The cell will then undergo NHEJ to repair the cut site. Due to the nature of NHEJ, one or more indels are introduced at the cut site, thereby silencing the target CBDA synthase gene. In some embodiments, an HDR template oligonucleotide may be used to direct the repair at the cut site to introduce a mutation of interest. The mutation of interest may be an insertion of a stop codon, a frameshift mutation, or a nonsense mutation that disrupts expression of the CBDA synthase gene. In some embodiments, the HDR oligonucleotide encodes a sequence comprising one or more the CBDA synthase gene SNPs recited herein or encodes a mutation in the CBDA synthase polypeptide sequence as demonstrated herein. In some embodiments, the guide RNAs direct cleavage of the CBDA gene such that all or a portion of the CBDA gene is removed. In some embodiments, the nuclease is a Cas nuclease. Suitable Cas nucleases are known and described in the art including, but not limited to, a Cas9 nuclease.

In some embodiments, the guide RNA targeting the CBDA gene is selected from SEQ ID NO:18 (GCTAGATCGAAAATCTATGG, forward gRNA gRF668), SEQ ID NO:19 (AAAGCATCCCACCTCTTCCA, forward gRNA gRF1621), SEQ ID NO:20 (TTTAGGACAGACATATACAA, reverse gRNA gRR172), SEQ ID NO:21 (GAAAGCACCGTTCTGCCCAG, reverse gRNA gRR1118), or combinations thereof. In some embodiments, the guide RNA sequences are cloned into a vector for introduction to the cell. In some embodiments, the vector also encodes a Cas nuclease (e.g., Cas9 nuclease). In some embodiments, one or more vectors encoding the guide RNA and the Cas nuclease are introduced into the cell in the presence of an HDR oligonucleotide. Cells positive for transformation and the desired CRISPR/Cas mediated editing results may be screened and selected for using standard molecular biology and sequencing techniques known in the art.

In some embodiments, both the THCA synthase and CBDA synthase genes are knocked out to produce a THC low or THC free *Cannabis* plant. The polypeptide sequence of the THCA synthase and CBDA synthase enzymes are approximately 84% identical and both contribute to THC production in *Cannabis*. Plants produced by knocking out both the THCA synthase and CBDA synthase genes have significantly increased production of cannabigerolic acid (CBG), which is the substrate for both THCA synthase and CBDA synthase, relative to a *Cannabis* plant with wild-type expression of THCA synthase and CBDA synthase. In some embodiments, both the THCA synthase and the CBDA synthase genes are knocked-out using CRISPR/Cas mediated gene editing as described herein. In some embodiments, guide RNAs targeting both the THCA synthase gene and the CBDA gene simultaneously are designed and used for CRISPR/Cas9 mediated gene editing. In some embodiments, the guide RNAs targeting both THCA synthase and CBDA synthase are selected from SEQ ID NO:22 (CATTTAAGGAAGTTTTCTCG, reverse gRNA gRR88), SEQ ID NO:23 (AAATGGGACTTGAGATATGT, reverse gRNA gRR259), SEQ ID NO:24 (CCCTTGGAGAAGTTTATTAT, forward gRNA gRF481), SEQ ID NO:25 (GTACCCTTACGGTGGTATAA, forward gRNA gRF1265), SEQ ID NO:26 (ATTCCAGCTCGATGAGGGAA, reverse gRNA gRR1291), SEQ ID NO:27 (TACACACAAGCACGTATTTG, forward gRNA gRF1515), and combinations thereof. In some embodiments, the guide RNA sequences are cloned into a vector for introduction to the cell. In some embodiments, the vector also encodes a Cas nuclease (e.g., Cas9 nuclease). In some embodiments, one or more vectors encoding the guide RNA and the Cas nuclease are introduced into the cell in the presence of an HDR oligonucleotide. Cells positive for transformation and the desired CRISPR/Cas mediated editing results may be screened and selected for using standard molecular biology and sequencing techniques known in the art.

In some embodiments, the heterologous nucleic acid of interest encodes a SOLO DANCERS (SDS) and BARNASE fusion gene. The SDS gene encodes a meiosis-specific cyclin and is required for homology interaction during meiotic prophase I in Arabidopsis. The BARNASE gene encodes a ribonuclease, is driven by a tapetum-specific promoter, and, when activated is toxic to and eliminates tapetal cells to create male sterile plants. Co-expression of SDS and BARNASE from a heterologous nucleic acid will create a male and female sterile plant. See, for example, Huang et al. ("Creating completely both male and female sterile plants by specifically ablating microspore and megaspore mother cells," Frontiers in Plant Science, 2016, 7(30)).

SDS gene from *Arabidopsis* (SEQ ID NO:60)

```
ATGAAGGAGATCGCGATGAGGAATTCAAAGCGCAAGCCTGAGCCGACG

CCGTTCGCCGGGAAGAAGCTCCGGTCGACGCGATTACGCCGGAAGAGA

GCACAGATCTCTCCCGTTCTTGTTCAATCACCTCTCTGGAGCAAACAA

ATCGGAGTCTCTGCTGCTTCTGTCGATTCCTGCTCCGATTTGCTAGCT

GATGACAACGTTTCCTGTGGTTCGAGCAGAGTCGAGAAGAGCTCGAAT

CCGAAGAAGACTCTAATTGAAGAGGTAGAAGTTTCTAAACCTGGTTAT

AATGTGAAGGAGACGATTGGTGATTCGAAATTTCGAAGGATTACGAGG

TCTTACTCTAAGCTACACAAGGAGAAGGAGGGAGATGAGATCGAAGTA

AGCGAATCGTCTTGTGTTGATTCGAATTCTGGTGCTGGATTAAGGAGA

TTGAATGTGAAGGGAAATAAAATTAACGACAACGATGAGATCTCTTTC

TCACGATCCGATGTGACCTTCGCCGGACATGTCTCCAACAGCCGGAGT

TTGAATTTCGAATCGGAGAATAAGGAGAGCGACGTCGTTTCTGTCATA

TCTGGAGTTGAGTACTGTTCCAAGTTCGGGAGCGTTACCGGAGGAGCT

GATAACGAAGAAATTGAAATCTCCAAGCCGAGCAGCTTCGTGGAAGCT

GATTCCTCTCTTGGATCGGCCAAGGAATTGAAGCCGGAGCTTGAGATA

GTCGGATGCGTCTCTGATCTCGCTTGCTCTGAGAAATTCTCGGAAGAG

GTTTCGGATTCTCTCGATGATGAGTCATCTGAGCAACGTTCAGAGATA

TATTCACAGTATTCCGACTTCGATTACTCGGATTACACTCCGTCCATC

TTCTTCGACTCTGGCAGCGAATTCTCTGAGAAATCTTCCTCTGATTCT
```

-continued

CCTATTTCACATTCTCGCTCTCTGTACCTCCAGTTCAAGGAACAGTTC

TGTAGATCCACGATTCCCAACGATTTTGGATCTTCTTGCGAGGAAGAA

ATTCACTCTGAATTGCTAAGGTTTGATGATGAGGAGGTGGAAGAGAGC

TATCTAAGGCTGAGGGAAAGAGAAAGAAGTCATGCATATATGCGGGAC

TGTGCTAAGGCATACTGCTCCAGGATGGACAATACTGGTCTCATCCCT

CGTCTACGCTCCATCATGGTTCAATGGATTGTAAAGCAATGTTCTGAC

ATGGGGCTTCAGCAAGAGACATTGTTTCTAGGAGTTGGTCTGTTGGAT

CGATTCCTGAGCAAAGGATCATTCAAAAGCGAAAGGACTCTAATACTA

GTCGGGATTGCGAGTCTTACTCTGGCCACCAGAATTGAAGAAAATCAA

CCTTACAACAGCATCCGGAAAAGGAACTTCACCATTCAGAACCTAAGA

TATAGCCGGCATGAAGTGGTGGCAATGGAGTGGCTGGTTCAAGAAGTC

CTCAACTTCAAATGCTTCACACCCACAATCTTCAACTTCTTGTGGTTC

TACTTAAAAGCTGCTCGAGCCAATCCAGAAGTTGAAAGGAAAGCCAAA

TCCTTGGCTGTTACCTCACTATCCGACCAAACTCAACTCTGTTTTTGG

CCCTCAACTGTAGCAGCTGCACTCGTGGTTCTCGCCTGCATCGAACAC

AACAAAATCTCTGCATACCAACGAGTCATAAAGGTCCATGTTAGAACA

ACAGATAACGAGTTGCCTGAATGCGTTAAGAGTCTGGACTGGTTGCTT

GGGCAGTAA

BARNASE gene (SEQ ID NO:61)

CTGGAAAACGTCACATTGCTTCCGCATATCGGGTCAGCAACGGCTAA

AATCCGCTTGAATATGTTCACACAAGCCGCTCAAAACATGATTGACG

CCGTATACGGAAGAACGCCGAAAAACCTTACTAAGGAATTTCAATAA

GAAGAAAATCCCGGTTGGTTCAGCCGGGGTTTATTTTTCGCTAGAT

AAAAAGTACTATTTTTAAATTCTTTCTATTCCTTTCTTTCGTTGCTG

ATACAATGAAAAGGAATCAGCTTCACATGATGAAAATGGGAGGTATT

GCTTTGAAAAAACGATTATCGTGGATTTCCGTTTGTTTACTGGTGCT

TGTCTCCGCGGCGGGATGCTGTTTTCAACAGCTGCCAAAACGGAAA

CATCTTCTCACAAGGCACACACAGAAGCACAGGTTATCAACACGTTT

GACGGGGTTGCGGATTATCTTCAGACATATCATAAGCTACCTGATAA

TTACATTACAAAATCAGAAGCACAAGCCCTCGGCTGGGTGGCATCAA

AAGGGAACCTTGCAGACGTCGCTCCGGGGAAAAGCATCGGCGGAGAC

ATCTTCTCAAACAGGGAAGGCAAACTCCCGGGCAAAAGCGGACGAAC

ATGGCGTGAAGCGGATATTAACTATACATCAGGCTTCAGAAATTCAG

ACCGGATTCTTTACTCAAGCGACTGGCTGATTTACAAAACAACGGAC

CATTATCAGACCTTTACAAAAATCAGATAACGAAAAAAACGGCTTCC

CTGCGGAGGCCGTTTTTTTCAGCTTTACATAAAGTGTGTAATAAATT

TTTCTTCAAACTCTGATCGGTCAATTTCACTTT

In some embodiments, provided herein is a *Cannabis* plant with increased trichomes that has increased expression of endogenous Cannabis lipid transfer protein 2 (LTP2) or includes a heterologous nucleic acid encoding *Brassica napus* LTP2 (BraLTP2). In some embodiments, a *Cannabis* cell is transformed with a heterologous polynucleotide encoding a polypeptide at least 80%, 85%, 90%, 95%, 98%, 99%, or 99.9% identical to SEQ ID NO:28. In some embodiments, a *Cannabis* cell is transformed with a heterologous polynucleotide encoding the polypeptide of SEQ ID NO:28. In some embodiments, the heterologous polynucleotide is at least 80%, 85%, 90%, 95%, 98%, 99%, or 99.9% identical to SEQ ID NO:29. The heterologous nucleic acid encoding BraLTP2 may be incorporated into a construct or vector as described herein. One embodiment for cloning BraLTP2 into a vector suitable for transformation using the methods described herein is demonstrated in FIG. 66. Trichomes in the transformed *Cannabis* plant may be at least 2 fold, 5 fold, 10 fold, or 15 fold higher than trichomes in a *Cannabis* plant that does not include the heterologous polynucleotide. In some embodiments, the modulation of the LTP2 gene in other plants, such as *Brassica napus* is described in the art. See, for example, Tian et al. (Tian et al., "Overexpression of BraLTP2, a lipid transfer protein of *Brassica napus*, results in increased trichome density and altered concentration of secondary metabolites," Int. J. Mol. Sci., 2018, 19:1733).

BraLTP2 protein sequence (SEQ ID NO:28)

MATGSRVLIGLANilLIISGELLVPGQGTCQGDIEGLMRECAVYVQR

PGPKVNPSAACCKVVKRSDIPCACGRITPSVQKMIDMNKVVLVTSFC

GRPLAHGTKCGSYIVP

BraLTP2 gene sequence GenBank: KM062522.1 (SEQ ID NO:29)

ATGGCGACAGGTTCTCGTGTTCTGATCGGTCTAGCAATGATCCTCAT

AATCTCAGGAGAACTGCTAGTTCCAGGGCAAGGAACGTGCCAAGGAG

ACATAGAGGGTCTGATGAGAGAATGTGCGGTCTACGTCCAGCGTCCA

GGCCCAAAGGTAAACCCATCCGCAGCGTGTTGCAAAGTCGTCAAGAG

ATCAGACATCCCCTGCGCATGTGGCCGTATCACACCCTCGGTTCAAA

AAATGATAGACATGAATAAGGTTGTTCTTGTCACTTCCTTTTGTGGG

AGGCCTCTCGCTCATGGTACCAAGTGTGGAAGCTACATTGTGCCATG

A

In some embodiments, the heterologous nucleic acid of interest modulates the expression or function of the endogenous *Cannabis* LTP2 gene. A heterologous nucleic acid is introduced into the *Cannabis* explant to upregulate, overexpress, or provide multiple copies of the LPT2 gene. *Cannabis* plants grown from the transformed *Cannabis* explant are characterized by a phenotype with an increase in trichomes compared to a wild-type plant as well as increased cannabidiol (CBD) production.

In some embodiments, the heterologous nucleic acid of interest modulates the expression or function of the endogenous *Cannabis sativa* prenyltransferase 1 (CsPT1) gene. A heterologous nucleic acid is introduced into the *Cannabis* explant to upregulate, overexpress, or provide multiple copies of the CsPT1 gene. In some embodiments, a *Cannabis* cell is transformed with a heterologous nucleic acid encoding a polypeptide at least 80%, 85%, 90%, 95%, 98%, 99%, or 99.9% identical to SEQ ID NO:30. In some embodiments, a *Cannabis* cell is transformed with a heterologous nucleic acid encoding the polypeptide SEQ ID NO:30. In some embodiments, a *Cannabis* cell is transformed with a heterologous nucleic acid comprising SEQ ID NO:31 or a sequence at least 80%, 85%, 90%, 95%, 98%, 99%, or 99.9% identical thereto. The heterologous nucleic acid encoding CsPT1 may be incorporated into a construct or vector as described herein. One embodiment for cloning CsPT1 into a vector suitable for transformation using the methods described herein is demonstrated in FIG. 67. *Cannabis* plants grown from the transformed *Cannabis* explant are characterized by a phenotype with increased cannabigerol (CBG) production and increased cannabidiol (CBD) production. The sequence and activity of the CsPT1 gene is known and described in the art. See, for example, Luo et al. (Luo et al., "Complete biosynthesis of cannabinoids and their unnatural analogues in yeast," Nature, 2019, 567) and U.S. Pat. No. 8,884,100.

CsPT1 protein sequence (SEQ ID NO:30)

MGLSSVCTFSFQTNYHTLLNPHNNNPKTSLLCYREIPKTPIKYSYNN

FPSKHCSTKSFEILQNKCSESLSIAKNSIRAATTNQIEPPESDNHSV

ATKILNFGKACWKLQRPYTIIAFTSCACGLFGKELLHNTNLISWSLM

FKAFFFLVAVLCIASFTTTINQIYDLHIDRINKPDLPLASGEISVNT

AWIMSIIVALFGLIITIKMKGGPLYIFGYCFGIFGGIVYSVPPFRWK

QNPSTAFLLNFLAIIIITNFTFYYASRAALGLPFELRPSFTFLLAFM

KSMGSALALIKDASDVEGDTKFGISTLASKYGSRNLTLFCSGIVLLS

YVAAILAGIIWPQAFNSNVMLLSHAILAFWLILQTRDFALTNYDPEA

GRRFYEFMVVKLYYAEYLVYVFI

Figure 68:
FIG. 68 shows embodiments of a cloning strategy for CsOMT1. From top to bottom, the sequences shown are: SEQ ID NO:33, SEQ ID NO:51, and SEQ ID NO:52.

CsPT1 cDNA sequence (SEQ ID NO:31)

atgggactctcatcagtttgtaccttttcatttcaaactaattaccata ctttattaaatcctcacaataataatcccaaaacctcattattatgtta tcgacaccccaaaacaccaattaaatactcttacaataattttccctct aaacattgctccaccaagagttttcatctacaaaacaaatgctcagaat cattatcaatcgcaaaaaattccattagggcagctactacaaatcaaac tgagcctccagaatctgataatcattcagtagcaactaaaattttaaac tttgggaaggcatgttggaaacttcaaagaccatatacaatcatagcat ttacttcatgcgcttgtggattgtttgggaaagagttgttgcataacac aaatttaataagttggtctctgatgttcaaggcattcttttttttggtg gctgtattatgcattgcttcttttacaactaccatcaatcagatttacg atcttcacattgacagaataaacaagcctgatctaccactagcttcagg ggaaatatcagtaaacacagcttggattatgagcataattgtggcactg tttggattgataataactataaaaatgaagggtggaccactctatatat ttggctactgttttggtattttggtgggattgtctattctgttccacc atttagatggaagcaaaatccttccactgcatttcttctcaatttcctg gcccatattattacaaatttcacattttattatgccagcagagcagctc ttggcctaccatttgagttgaggccttatttactttcctgctagcattt atgaaatcaatgggttcagctttggctttaatcaaagatgcttcagacg ttgaaggcgacactaaatttggcatatcaaccttggcaagtaaatatgg ttccagaaacttgacattattttgttctggaattgttctcctatcctat gtggctgctatacttgctgggattatctggccccaggctttcaacagta acgtaatgttactttctcatgcaatcttagcattttggttaatcctcca gactcgagattttgcgttaacaaattacgacccggaagcaggcagaaga ttttacgagttcatgtggaagctttattatgctgaatatttagtatatg ttttcatataa In some embodiments, the heterologous nucleic acid of interest modulates the expression or function of the endogenous *Cannabis sativa* O-methyltransferase (CsOMT21) gene. A heterologous nucleic acid is introduced into the *Cannabis* explant to upregulate, overexpress, or provide multiple copies of the CsOMT21 gene. In some embodiments, a *Cannabis* cell is transformed with a heterologous nucleic acid encoding a polypeptide at least 80%, 85%, 90%, 95%, 98%, 99%, or 99.9% identical to SEQ ID NO:32. In some embodiments, a *Cannabis* cell is transformed with a heterologous nucleic acid encoding the polypeptide SEQ ID NO:32. In some embodiments, a *Cannabis* cell is transformed with a heterologous nucleic acid comprising SEQ ID NO:33 or a sequence at least 80%, 85%, 90%, 95%, 98%, 99%, or 99.9% identical thereto. The heterologous nucleic acid encoding CsOMT21 may be incorporated into a construct or vector as described herein. One embodiment for cloning CsOMT21 into a vector suitable for transformation using the methods described herein is demonstrated in FIG. 68. *Cannabis* plants grown from the transformed *Cannabis* explant are characterized by a phenotype with increased chrysoeriol production and increased cannflavin A and cannflavin B production. The sequence and activity of the CsOMT21 gene is known and described in the art. See, for example, Rea et al. Phytochemistry 2019: "Biosynthesis of cannflavins A and B from *Cannabis sativa* L."

CsOMT21 (PK24150) (SEQ ID NO:32)

MGSTGIETQMTPTQISDEEANLFAMQLASASVLPMVLKAALELDLLEI

TAKAGPGAFLSPSDIAQQLPTQNPDAPVMLDRMLRLLASYNVVTYSLR

ERETAEEEGKVERLYGLAPVSKYLTKNEDGVSIAPLCLMNQDKVLMES

WYEILKDAVLDGGIPFNKAYGMTAFEYHGTDQRFNKIFNRGMSDHSTI

TMKKILETYKGFEGLNSIVDVGGGTGAVVNMIVSKYPTIKGINFDLPH

VIEDAPPLTGVEHVGGDMFVSVPKGDAIFMKWICHDWSDEHCLKFLKN

CHAALPEHGKVIVAECILPVAPDSSLATKSTVHIDVIMLAHNPGGKER

TEKEFEALAKGAGFKGFKVHCNAFNTHIMEFLKTI

*Cannabis sativa* PK24150.1_1.CasaPuKu, GenBank: JP459899.1 (SEQ ID NO:33)

ATGGGTTCAACAGGAATAGAGACCCAAATGACCCCAACCCAAATATCC

GACGAAGAAGCCAACCTCTTCGCCATGCAATTAGCCAGTGCCTCAGTC

TTACCCATGGTTCTCAAAGCAGCTTTAGAGCTCGACCTCTTGGAGATC

ATAGCCAAGGCCGGTCCAGGCGCGTTTCTCTCACCTTCCGACATAGCT

CAACAGCTTCCGACTCAGAACCCAGACGCCCCGGTGATGCTGGACCGG

ATGCTGAGACTGTTGGCTAGCTACAACGTGGTGACGTACTCGCTGCGT

-continued
GAGCGTGAGACGGCGGAAGAGGAAGGGAAGGTGGAGAGGCTTTATGGG

TTGGCTCCGGTGAGTAAATATCTGACGAAGAATGAAGATGGAGTCTCC

ATTGCTCCTCTTTGTCTCATGAACCAGGATAAGGTTCTTATGGAGAGT

TGGTATCACTTAAAAGATGCAGTACTTGATGGAGGAATACCTTTCAAC

AAGGCATATGGAATGACAGCATTTGAATATCATGGAACCGATCAAAGG

TTCAATAAAATCTTTAATAGAGGAATGTCCGACCACTCGACTATTACC

ATGAAAAAAATCCTCGAAACTTACAAGGGTTTCGAGGGTCTTAACTCG

ATTGTTGATGTTGGTGGTGGTACTGGAGCTGTTGTTAACATGATCGTC

TCTAAGTACCCTACTATTAAGGGTATTAACTTCGATTTGCCTCATGTC

ATCGAAGATGCACCTCCATTGACCGGTGTAGAGCATGTTGGAGGAGAC

ATGTTTGTAAGTGTACCAAAAGGAGATGCAATTTTCATGAAGTGGATT

TGCCATGATTGGAGCGATGAACACTGCTTGAAATTCTTGAAGAACTGC

CACGCTGCACTGCCCGAACACGGAAAAGTGATCGTGGCGGAGTGCATT

CTTCCGGTGGCACCGGACTCGAGCCTTGCCACAAAGAGTACGGTCCAC

ATTGATGTGATCATGTTGGCCCATAACCCTGGTGGCAAAGAGAGAACA

GAGAAAGAGTTTGAGGCATTGGCTAAGGGAGCTGGCTTTAAAGGCTTC

AAAGTCCATTGCAATGCTTTCAATACCCATATCATGGAATTTCTCAAG

ACCATTTAA

Figure 69:
FIG. 69 shows embodiments of a cloning strategy for CsPT3. From top to bottom, the sequences shown are: SEQ ID NO:35, SEQ ID NO:53, and SEQ ID NO:54.

In some embodiments, the heterologous nucleic acid of interest modulates the expression or function of the endogenous *Cannabis sativa* prenyltransferace 3 (CsPT3) gene. A heterologous nucleic acid is introduced into the *Cannabis* explant to upregulate, overexpress, or provide multiple copies of the CsPT3 gene. In some embodiments, a *Cannabis* cell is transformed with a heterologous nucleic acid encoding a polypeptide at least 80%, 85%, 90%, 95%, 98%, 99%, or 99.9% identical to SEQ ID NO:34. In some embodiments, a *Cannabis* cell is transformed with a heterologous nucleic acid encoding the polypeptide SEQ ID NO:34. In some embodiments, a *Cannabis* cell is transformed with a heterologous nucleic acid comprising SEQ ID NO:35 or a sequence at least 80%, 85%, 90%, 95%, 98%, 99%, or 99.9% identical thereto. The heterologous nucleic acid encoding CsPT3 may be incorporated into a construct or vector as described herein. One embodiment for cloning CsPT3 into a vector suitable for transformation using the methods described herein is demonstrated in FIG. 69. *Cannabis* plants grown from the transformed *Cannabis* explant are characterized by a phenotype with increased cannabigerol (CBG) production and increased cannabidiol (CBD) production.

CsPT3 (PK17697) (SEQ ID NO:34)

MVFSSVCSFPSSLGTNFKLVPRSNFKASSSHYHEINNFINNKPIKFSY

FSSRLYCSAKPIVHRENKFTKSFSLSEILQRKSSIKAHGEIEADGSNG

TSEFNVMKSGNAIWRFVRPYAAKGVLFNSAAMFAKELVGNLNLFSWPL

MFKILSFTLVILCIFVSTSGINQIYDLDIDRLNKPNLPVASGEISVEL

AWLLTIVCTISGLTLTIITNSGPFFPFLYSASIFFGFLYSAPPFRWKK

NPFTACFCNVMLYVGTSVGVYYACKASLGLPANWSPAFCLLFWFISLL

-continued
SIPISIAKDLSDIEGDRKFGIITFSTKFGAKPIAYICHGLMLLNYVSV

MAAAIIWPQFFNSSVILLSHAFMAIWVLYQAWILEKSNYATETCQKYY

IFLWIIFSLEHAFYLFM

*Cannabis sativa* PK17697.1_1.CasaPuKu, GenBank: JP460361.1, (SEQ ID NO:35)

atggtgttctcatcagtttgtagttttccatcctcccttggaactaat tttaaattagttcctcgtagtaattttaaggcatcatcttctcattat catgaaataaataattttattaataataaaccaattaaattctcatat tttcttcaagactatattgctctgccaaaccaattgtacacagagaa aacaaattcacaaaatcattttcactcagccacctccaaaggaaaagc tccataaaggcacatggtgaaattgaagctgatgggagtaatggcaca tctgaatttaatgtaatgaaaagtggaaacgcaatttggagatttgta aggccatatgcagccaagggagtattgtttaactctgctgctatgttt gcaaaagagttggtggggaacctaaatctatttagttggcattgatgt ttaagatactctcttttacattggttattttatgcattttgtaagta caagtggcatcaatcaaatttatgatctcgacatcgacaggttaaaca aacctaatttgccagtagcatcaggagaaatttcagttgaattggcat ggttgttgactatagtttgtacaataagtggcctcacattaacaatta taacgaactcagggccattcttcccttttctctactctgctagtatct ttttggctttctctattctgctcctccattcagatggaagaagaatc cttttacagcatgtttctgtaatgttatgttgtatgttggcacaagcg ttggtgtctattatgcttgtaaggctagtctcgggcttccagccaact ggagccctgcttttgtttgctcttttggtttatttcattgttgagta tacccatctccattgcaaaagatcttcagacatagaaggtgaccgca agtttggaatcataaccttctcaactaaatttggagcaaaacccatag catatatttgtcatggactcatgcttctgaattacgtgagtgttatgg ctgcagctattatttggccacagttttttcaacagtagcgtaatattgc tttctcatgcattcatggcaatttgggtattatatcaggcttggatat tggagaaatcaaattacgccacggagacgtgccaaaaatactatatat tcctttggataattttttctcttgaacatgccttctatttgttcatgt ag In some embodiments, the heterologous nucleic acid of interest produces a glyphosate resistant *Cannabis* plant following transformation. To create a glyphosate resistant *Cannabis* plant, a *Cannabis* cell is transformed as described herein with a heterologous nucleic suitable for mutating the *Cannabis sativa* gene encoding 3-phosphoshikimate 1-carboxyvinyltransferase 2 (EPSP synthase) such that when expressed, the EPSP synthase enzyme is not inhibited by the herbicide glyphosate. Without wishing to be bound by any particular theory or embodiment, glyphosate is a competitive inhibitor of phosphoenolpyruvate (PEP) in EPSP, acting as a transition state analog that binds more tightly to the EPSPS-S3P (shikimate-3-phosphate bound EPSP synthase) complex than PEP. Upon exposure to glyphosate, the EPSP synthase enzyme is non-functional or severely inhibited resulting in plant death. However, it is possible to mutate the EPSP synthase enzyme such at it does not bind glyphosate but still catalyzes the synthesis of 5-enol-pyruvylshikimate-3-phosphate.

In some embodiments, the *Cannabis sativa* gene encoding EPSP synthase is mutated using prime editing guide RNA (pegRNA) together with a Cas9 nuclease and reverse transcriptase fusion protein. In some embodiments, the Cas9 nuclease is a mutated Cas9 nuclease that only cleaves a single strand of the target DNA. In some embodiments, the mutated Cas9 nuclease is a Cas9 H840A nickase or a Cas9 D10A nickase (Cas9n). pegRNA are designed with the desired genetic mutation and to target the *Cannabis sativa* EPSPS gene loci of interest. A nucleic acid encoding the pegRNA and the Cas9 nuclease/reverse transcriptase fusion protein is introduced into a *Cannabis sativa* cell. Cells positive for transformation and the desired prime editing mutations may be screened and selected for using standard molecular biology and sequencing techniques known in the art.

In some embodiments, the Cannabis EPSPS gene (SEQ ID NO:40) is mutated at positions 1790, 1801, 3620, and 3621 to encode an EPSP synthase that is glyphosate resistant and includes T181I, P185S, and P460L mutations relative to the wild-type sequence. In some embodiments, the pegRNA for the mutations at positions 1790 and 1801 comprises the gRNA sequences tgaagactttgcaCAACTTTTCCTTG-GAAATGCgtttaagtcttct (forward, SEQ ID NO:41) and AGAAGACTTAAACGCATTTC-CAAGGAAAAGTTGTGCAAAGTCTTCA (reverse, SEQ ID NO:42) and the sequence ACCTGCTATAGTGCT-GAGTGAACGCATTGCTATTCCAGCATTTC-CAAGGAAACATAT AGCAGGT (SEQ ID NO:43) encoding the two C→T mutations at positions 1790 and 1801. See, FIG. 70. In some embodiments, the pegRNA for the mutations at positions 3620 and 3621 comprises the gRNA sequences tgaagactttgcaCTTGGAGCAACAGTTGAG-GAgtttaagtcttct (forward, SEQ ID NO: 44) and AGAA-GACTTAAACTCCTCAACTGTTGCTC-CAAGTGCAAAGTCTTCA (reverse, SEQ ID NO:45) and the sequence ACCTGCTATAGTGCCACGCAGTAAT-CAAGTCCTTCCTCAACTGTTGAACATATAGCA GGT (SEQ ID NO:46) encoding the two C→T mutations at positions 3620 and 3621. See, FIG. 71.

Cannabis EPSP synthase (SEQ ID NO:36)

MAQVSKICSNGAQTILTLPNISKSHTPRSLNSVSLRSPFLGSSNSLSL

KIGTEFGGCSTVGKAMAGPVMASAVTAEKPSKVPEIVLQPIKDISGTV

KLPGSKSLSNRILLLAALSEGTTVVDNLLDSDDIHYMLGALETLGLRV

EADKESKRAIVEGCAGQFPAGKESVDEVQLFLGNAGTAMRPLTAAVTV

AGGNASYVLDGVPRMRERPIGDLVTGLKQLGADVDCFHGTDCPPVRVL

GKGGLPGGKVKLSGSISSQYLTALLMAAPLALGDVEIEIIDKLISVPY

VDMTLKLMARFGVTVEHSDSWDRFLVKGGQKYKSPGNAYVEGDASSAS

YFLAGAAVTGGTVTVEGCGTSSLQGDVKFAEVLEKMGAKVSWTENSVT

VTGPPRDSVKSKHLKAIDVNMNKMPDVAMTLAVVALFADGPTAIRDVA

SWRVKETERMIAICIELRKLGATVEEGPDYCVITPPEKLNITAIDTYD

DEIRMAMAFSLAACSDVPVTIKDPGCTRKTFPDYFEVLERFTKH

Glyphosate resistant Cannabis EPSP synthase (SEQ ID NO:37), mutations relative to SEQ ID NO:36 shown in bold underline including T181I, P185S, P460L

MAQVSKICSNGAQTILTLPNISKSHTPRSLNSVSLRSPFLGSSNSLSL
KIGTEFGGCSTVGKAMAGPVMASAVTAEKPSKVPEIVLQPIKDISGTV
KLPGSKSLSNRILLLAALSEGTTVVDNLLDSDDIHYMLGALETLGLRV
EADKESKRAIVEGCAGQFPAGKESVDEVQLFLGNAGIAMRSLTAAVTV
AGGNASYVLDGVPRMRERPIGDLVTGLKQLGADVDCFHGTDCPPVRVL
GKGGLPGGKVKLSGSISSQYLTALLMAAPLALGDVEIEIIDKLISVPY
VDMTLKLMARFGVTVEHSDSWDRFLVKGGQKYKSPGNAYVEGDASSAS
YFLAGAAVTGGTVTVEGCGTSSLQGDVKFAEVLEKMGAKVSWIENSVT
VTGPPRDSVKSKHLKAIDVNMNKMPDVAMTLAVVALFADGPTAIRDVA
SWRVKETERMIAICTELRKLGATVEEGLDYCVITPPEKLNITAIDTYD
DEIRMAMAFSLAACSDVPVTIKDPGCTRKTFPDYFEVLERFTKH

Cannabis EPSP synthase cDNA (SEQ ID NO:38)

```
ATGGCCCAAGTGAGCAAAATCTGTAGCAATGGAGCTCAAACTATCCTTA
CTCTCCCAAATATATCTAAGTCTCATACACCAAGATCCCTAAATTCAGT
TTCGTTGAGATCACCGTTTTTGGGTTCATCTAACTCTTTGAGTTTGAAG
ATTGGAACTGAATTTGGGGGTTGTTCTACGGTTGGTAAAGCTATGGCTG
GTCCAGTCATGGCTTCAGCTGTCACAGCGGAGAAGCCTTCAAAGGTACC
GGAGATTGTGTTGCAGCCCATTAAAGATATCTCTGGCACTGTCAAGTTG
CCGGGTTCCAAGTCACTATCGAATCGGATTCTACTCCTGGCTGCTCTTT
CTGAGGGGACAACTGTTGTGGACAACTTGTTAGATAGTGATGACATTCA
CTACATGCTTGGTGCCTTGGAAACCCTTGGTCTTCGTGTTGAAGCAGAC
AAGGAAAGCAAACGAGCAATTGTGGAAGGTTGTGCGGGTCAGTTTCCTG
CAGGTAAAGAATCTGTTGACGAAGTTCAACTTTTCCTTGGAAATGCTGG
AACAGCAATGCGTCCACTCACAGCTGCGGTGACTGTTGCTGGTGGAAAT
GCTAGCTACGTACTTGATGGTGTTCCTCGAATGAGAGAAAGACCAATTG
GAGATTTGGTGACTGGTCTTAAGCAGCTTGGTGCAGATGTTGATTGTTT
TCATGGTACGGATTGTCCCCCTGTTCGTGTGCTTGGAAAAGGAGGCCTT
CCTGGGGGCAAGGTGAAACTTTCTGGATCAATTAGCAGTCAATATTTGA
CAGCCTTGCTTATGGCAGCTCCCTTGGCTCTTGGAGATGTTGAAATCGA
GATAATTGATAAATTGATCTCGGTTCCCTATGTTGATATGACTTTGAAG
TTGATGGCACGTTTTGGGGTTACTGTTGAACACAGTGATAGCTGGGATC
GATTTTTAGTTAAAGGAGGTCAAAAGTACAAATCTCCTGGAAACGCTTA
TGTTGAAGGTGATGCTTCAAGTGCTAGTTACTTCCTAGCTGGTGCTGCA
GTCACTGGTGGTACAGTCACCGTAGAAGGTTGTGGGACTAGTAGTTTAC
AGGGAGACGTAAAATTTGCTGAAGTTCTTGAGAAAATGGGTGCTAAAGT
TAGCTGGACAGAGAACAGTGTCACGGTCACTGGACCACCACGAGATTCT
GTAAAAAGTAAACACTTGAAAGCCATTGATGTCAACATGAACAAAATGC
CTGATGTTGCCATGACTCTTGCTGTAGTTGCTCTTTTTGCTGATGGCCC
CACTGCTATAAGAGATGTGGCAAGTTGGAGAGTCAAGGAGACAGAGAGA
ATGATTGCCATCTGCACTGAACTCAGAAAGCTTGGAGCAACAGTTGAGG
```

AAGGACCCGATTACTGCGTGATCACTCCACCAGAGAAACTAAATATCAC

AGCAATAGACACATACGACGACCACAGGATGGCTATGGCGTTCTCTCTT

GCAGCTTGTTCAGATGTGCCAGTTACCATTAAGGATCCTGGTTGCACCC

GAAAAACTTTCCCAGATTACTTTGAAGTCCTTGAGAGATTTACAAAGCA

CTGA

Glyphosate resistant Cannabis EPSP synthase cDNA (SEQ ID NO:39), mutations relative to SEQ ID NO:38 shown in bold underline, including C542T, C553T, C1379T, and C1380T

ATGGCCCAAGTGAGCAAAATCTGTAGCAATGGAGCTCAAACTATCCTTA

CTCTCCCAAATATATCTAAGTCTCATACACCAAGATCCCTAAATTCAGT

TTCGTTGAGATCACCGTTTTTGGGTTCATCTAACTCTTTGAGTTTGAAG

ATTGGAACTGAATTTGGGGGTTGTTCTACGGTTGGTAAAGCTATGGCTG

GTCCAGTCATGGCTTCAGCTGTCACAGCGGAGAAGCCTTCAAAGGTACC

GGAGATTGTGTTGCAGCCCATTAAAGATATCTCTGGCACTGTCAAGTTG

CCGGGTTCCAAGTCACTATCGAATCGGATTCTACTCCTGGCTGCTCTTT

CTGAGGGGACAACTGTTGTGGACAACTTGTTAGATAGTGATGACATTCA

CTACATGCTTGGTGCCTTGGAAACCCTTGGTCTTCGTGTTGAAGCAGAC

AAGGAAAGCAAACGAGCAATTGTGGAAGGTTGTGCGGGTCAGTTTCCTG

CAGGTAAAGAATCTGTTGACGAAGTTCAACTTTTCCTTGGAAATGCTGG

AATAGCAATGCGTTCACTCACAGCTGCGGTGACTGTTGCTGGTGGAAAT

GCTAGCTACGTACTTGATGGTGTTCCTCGAATGAGAGAAAGACCAATTG

GAGATTTGGTGACTGGTCTTAAGCAGCTTGGTGCAGATGTTGATTGTTT

TCATGGTACGGATTGTCCCCCTGTTCGTGTGCTTGGAAAAGGAGGCCTT

CCTGGGGGCAAGGTGAAACTTTCTGGATCAATTAGCAGTCAATATTTGA

CAGCCTTGCTTATGGCAGCTCCCTTGGCTCTTGGAGATGTTGAAATCGA

GATAATTGATAAATTGATCTCGGTTCCCTATGTTGATATGACTTTGAAG

TTGATGGCACGTTTTGGGGTTACTGTTGAACACAGTGATAGCTGGGATC

GATTTTTAGTTAAAGGAGGTCAAAAGTACAAATCTCCTGGAAACGCTTA

TGTTGAAGGTGATGCTTCAAGTGCTAGTTACTTCCTAGCTGGTGCTGCA

GTCACTGGTGGTACAGTCACCGTAGAAGGTTGTGGGACTAGTAGTTTAC

AGGGAGACGTAAAATTTGCTGAAGTTCTTGAGAAAATGGGTGCTAAAGT

TAGCTGGACAGAGAACAGTGTCACGGTCACTGGACCACCACGAGATTCT

GTAAAAAGTAAACACTTGAAAGCCATTGATGTCAACATGAACAAAATGC

CTGATGTTGCCATGACTCTTGCTGTAGTTGCTCTTTTTGCTGATGGCCC

CACTGCTATAAGAGATGTGGCAAGTTGGAGAGTCAAGGAGACAGAGAGA

ATGATTGCCATCTGCACTGAACTCAGAAAGCTTGGAGCAACAGTTGAGG

AAGGACTTGATTACTGCGTGATCACTCCACCAGAGAAACTAAATATCAC

AGCAATAGACACATACGACGACCACAGGATGGCTATGGCGTTCTCTCTT

GCAGCTTGTTCAGATGTGCCAGTTACCATTAAGGATCCTGGTTGCACCC

GAAAAACTTTCCCAGATTACTTTGAAGTCCTTGAGAGATTTACAAAGCA

CTGA

Cannabis EPSP synthase gene, Cannabis sativa chromosome 2, cs10, whole genome shotgun sequence, Cannabis sativa 3-phosphoshikimate 1-carboxyvinyltransferase 2 (LOC115705599), (SEQ ID NO:40), possible glyphosate resistant mutation target loci indicated in bold underline italics including positions 1790, 1801, 3620, and 3621.

GGTTGGTAAGCCCTCCTACCCTCTTTGAAAATTGAAAGAGAGTCAATGTCGACCTACAGCAG

CAGCATCCATTAACGTTACCATTGCCACCAAAAATCCAACCTTTATTTGTATAGAGAATC

AGAGAAGGTTTGGGTTTCAGAGAGAGAGAGAAGAAGAACAAAAAAATGGCCCAAGTGAGCAA

AATCTGTAGCAATGGAGCTCAAACTATCCTTACTCTCCCAAATATATCTAAGTCTCATACA

CCAAGATCCCTAAATTCAGTTTCGTTGAGATCACCGTTTTTGGGTTCATCTAACTCTTTGAG

TTTGAAGATTGGAACTGAATTTGGGGGTTGTTCTACGGTTGGTAAAGCTATGGCTGGTCCAG

TCATGGCTTCAGCTGTCACAGCGGAGAAGCCTTCAAAGGTACCGGAGATTGTGTTGCAGCCC

ATTAAAGATATCTCTGGCACTGTCAAGTTGCCGGGTTCCAAGTCACTATCGAATCGGATTCT

ACTCCTGGCTGCTCTTTCTGAGGTATATTTCATTTTTTTAAAACGTCAAACATGTATTTTT

GTCGAGGAAGTTTTCTGTATATACAAAGATAAGAGAGTAAAAATATGGAACATCAATACCAA

AATGAACCAAAACTAGGCTAAGCTATCAAATCATGTCATGGTATGCCATACTCTACTTTCCT

ATCTCAAGCTCCACAGCTATAAAATACTATATCGTAATTATTTTGTCAACTGCTTTCATATT

CCTTGTAATTTCCCTCATTCCCACTAAAACTAGTTCCAATGGATTGTGTGGCTGGAAACTGT

AGTTAGTTACATTAGCTAGATCTGAACCATGATCAGCATCGACTGCCCAACTGGTAAACCAT

GTAATTGCATGGAATTCTTCCTTTGTTATCCACAAATTTGAAAAGTATTTTTGAGGTATACA

AAGATTGTGCTTTTTATGAGCAATTTTCTTTTAGTTTTATGTTAAGAGTTTGTAGCGATGGG

-continued

```
ATGTTTTTTTCTAGAAAATGGACAGTAAAGCTTAGCATTTTTACTTTATTGGTGTAAATGA
ATAGTGTTCATTGAAGCTGAACTCATGCCCTTAATTGGGAGGAAAATTGAGAGAAATGGAGT
AAAGTAATATGATATTTTGGTTAAATTCGTAAGAATATGATGGAAATAAAAAATGCAACTCA
ACTGGGTTACTGAAGTTATATTTCTGGTCTCAGTTGTGCTTTTACAACTTTAGTCTAGAGCT
CCACGCTGCGGAGAGATTCGGAGTCCTTACAGTTTATTTTGATAATGATTTATGAGAATTTC
ATAACTCTACGCTTTTGTTACATTATATATGAGGTGTTTCGTTGGTGCATTGTCTCACCTGA
ACTCCCTAAATTTTAGAATGTGGGATTTAGAATGAAGTTATACTATTAGTGTTTGAGTCATC
TAGAATTTGTAGCTGCTCATTCTCCATATACTCTTTCTCTATTTCCTCCCCATATTTTGGCG
CTACTACTTATCTTTACAGTTCATGTTATTTTCATGTACTTGAGTTTTTTGCCCTATAAAT
ATTTTGAGCGGTGGGAAGTAACTGTTTTTTTTGTTATAATTATCCAGGGGACAACTGTTGTG
GACAACTTGTTAGATAGTGATGACATTCACTACATGCTTGGTGCCTTGGAAACCCTTGGTCT
TCGTGTTGAAGCAGACAAGGAAAGCAAACGAGCAATTGTGGAAGGTTGTGCGGGTCAGTTTC
CTGCAGGTAAAGAATCTGTTGACGAAGTTCAACTTTTCCTTGGAAATGCTGGAACAGCAATG
CGTCCACTCACAGCTGCGGTGACTGTTGCTGGTGGAAATGCTAGGTTTGTCTTCATTGCAAT
TGCTTTTGAATATAAAGTACTTCTAATGCAGTGAATTTATGCTCTTGTTTTTCTTACTGGCC
GAGTAGCTCTTACATTTTAGGTAAAGAAAGTCACTTTTGCTAACAACATCACCATTTATACT
TCCCTCTTTACTTTGATGTGGTTATGCTAGAAATTACATGTTGGAAATGAACTAGCACATAT
CATAAATTATTTTGTATGCTGTTATTACATTTTCTCAGTAACCTCTTAACTTCTATATCTCA
GCTACGTACTTGATGGTGTTCCTCGAATGAGAGAAAGACCAATTGGAGATTTGGTGACTGGT
CTTAAGCAGCTTGGTGCAGATGTTGATTGTTTTCATGGTACGGATTGTCCCCCTGTTCGTGT
GCTTGGAAAAGGAGGCCTTCCTGGGGGCAAGGTGAGGCTTGCATTGCTTCTTCTTATTCTTT
TTGGCCATAAAACATCATTGTAATAGTGGTTTTATGTTATGAAATCCATTGACTGGTTTATT
TTTAGGTTGTTGTTTTGCTTTTAAATAAAAACAATATTGTCAAATGATGCATAAGTAGTGAT
TACATCTACATCATTTAATTTATTATCTTAAATGATGACAAACTTCATCATTTTGACTCAGA
ATTATGTAATATTACCCTTTGCAGGTGAAACTTTCTGGATCAATTAGCAGTCAATATTTGAC
AGCCTTGCTTATGGCAGCTCCCTTGGCTCTTGGAGATGTTGAAATCGAGATAATTGATAAAT
TGATCTCGGTTCCCTATGTTGATATGACTTTGAAGTTGATGGCACGTTTTGGGGTTACTGTT
GAACACAGTGATAGCTGGGATCGATTTTTAGTTAAAGGAGGTCAAAAGTACAAGTAGGTTTC
TTCTGAATATAGTTGATAGTATTGTTACATTACATCTGGTTATGTCAAAGAGTAATAAATTG
AAAAATAAAAATCTGTCAGATCTCCTGGAAACGCTTATGTTGAAGGTGATGCTTCAAGTGCT
AGTTACTTCCTAGCTGGTGCTGCAGTCACTGGTGGTACAGTCACCGTAGAAGGTTGTGGGAC
TAGTAGTTTACAGGTATTTTGCTTAGACCTTGAAATCTCTTATTCTTGTACTTGTGTTTACA
TAGAATCTAAGATTAAGTGTATTTACATACATTAACTGGTGTTTAATAAAGGGAGACGTAAA
ATTTGCTGAAGTTCTTGAGAAAATGGGTGCTAAAGTTAGCTGGACAGAGAACAGTGTCACGG
TCACTGGACCACCACGAGATTCTGTAAAAAGTAAACACTTGAAAGCCATTGATGTCAACATG
AACAAAATGCCTGATGTTGCCATGACTCTTGCTGTAGTTGCTCTTTTTGCTGATGGCCCCAC
TGCTATAAGAGATGGTATGTTTTTCCTTAAATTTGTGAGATGGTAAAATGGGGCAGTCGGTT
TGGGTTGGGGTAGATTATCGGTTCTCGTCTGCCATAATAAAAAATAATCTGCTCATTTGCAA
TAAATTTCACAGACACAAAAATGAAACCAATAAAATATTATTTTGTTTAGAGGATTAAATA
CTCATTTCTTGCCTTTCCTAATTCCCAGTGGCAAGTTGGAGAGTCAAGGAGACAGAGAGAAT
GATTGCCATCTGCACTGAACTCAGAAAGGTTAGTTTTTATGCTGTTTTATGTACTTGTTATG
```

```
TCATGCGCCTTGGAATGTAATGGCTGATAGCTATCTGTTCTTATGGGAACAAACATTTCAGC

TTGGAGCAACAGTTGAGGAAGGACCCGATTACTGCGTGATCACTCCACCAGAGAAACTAAAT

ATCACAGCAATAGACACATACGACGACCACAGGATGGCTATGGCGTTCTCTCTTGCAGCTTG

TTCAGATGTGCCAGTTACCATTAAGGATCCTGGTTGCACCCGAAAAACTTTCCCAGATTACT

TTGAAGTCCTTGAGAGATTTACAAAGCACTGAATGAGTATTTATTAACTGGATAGAGAACAA

TAGCATCGGCTACTGTCATTACAACTAAAGCAGTTGGGAGGCAGGCAATCCTTTTCAATTAT

CATGTGTTTGATTTTGGTCGACTGTATTGCAAGTTGAGCTTCTCATTATTATTAAGACTGTA

ATCGTAGTTATTTGTTGTAACTTCTGCAAACCCTTCATGTTATTTTTTCACCCTTCTAATAA

GCCAGTGGGGCAAATTCTATATCTGCTATATGAGCTTGAGTGTAGAGAGAACTTTTGTCAAT

GTATAGGTTTCTAGCAGAAGCACCATCCCTAATATGCTTTATTATAAGAGTTGCTGTGATCG

TGTAGTGTTATTTTATTGAAAGTAACCGACGCATCTCATATTA
```

As used herein, the terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of natural or synthetic origin (which may be single-stranded or double-stranded and may represent the sense or the antisense strand). The polynucleotides may be cDNA or genomic DNA.

As used herein, the term "construct" refers to recombinant polynucleotides including, without limitation, DNA and RNA, which may be single-stranded or double-stranded and may represent the sense or the antisense strand. Recombinant polynucleotides are polynucleotides formed by laboratory methods that include polynucleotide sequences derived from at least two different natural sources or they may be synthetic. Constructs thus may include new modifications to endogenous genes introduced by, for example, genome-editing technologies. Constructs may also include recombinant polynucleotides created using, for example, recombinant DNA methodologies.

The constructs provided herein may be prepared by methods available to those of skill in the art. Notably each of the constructs used or claimed are recombinant molecules and as such do not occur in nature. Generally, the nomenclature used herein and the laboratory procedures utilized in the present invention include molecular, biochemical, and recombinant DNA techniques that are well known and commonly employed in the art. Standard techniques available to those skilled in the art may be used for cloning, DNA and RNA isolation, amplification and purification. Such techniques are thoroughly explained in the literature.

The constructs provided herein may include a promoter operably linked to any one of the polynucleotides described herein. The promoter may be a heterologous promoter or an endogenous promoter associated with the heterologous gene, nucleic acid, or polypeptide of interest.

As used herein, the terms "heterologous promoter," "promoter," "promoter region," or "promoter sequence" refer generally to transcriptional regulatory regions of a gene, which may be found at the 5' or 3' side of the polynucleotides described herein, or within the coding region of the polynucleotides, or within introns in the polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

In some embodiments, the heterologous polynucleotides of interest are operably connected to the promoter. As used herein, a polynucleotide is "operably connected" or "operably linked" when it is placed into a functional relationship with a second polynucleotide sequence. For instance, a promoter is operably linked to a polynucleotide if the promoter is connected to the polynucleotide such that it may effect transcription of polynucleotides. In various embodiments, the polynucleotides may be operably linked to at least 1, at least 2, at least 3, at least 4, at least 5, or at least 10 promoters.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter. Suitable promoters for expression in plants include, without limitation, the 35S promoter of the cauliflower mosaic virus, ubiquitin, tCUP cryptic constitutive promoter, actin, the Rsyn7 promoter, pathogen-inducible promoters, the maize In2-2 promoter, the tobacco PR-1a promoter, glucocorticoid-inducible promoters, estrogen-inducible promoters and tetracycline-inducible and tetracycline-repressible promoters. Other promoters include the T3, T7 and SP6 promoter sequences, which are often used for in vitro transcription of RNA. Those of skill in the art are familiar with a wide variety of additional promoters for use in various cell types. In some embodiments, the heterologous promoter includes a plant promoter, either endogenous to the plant host or heterologous.

Vectors including any of the constructs or polynucleotides described herein are provided. The term "vector" is intended to refer to a polynucleotide capable of transporting another polynucleotide to which it has been linked. In some embodiments, the vector may be a "plasmid," which refers to a circular double-stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome, such as some viral vectors or transposons. Plant mini-chromosomes are also included as vectors. Any suitable vector design known in the art may be used with the explants of the present invention.

Vectors may carry genetic elements, such as those that confer resistance to certain drugs or chemicals. In some embodiments, the vector will additionally include one or more selectable or screenable markers. The selectable or screenable marker may confer upon the plant tissue resistance to an otherwise toxic compound. A number of screenable or selectable marker are known in the art and can be used in the present invention. The screenable marker may be fluorescent (e.g., RFP) or non-fluorescent (e.g., GUS). More than 20 selectable marker genes have been reported in the transformation of higher plants (Komari T, Takakura Y, Ueki J, Kato N, Ishida Y, Hiei Y (2006) Binary vectors and super-binary vectors. In: KanWang (ed.), and *Methods in Molecular Biology*, vol. 343: *Agrobacterium Protocols*, Vol. 1, Second Edition. Humana Press Inc., Totowa, NJ, pp. 15-41). In some embodiments, the selectable or screenable marker is selected from the group consisting of RFP, GUS, aadA, spectinomycin, streptomycin, and imazapyr. In some embodiments, the vector is a DICOTBINARY-19 plasmid. In some embodiments, the vector is a DICOTBINARY-22 plasmid.

In some aspects, provided herein are methods for transforming *Cannabis* using floral dip transformation. Female *Cannabis* flowers are exposed to *Agrobacterium* cultures suitable for flower dip transformation. In some embodiments, Cannabis flowers are submerged in an Agrobacterium culture under vacuum to induce transformation. In some embodiments, the *Agrobacterium* culture comprises *Agrobacterium* comprising the heterologous gene or nucleic acid of interest, a wetting agent, and a carrier. In some embodiments, the heterologous gene or nucleic acid of interest is included on a vector such as the DICOTBINARY-22 vector described herein. Other suitable vectors are known in the art. In some embodiments, the *Agrobacterium* strain is Ar18r12v, although other suitable *Agrobacterium* strains are known and used in the art. In some embodiments, the *Agrobacterium* used is a constitutively active variant or virG mutant of *Agrobacterium* (e.g., N45D mutant *Agrobacterium*). In some embodiments, the carrier is a cell culture medium suitable for the survival of the *Agrobacterium*. In some embodiments, the carrier is 5% sucrose. In some embodiments, the wetting agent is 0.05% silwet L-77. In some embodiments, the *Agrobacterium* culture includes Triton X-100, NP-40, Tween, or combinations thereof. In some embodiments, the *Agrobacterium* culture additionally comprises acetosyringone, galacturonic acid, cinnamic acid, coumarin, vanillin, other phenolic compounds, or combinations thereof. Suitable surfactants for plant floral dip transformations are known in the art. Following application of the *Agrobacterium* culture to the female *Cannabis* flower, the flowers are pollinated with male pollen from a suitable donor plant. In some embodiments, female *Cannabis* flowers are exposed to the *Agrobacterium* culture for at least 1, at least 2, at least 5, at least 10, at least 12, at least 15, at least 16, or at least 18 days before pollination. In some embodiments, the female *Cannabis* flowers are pollinated using a paintbrush.

In some embodiments of the floral dip transformations, DNA is delivered directly to the *Cannabis* ovules. In some embodiments, DNA is complexed with cell penetrating peptides prior to administration to *Cannabis* ovules.

In some aspects, provided herein are methods for transforming *Cannabis* nodes, internodes, leafs, petioles, hypocotyls, and buds. Sanitized and imbibed seeds are plated on non-selective medium (e.g., B5 medium) and grown for approximately 6 weeks or until explants suitable for transformation are formed. Resulting explants are inoculated with a heterologous gene or nucleic acid of interest. In some embodiments, the explants are inoculated using a force treatment as described herein. In some embodiments, the explants are inoculated by sonication with a vector comprising the heterologous gene or nucleic acid of interest. In some embodiment, the vector additionally comprises a selectable markers.

Following inoculation, node and bud explants are co-cultured in a culture medium that supports growth and survival of the node or bud for at least about 4 days. In some embodiments, the culture medium that supports the growth and survival of the node or bud is WCIC INO medium. In some embodiments, the medium additionally comprises nystatin, TBZ, and meta-topolin (mT). Following co-culture of at least about 4 days, the nodes and buds are transferred to a second culture medium suitable for the growth and survival of the nodes or buds. In some embodiments, the second culture medium is hemp node medium described herein in Table 7. In some embodiments, the hemp node medium additionally comprises a selection agent. In some embodiments, the hemp node medium additionally comprises activated charcoal.

Following inoculation, internode, leaf, hypocotyl, and petiole explants are co-cultured in a culture medium that supports growth and survival of the internode, leaf, hypocotyl, or petiole for at least about 4 days. In some embodiments, the culture medium that supports the growth and survival of the internode, leaf, hypocotyl, or petiole is WCIC INO medium. In some embodiments, the medium additionally comprises nystatin, TBZ, meta-topolin (mT), napthylacetic acid (NAA) and GA3. Following co-culture for at least about 4 days, leaf, petiole, hypocotyl, and internode explants are transferred to a second culture medium suitable for the growth and survival of the leaf, petiole, or internode. In some embodiments, the second culture medium is hemp internode medium described herein in Table 12. In some embodiments, the medium additionally includes a selection agent.

In some aspects, provided herein are methods for transforming *Cannabis* pollen or anther cultures. *Cannabis* pollen is harvested by shaking branches of male plants and collecting the pollen. In some embodiments, after harvest and collection, the pollen may be sized by passing the pollen through a sieve (e.g., a #80 sieve). Pollen may be used immediately for transformation, or may be stored prior to use. Pollen may be stored at a temperature between about 4° C. and about 20° C. The pollen may be stored in the presence of a storage medium. In some embodiments, the storage medium is medium suitable for pollen germination. In some embodiments, the storage medium includes boric acid, calcium chloride, potassium phosphate, and water. In some embodiments, the storage medium additionally includes glycerol.

Pollen may be transformed using particle bombardment, high velocity microprojection, microinjection, electroporation, direct DNA uptake, cell-penetrating peptides, silica carbide fibers, nanoparticles, and bacterially-mediated transformation. In some embodiments, pollen is transformed using silica carbide fibers. In some embodiments, pollen is transformed using cell-penetrating peptides. Following transformation, pollen is co-cultured and germinated on medium suitable for the survival of the pollen. The medium may include a suitable selection agent. In some embodiments, transformed pollen is used to pollenate female flowers for rapid generation of transgenic T1 progeny.

In some aspects, provided herein are methods for transforming Cannabis callus tissue or embryogenic suspension cells. In general, Cannabis leaf tissue is cultured on plant medium containing hormones suitable to induce embryogenic calli formation. Embryogenic calli are then transformed using any of the suitable transformation methods as described herein. Calli are then grown a suitable plant medium containing hormones suitable for induction of shooting in the plant. Suspension cells may similarly be transformed in suspension as single cells then subsequently grown into plants using suitable medium including suitable hormones. Suitable medium and hormones are known and described in the art.

The present invention has been described in terms of one or more preferred embodiments, and it should be appreciated that many equivalents, alternatives, variations, and modifications, aside from those expressly stated, are possible and within the scope of the invention.

Example 1

The embodiment described here demonstrates *Cannabis* meristem explant transformation.

Seeds of variety Elektra x Chardonnay were surface sanitized with 20% Clorox for 5 minutes, rinsed, and sat for ~2 hrs before overnight imbibition with WCIC Bean Germination Media (BGM).

TABLE 1

| WCIC Bean Germination Media (BGM) | |
|---|---|
| Ingredients and Notes | Amount to add per liter (grams) |
| Phytotechnology Laboratories WPM L449 | 2.41 |
| Sucrose | 20 |
| pH to 5.8 with 1N KOH and autoclave | |
| Add the following prior to use: | |
| Captan fungicide (50WP) | 0.06 |
| Bravo fungicide (Daconil) (82DP) | 0.03 |
| Cefotaxime (100 mg/ml) | 1.25 ml |

The next day, meristem explants were aseptically excised from seed and incubated for approximately 2 hrs in 20% PEG4000 with 60 mg/L Captan and 30 mg/L Bravo fungicides. Explants were then rinsed and inoculated with Agrobacterium strain Ar18r12v harboring the binary plasmid DICOTBINARY-19. During inoculation, explants were exposed to 20 seconds of sonication at ~45 kHz. Explants were co-cultured in either 1.75 ml or 2.0 ml WCIC INO media with 100 uM acetosyringone, 50 mg/L nystatin, 10 mg/L TBZ, and 95 uM lipoic acid for 4 days at 23 C 16/8 photoperiod. Thidiazuron (TDZ) was added to some co-culture treatments at 1 mg/L.

TABLE 2

| WCIC INO media | |
|---|---|
| Ingredients and Notes | Amount to add per liter (grams) |
| Gamborg B5 Phytotechnology Laboratories G398 | 1.284 |
| Glucose | 30 |
| MES | 2.8 |
| pH to 5.4 with 1N KOH and autoclave | |

After 4 days of co-culture, transient GUS expression was evaluated in explants. Explants were then transferred to either 10 mg/L spectinomycin or 150 mg/L spectinomycin WCIC Gamborg B5 medium (Table 3) for selection. Explants on 10 mg/L spectinomycin B5 were transferred to 150 mg/L spectinomycin B5 approximately 1 week later, and then explants from all treatments were transferred to 50 mg/L spectinomycin B5 1 month later. Additional transfers have been made with explants remaining green on spectinomycin. A summary of this experiment is given in Table 4.

TABLE 3

| WCIC Gamborg B5 Medium | |
|---|---|
| Ingredients and Notes | Amount to add per liter (grams) |
| Phytotechnology Laboratories B5 salts G398 | 2.41 |
| Sucrose | 20 |
| Cleary's 3336 (50WP) | 0.06 |
| Ca Gluconate | 1.29 |
| pH to 5.8 with 1N KOH | |
| Phytagel | 3.50 |
| autoclave | |
| Add the following fresh before use: | |
| Timetin (150 mg/ml stock) | Use 1 mL per Liter (150 mg/L) |
| Cefotaxime (100 mg/ml stock) | Use at 2 ml per Liter (200 mg/L) |
| Carbenicillin (100 mg/ml stock) | Use at 4 ml per Liter (400 mg/L) |
| Selective Agent | as needed |

TABLE 4

Description and summary of *Cannabis* meristem explant transformation experiments.

| Co-Culture conditions | Experiment ID | # embryos to Selection | Selection Media | 2nd media | 3rd media | Notes | Notes |
|---|---|---|---|---|---|---|---|
| Filter paper in plantcon with 1.75 ml INO + 50 ppm nystatin + 10 ppm TBZ + lipoic acid; 23 C. 16/8 photoperiod | Hemp 3/22-1A | 7 | 10 ppm spec B5; 28 C. 16/8 photoperiod; | 150 ppm spec B5; 28 C. 16/8 photoperiod; | 50 ppm spec B5; 28 C. 16/8 photoperiod; | 1 greening explant transferred to non-selective BRM | |

TABLE 4-continued

Description and summary of *Cannabis* meristem explant transformation experiments.

| Co-Culture conditions | Experiment ID | # embryos to Selection | Selection Media | 2nd media | 3rd media | Notes | Notes |
|---|---|---|---|---|---|---|---|
| Filter paper in plantcon with 1.75 ml INO + 50 ppm nystatin + 10 ppm TBZ + lipoic acid; 23 C. 16/8 photoperiod | Hemp 3/22-1B | 4 | 150 ppm spec B5; 28 C. 16/8 photoperiod; | NA | 50 ppm spec B5; 28 C. 16/8 photoperiod; | 1 greening explant transferred to non-selective BRM | |
| Filter paper in plantcon with 2 ml INO + 50 ppm nystatin + 10 ppm TBZ + lipoic acid; 23 C. 16/8 photoperiod | Hemp 3/22-2A | 9 | 10 ppm spec B5; 28 C. 16/8 photoperiod; | 150 ppm spec B5; 28 C. 16/8 photoperiod; | 50 ppm spec B5; 28 C. 16/8 photoperiod; | 1 greening explant transferred to 10 ppm spec B5 | |
| Filter paper in plantcon with 2 ml INO + 50 ppm nystatin + 10 ppm TBZ + lipoic acid; 23 C. 16/8 photoperiod | Hemp 3/22-2B | 10 | 150 ppm spec B5; 28 C. 16/8 photoperiod; | NA | 50 ppm spec B5; 28 C. 16/8 photoperiod; | 1 chimeric RFP+ explant (primary leaves) transferred to B5 | 1 greening explant transferred to non-selective BRM |
| Filter paper in plantcon with 1.75 ml INO + 50 ppm nystatin + 10 ppm TBZ + lipoic acid + 1 ppm TDZ; 23 C. 16/8 photoperiod | Hemp 3/22-3A | 9 | 10 ppm spec B5; 28 C. 16/8 photoperiod; | 150 ppm spec B5; 28 C. 16/8 photoperiod; | 50 ppm spec B5; 28 C. 16/8 photoperiod; | | |
| Filter paper in plantcon with 1.75 ml INO + 50 ppm nystatin + 10 ppm TBZ + lipoic acid + 1 ppm TDZ; 23 C. 16/8 photoperiod | Hemp 3/22-3B | 10 | 150 ppm spec B5; 28 C. 16/8 photoperiod; | NA | 50 ppm spec B5; 28 C. 16/8 photoperiod; | 1 chimeric RFP + explant (primary leaves) transferred to B5 | 4 greening explant transferred to non-selective BRM; GUS positive leaf imaged |
| Filter paper in plantcon with 2 ml INO + 50 ppm nystatin + 10 ppm TBZ + lipoic acid + 1 ppm TDZ; 23 C. 16/8 photoperiod | Hemp 3/22-4A | 9 | 10 ppm spec B5; 28 C. 16/8 photoperiod; | 150 ppm spec B5; 28 C. 16/8 photoperiod; | 50 ppm spec B5; 28 C. 16/8 photoperiod; | RFP positive shoot imaged | |
| Filter paper in plantcon with 2 ml INO + 50 ppm nystatin + 10 ppm TBZ + lipoic acid + 1 ppm TDZ; 23 C. 16/8 photoperiod | Hemp 3/22-4B | 12 | 150 ppm spec B5; 28 C. 16/8 photoperiod; | NA | 50 ppm spec B5; 28 C. 16/8 photoperiod; | 5 greening explants transferred to 10 ppm spec B5 | |

Stable RFP (tdTomato) was imaged several explants 3 weeks after inoculation, but was confined primarily to primary leaves and cotyledonary remnants. The stable RFP signal in the chimeric plantlet that appeared to be from new growth was from treatment 4A (treatment bolded in Table 4—2 ml co-culture volume with TDZ, and initial transfer to 10 mg/L spectinomycin B5), shown again in FIG. 1. This plant did not survive tissue culture, which may have been result of its chimerism in response to selection, or possibly non-optimal media conditions.

Figure 16:
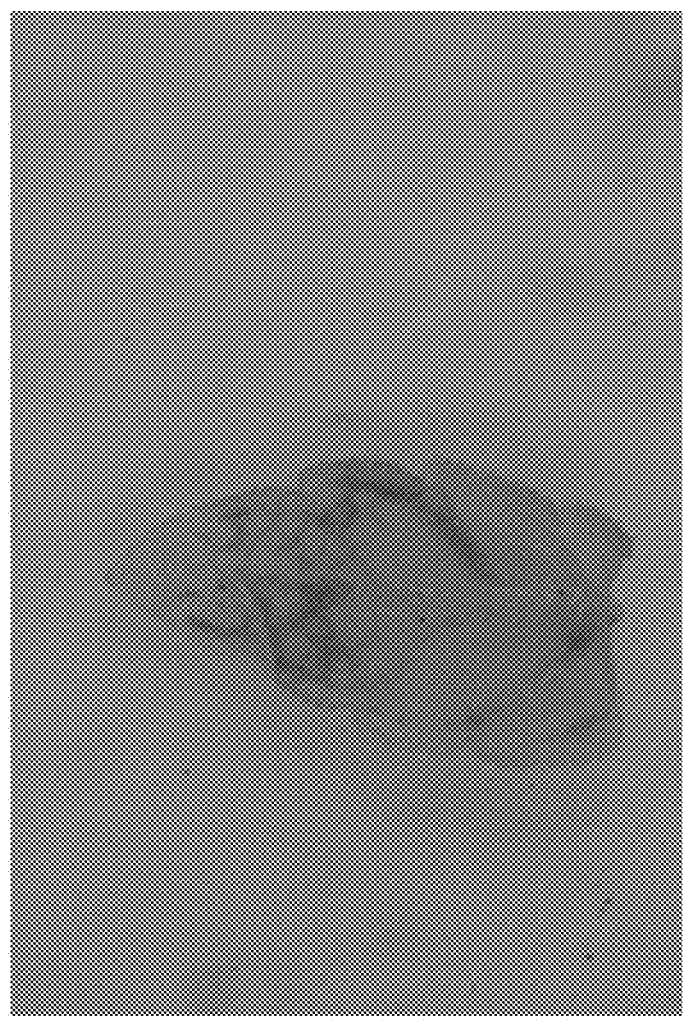
FIG. 16 shows stable GUS expression in a plantlet derived from the treatment Hemp 3/22-3B described in Example 1. One of the leaves in a plantlet transferred to non-selective BRM expressed GUS in leaf stably.

We have also observed stable GUS expression in a plantlet derived from this experiment in treatment Hemp 3/22-3B. One of the leaves in a plantlet transferred to non-selective BRM expressed GUS in leaf stably. The leaf shown in FIG. 16 was imaged 2 months after inoculation after clearing with 70% ethanol.

Figure 2:
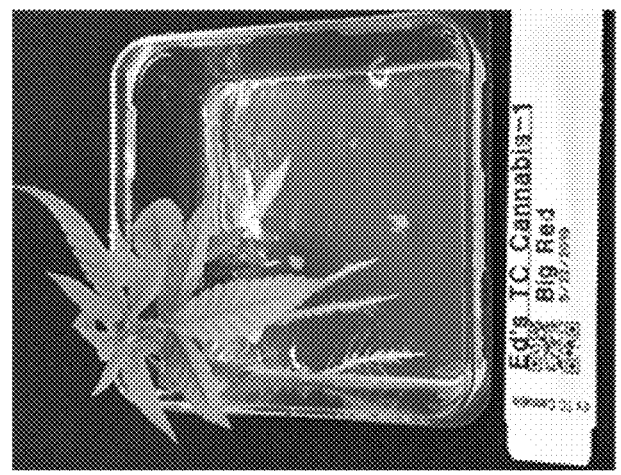
FIG. 2 shows a non-transgenic *Cannabis* plant derived from meristem explant in tissue culture.

The non-inoculated control meristem explant was sent to the greenhouse as a proof of concept of tissue culture (TC) regeneration of a plant from a meristem explant (rooted on non-selective B5 media). See FIG. 2.

Additional experiments with additional varieties of *Cannabis* inoculated with Ar18r12v/DICOTBINARY-19 and a 4 day co-culture are outlined in Table 5. The co-culture volume was increased as we noted in the prior tests explants were very dry post co-culture. Some of these experiments used meta-topolin in co-culture, which has been demonstrated to encourage propagation in *Cannabis* nodal cultures (H. Lata et al./Journal of Applied Research on Medicinal and Aromatic Plants 3 (2016) 18-26); some used a full-strength formulation of B5 media for selection; and some used an MS-based selection media with meta-topolin (mT) based on Lata 2016 but without activated charcoal.

TABLE 5

Description and summary of follow-up experiments with *Cannabis* meristem explants.

| *Cannabis sativa* Genotype/ Line | Comments | Experiment ID | Strain | Binary | # embryos to Selection | Notes |
|---|---|---|---|---|---|---|
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ; 23 C. 16/8 photoperiod | Hemp 5/9-1 | Ar18r12v | DICOT-BINARY-19 | 35 | 10 ppm spec 100% B5; 28 C. 16/8 photoperiod; |
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ + 1 ppm meta-topolin (mT); 23 C. 16/8 photoperiod | Hemp 5/9-2 | Ar18r12v | DICOT-BINARY-19 | 25 | 10 ppm spec 100% B5; 28 C. 16/8 photoperiod; |
| Fiber Hemp | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ; 23 C. 16/8 photoperiod | Hemp 5/9-3 | Ar18r12v | DICOT-BINARY-19 | 21 | 10 ppm spec 100% B5; 28 C. 16/8 photoperiod; |
| Fiber Hemp | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ + 1 ppm meta-topolin (mT); 23 C. 16/8 photoperiod | Hemp 5/9-4 | Ar18r12v | DICOT-BINARY-19 | 12 | 10 ppm spec 100% B5; 28 C. 16/8 photoperiod; |
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ 1 ppm TDZ; 23 C. 16/8 photoperiod | Hemp 5/16-1 | Ar18r12v | DICOT-BINARY-19 | 59 | 10 ppm spec 100% B5; 28 C. 16/8 photoperiod; |
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper on top of semisolid INO (8 g/L agarose I) + 60 ppm Cleary's + 1 ppm TDZ; 23 C. 16/8 photoperiod | Hemp 5/16-2 | Ar18r12v | DICOT-BINARY-19 | 19 | 10 ppm spec 100% B5; 28 C. 16/8 photoperiod; |
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ 1 ppm TDZ; 23 C. 16/8 photoperiod | Hemp 5/30-1 | Ar18r12v | DICOT-BINARY-19 | 5 | non-selective hemp node media (minus activated charcoal) |
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ 1 ppm TDZ; 23 C. 16/8 photoperiod | Hemp 5/30-2 | Ar18r12v | DICOT-BINARY-19 | 36 | 10 ppm sec hemp node media (minus activated charcoal) |
| Honey Gold 3WS | Hand excised from seed surface sanitized in 20% Clorox 5 min; rinsed; imbibed for ~20 h in BGM; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ + 1 ppm TDZ; 23 C. 16/8 photoperiod | Hemp 5/30-3 | Ar18r12v | DICOT-BINARY-19 | 43 | 50 ppm sec hemp node media (minus activated charcoal) |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ + 1 ppm TDZ; 23 C. 16/8 photoperiod | Hemp 6/6-1 | Ar18r12v | SOYTEST-2 | 36 | 50 ppm sec hemp node media (minus activated charcoal) |

TABLE 5-continued

Description and summary of follow-up experiments with *Cannabis* meristem explants.

| *Cannabis sativa* Genotype/ Line | Comments | Experiment ID | Strain | Binary | # embryos to Selection | Notes |
|---|---|---|---|---|---|---|
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 2 min 45 kHz; incubated 30 min, inoculum removed; explants co-cultured on filter paper in plantcon with 2.5 ml INO + 60 ppm Cleary's + 50 ppm nystatin + 10 ppm TBZ + 1 ppm TDZ; 23 C. 16/8 photoperiod | Hemp 6/6-2 | Ar18r12v | SOYTEST-2 | 36 | 50 ppm sec hemp node media (minus activated charcoal) |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 50 ppm nystatin + 10 ppm TBZ + 1 ppm TDZ; 23 C. 16/8 photoperiod | Hemp 6/13-1 | Ar18r12v | SOYTEST-2 | 44 | 50 ppm sec hemp node media (minus activated charcoal) |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 2 min 45 kHz; incubated 30 min, inoculum removed; explants co-cultured on filter paper in plantcon with 2.5 ml INO + 50 ppm nystatin + 10 ppm TBZ + 1 ppm TDZ; 23 C. 16/8 photoperiod | Hemp 6/13-2 | Ar18r12v | SOYTEST-2 | 45 | 50 ppm sec hemp node media (minus activated charcoal) |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ; 23 C. 16/8 photoperiod | Hemp 6/20-1A | Ar18r12v | SOYTEST-2 | 20 | 10 ppm sec B5; 28 C. 16/8 photocopied; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ; 23 C. 16/8 photoperiod | Hemp 6/20-1B | Ar18r12v | SOYTEST-2 | 10 | 10 ppm sec node-AC; 28 C. 16/8 photocopied; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ; 23 C. 16/8 photoperiod | Hemp 6/20-1C | Ar18r12v | SOYTEST-2 | 10 | 50 ppm sec B5; 28 C. 16/8 photocopied; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 60 ppm Cleary's + 50 ppm nystatin + 10 ppm TBZ; 23 C. 16/8 photoperiod | Hemp 6/20-1D | Ar18r12v | SOYTEST-2 | 10 | 50 ppm strep node-AC; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 1 ppm TDZ, 60 ppm Cleary's + 50 ppm nystatin + 10 ppm TBZ; 23 C. 16/8 photoperiod | Hemp 6/20-2A | Ar18r12v | SOYTEST-2 | 10 | 10 ppm spec B5; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 1 ppm TDZ, 60 ppm Cleary's + 50 ppm nystatin + 10 ppm TBZ; 23 C. 16/8 photoperiod | Hemp 6/20-2B | Ar18r12v | SOYTEST-2 | 10 | 10 ppm spec node-AC; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 1 ppm TDZ, 60 ppm Cleary's + 50 ppm nystatin + 10 ppm TBZ; 23 C. 16/8 photoperiod | Hemp 6/20-2C | Ar18r12v | SOYTEST-2 | 10 | 50 ppm spec B5; 28 C. 16/8 photoperiod; |

TABLE 5-continued

Description and summary of follow-up experiments with *Cannabis* meristem explants.

| *Cannabis sativa* Genotype/ Line | Comments | Experiment ID | Strain | Binary | # embryos to Selection | Notes |
|---|---|---|---|---|---|---|
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.5 ml INO + 1 ppm TDZ, 60 ppm Cleary's + 50 ppm nystatin + 10 ppm TBZ; 23 C. 16/8 photoperiod | Hemp 6/20-2D | Ar18r12v | SOYTEST-2 | 10 | 50 ppm strep node-AC; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.25 ml INO + 60 ppm Cleary's + 50 ppm nystatin + 10 ppm TBZ + 1 ppm TDZ; 23 C. 16/8 photoperiod | Hemp 6/27-1 | GV3101 | SOYTEST-2 | 48 | 50 ppm spec meristem regeneration; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.25 ml INO + 60 ppm Cleary's + 50 ppm nystatin + 10 ppm TBZ + 1 ppm TDZ; 23 C. 16/8 photoperiod | Hemp 6/27-2 | GV3101 | SOYTEST-2 | 36 | 50 ppm spec meristem regeneration with 0.5 ppm MT; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper in plantcon with 2.25 ml INO + 60 ppm Cleary's + 1 ppm TDZ; 23 C. 16/8 photoperiod | Hemp 7/3-1 | Ar18r12v | SOYTEST-2 | 83 | 10 ppm spec meristem regeneration; 28 C. 16/8 photoperiod; |
| Honey Gold 3WS | Hand excised from seed surface sanitized in 20% Clorox 5 min; rinsed; imbibed for ~20 h in BGM at 37 C.; explants placed in 20% PEG4000 with Captan/Bravo for 1.5-2.5 h, rinsed, inoculated and sonicated 20 s 45 kHz; incubated 30 min, inoculum removed; explants co-cultured on filter paper on semisolid INO (8 g/L agarose I) + 60 ppm Cleary's 1 ppm TDZ; 23 C. 16/8 photoperiod | Hemp 7/8-1 | Ar18r12v | SOYTEST-2 | 48 | 50 ppm spec meristem regeneration with 0.5 ppm mT; 28 C. 16/8 photoperiod; |

TABLE 6

WCIC TRUE Gamborg B5 Media

| Ingredients and Notes | Amount to add per liter (grams) |
|---|---|
| Phytotechnology Laboratories B5 salts G398 | 3.21 |
| Sucrose | 20 |
| Cleary's 3336 (50WP) | 0.06 |
| Ca Gluconate | 1.29 |
| pH to 5.8 with 1N KOH | |
| Phytagel | 3.50 |
| autoclave | |
| Add the following fresh before use: | |
| Timetin (150 mg/ml stock) | Use 1 mL per Liter (150 mg/L) |
| Cefotaxime (100 mg/ml stock) | Use at 2 ml per Liter (200 mg/L) |
| Carbenicillin (100 mg/ml stock) | Use at 4 ml per Liter (400 mg/L) |
| Selective Agent | as needed |

TABLE 7

WCIC Hemp Node Media (modified from Lata 2016)

| Ingredients and Notes | Amount to add per liter (grams) |
|---|---|
| MS Salts complete with vitamins (PhytoTech M519) | 4.43 |
| Sucrose | 30 |
| Cleary's 3336 | 0.06 |
| pH to 5.7 with 1N KOH | |
| Agar (Sigma A7921) | 8 |
| autoclave | |
| Meta-topolin (mT) (1 mg/ml) | 0.5 ml |
| Carbenicillin (200 mg/ml) | 1.25 ml |
| Cefotaxime (100 mg/ml) | 2 ml |
| Selection | as needed |

Figure 3:
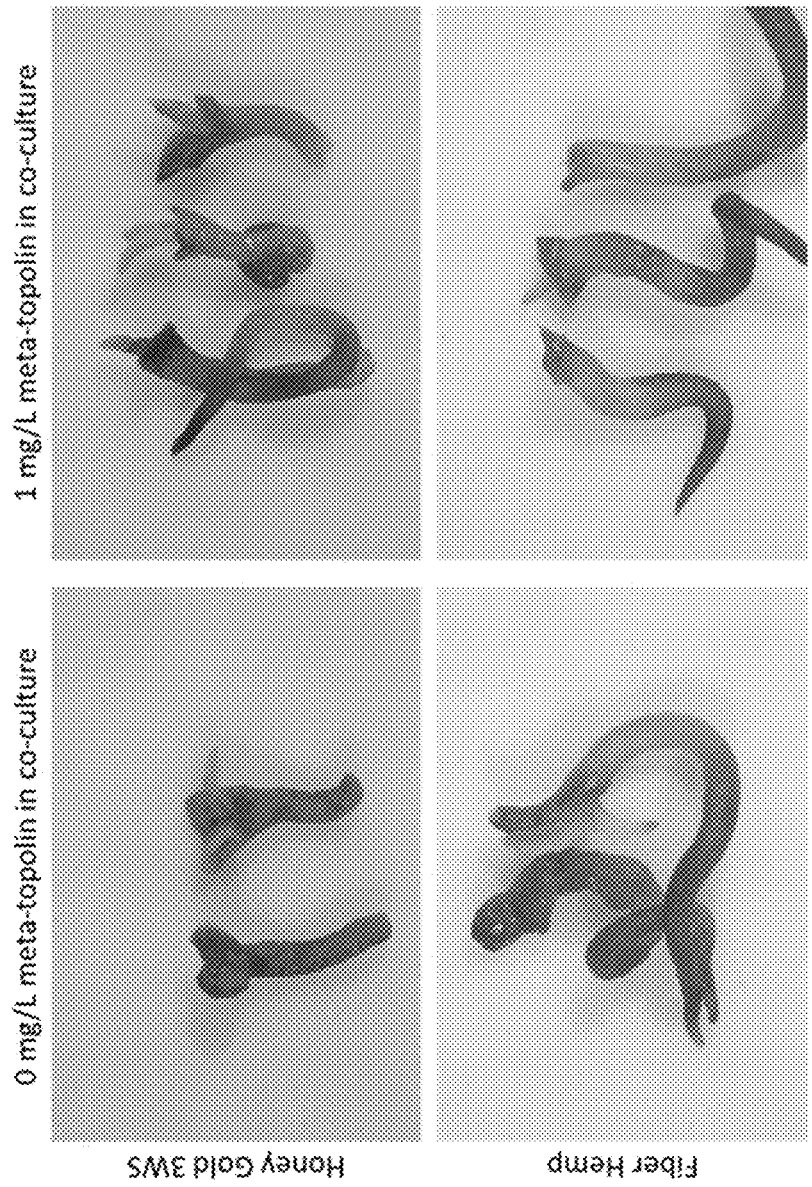
FIG. 3 shows transient GUS expression in *Cannabis* meristem explants varieties Honey Gold 3WS and Fiber Hemp inoculated with Ar18r12v/DICOTBINARY-19.
Figure 4:
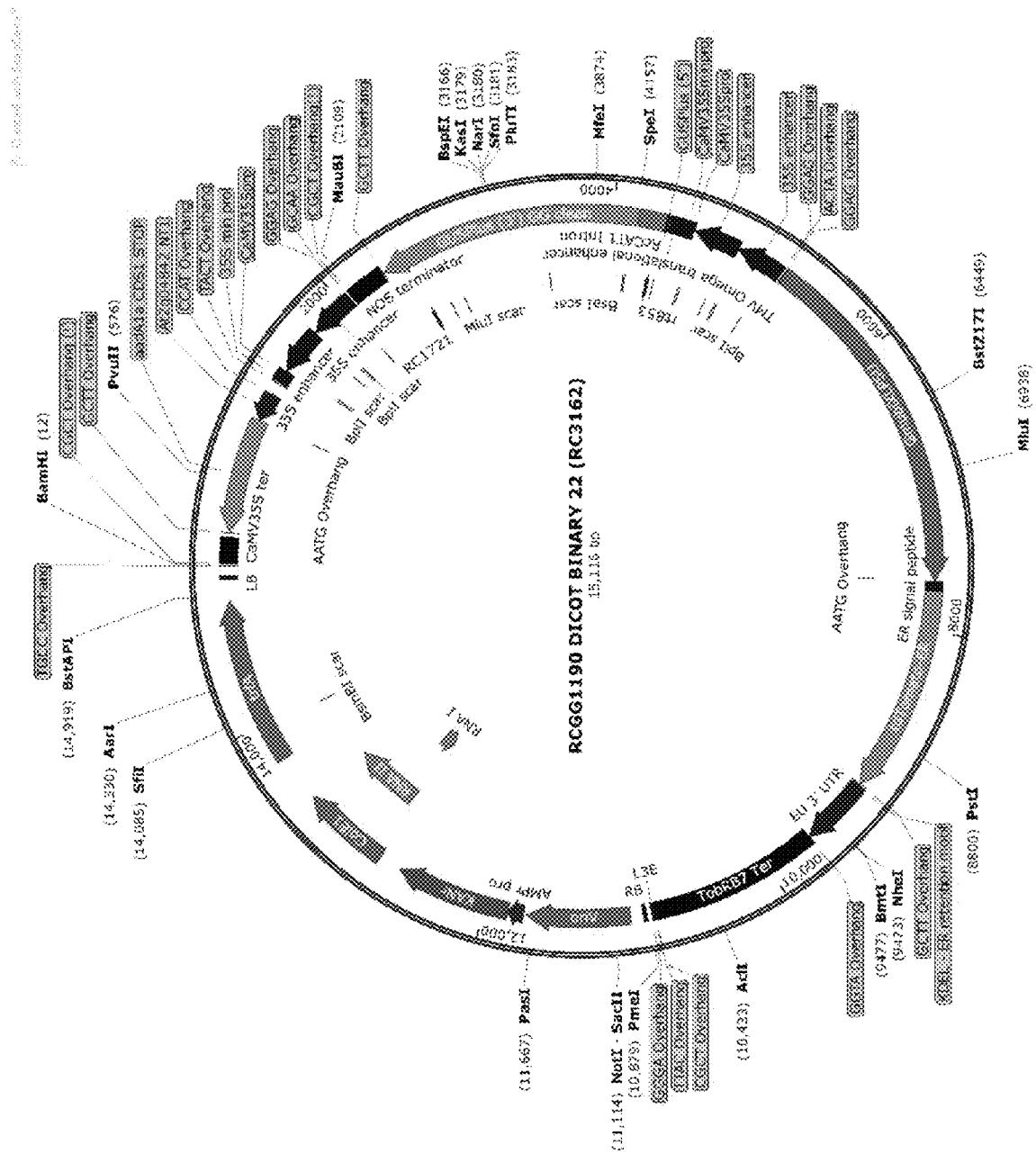
FIG. 4 shows the plasmid map of the DICOTBINARY-22 vector.

We did obtain strong GUS transients using both *Cannabis* varieties Honey Gold 3WS and the Fiber Hemp (in addition to the transients shown for Elektra x Chardonnay in initial disclosure). See FIG. 3.

Figure 17:
FIG. 17 shows *Cannabis* seeds imbibed at 37° C.

Additionally, *Cannabis* seeds were also imbibed at 37° C. to facilitate excision of the meristem explants. With an overnight imbibition at 37° C. the radical begins to emerge from the seed which makes a natural crack in the hard seed coat. This makes isolating the *Cannabis* mature embryo/meristem explant easier. See FIG. 17.

It is also possible to mechanically excise the *Cannabis* meristem explants from the seen. 10 g *Cannabis* seed from the Fiber variety were surface sterilized with 20% bleach solution for 5 minutes, then rinsed with sterile distilled water for 2 minutes. Seed were then imbibed in sterile distilled water at 37 degrees C. for approximately 24 hours. Seed was then rinsed with sterile distilled water for 2 minutes and weighed (collected rehydrated weight was 18 grams). Seed was then split into two 9 gram samples and spread on sterile filter paper in petri dishes and dried in laminar flow hood. One sample was removed 24 hrs later, the other 49 hours later. The collected dry weight of each sample was 4.8 grams.

A portion of this dry hemp seed from the 49 hour dried material was used for machine excision experiments. Seed were placed through a Perten Instruments Laboratory Mill 3310 using seven different gap settings (0 to 6, smallest to largest gap) with 20 seeds per gap setting. Ground material was collected and embryonic parts were counted under a microscope. While the Perten Lab mill was used for these examples, excision of embryos and explants can be performed using and dry mill or equivalent instrumentation known in the art, for example, roller mills, hammer mills, and bladed mills or other suitable means described herein. Equivalent wet mill processing is also envisioned.

TABLE 8

Embryonic parts produced using various gap setting on the Perten Instruments Laboratory Mill 3310

| Gap Setting | Embryonic Parts Produced |
| --- | --- |
| 6 | 20 |
| 5 | 14 |
| 4 | 14 |
| 3 | 5 |
| 2 | 3 |
| 1 | 4 |
| 0 | 0 |

Figure 18:
FIG. 18 shows embryonic parts produced by mechanical excision.

Further experimentation will be carried out using gap setting 6 for grinding hemp varieties. Following embryonic part production, regeneration of the embryonic material will be checked on non-selective medium. Embryonic parts generated using the gap 6 setting on Perten is shown in FIG. 18.

Additionally, MS-based medium with or without meta-topolin may be used with meristem explants. When TDZ is used in co-culture with Agrobacterium, the use of meta-topolin during selection/regeneration may not be necessary.

TABLE 9

Hemp Meristem Regeneration Medium

| Ingredients and Notes | Amount to add per liter (grams) |
| --- | --- |
| MS Salts complete with vitamins (PhytoTech M519) | 4.43 |
| Sucrose | 30 |
| Cleary's 3336 | 0.06 |
| pH to 5.7 with 1N KOH | |
| Agar (Sigma A7921) autoclave | 8 |
| Meta-topolin (mT) (1 mg/ml) | as needed |
| Carbenicillin (100 mg/ml) | 2 ml |
| Cefotaxime (100 mg/ml) | 2 ml |
| Timetin (150 mg/ml) | 1 ml |
| Selection | as needed |

Figure 19:
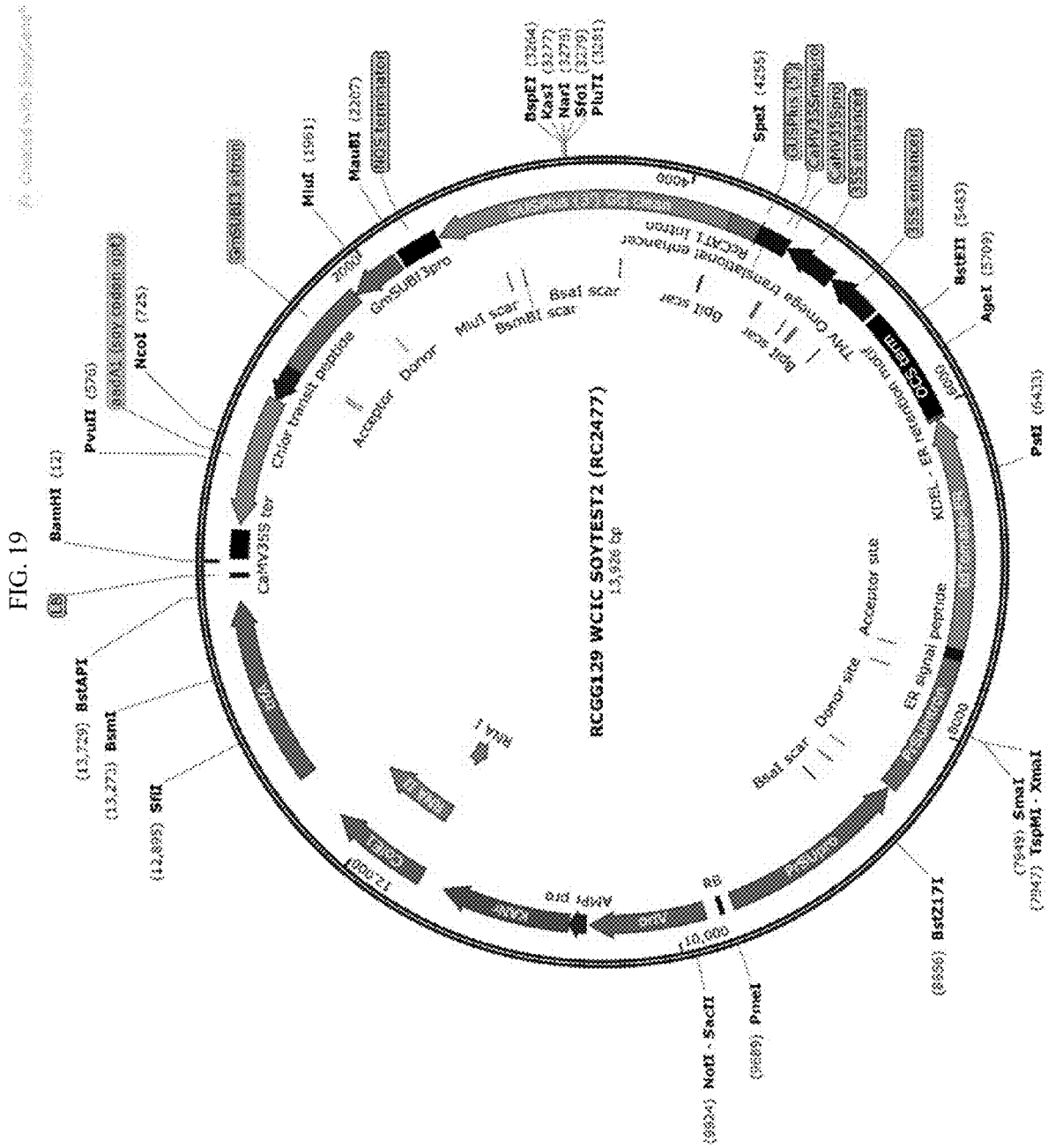
FIG. 19 shows the plasmid map of control binary construct SOYTEST-2.

Additional control binary constructs have also been testing including SOYTEST-2. SOYTEST-2 has a different promoter driving tdTomato to test impacts on RFP visualization (DICOTBINARY-19 uses the *Glycine max* Ubiquitin 3 XL promoter driving tdTomato, where SOYTEST-2 uses *Pinus radiata* Super Ubiquitin promoter driving tdTomato). See FIG. 19.

Figure 20:
FIG. 20 shows positive GUS transients in *Cannabis* meristem explants (3WS variety) using SOYTEST-2 in both the Ar18r12v (left) and GV3101 (right) strains of *Agrobacterium*, demonstrating transfection of *Cannabis* meristems using disarmed strains of both *Agrobacterium rhizogenes* (Ar18r12v) and *Agrobacterium tumefaciens* (GV3101).

We have obtained positive GUS transients in *Cannabis* meristem explants (3WS variety) using SOYTEST-2 in both the Ar18r12v and GV3101 strains of *Agrobacterium* (see FIG. 20), demonstrating transfection of *Cannabis* meristems using disarmed strains of both *Agrobacterium rhizogenes* (Ar18r12v) and *Agrobacterium tumefaciens* (GV3101).

Figure 21:
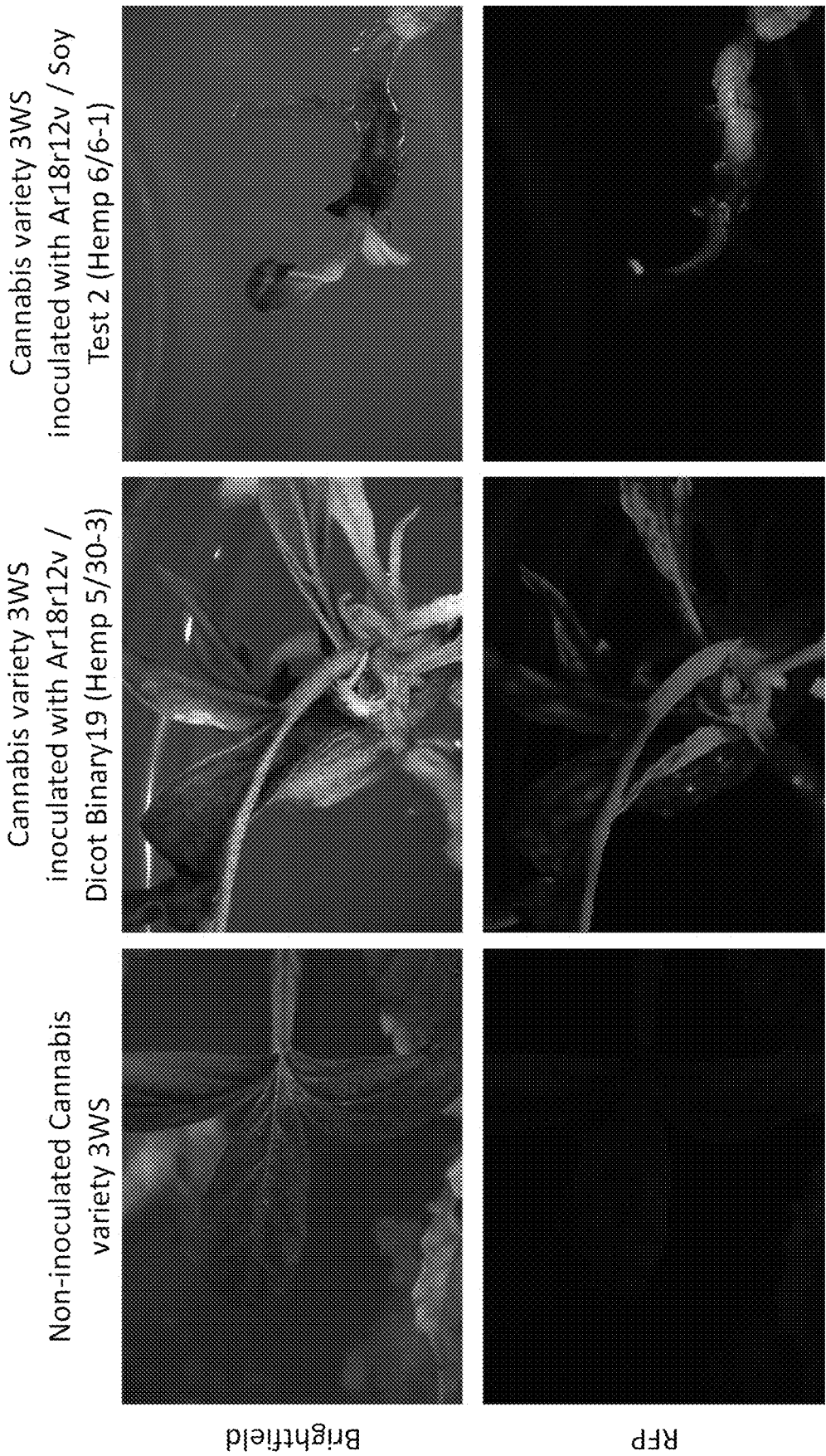
FIG. 21 additional stable RFP expressing *Cannabis* (Plant WP421-1) from experiments in the Honey Gold 3WS variety. The plantlet in the center is rooting on 50 mg/L streptomycin hemp node media (after being on 50 mg/L spectinomycin hemp node media for approximately 1 month).
Figure 22:
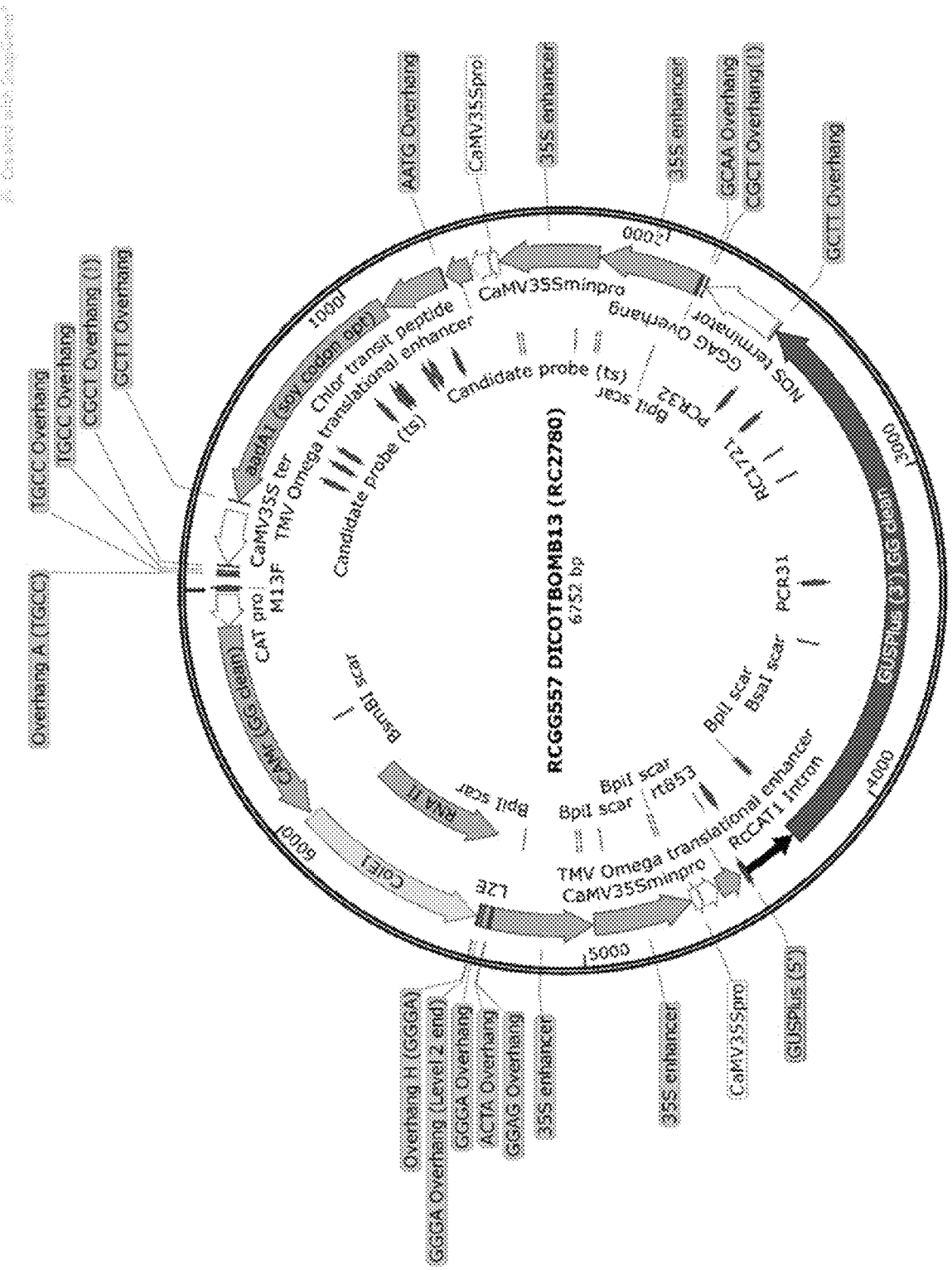
FIG. 22 shows the plasmid map of the DICOTBOMB-13 vector.

We have obtained additional stable RFP expressing *Cannabis* from experiments in the Honey Gold 3WS variety. The plantlet in the center of FIG. 21 (*Cannabis* plant WP421-1) is rooting on 50 mg/L streptomycin hemp node media (after being on 50 mg/L spectinomycin hemp node media for approximately 1 month).

Figure 27:
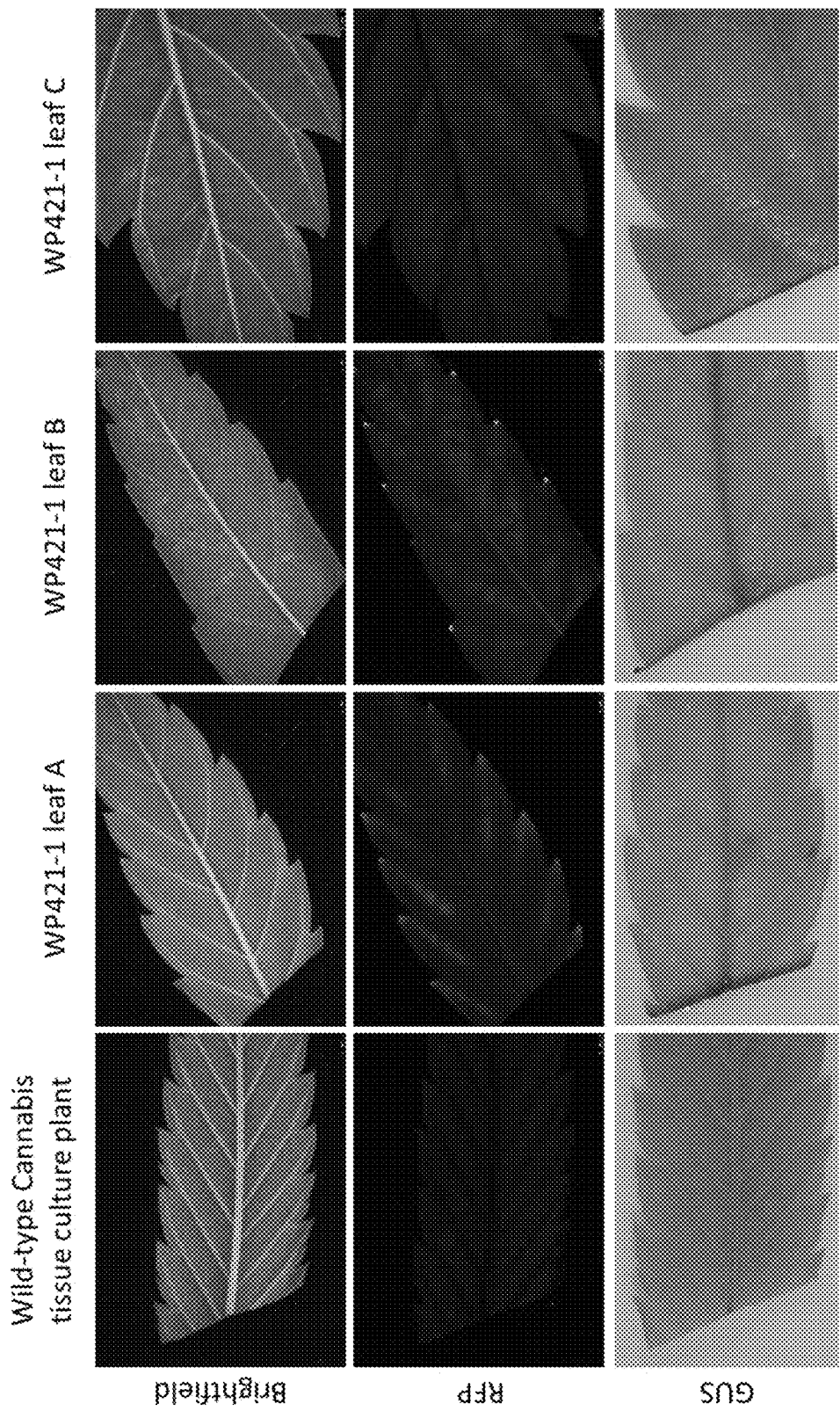
FIG. 27 shows stable RFP and GUS expression in leaves of T0 *Cannabis* plant WP421-1 derived from meristem transformation.
Figure 28:
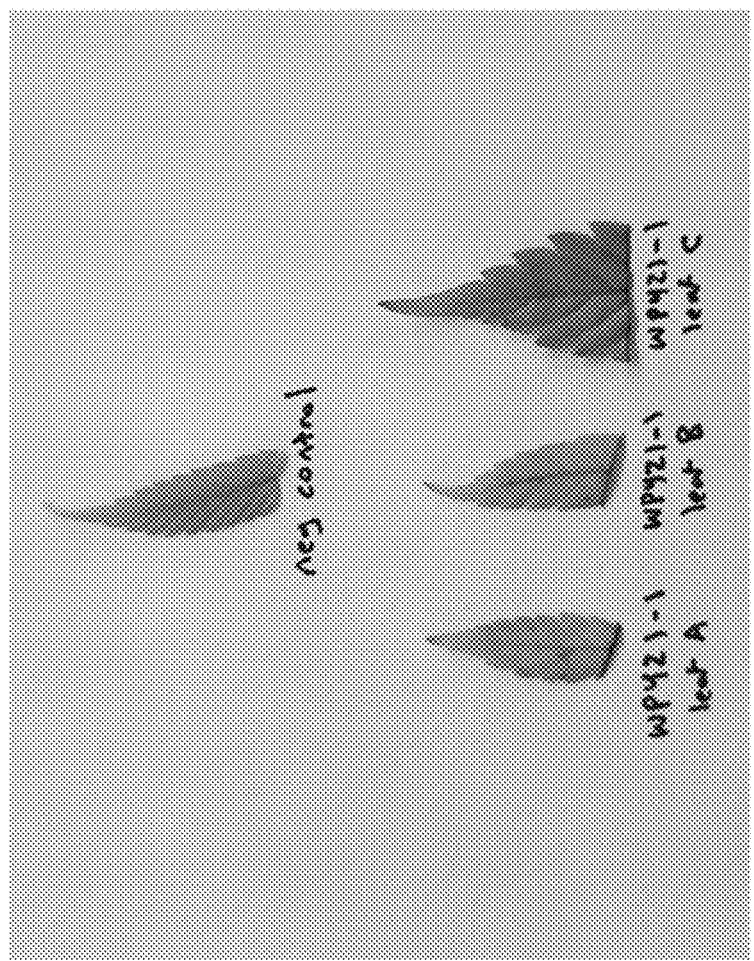
FIG. 28 shows stable GUS expression of leaves of T0 *Cannabis* plant WP421-1 derived from meristem transformation.
Figure 31:
FIG. 31 shows transgenic T0 plant WP421-1 after 7 weeks in the greenhouse.

Plant WP421-1 was transferred to the greenhouse and imaged the day of transfer, approximately 4 weeks later (FIG. 26), and approximately 7 weeks later (FIG. 31). Three leaves from WP421-1 were sampled after it had been in greenhouse for 4 weeks. Two of the three leaves were stably expressing RFP (FIG. 27), while all three were stable expressing GUS (FIGS. 27 and 28). RFP expression was relatively weaker than when we initially sent the plant, which is likely due to tissue age. That all three randomly selected leaves are stably expressing GUS is a good indicator WP421-1 is not overly chimeric.

Figure 32:
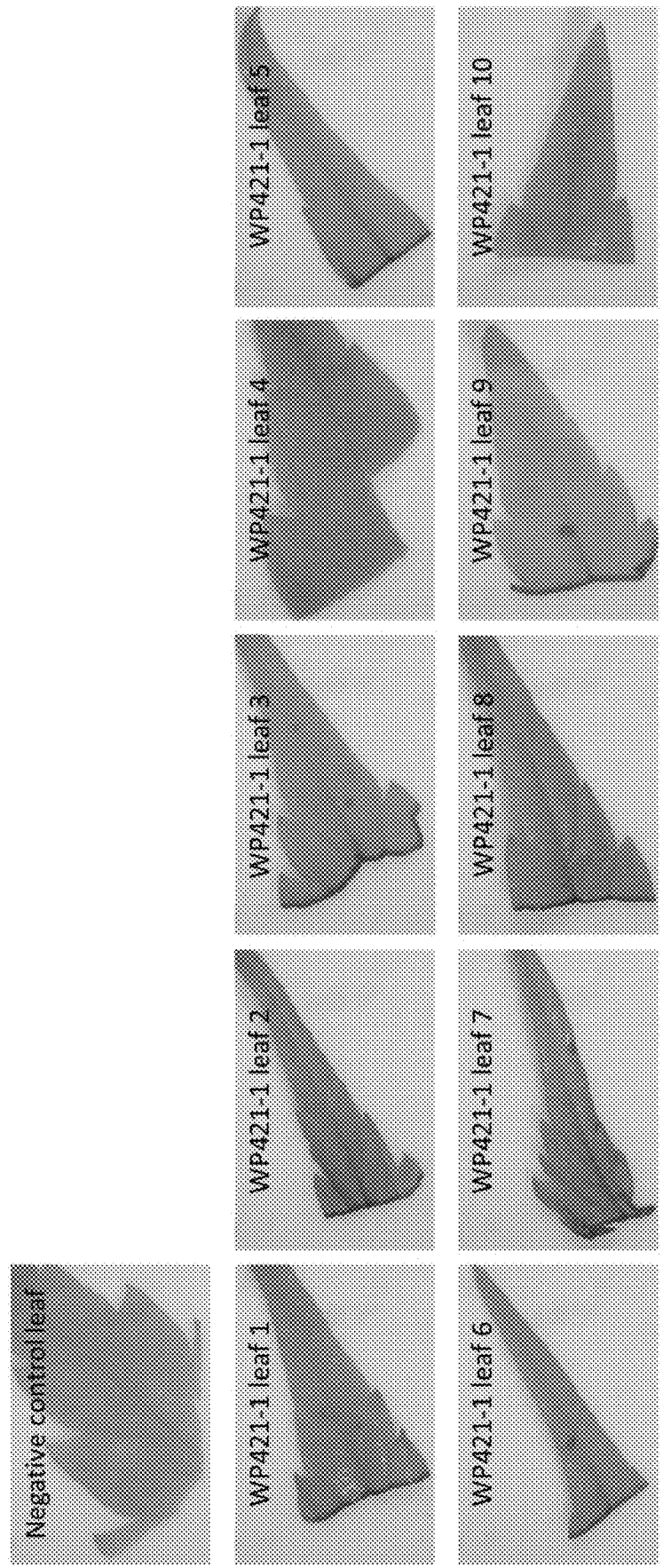
FIG. 32 shows GUS expression in leaf samples from WP421-1. Nine out of the ten leaf samples showed positive GUS expression confirming minimal chimerism.
Figure 33:
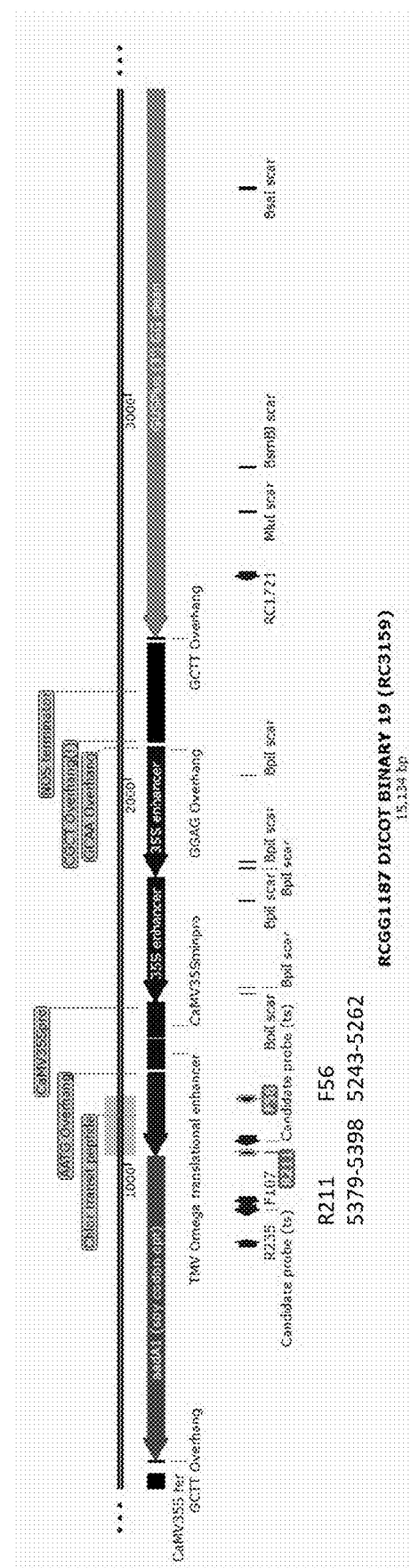
FIG. 33 shows the PCR amplification scheme for PCR of leaf samples from WP421-1. A 156 bp fragment within the aadA1a expression cassette of DICOTBINARY-19 was amplified using primers designated F56 and R11. The fragments and the resulting amplicon is highlighted in blue.
Figure 34:
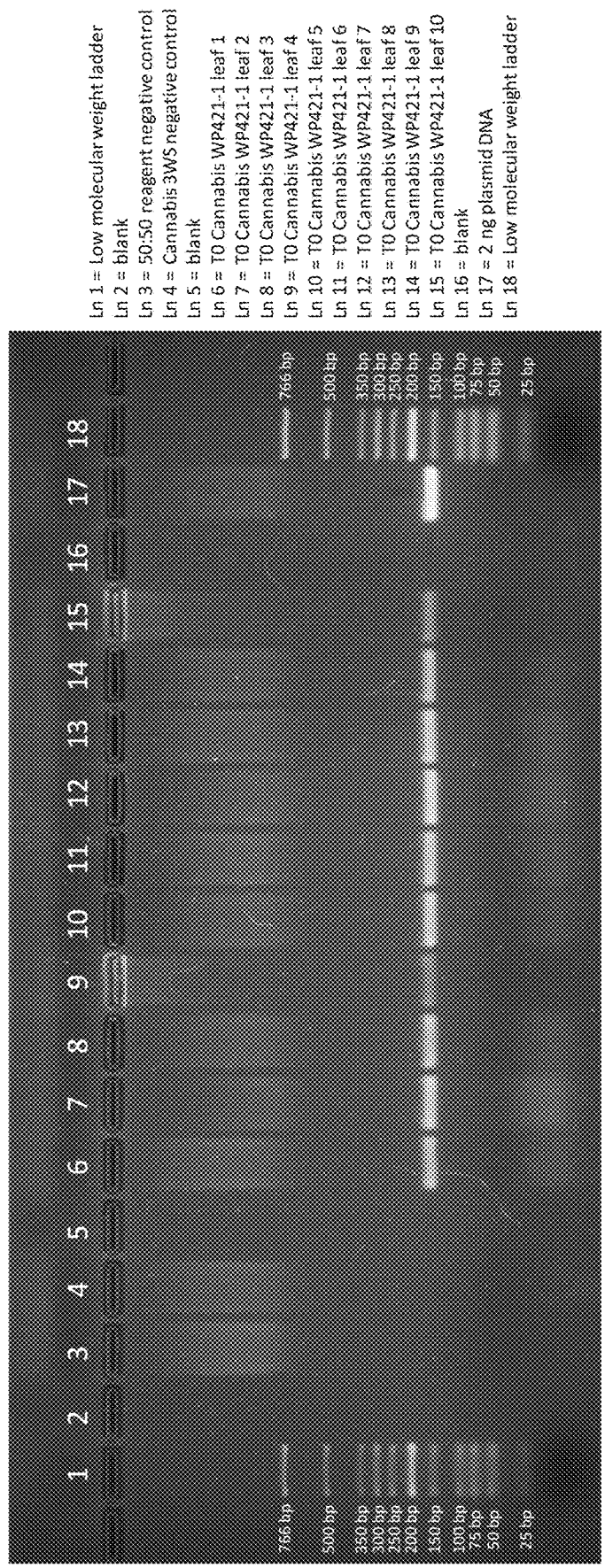
FIG. 34 shows the results of PCR amplification of a 156 bp fragment of the aadA1a expression cassette. All 10 leaf samples were positive.

Additional data in FIGS. 32-34 confirms the chimerism in the WP421-1 plant. 10 leaf samples were taken from EP421-1 and divided for PCR (FIGS. 33-34) and GUS expression (FIG. 32) analysis. For PCR, we amplified a 156 bp fragment within the aadA expression cassette of DICOTBINARY-19 using primers designated F56 and R11 (fragments and amplicon highlighted in blue in FIG. 33). Leaf DNA from WP421-1 was extracted using the REDExtract-N-Amp™ Plant PCR Kit (Sigma-Aldrich XNAP-1KT) following manufacturer's instructions. PCR reaction was run with following:
1. 3 minutes at 94 C for initial denaturation
2. 30 seconds at 94 C for denaturation
3. 30 seconds at 55 C for annealing
4. 1 minute at 72 C for primer extension
5. Cycle steps 2-4 34 more times (35 total cycles)
6. 10 minutes at 72 C for final primer extension PCR products were run on 1.5% agarose gel in SB buffer. All 10 leaf samples gave the expected 156 bp product, confirming minimal chimerism in this event We have also blasted DNA into *Cannabis* meristem explants using PDS-1000 Helium gun with a plasmid designated DICOTBOMB-13. For particle bombardment experiments, gold-DNA "bead prep" was prepared by first washing 50 mg 0.6 um gold microcarriers (BioRad part #1652262) in 1 ml 100% ethanol and sonicating for 1 min 45 kHz. Gold was pelleted by centrifugation at 5000 rpm in microfuge (~2300×g) and ethanol removed. Gold was then resuspended in 1 ml 100% ethanol and stored at −20 C until use. To precipitate DNA onto beads, the 50 mg gold/1 ml ethanol stock was sonicated for 1 min 45 kHz. 42 ul of this stock was transferred to an Eppendorf tube, then pelleted by centrifugation at 2500 rpm for 10 seconds, after which ethanol was removed. 500 uL sterile water was added and mixture sonicated 1 min 45 kHz. Gold was again pelleted by centrifugation at 2500 rpm for 10 seconds and water removed. 25 ul sterile water was then added, followed by sonication for 1 min 45 kHz. 2.6 ug DICOTBOMB-13 DNA was added, then sterile water to bring volume up to 245 ul. 250 ul cold 2.5 M $CaCl_2$ was added, followed by 50 ul 0.1 M spermidine. Solution was mixed by low speed vortexing. Tube was incubated on ice for approximately 1 hour with gentle inversions every 5-10 minutes. DNA/gold was pelleted at 1000 rpm (~100×g) for 2 min and supernatant removed. Pellet was then washed with 1 ml 100% EtOH w/ pipette tip, then pelleted again at 1000 rpm (~100×g) for 2 min and supernatant removed 36 ul 100% EtOH was added to tube and gold completely resuspended with low-speed vortexing. Bead prep was stored at −20 C until used, with 5 ul used per bombardment. This corresponds to 360 ng DNA per blast; 290 ug gold per blast (1.2 ng DNA per ug gold).

Figure 23:
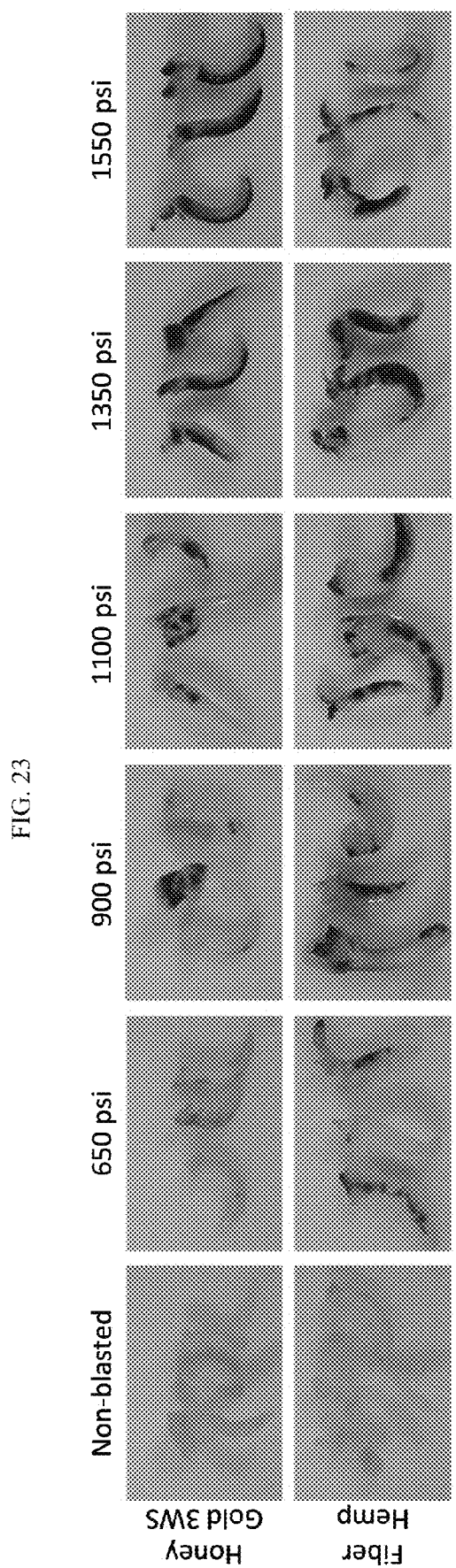
FIG. 23 shows GUS transient expression in *Cannabis* meristem explants bombarded with DICOTBOMB-13.
Figure 25:
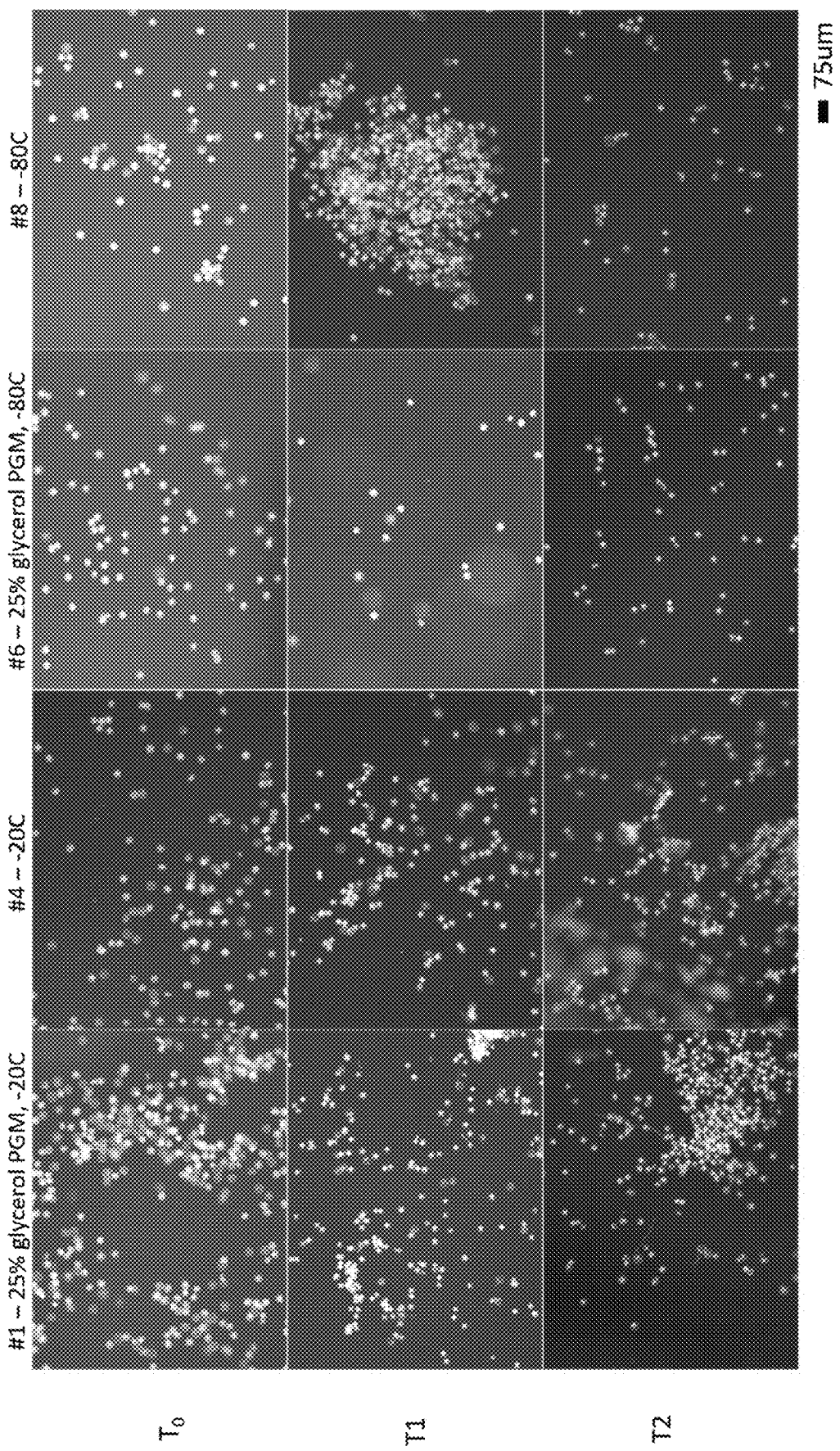
FIG. 25 shows pollen germination results. T0=initial germination after 1 hr treatment; T1=germination after 4 hr treatment; T2=germination after overnight treatment (22 h).

*Cannabis* meristem explants were excised from seed and precultured on EJW1 media overnight at 28 C 16/8 photoperiod, arranged on 12% xanthan gum targeting plates (with 60 mg/L Cleary's 3336 fungicide), blasted at 6 cm from the launch assembly using 5 uL bead prep per target and a range of rupture disks (650 psi-1550 psi), then allowed to rest on EJW1 media overnight. Transients were taken the next day. GUS transient expression in *Cannabis* meristem explants bombarded with DICOTBOMB-13 is shown in FIG. 23.

TABLE 10

| Preculture Medium EJW1 | |
|---|---|
| Ingredients and Notes | Amount to add per liter (grams) |
| MS salts no vitamins | 4.3 |
| Sucrose | 30 |
| 2,4-D (1 mg/ml stock) | 0.2 ml |
| MES | 2 |
| Cleary's 3336 | .03 |
| pH | 5.6 |
| Agarose | 4 |
| Autoclave | |
| Carbenicillin (100 mg/ml) | .25 |
| TDZ (1 mg/ml stock) | 1 ml |

Example 2

The embodiments described herein demonstrate *Cannabis* floral dip experiments.

We used strain Ar18r12v based on positive GUS transients in meristem explants, harboring DICOTBINARY-22, which has the aadA1a protein targeted to both plastid and mitochondria in the plants. *Agrobacterium* cultures were resuspended in 5% sucrose with 0.05% silwet L-77 as a wetting agent. One of the cultures was induced with 100 uM acetosyringone and one was not. These cultures were applied directly to female flowers (some flowers received only 5% sucrose+0.05% silwet L-77 "blank"). Experiment is summarized in Table 11.

Figure 5:
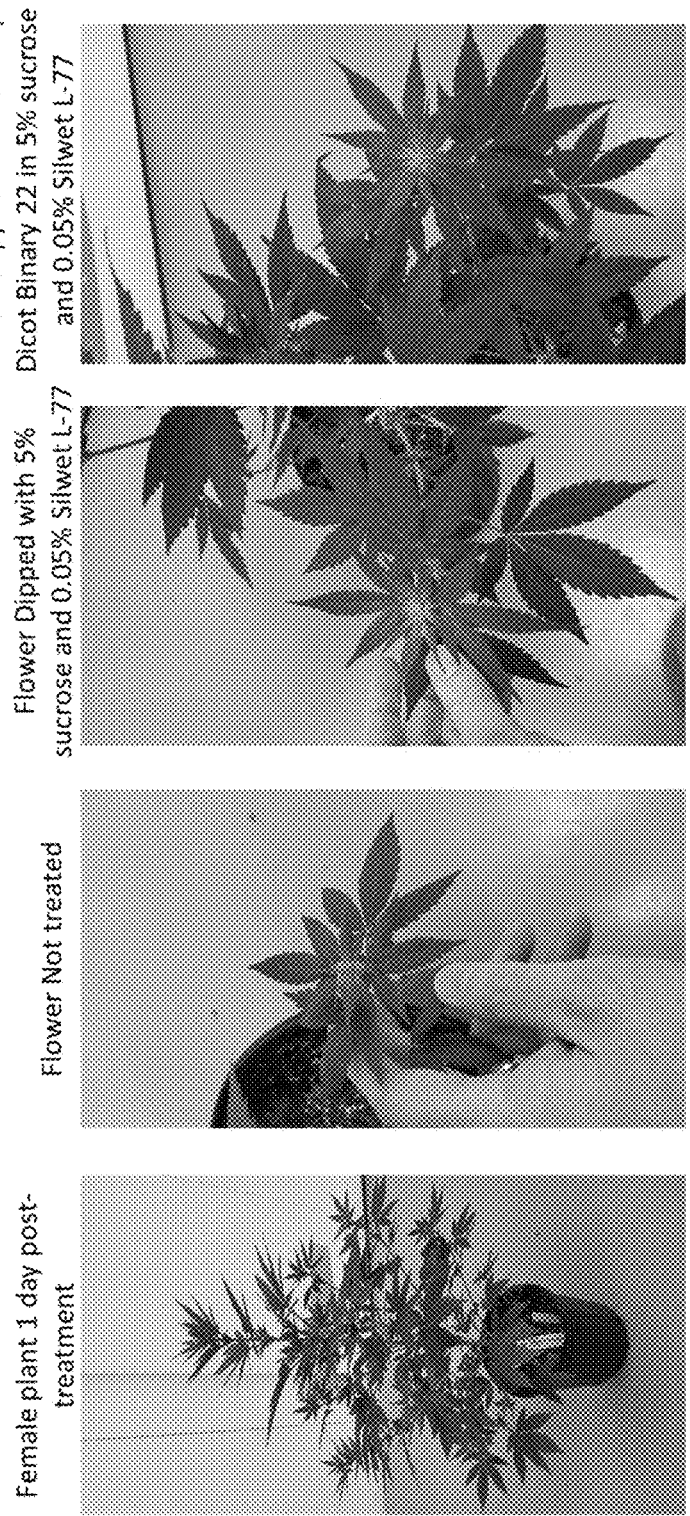
FIG. 5 shows flower phenotypes post inoculum application (1 day).

We noted no obvious ill effects of the inoculum application to the flowers one-day post-application. See FIG. 5. Female flowers were then pollinated with male pollen from donor plants by dusting the plants with pollen; as well as using a paint brush to apply pollen earlier.

Example 3

The embodiments described herein demonstrate *Cannabis* node, internode, leaf, and petiole transformation experiments.

Figure 6:
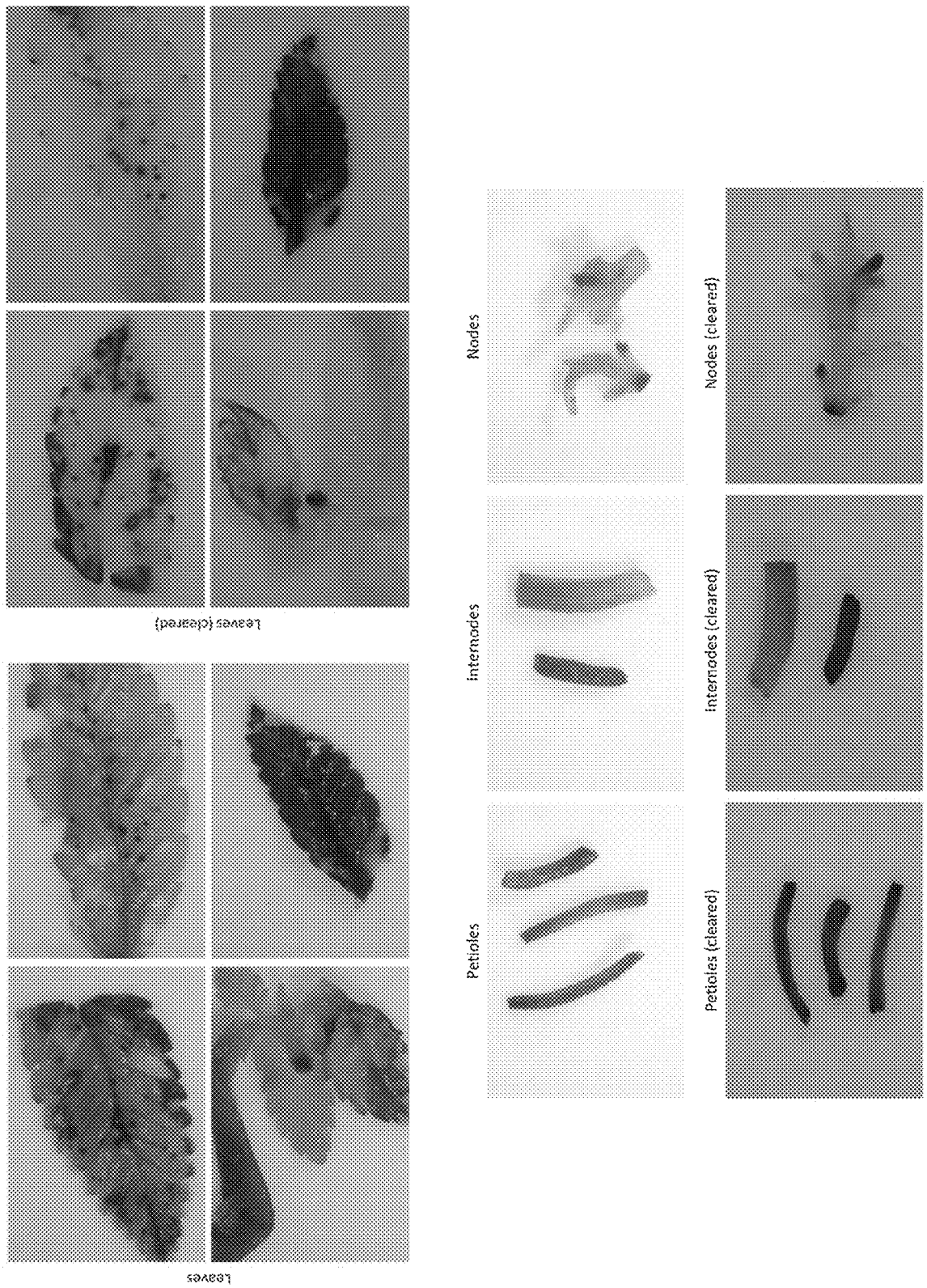
FIG. 6 shows GUS transient expression in *Cannabis* leaves, petioles, internodes, and nodes inoculated with Ar18r12v/DICOTBINARY-19.
Figure 7:
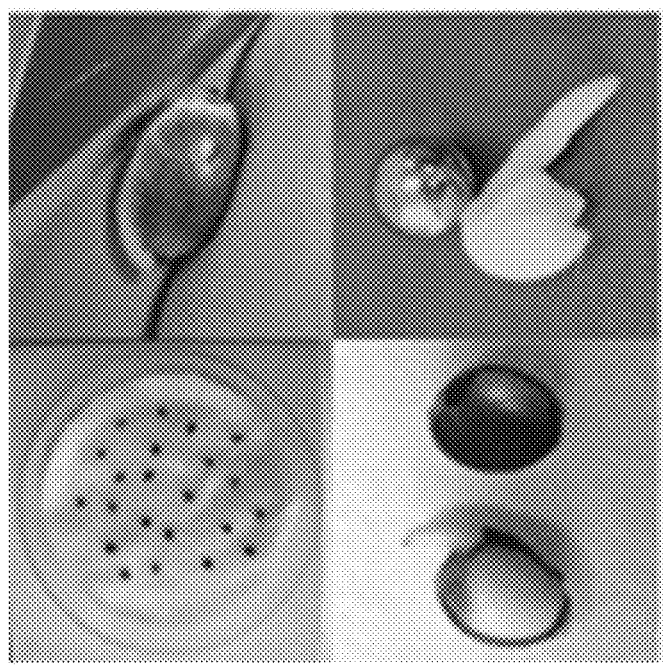
FIG. 7 shows mature *Cannabis* seed and embryo.
Figure 8:
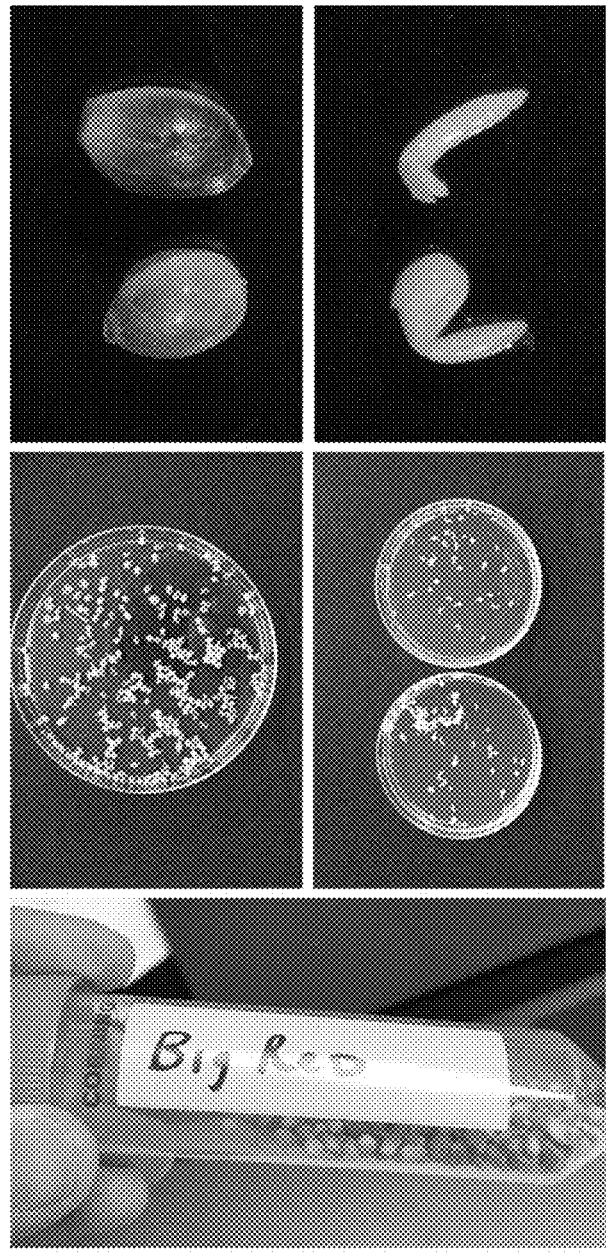
FIG. 8 shows *Cannabis* seeds and meristem explants.
Figure 9:
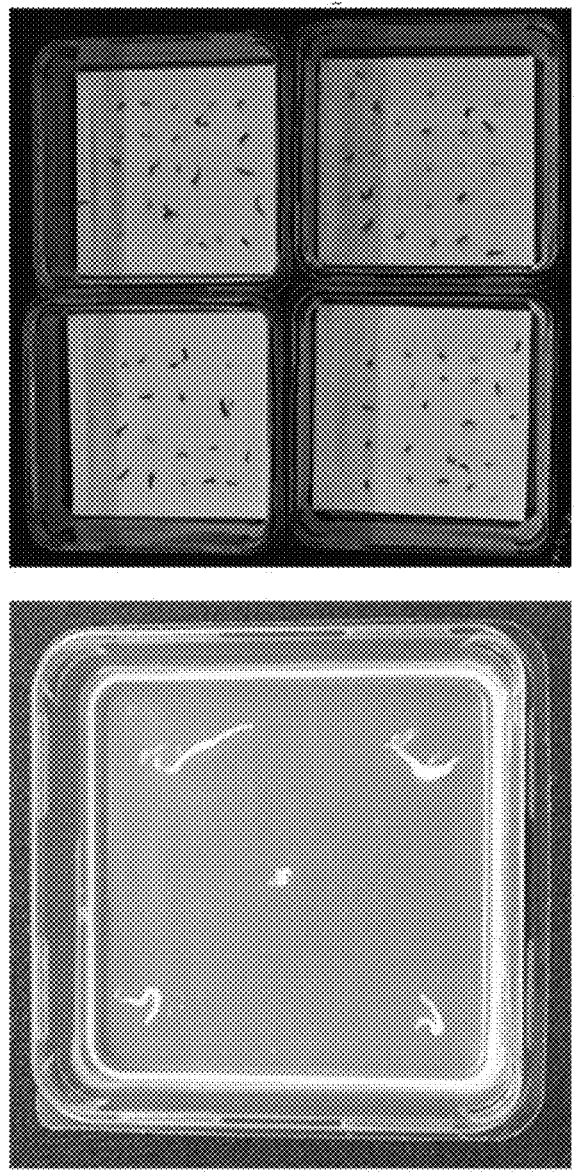
FIG. 9 shows *Cannabis* meristem explants on B5 medium and after 4 days in co-culture after inoculation with Ar18r12v/DICOTBINARY-19.
Figure 9:
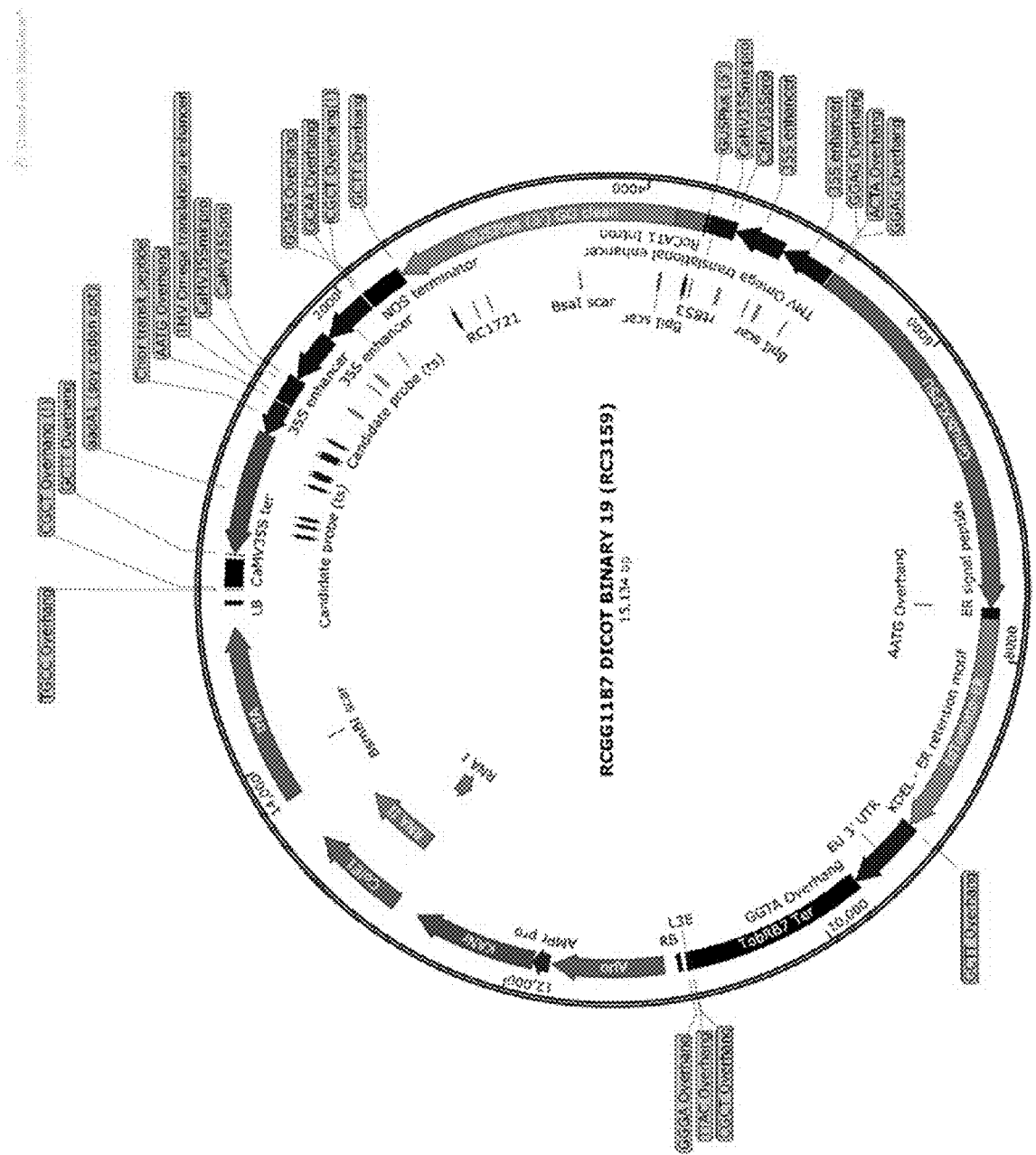
Figure 10:
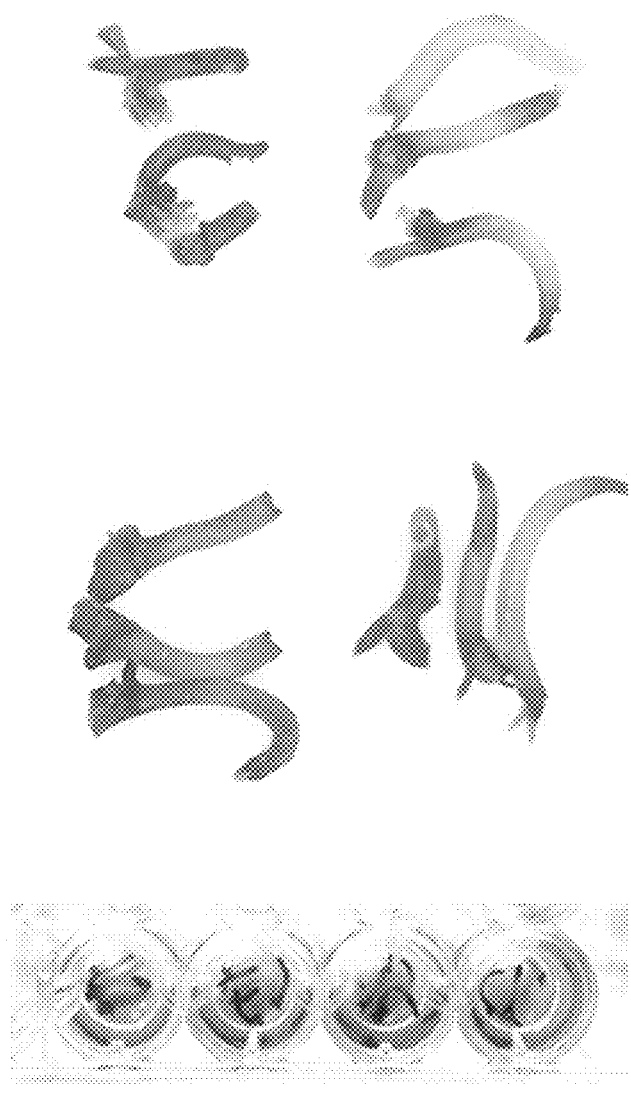
FIG. 10 shows transient GUS expression in *Cannabis* meristem explants transformed with Ar18r12v/DICOTBINARY-19.
Figure 11:
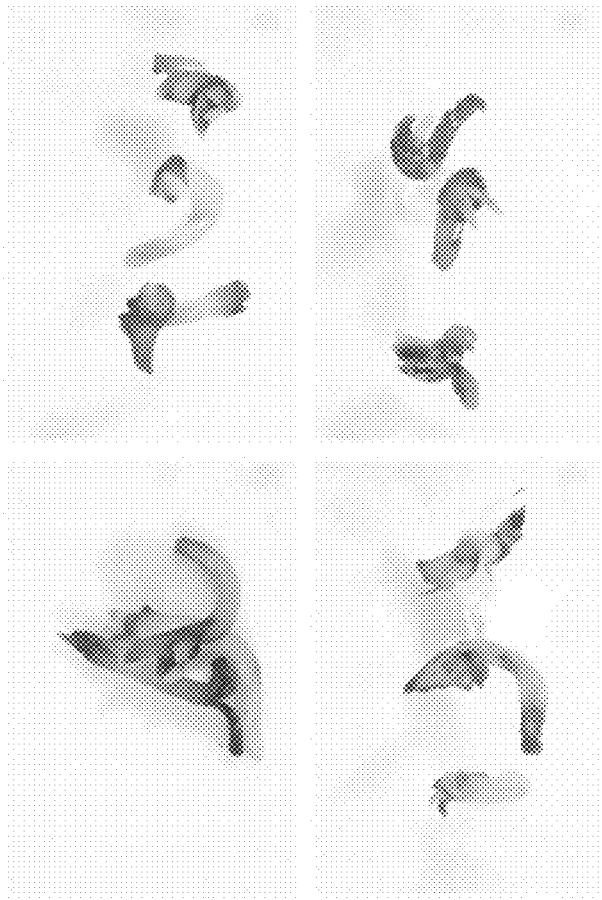
FIG. 11 shows transient GUS expression in *Cannabis* meristem explants transformed with Ar18r12v/DICOTBINARY-19 and de-stained in 70% EtOH.
Figure 12:
FIG. 12 shows a non-inoculated *Cannabis* seed sanitized in 20% Clorox on B5 medium (left) and a non-inoculated meristem explant on B5 medium (right).
Figure 13:
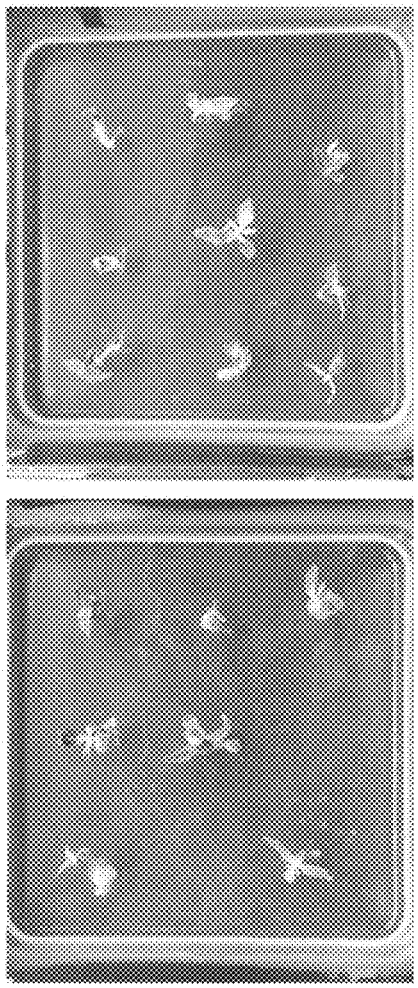
FIG. 13 shows spectinomycin sensitive (bleaching) phenotype visible in inoculated *Cannabis* meristem explants on 150 mg/L spectinomycin B5.
Figure 15:
FIG. 15 shows greening, regenerating *Cannabis* explants that were dried, stored, and regenerated (right) against freshly excised explants (left) that were plated on Hemp Node medium (Table 7) the day of excision. Explants were imaged approximately 3 weeks after excision.

We inoculated node, internode, leaf, and petiole explants of *Cannabis* variety Elektra x Chardonnay. We used aseptically grown plantlets from sanitized and imbibed seed plated on non-selective B5 media for approximately 6 weeks. Explants were sonicated for 20 seconds at ~45 kHz in the presence of Ar18r12v/DICOTBINARY-19. Nodal explants were co-cultured on 2.5 ml WCIC INO media with 50 mg/L nystatin, 10 mg/L TBZ, and 0.5 mg/L meta-topolin (mT). Internode, leaf, and petiole explants were co-cultured on 2.5 ml WCIC INO media with 50 mg/L nystatin, 10 mg/L TBZ, 1 mg/L meta-topolin (mT), 1 mg/L napthylacetic acid (NAA), and 0.2 mg/L GA3. After 4 days of co-culture at 23 C 16/8 photoperiod, GUS transient expression was observed in all explant types. See FIG. 6.

After co-culture, nodal explants were transferred to 100 mg/L spectinomycin hemp node media (Table 7) supplemented with 500 mg/L activated charcoal. Leaf, petiole, and internode explants were transferred to 100 mg/L spectinomycin hemp internode media, which is a modification of potato ZIG media (Cearley J A, Bolyard M G: Regeneration of *Solanum tuberosum* cv. Katandin from leaf explants in vitro. Am Potato J 74: 125-129 (1997)). A summary of these experiments is provided in Table 13.

TABLE 12

| WCIC Hemp Internode Media (modified from Cearley 1997) | |
|---|---|
| Ingredients and Notes | Amount to add per liter (grams) |
| MS Salts complete with vitamins (PhytoTech M519) | 4.43 |
| Sucrose | 20 |
| Cleary's 3336 | 0.06 |
| pH to 5.7 with 1N KOH | |
| Gelrite (or Phytagel), then autoclave | 2 |
| Meta-topolin (mT) (1 mg/ml) | 1 ml |

TABLE 11

| Description and summary of experiments with Cannabis floral dip | | | | |
|---|---|---|---|---|
| Experiment ID | Comments | AS | Co-Culture Duration (Days) | Observations and Comments |
| Hrmp 4/17-1 | Agro washed once with sterile water; spun 10 min, resuspended in 5% sucrose; Silwet L-77 added to 0.05% | none | Agro applied directly to flowers; 1 d dark in high humidity LEDA; then moved to GH7 with 3 males | 5 female plants; 3 hermaphrodites (red/white twist tie below flower for inoculated, white for blank) |
| Hemp 4/17-2 | Agro washed once with sterile water; spun 10 min, resuspended in 5% sucrose; Silwet L-77 added to 0.05% | 100 uM AS | Agro applied directly to flowers; 1 d dark in high humidity LEDA; then moved to GH7 with 3 males | 5 female plants; 3 hermaphrodites (green twist tie below flower for inoculated, white for blank) |

TABLE 12-continued

WCIC Hemp Internode Media (modified from Cearley 1997)

| Ingredients and Notes | Amount to add per liter (grams) |
|---|---|
| Napthylacetic acid (NAA) (1 mg/ml) | 1 ml |
| GA3 (FS) Sigma Prod G7645 (1 mg/ml) | 0.2 ml |
| Carbenicillin (200 mg/ml) | 1.25 ml |
| Cefotaxime (100 mg/ml) | 2 ml |
| Selection | as needed |

TABLE 13

Description and summary of experiments with Cannabis nodes, leaves, petioles, and internodes.

| Experiment ID | Comments | # embryos to Selection | Notes | # explants to second media | 2nd media |
|---|---|---|---|---|---|
| Hemp 5/2-1 | Nodes from hemp seed sanitized and imbibed; germinated on B5 3/22/19; harvested in INO; inoculated and sonicated 20 s 45 kHz; co-cultured in plantcons with filter paper + 2.5 ml INO with 50 ppm nystatin +10 ppm TBZ + .5 ppm meta-topolin (mT); 23 C. 16/8 photoperiod | 11 | 100 ppm spec hemp node media; 28 C. 16/8/photoperiod | NA | NA |
| Hemp 5/2-2 | Leaves from hemp seed sanitized and imbibed; germinated on B5 3/22/19; harvested in INO; inoculated and sonicated 20 s 45 kHz; co-cultured in plantcons with filter paper + 2.5 ml INO with 50 ppm nystatin + 10 ppm TBZ + 1 ppm meta-topolin (mT) + 1 ppm NAA + 0.2 ppm GA3; 23 C. 16/8 photoperiod | 68 | 100 ppm spec hemp internode media; 28 C. 16/8/photoperiod | 18 | non selective hemp node media; 28 C. 16/8/photoperiod |
| Hemp 5/2-2 | Petioles from hemp seed sanitized and imbibed; germinated on B5 3/22/19; harvested in INO; inoculated and sonicated 20 s 45 kHz; co-cultured in plantcons with filter paper + 2.5 ml INO with 50 ppm nystatin + 10 ppm TBZ + 1 ppm meta-topolin (mT) + 1 ppm NAA + 0.2 ppm GA3; 23 C. 16/8 photoperiod | 68 | 100 ppm spec hemp internode media; 28 C. 16/8/photoperiod | 3 | non selective hemp node media; 28 C. 16/8/photoperiod |
| Hemp 5/2-2 | Internodes from hemp seed sanitized and imbibed; germinated on B5 3/22/19; harvested in INO; inoculated and sonicated 20 s 45 kHz; co-cultured in plantcons with filter paper + 2.5 ml INO with 50 ppm nystatin + 10 ppm TBZ + 1 ppm meta-topolin (mT) + 1 ppm NAA + 0.2 ppm GA3; 23 C. 16/8 photoperiod | 68 | 100 ppm spec hemp internode media; 28 C. 16/8/photoperiod | 3 | non selective hemp node media; 28 C. 16/8/photoperiod |

Example 4

Cannabis meristem explants were excised, dried, and stored at −20 C. Cannabis meristem explants of variety 3WS were excised from seed and then dried on the surface of filter paper in a laminar flow hood for 26 hours. Dried Cannabis meristem explants were then stored at −20 C for 3 days. Explants were then rehydrated in 20% PEG4000 with 60 mg/L Captan and 30 mg/L Bravo fungicides, rinsed, and plated on Hemp Node media without activated charcoal (Table 7).

Example 5

This embodiment describes the transformation of Cannabis pollen, in particular the advantages provided when pollen from male plants can be stored. Cannabis pollen was harvested in by shaking branches of male plants onto a creased sheet of blue paper (high visibility of yellow on blue). Pollen was poured through a #80 sieve into a 50 mL conical tube. A small, visible amount of pollen was added to 7 1.5 mL microfuge tubes comprising the following treatments:
1. 25% glycerol (w/v) PGM, inverted several times to mix and stored at −20 C.
2. 25% glycerol (w/v) PGM, inverted several times to mix and stored at 4 C
3. Untreated, fresh pollen, stored at 4 C
4. Untreated pollen, stored at −20 C
5. Pollen placed in 1.5 mL microfuge tube, placed in sweater box with MgNO3 solution. Moved to −20 C on 5/3 at 11 am.
6. 25% w/g glycerol PGM, 1 hour incubation at RT, followed by storage at −80 C
7. One hour untreated at room temperature in 50 mL tube.

The same day pollen was harvested, pollen from tubes #6,7 were placed onto solid PGM after one hour of incubation at room temperature. Plates were then wrapped in parafilm and placed in dark room and examined under microscope for germination in the form of pollen tube expansion. Germination of tubes was visible on both. Tube emerged more quickly from pollen from tube #6, which may be due to the liquid PGM matrix. Germination continue onto the next day, 22 hours after plating. See FIG. 24.

Figure 35:
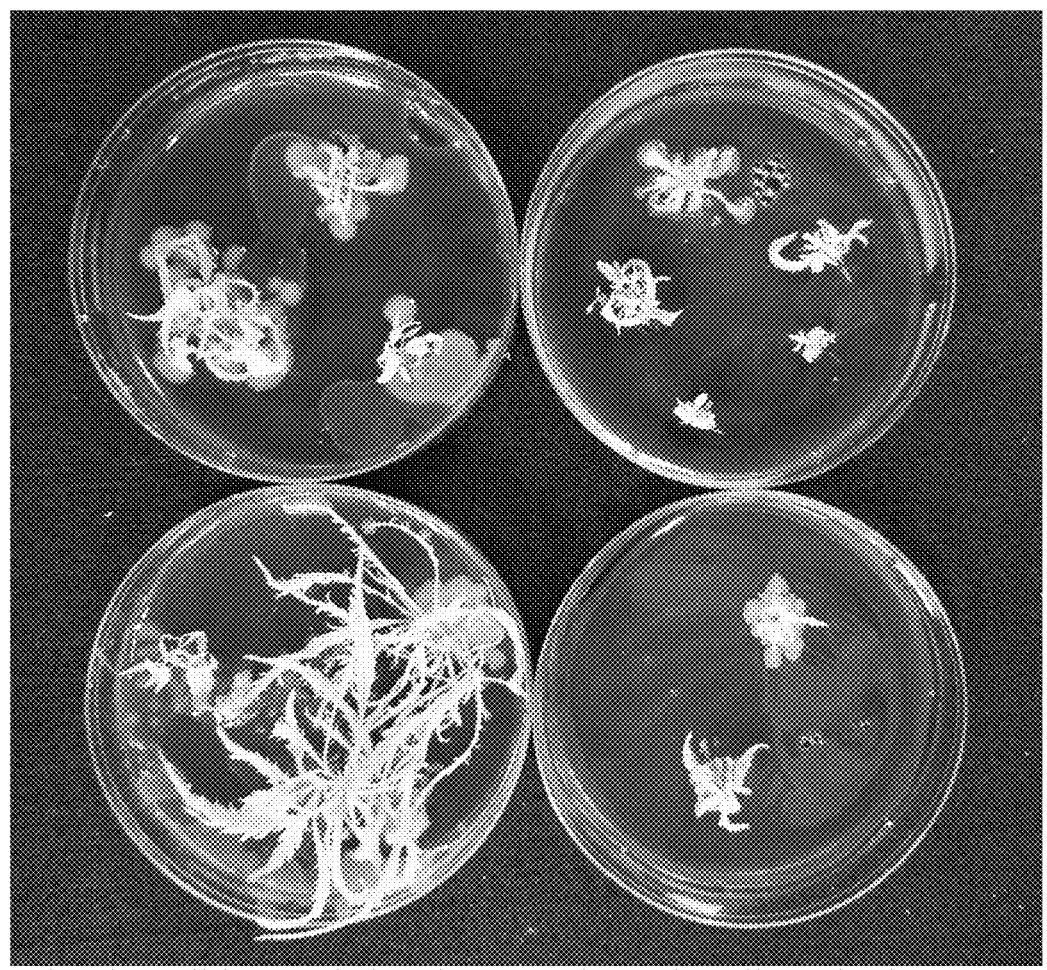
FIG. 35 shows bleached *Cannabis* meristem explants after 1 month on 100 mg/L spectinomycin node medium. RFP negative *Cannabis* meristem explants that were previously greening on 10-50 mg/L spectinomycin were transferred to hemp node medium containing 100 mg/L spectinomycin.

To test for overnight storage, we assayed pollen for germination the next day. Pollen from tubes 1,4 and 6 were placed on ice to thaw. After half an hour, a small amount of pollen from each was added to a PGM plate partition. 50 uL of pollen was taken from 1 & 6. Tube 6 was noticeably more opaque than tube 1. Tube germination was visible only in treatment #1. Multiple, branched tube-like structures were visible in treatment #4 at T2 (overnight storage) which may have been aberrant germination or the first indications of fungal hyphae. Following 24H of incubation, tube germination was visible in the −20° C. stored pollen that was stored in 25% (w/v) glycerol PGM. No survival was observed in either −80° C. treatment, which perhaps indicates that a slower rate of freezing is important for retaining viability. See FIG. 35.

TABLE 14

Pollen Germination Medium - Salts II Solution (PGM2 Salts)
Pollen Germination Medium Salts II Solution (PGM2 Salts)

| Stock (100X) Reagent | CAS | Volume: 10 mL g/10 mL | Original Units | 100 mL stock grams added |
|---|---|---|---|---|
| Boric Acid (H3BO3) | 0043-35-3 | 0.05 | 0.005% | 0.5 |
| CaCl2 * 2H2O | 10035-04-8 | 1.47 | 10 mM | 14.7 |
| Potassium Phosphate, monobasic (KH2PO4) | 7778-77-0 | 0.00680 | 0.05 mM | 0.068 |
| ddH2O (dissolve salts) dissolve by stirring and/or sonication | | Add 8 mL | | Add 80 mL |
| ddH2O | | Fill to 10 mL w/ graduated cylinder | | Fill to 100 mL w/ graduated cylinder |

TABLE 15

2X PGM (Pollen Germination Medium)
2X Pollen Germination Medium

| | 1 L | |
|---|---|---|
| Volume | amount | units |
| PGM Salts | 10 | mL |
| Sucrose | 100 | g |
| PEG 4000 | 600 | g |
| ddH2O | Fill to 1 L | |
| Heat to 70 C. for 10 minutes on stir plate. | | |
| Filter sterilize. | | |
| Store at 4 C. | | |

TABLE 16

Solid Pollen Germination Medium
Solid Pollen Germination Medium

| | 1 L | |
|---|---|---|
| Volume | amount | units |
| 2X PGM | 500 | mL |
| 0.6% Noble Agar | 500 | mL |

TABLE 17

25% glycerol PGM
25% glycerol PGM

| | 1 L | |
|---|---|---|
| Volume | amount | units |
| 2X PGM | 500 | mL |
| 50% (w/y) glycerol | 500 | mL |

Example 6

Figure 29:
FIG. 29 shows *Cannabis* VAEs after 5 weeks (left) compared to freshly excised *Cannabis* meristem explants (right).
Figure 30:
FIG. 30 shows machine excised *Cannabis* meristem explants imaged after approximately two weeks on non-selective B5 medium.

*Cannabis* value added explants (VAEs) were generated by hand excising meristem tissue from seeds surface sanitized in 20% Clorox for 5 min, rinsed, and imbibed for ~20 h in BGM. *Cannabis* VAEs of variety 3WS were excised from seed, then dried on the surface of a filter paper in a laminar flow hood for 26 hours. Dried *Cannabis* meristem explants were then stored at −20 C for 3 days. Explants were then rehydrated in 20% PEG4000 with 60 mg/L Captan and 30 mg/L Bravo fungicides, rinsed, and plated on Hemp Node media without activated charcoal. FIG. 29 shows dried *Cannabis* VAEs after 5 weeks plated on non-selective medium. FIG. 30 shows machine excised *Cannabis* meristem explants on non-selective medium for 2 weeks.

*Cannabis* VAEs may also be primed with WCIC INO or other medium prior to drying. Examples of priming and drying conditions are outlined below. These examples are for soybean transformations but are applicable to *Cannabis* VAE priming and drying and the same or similar conditions may be used with *Cannabis* explants.

TABLE 18

Priming and Drying of Explants
(Soybean genotype W28, strain GV3101)

| VAE Batch/Priming | Co-culture | Ex-plants | Shoots harvested | T0 plants to GH | TF |
|---|---|---|---|---|---|
| Fresh explants giving rise to S92 series | 1 ppm TDZ | 75 | 6 | 3 | 4.0% |
| Fresh explants giving rise to S92 series | no TDZ | 71 | 3 | 3 | 4.2% |
| S92A (std dry) | 1 ppm TDZ | 75 | 8 | 4 | 5.3% |
| S92B (3 hr prime in INO, then dry) | 1 ppm TDZ | 50 | 10 | 10 | 20.0% |
| S92C (3 hr prime in INO with 1 ppm TDZ, then dry) | 1 ppm TDZ | 75 | 9 | 6 | 8.0% |
| S92D (3 hr prime in INO with 10 ppm TDZ, then dry) | 1 ppm TDZ | 50 | 0 | 0 | 0.0% |
| S92E (3 hr prime in INO with 50 ppm TDZ, then dry) | 1 ppm TDZ | 63 | 0 | 0 | 0.0% |
| S92E (3 hr prime in INO with 100 ppm TDZ, then dry) | 1 ppm TDZ | 50 | 0 | 0 | 0.0% |

Example 7

This example demonstrates additional embodiments of the transformation methods and transgenic *Cannabis* plants described herein.

Figure 36:
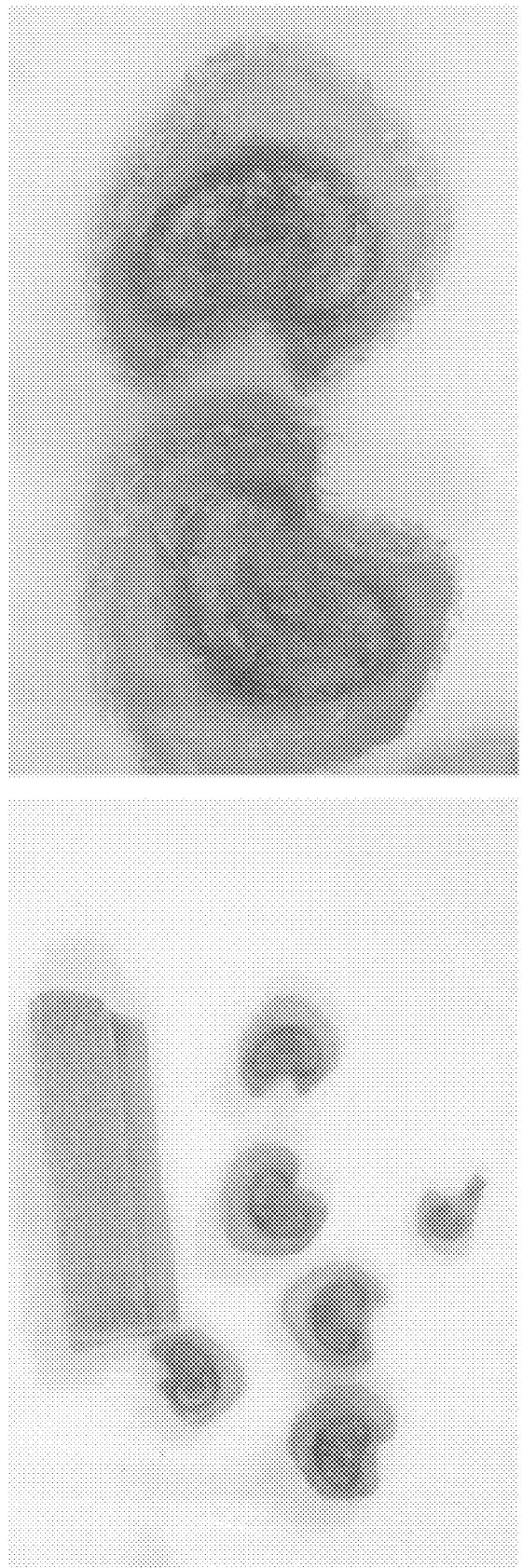
FIG. 36 shows GUS expression in vascular tissue (petiole sections) of *Cannabis* T0 event WP421-1 ("Candice").

T1 data/POC of germline transformation of *Cannabis* using meristem explants: A leaf sample of *Cannabis* T0 event WP421-1 (plant "Candice") was taken for long-term storage at −80 for further genetic analysis, and at this time we took sections of the petiole as well for GUS expression analysis. FIG. 36 shows GUS expression in the vascular tissue of WP421-1, which is an indicator of germline status for the transgene.

Figure 37:
FIG. 37 shows pollination of WP421-1 by 3WS wild-type plant.
Figure 38:
FIG. 38 shows flower of WP421-1 pollinated by 3WS wild-type plant.
Figure 39:
FIG. 39 shows cuttings of WP421-1.

WP421-1 was moved to short days in GH15 approximately 9 weeks after plant handoff to greenhouse. 10 cuttings were taken 2 days later. Some cuttings had roots approximately 2 weeks after cuttings were taken. First flowers (female) observed 5 days after moving plant to short days. WP421-1 was move into GH9 2 weeks after being put in short-day to be exposed to pollen from the 3WS 2-5 auto-flowering male. FIG. 37 shows WP421-1 adjacent to the male pollen donor wild-type 3WS plant.

2.5 weeks after pollination with male 3WS plant, immature T1 seed of WP421-1 was planted. We noted RFP+ expression (tdTomato) in one of the seedlings 3.5 weeks after this (in plantlet "Carly"), confirming germline transmission of transgene. (FIG. 40)

Figure 41:
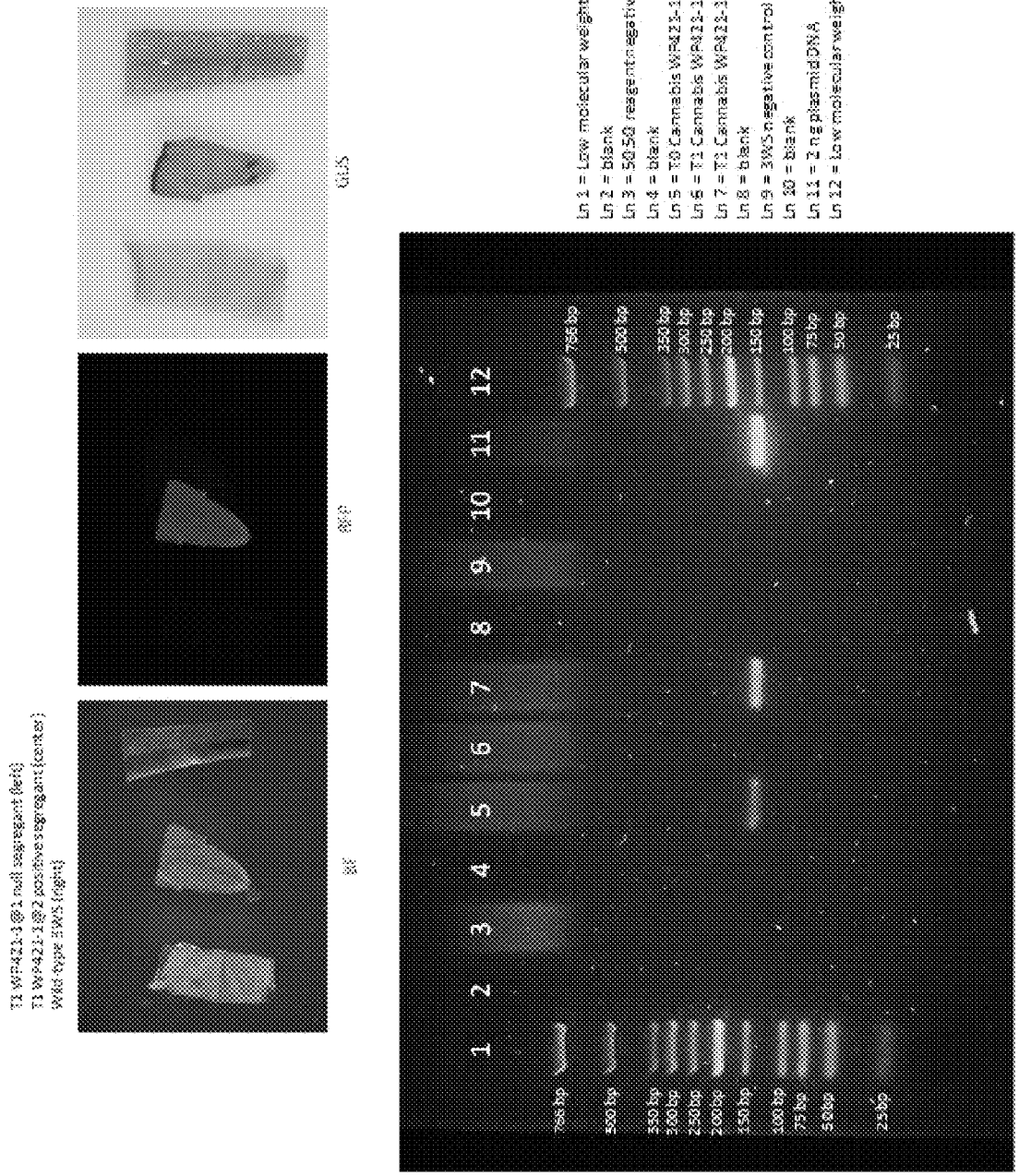
FIG. 41 shows germline confirmation of *Cannabis* meristem transformation through RFP, GUS expression, and aadA1a PCR.
Figure 42:
FIG. 42 shows T1 *Cannabis* plants WP421-1@1 and WP421-1@2 after 2 months in greenhouse.
Figure 43:
FIG. 43 shows T1 seed of WP421-1.
Figure 44:
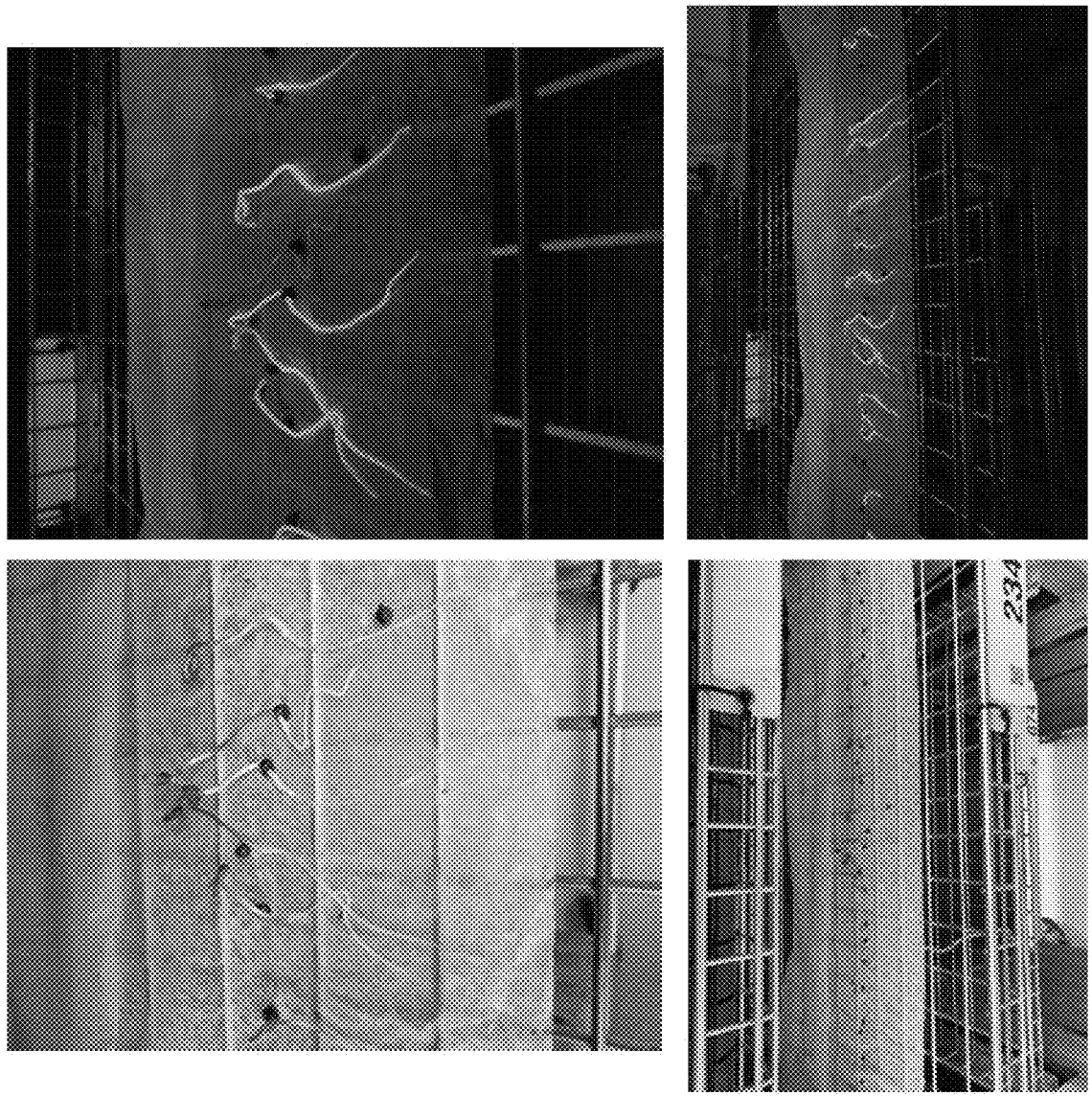
FIG. 44 shows stable RFP expression (tdTomato) in T1 seedlings of WP421-1 (germinated on germination paper).
Figure 46:
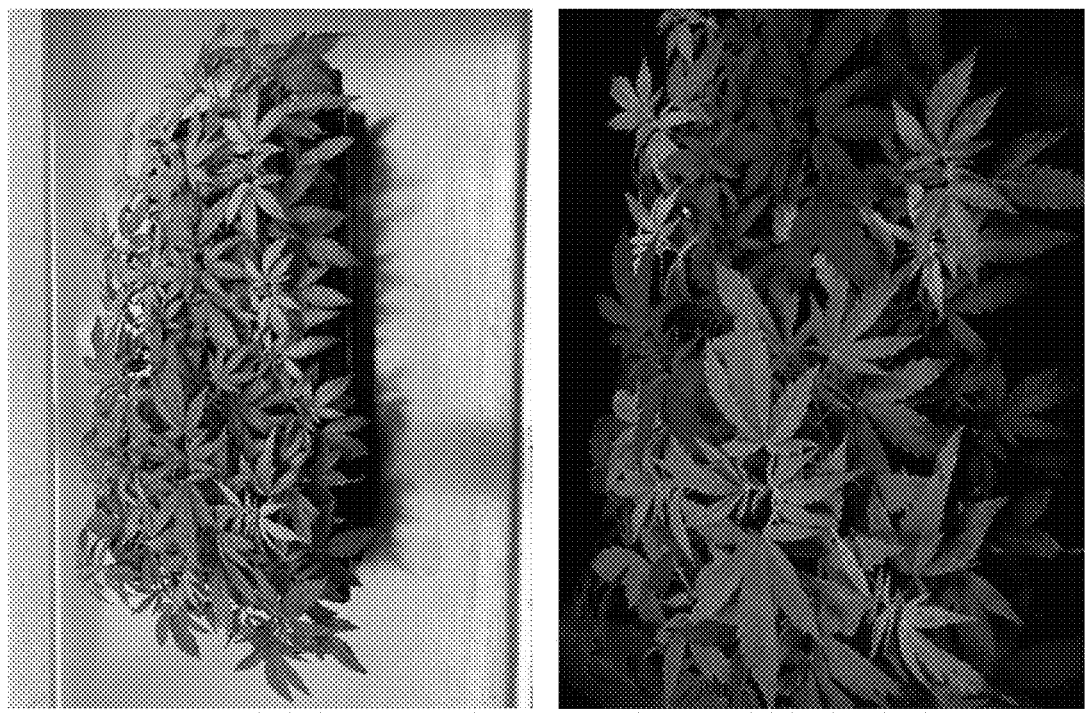
FIG. 46 shows stable RFP expression (tdTomato) in T1 seedlings of WP421-1 (germinated in flats).
Figure 47:
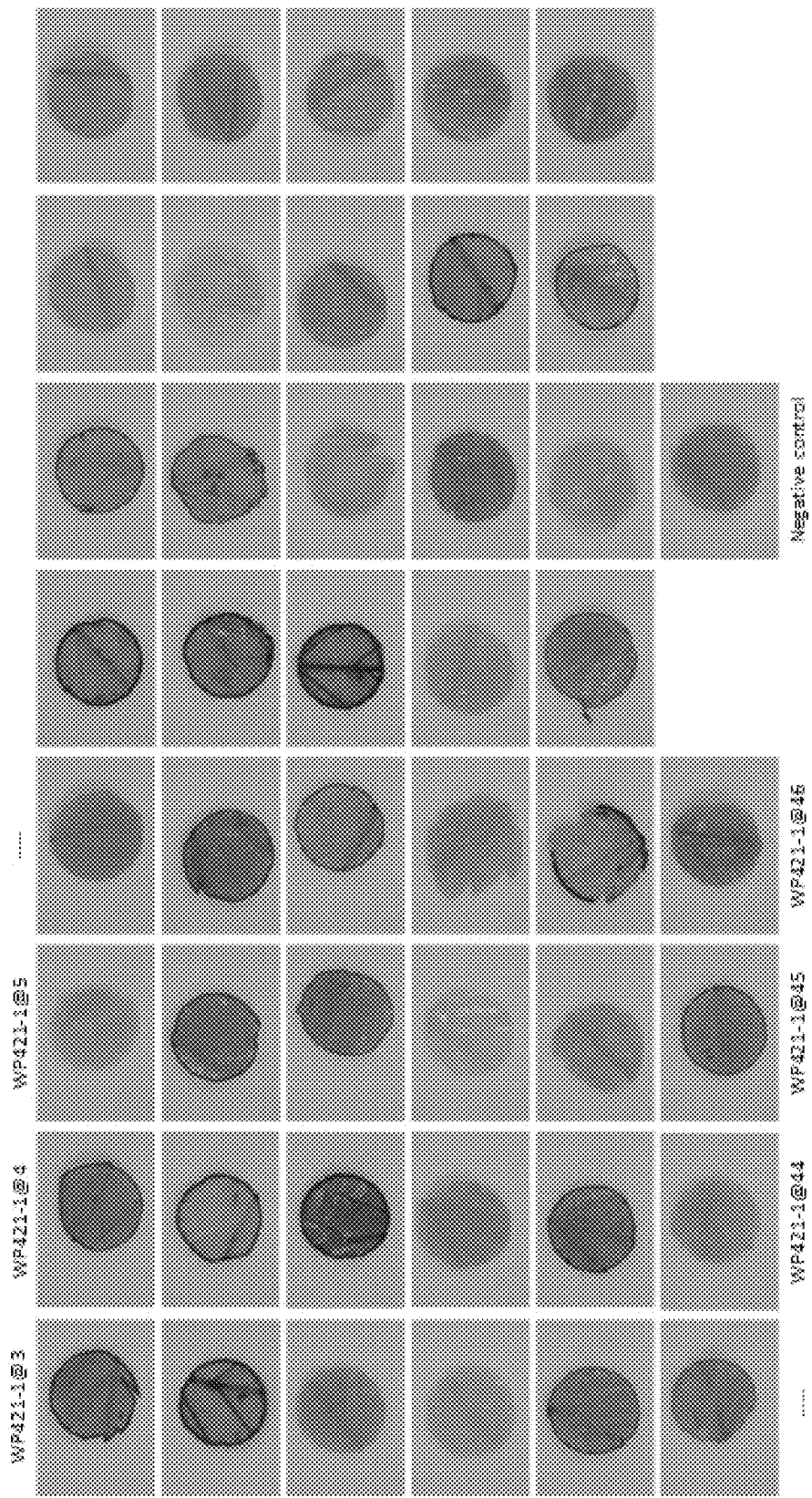
FIG. 47 shows stable GUS expression in T1 seedlings of WP421-1 (germinated in flats).

We followed this observation up with additional RFP expression (tdTomato) observations (eliminating background in a null segregant and in a wild-type leaf), GUS expression, and an aadA1a PCR that produced the expected 156 bp amplicon. (FIGS. 41 and 42). Approximately 5250 T1 seed were harvested from WP421-1 approximately 2 months after pollination was initiated (FIG. 43). We germinated T1 seed of WP421-1 on germination paper and planted a flat of T1 seed to examine more plants for RFP expression (tdTomato) and segregation. RFP expression (tdTomato) was apparent along with null segregants (FIG. 44).

Of the 48 T1 WP421-1 seed planted in flats, 44 germinated and were designated WP421-1@3 through WP421-1@46. 22 of these 44 expressed RFP (tdTomato) and GUS, giving the expected 1:1 segregation ratio for this cross. (FIG. 45)

Figure 48:
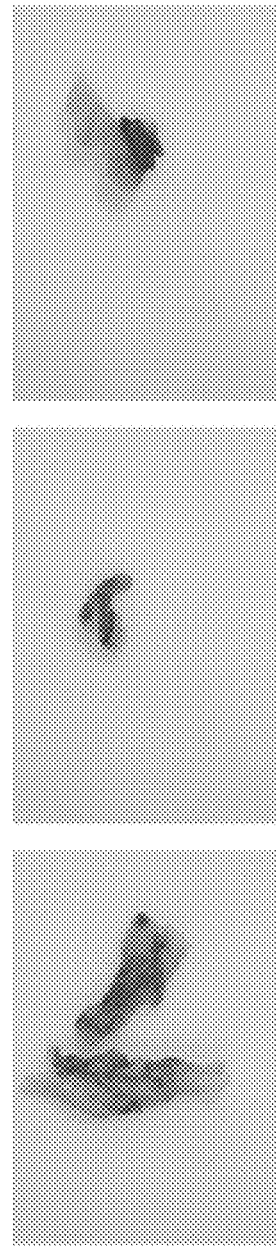
FIG. 48 shows GUS expression 7-8 weeks post-inoculation in chimeric *Cannabis* shoots (3WS variety) regenerated on 75 mg/L spectinomycin.
Figure 49:
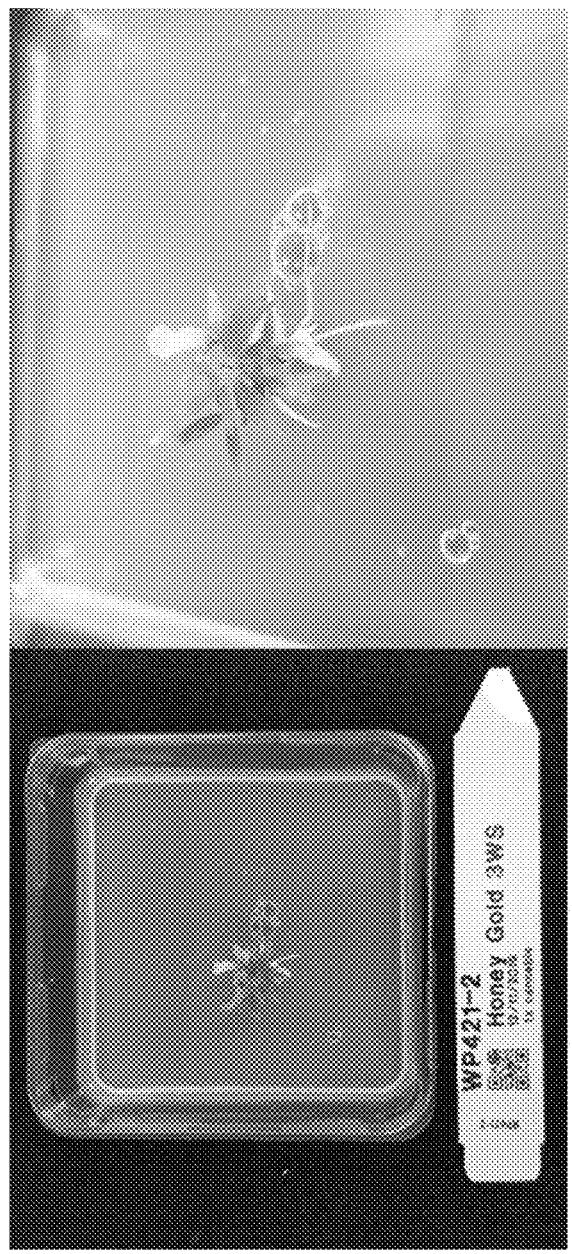
FIG. 49 shows T0 *Cannabis* plant WP421-2 (Honey Gold 3WS+DICOTBINARY-19).
Figure 50:
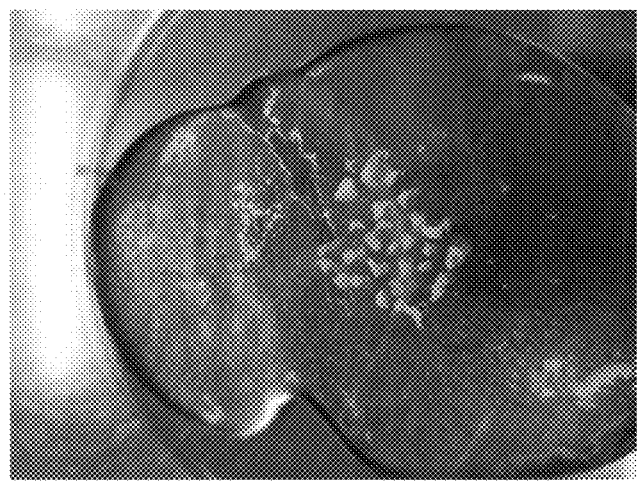
FIG. 50 shows *Cannabis* meristem explants targeted on carboxymethylcellulose media for particle bombardment.

Additional *Cannabis* transformation experiments using meristem explants: Additional experiments with *Cannabis* meristem explants inoculated with Ar18r12v/DICOTBINARY-19 using 75 mg/L spectinomycin selection have yielded plantlets chimeric for GUS as well as greening plantlets that are GUS negative. These chimeric plantlets did not root on the subsequent 50 mg/L streptomycin media and were instead transferred to selection-free BRM (FIG. 48). One chimeric GUS+ plant (center photo in FIG. 48) from this set rooted on selection-free BRM and was sent to the greenhouse as the T0 plant WP421-2, but we could not detect positive GUS or RFP expression or transgene integration by PCR in subsequent tests of WP421-2, possibly indicating negative sectors of the plant outcompeted transgenic sector (FIG. 49).

We have regenerated a transgenic *Cannabis* plantlet from particle-mediated transformation that is stably expressing GUS in all it leaves. *Cannabis* explants prepared from seed germinated at 37 C overnight of variety 3WS were precultured on EJW1 overnight and blasted on carboxymethylcellulose media using DICOTBOMB-13 (at 1.2 ng DNA/ug gold; 0.6 um gold; 1 cm gap, 6 cm distance, and 1350 psi).

Figure 51:
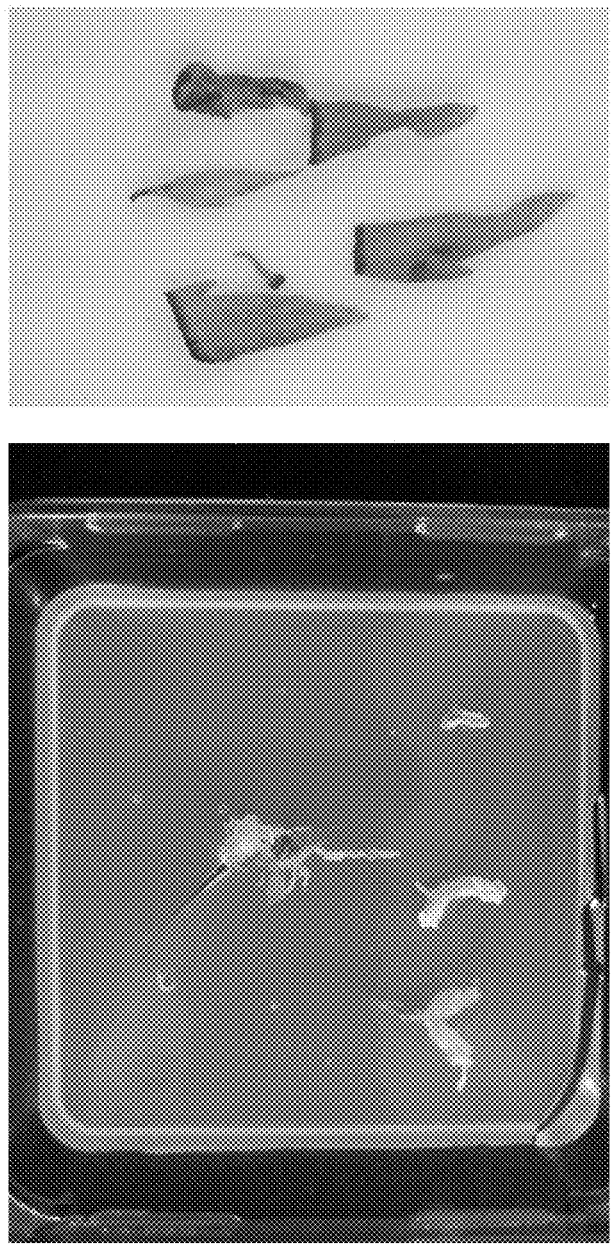
FIG. 51 shows phenotype and stable GUS expression in transgenic 3WS *Cannabis* derived from particle-mediated transformation of meristem explants (imaged approximately 2 months post-blast).

Explants were rested on EJW1 overnight, then transferred to 100 mg/L spectinomycin hemp node media without activated charcoal for 1 month. Explants were then transferred to 50 mg/L streptomycin hemp regeneration media with 1 mg/L meta-topolin (mT). Leaves were sampled from greening explant and incubated in X-gluc at 37 C. Stable GUS expression was present in every leaf, demonstrating POC of particle-mediated transformation of *Cannabis* meristem explants (FIG. 51).

Example 8

Figure 52:
FIG. 52 shows phenotype and stable GUS expression in T0 transgenic 3WS *Cannabis* plant WP-001181-1a ("Fernanda") derived from particle-mediated transformation of meristem explants.

Transgenic T0 *Cannabis* Plant Generation Using Particle-Mediated Transformation of *Cannabis* Meristem Explants The regenerating transgenic *Cannabis* plantlet from particle-mediated transformation stably expressing GUS in all it leaves from last report has rooted and been sent to GH as T0 plant WP-001181-1. This T0 plant was derived from *Cannabis* meristem explants prepared from seed germinated at 37 C overnight of variety 3WS. Meristem explants were precultured on EJW1 overnight and blasted on carboxymethylcellulose media using DICOTBOMB-13 (at 1.2 ng DNA/ug gold; 0.6 um gold; 1 cm gap, 6 cm distance, and 1350 psi). Explants were rested on EJW1 overnight, then transferred to 100 mg/L spectinomycin hemp node media without activated charcoal for 1 month (media previously described). Explants were then transferred to 50 mg/L streptomycin hemp regeneration media with 1 mg/L meta-topolin (mT) for 6 weeks (media previously described). We then attempted to root this explant by transferring it to: (i) 4 weeks on 50 mg/L streptomycin hemp node media after cutting hypocotyl to remove necrotic tissue; (ii) 2 weeks on non-selective B5 media; (iii) 6 weeks on non-selective dicot BRM media (½ MS salts with 0.1 mg/L IAA); (iv) Explant split into two; hypocotyl cut on each piece to remove necrotic tissue; and (v); 4 weeks (plant "A") to 7 weeks (plant "B") on non-selective dicot BRM media. We re-assayed leaves for GUS and found all leaves remained GUS+. (FIG. 52).

Figure 53:
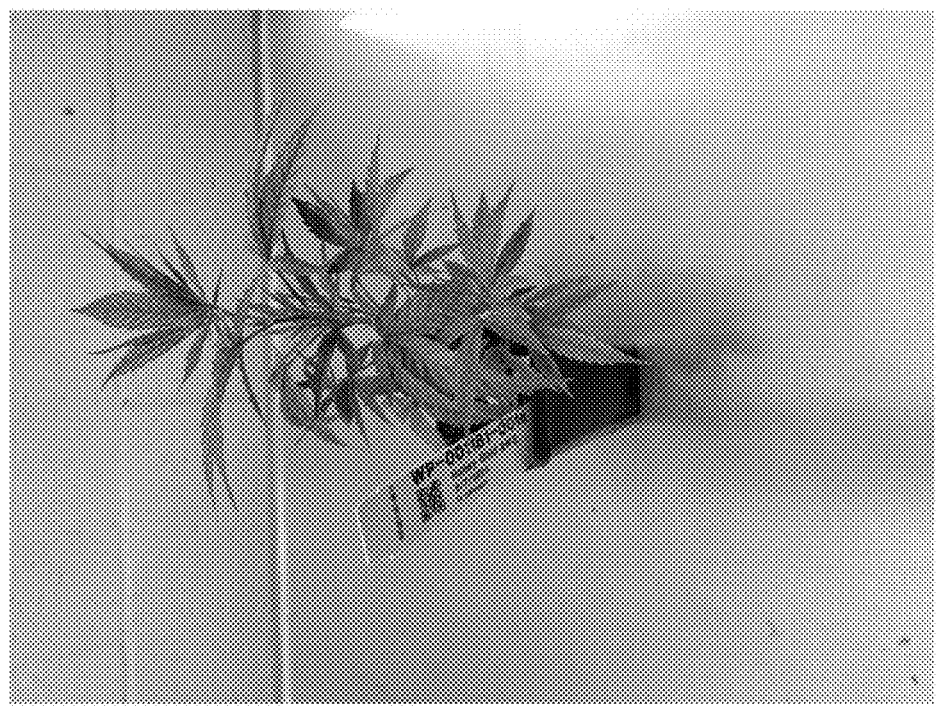
FIG. 53 shows phenotype of T0 transgenic 3WS *Cannabis* plant WP-001181-1a "Fernanda" derived from particle-mediated transformation of meristem explants after approximately 3 weeks in greenhouse.
Figure 54:
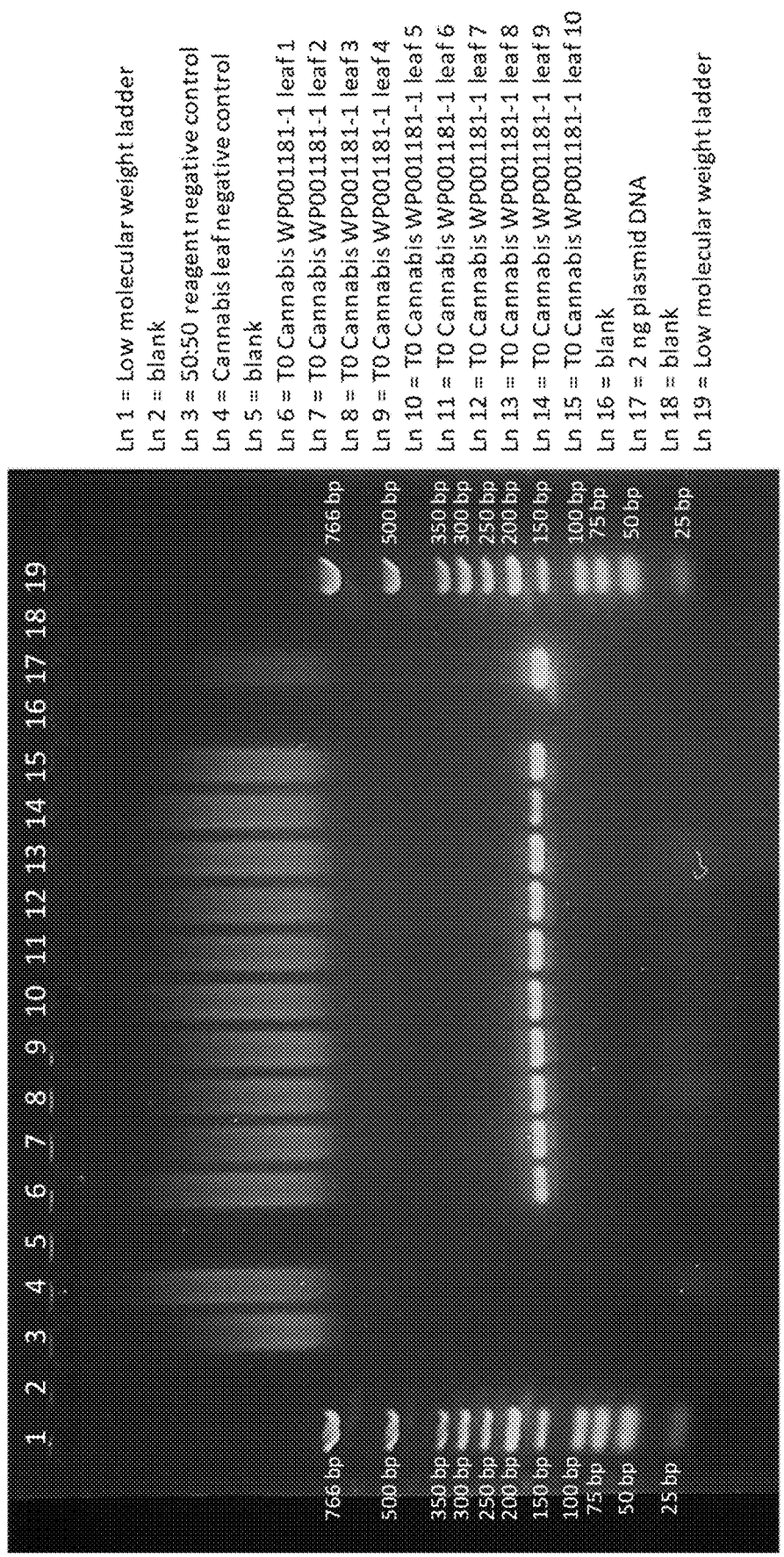
FIG. 54 shows *Cannabis* WP001181-1a particle gun T0 event aadA1a PCR.
Figure 55:
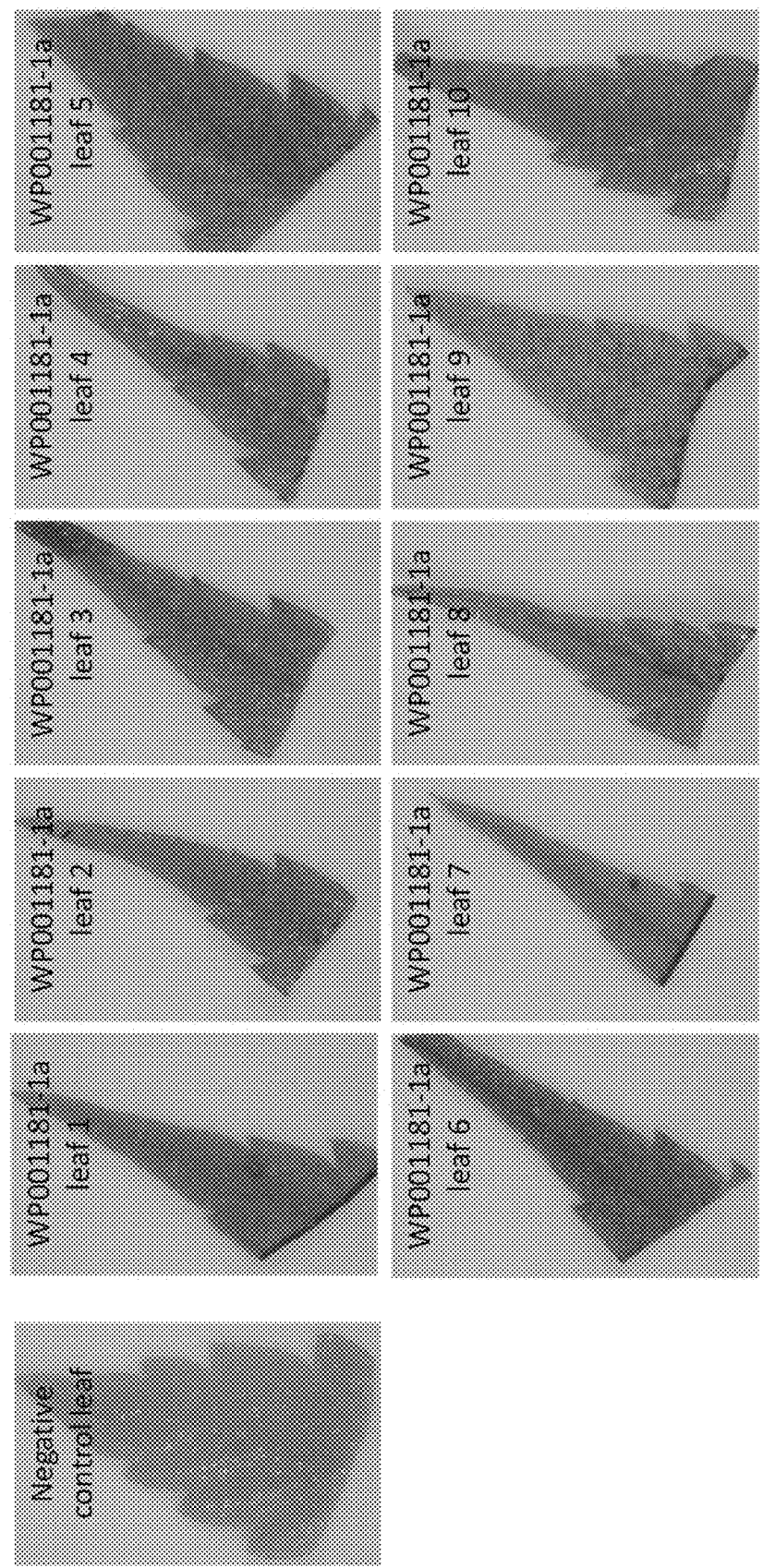
FIG. 55 shows *Cannabis* WP001181-1a particle gun T0 event GUS expression.

After the WP-001181a event had been in the greenhouse for 3 weeks, we used the previously described primer set and PCR conditions to amplify a 156 bp fragment of the aadA1a gene from 10 separate leaves. At the same time, we assayed these leaves for GUS expression (each leaf sample was divided in 2, one sample for PCR, one for GUS assay). All 10 leaves tested positive for aadA1a by PCR, and all 10 were GUS positive (FIG. 53).

Figure 56:
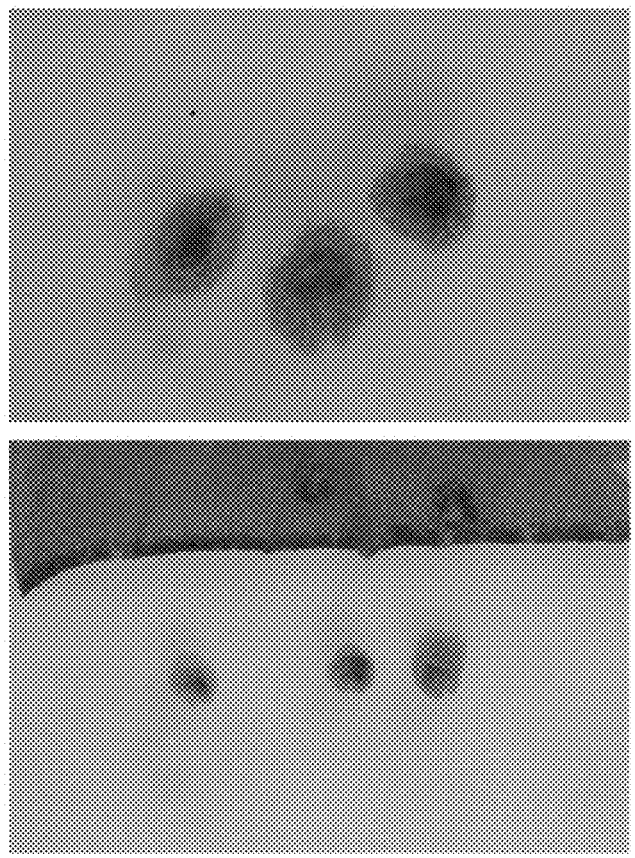
Figure 57:
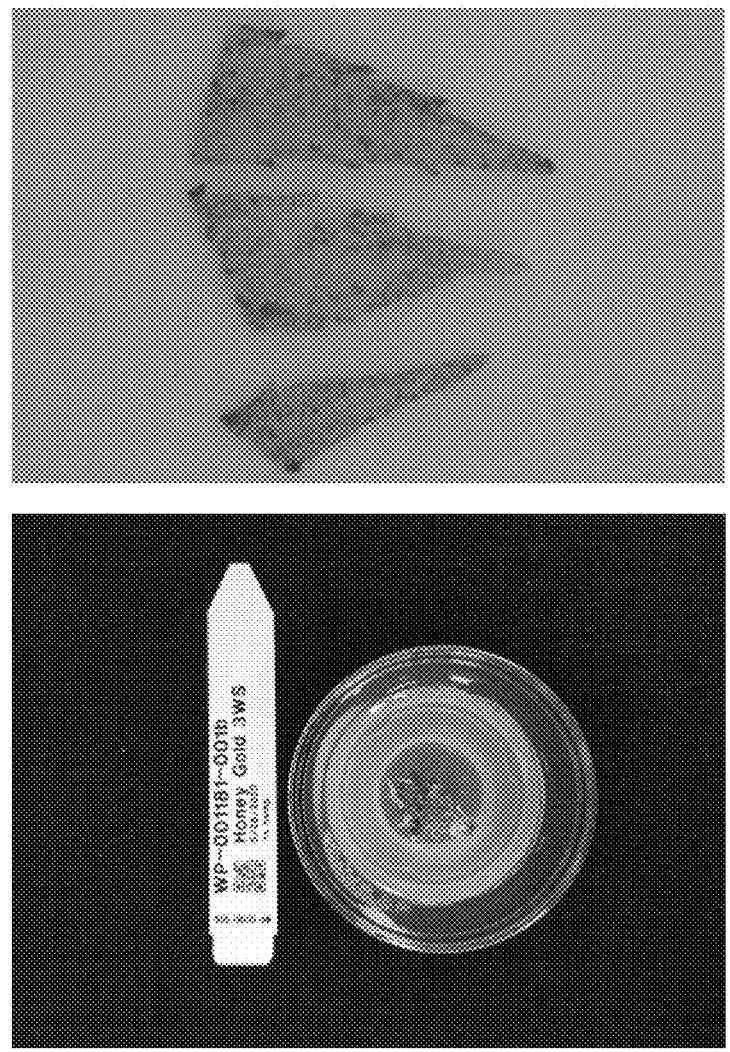
FIG. 57 shows phenotype and stable GUS expression in T0 transgenic 3WS *Cannabis* plant WP-001181-1b ("Hernanda") derived from particle-mediated transformation of meristem explants.

Previous examples described taking petiole sections of the *Cannabis* T0 event WP421-1 to examine GUS expression in vascular tissue, which appeared to be an early indicator of germline status in the *Cannabis* WP421-1 T0 event, and found GUS expression to be present in vascular tissue of WP001181-1a as well (FIG. 56). The second piece of this explant rooted approximately 3 weeks after the first, and was sent to greenhouse after finding all leaves GUS+ (FIG. 57). The ability to split the event into two T0 plants in the meristem transformation system may offer some downstream advantages. It may be possible to feminize either the WP-001181-1a or WP-001181-1b to make subsequent flowers male (process described later). Crosses from −1a onto −1b would then yield homozygotes in the T1 progeny, which may offer timing advantages for transgenic *Cannabis* breeding programs (and advantages to attempting to make hermaphroditic plants for same purpose).

DNA complexed with gold "bead prep" was made by these steps:

Sonicate 50 mg/1 ml EtOH gold suspension for 3 min 45-55 kHz to resuspend gold.

Transfer 42 ul to a new tube. Pellet by centrifugation at 2500 rpm for 10 seconds, remove EtOH.

Add 500 uL sterile water, sonicate 3 min 45-55 kHz. Pellet by centrifugation at 2500 rpm for 10 seconds, remove water.

Add 25 ul sterile water (wash sides of tube with pipette tip). Sonicate 3 min 45-55 kHz.

Add 2.6 ug DNA

Add cold sterile water to bring volume up to 245 ul.

Add 250 ul cold 2.5 M CaCl2.

Add 50 ul 0.1 M spermidine

Mix solution by low speed vortexing. Incubate tube on ice for at least 45 min (I usually go 1.5 hrs). Invert tube every 5-10 minutes.

Once coating is done, pellet the DNA/gold at 1000 rpm (~100×g) for 2 min. Remove supernatant.

Wash pellet with 1 ml 100% EtOH w/ pipette tip. Pellet DNA/gold at 1000 rpm (~100×g) for 2 min. Remove EtOH.

Add 36 ul 100% EtOH, completely resuspend gold with low-speed vortexing.

Store at −20 C, we generally use 5 ul of this prep per bombardment.

This DNA prep gives a DNA Loading Rate of 1.2 ng DNA/ug gold (360 ng DNA per blast, 290 ug gold per blast).

CMC targeting media includes 8% low viscosity carboxymethylcellulose, 2% medium viscosity carboxymethylcellulose, and 0.4% washed agar. CMC was made by adding washed agar to water, autoclaving, pouring into blender, adding carboxymethylcellulose, blending, pouring into bottle, then re-autoclaving, then poured into plates or stored.

EJW1 media is shown above in Table 10.

TABLE 19

BRM media

| Ingredients and Notes | Amount to add per liter (grams) |
| --- | --- |
| MS Salts no vitamins M524 | 2.15 |
| myo-inositol | 0.1 |
| sucrose | 30 |
| pH 5.8 with KOH | |
| Agar, Sigma A7921 | 8 |
| Autoclave | |
| Add after autoclaving | |
| Cysteine (100 mg/ml) - make stock fresh | Use at 1.0 ml per Liter (100 mg/L) |
| Cefotaxime (100 mg/ml) | Use at 2.0 ml per Liter (200 mg/L) |
| IAA (1 mg/ml) | Use at 0.1 ml per Liter (0.1 mg/L) |
| MS Vitamins (1000X) | Use at 1.0 ml per Liter |
| Selection | as needed |

It should also be possible to transform Cannabis meristem explants with free DNA methods where the explants do not require targeting (i.e. nanotechnology such as cell penetrating peptides, silica carbide fibers or others; as well as use of lipid and/or cationic lipid compounds).

Figure 58:
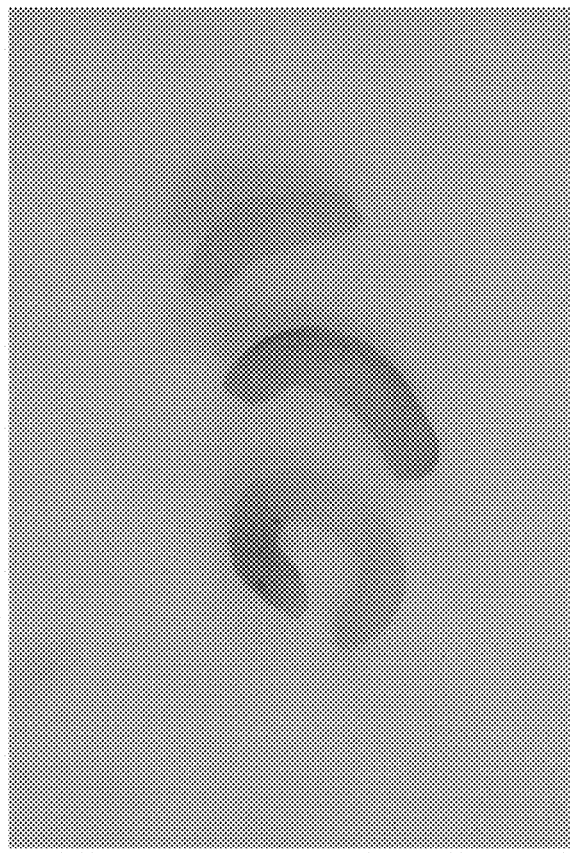
FIG. 58 shows GUS transient expression in automated-excised *Cannabis* meristem explants of Fiber Hemp variety post co-culture.

Transient transformation of storable Cannabis meristem explants excised from seed using automation: We have demonstrated transient expression of GUS in meristem explants of the Fiber Hemp variety using meristem explants excised from seed using automation (described in comments to application sent in July 2019) with H1-H5 fractions pooled. These explants had been stored at −20 C for x weeks before rehydration in INO+60 mg/L Cleary's and inoculation with Ar18r12v/DICOTBINARY-19. Presence of GUS also indicates cells remained viable during this ~8 month storage time. (FIG. 58).

Figure 59:
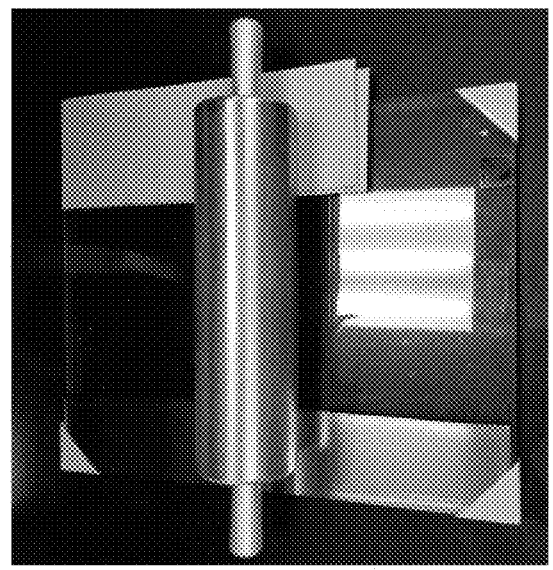
FIG. 59 shows metal rolling pin with glass plate; optional gap can be set by adding/removing shims (metal shims shown on left, paper on right).

Cannabis seeds can also be crushed to extract mature embryos using a metal rolling pin on a glass plate, with an adjustable gap made using shims (FIG. 59). Cannabis seed of the Abacus variety was sanitized and imbibed overnight at 23 C. Seed was then either crushed under the rolling pin, with crushed material allowed to dry in a laminar flow hood for 72 hours; or seed was dried first for 72 hours in laminar flow hood and then crushed. Crushed material was stored at −20 C for 2 months, then rehydrated in INO media with 60 mg/L Cleary's fungicide. Explants were inoculated with Ar18r12v/DICOTBINARY-19 and co-cultured as previously described. We noticed transient GUS expression in meristem explants, again indicating cells were capable of surviving storage as well as maintaining some competency for Agrobacterium transformation (FIG. 60). This crushing technology and roller technology can be applied to wet or dry Cannabis seed, and can be used in conjunction with other treatments to compromise seed coat (ex. seed placed in paint shaker with a metal bead or beads).

Figure 61:
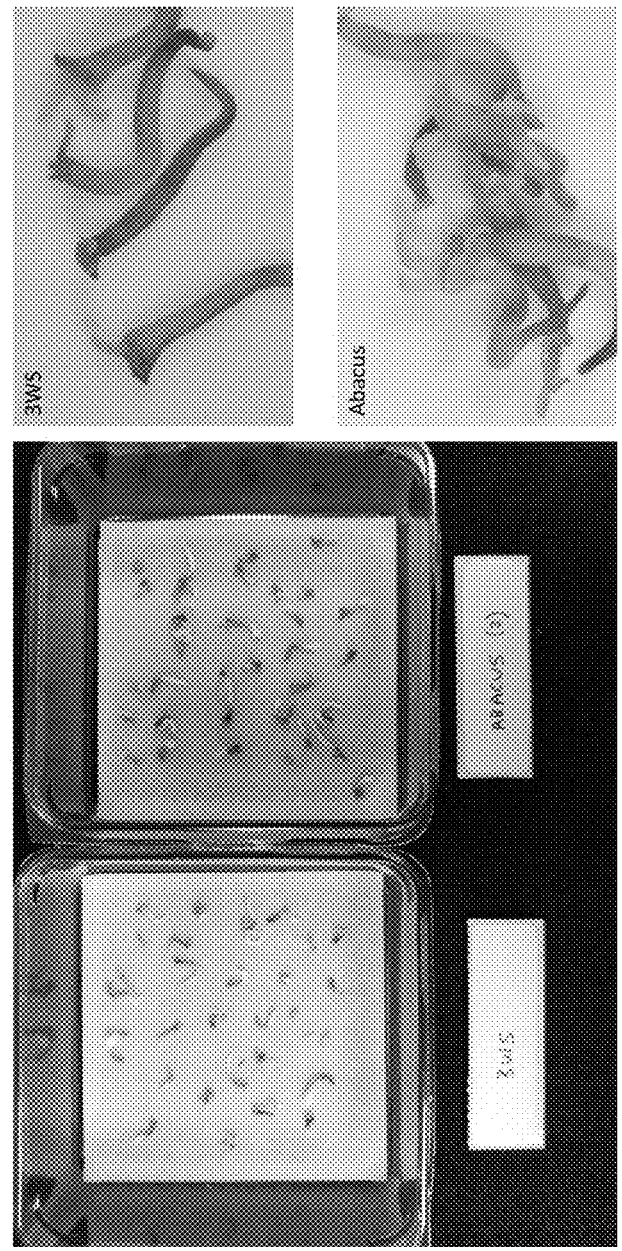
FIG. 61 shows GUS transient expression in *Cannabis* meristem explants of variety 3WS and Abacus post co-culture.
Figure 62:
FIG. 62 shows RFP (tdTomato) segregation in the T2 generation of transformed *Cannabis* (derived from T0 event WP421-1).
Figure 63:
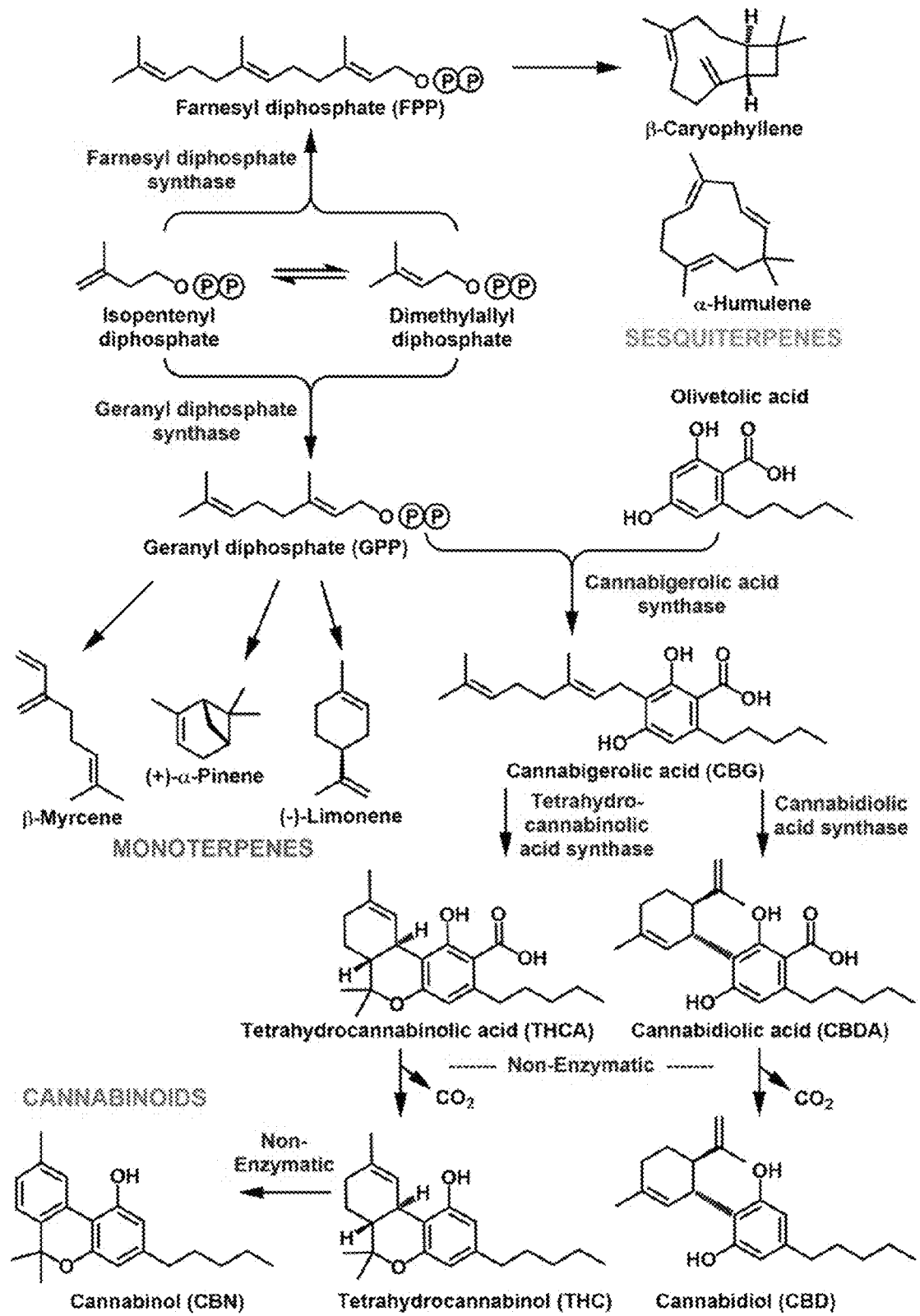
FIG. 63 shows a schematic of the gene networks underlying cannabinoid and terpenoid accumulation in *Cannabis*. Zager et al., Plant Physiology, 2019, 180(4):1877-1897.

Transient transformation of elite Abacus Cannabis variety using Agrobacterium-mediated transformation of meristem explants: We have also demonstrated transient expression of GUS in meristem explants of the elite Abacus variety using meristem explants inoculated with Ar18r12v/DICOTBINARY-19 (derived from seed imbibed overnight at 23 C) (FIG. 61).

Transmission of transgenes into T2 generation of Cannabis 3WS variety (from initial T0 event WP421-1): The previously described GUS positive, RFP (tdTomato) positive, and aadA positive T1 plant WP421-1@2 and cuttings from this plant (WP421-1-08C; WP421-1-10C; WP421-1-07C; WP421-1-02C) were used to examine transmission of transgenes into the T2 generation. This T1 plant and its cuttings were pollinated with pollen from a separate GUS positive and RFP positive feminized WP421-1 T1 plant. Feminization stresses the female plant out enough that it is making male structures that have female genetic pollen, Seed is feminized from the subsequent crosses (all female). Three main substances can be used: Colloidal Silver Solution (~120 ppm); Silver Thiosulfate/Silver Nitrate (STS); or GA3. These chemicals reduce ethylene production that ordinarily helps ripening and the production of female flowers. Temperature or other stresses can cause feminization as well. This T1 plant was feminized by the following procedure. 5 days before moving plants to short days (i.e., 12 hour light periods), all branches and leaves of the plants were sprayed to saturation with ether the STS or Colloidal Silver solution. The spraying was repeated every 5 days until major male flower formation has begun. Usually male flowers begin showing at about 16-20 days after initial spraying and spraying finished after 25-30 days. Resulting T2 seeds were harvested and germinated and imaged for RFP expression. These crosses gave rise to the expected 3:1 segregation ratio (from both parents segregating 1:1), and the 3:1 ratio should include 1 homozygote, 2 hemizygotes and 1 null at T2.

TABLE 20

RFP segregation ratios in T2 Cannabis lines derived from transformed meristem explants.

| Cannabis line | Ratio |
| --- | --- |
| WP421-1@2 | 10/15 positive |
| WP421-1-08C | 13/18 positive |
| WP421-1-10C | 16/18 positive |
| WP421-1-07C | 13/18 positive |
| WP421-1-02C | 12/16 positive |
| Total | 64/85 positives |

Example 9

The reduction or elimination of THC will be accomplished by knocking out the THCA synthase gene using a CRISPR/Cas9 gene editing approach. Cannabis has two genes that contribute to THC production, namely THCA synthase (primary) and CBDA synthase (secondary). It is postulated that in high CBD varieties of Cannabis, the THCA synthase gene(s) are either inactive or highly suppressed. Since CBDA synthase has about an 84% amino acid similarity to THCA synthase, it is also possible that it also plays a role in producing the low amounts of THC seen in these varieties. The proposed CRISPR approach includes a gRNAs designed to target both the THCA synthase as well as the CBDA synthase resulting in plants with single gene knockouts as well as knockouts for both genes. Plants produced from this editing approach would be analyzed with our UPLC to determine the content of 13 different cannabinoids including THCA, CBDA, and CBG. In general, high CBD varieties of cannabis have a CBDA:THCA ratio of 20:1 to 27:1 and these compounds are tightly related to each other (i.e. as CBDA goes up so does THCA). A potential outcome of this editing approach may also be a plant that is skewed with a higher ratio of CBDA:THCA, again reducing the risk to the grower of cultivating plants producing THC as well as producing more CBDA. Another possible outcome of knocking out both THCA synthase and CBD synthase would be the accumulation of the precursor compound CBG. A plant high in CBG is also a highly valued product due to the fact that the plant would normally make very little CBG and thus is a cannabinoid in higher demand.

A big risk to farmers trying to maximize their CBD amounts in their Cannabis plants, is pollination from male plants in the population or form adjacent fields. Pollination of female plants substantially reduces the amount of CBD made by the plants due to the reduction of trichome producing pistils and energy going toward making seed, which is low in CBD. Huang et al. successfully expressed the Solo Dancers and Barnase genes using a fusion gene, which resulted in fully sterile male/female flowers in *Arabidopsis* and tobacco without affecting growth or development. Since *Cannabis* can be easily cloned from a "mother" plant as demonstrated herein, a female sterile plant could be of high value to the grower in eliminating the risk of pollination to the crop.

Increasing trichome numbers: Cannabinoids are mainly made and secreted in the trichomes of the cannabis plant, and more specifically the trichomes associated with female flowers (pistils) of the plant. Increasing the number of trichomes will increase the total cannabinoid production in the plant. Tian, et al. successfully overexpressed the BraLTP2, a lipid transfer protein from *Brassica napus*, resulting in a 10-fold increase of trichomes in *B. napus*. The transgenic lines also produce elevated levels of 43 different secondary metabolites, which could also prove interesting to the amount and type of cannabinoids made in a transgenic cannabis plant with overexpression of this type of gene. LTPs belong to a large multigene family with many complex physiological functions. We have identified similar genes in the cannabis genome and propose to overexpress both the *B. napus* BraLTP2 as well as some homologues from cannabis. These genes could be driven by either a constitutive or flower/pistil specific promoter to drive these potential outcomes. Transgenic plants would be visually screened for an increase in trichomes as well as tested for cannabinoid content using our UPLC.

High CGBA plants: The CsPT1 ((geranylpyrophosphate: olivetolate geranyltransferase (GOT)) gene is involved in the production of CBGA, the precursor to THCA and CBDA. By overexpressing this gene, it may be possible to increase the amount of CBGA in the plant resulting in the increase of the downstream cannabinoids CBDA ad THCA. This approach could also be used in conjunction with knocking out the THCA synthase gene and ultimately making a very high CBDA plant with little or no THCA.

Herbicide resistant plants: Like many other plants, cannabis has an EPSP Synthase gene. It is known that changes to 1-3 amino acids in this gene tend to confer glyphosate resistance to the plant. Since weed pressure in cannabis is high due to the competition of weeds before its canopy is established, this would be a good target. Currently there are no federally registered pesticides for cannabis. A gene editing is used to make the required amino acid substitutions, and produce a glyphosate resistant cannabis plant.

Example 10

Figure 72:
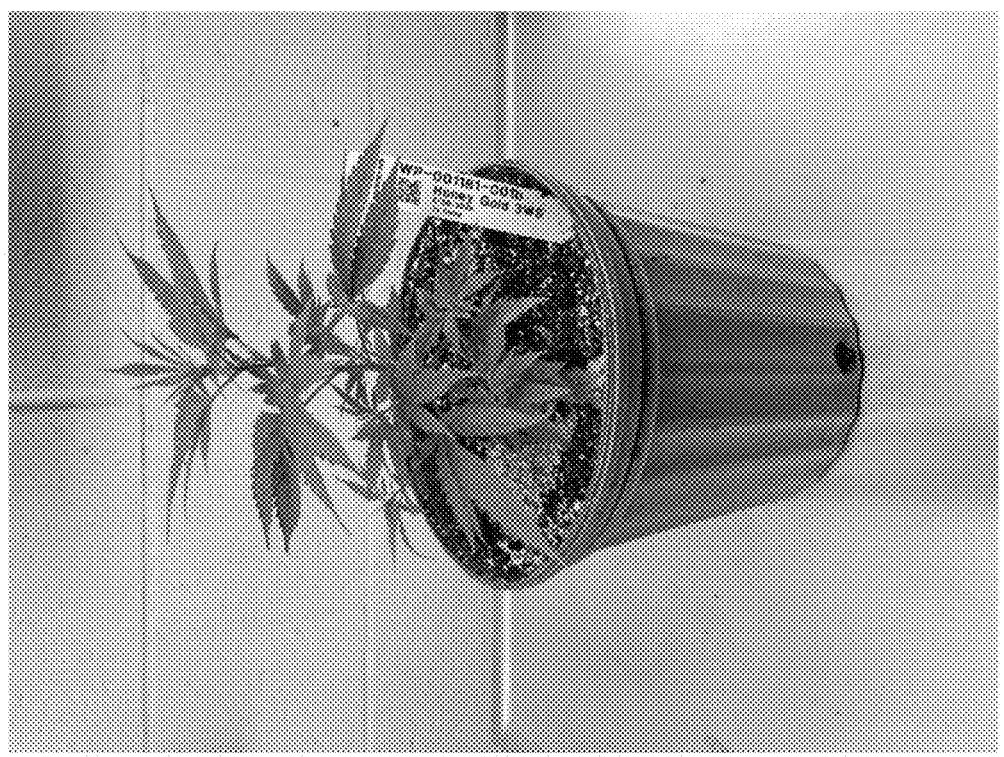
FIG. 72 shows the phenotype of T0 transgenic 3WS *Cannabis* plant WP-001181-1b ("Hernanda") derived from particle-mediated transformation of meristem explants after transplant to large pot.
Figure 73:
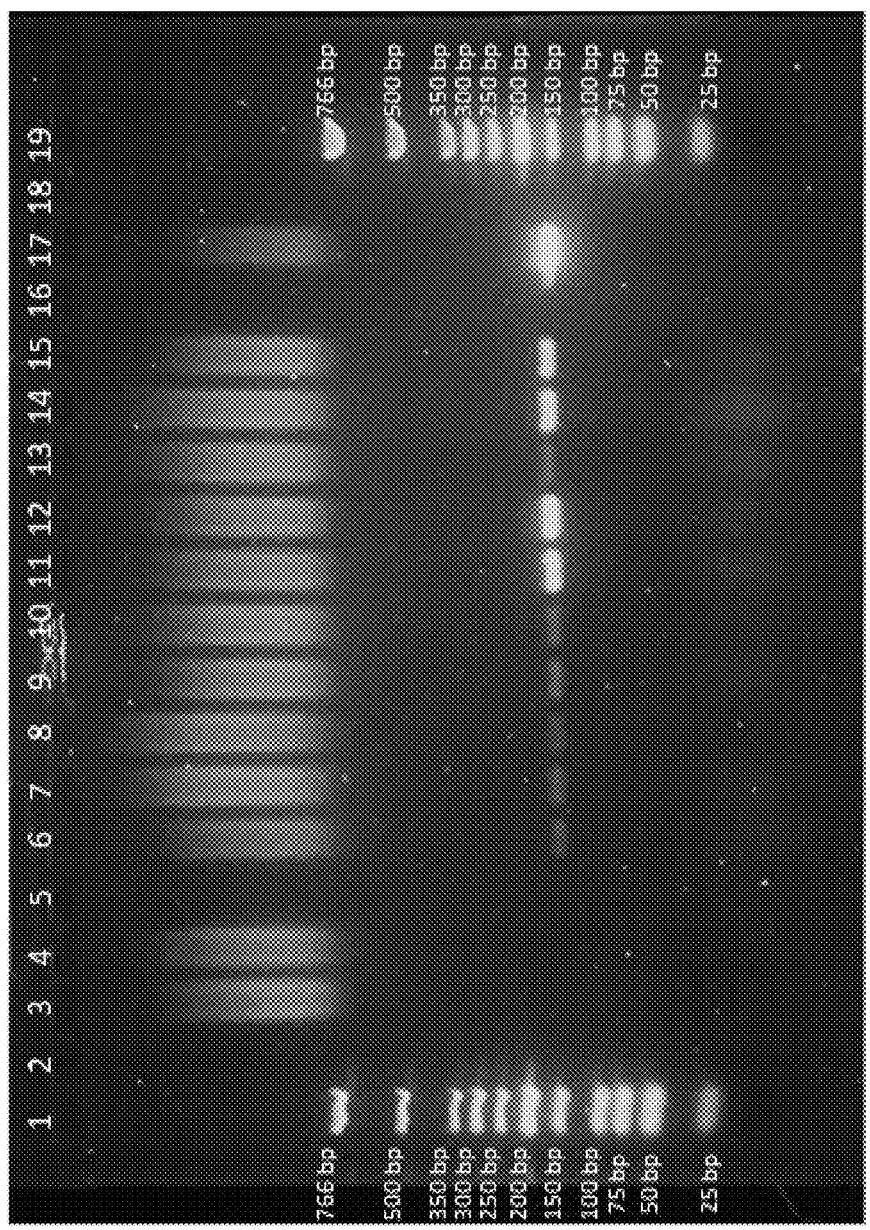
FIG. 73 shows *Cannabis* WP001181-1b particle gun T0 event aadA1a PCR.
Figure 74:
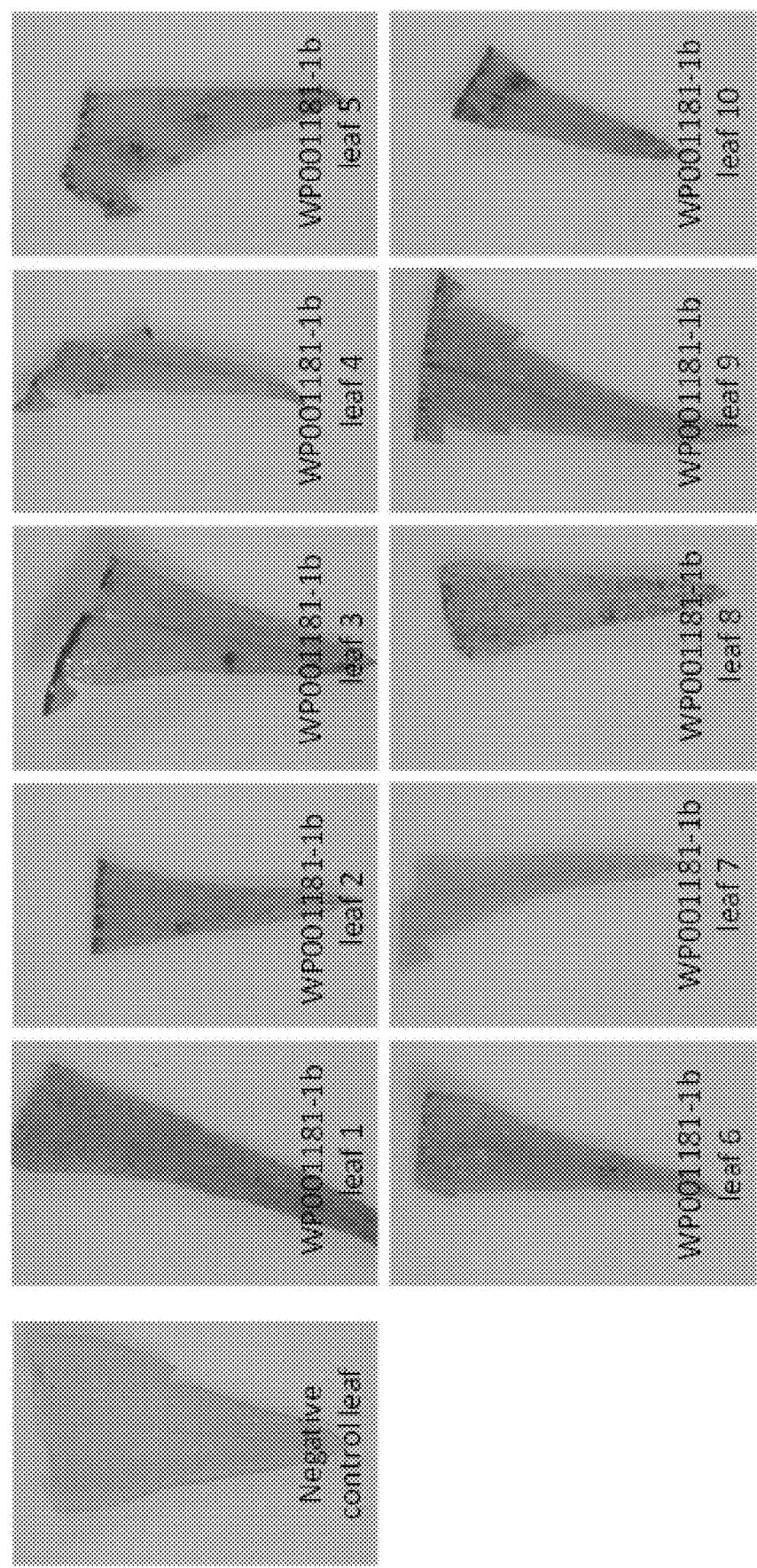
FIG. 74 shows *Cannabis* WP001181-1b particle gun T0 event GUS expression.

Transgenic T0 *Cannabis* plant generation using particle-mediated transformation of *Cannabis* meristem explants—We tested 10 leaves of the twin particle gun event described in Example 8, WP-001181-1b "Hernanda" for aadA1a by PCR and GUS by expression and all 10 leaves were positive. (FIGS. 72-74). As described herein (Example 2), it is also possible to transform plastids and/or proplastids of *Cannabis* meristem explants using plastid specific promoters driving aadA (and GOI) such as the large subunit promoter of RUBISCO; or a suitable prokaryotic promoter. This would give advantages of plastid transformation (maternal inheritance with null pollen, whole operon engineering, greater protein expression, etc.) in *Cannabis* and *Cannabis* breeding.

Figure 75:
FIG. 75 shows a *Cannabis* seed (Badger variety) surface sanitized followed by incubation at 37° C. without imbibition (note radical emergence in seed on left).

Alternate seed conditioning without imbibition—We were able to get radical emergence from *Cannabis* seed of the Badger variety using seed sanitization followed by incubation at 37° C. without imbibition. This enables new forms of both hand and machine excision and storage (as seed coat is split but at relatively low moisture compared with imbibed seed). (FIG. 75)

Figure 76:
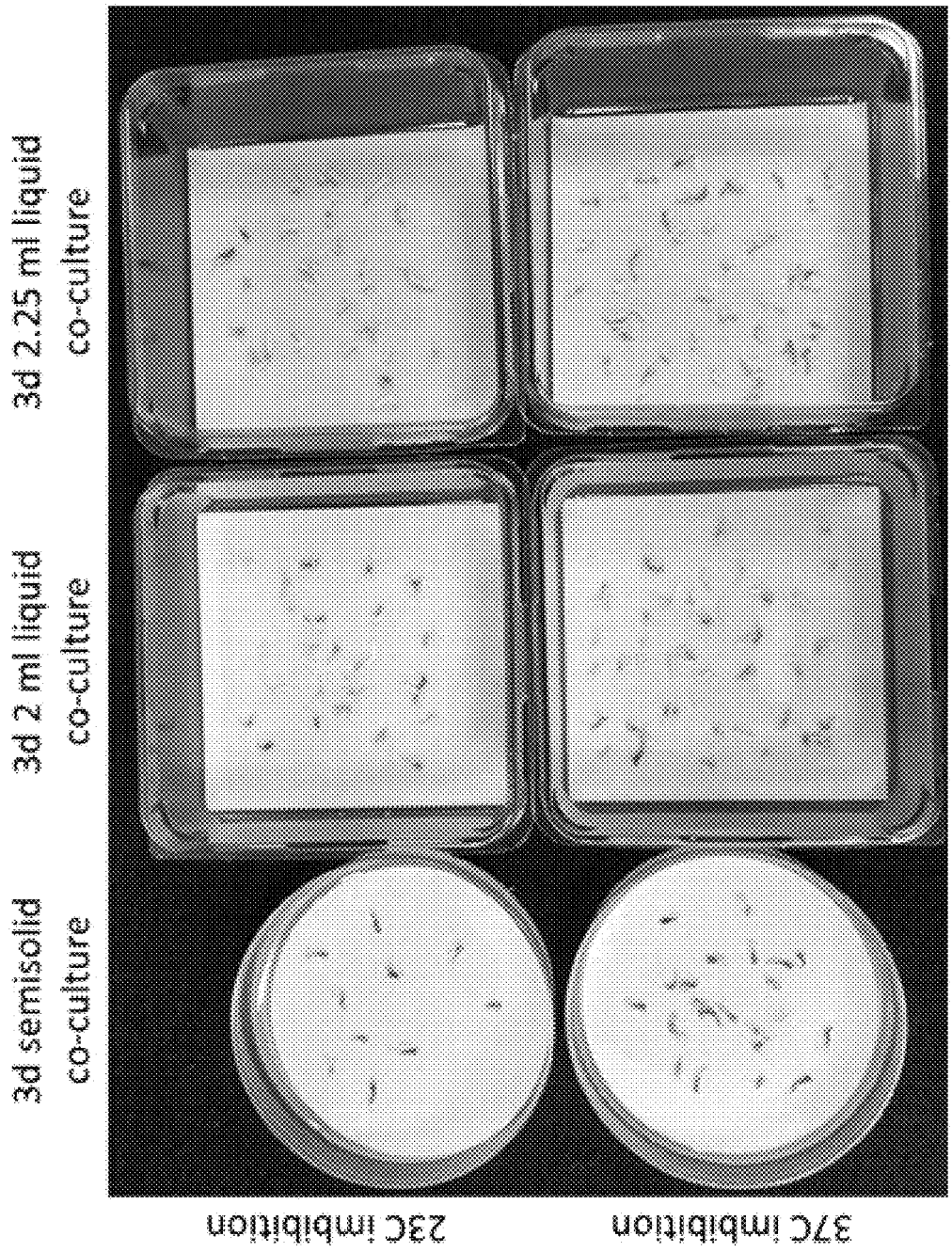
FIG. 76 shows the phenotype of *Cannabis* meristem explants of Badger variety after 3-day co-culture.
Figure 77:
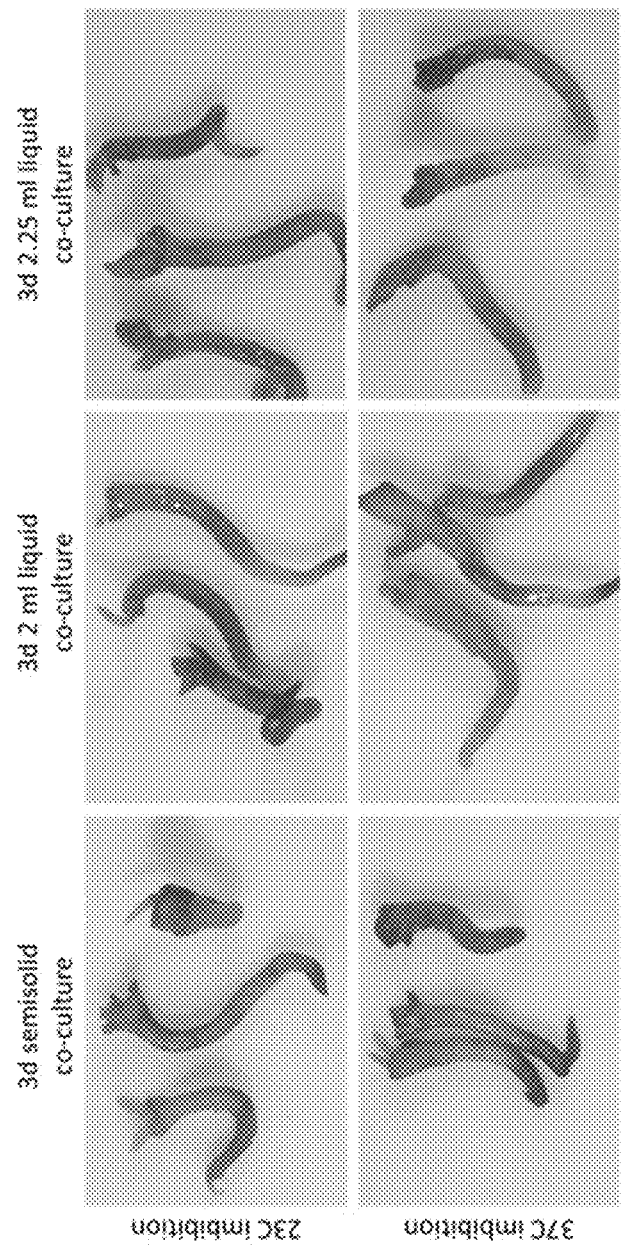
FIG. 77 shows transient GUS expression in *Cannabis* meristem explants of Badger variety after 3-day co-culture.
Figure 78:
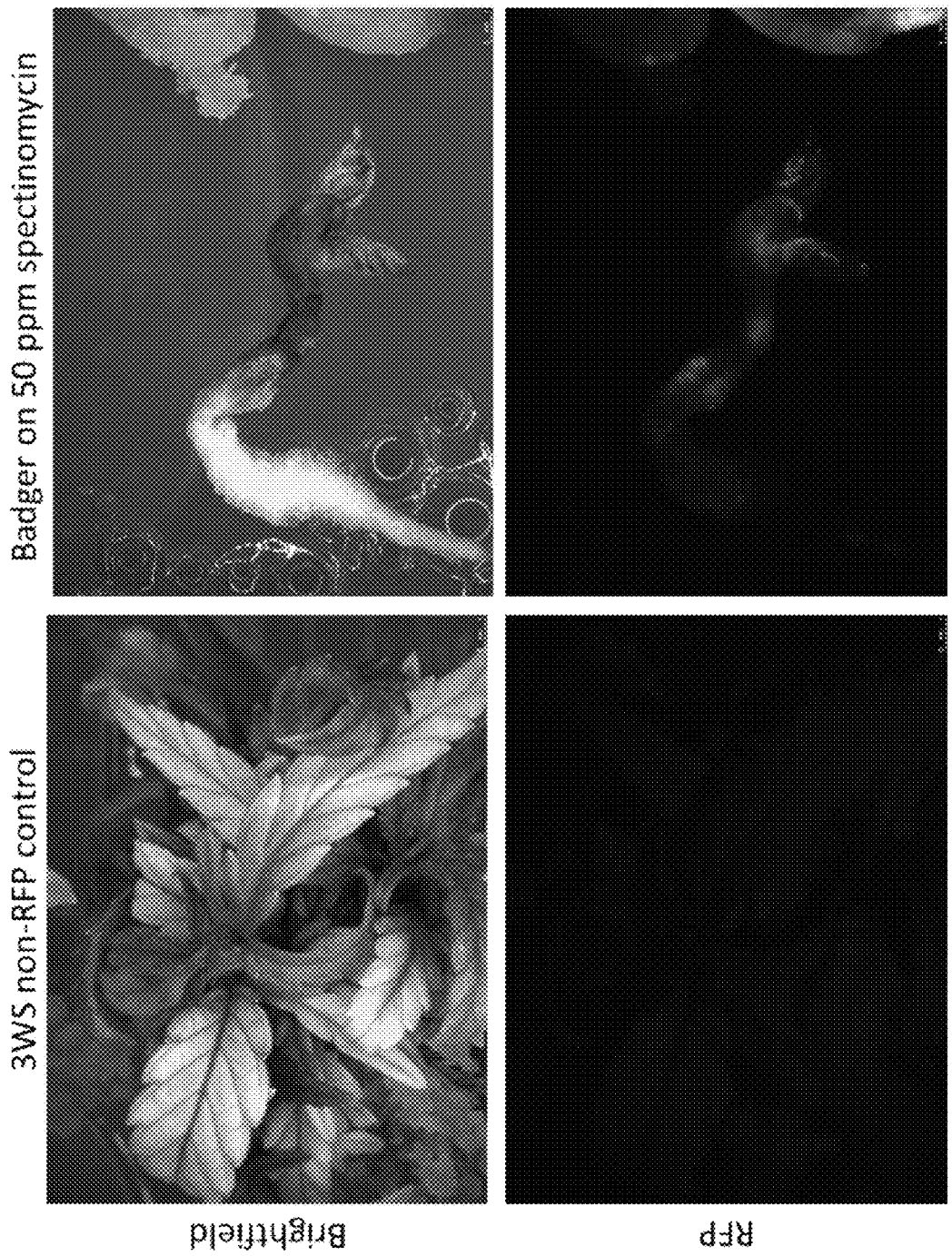
FIG. 78 shows stable RFP (tdTomato) expression in *Cannabis* meristem explants (variety Badger).
Figure 79:
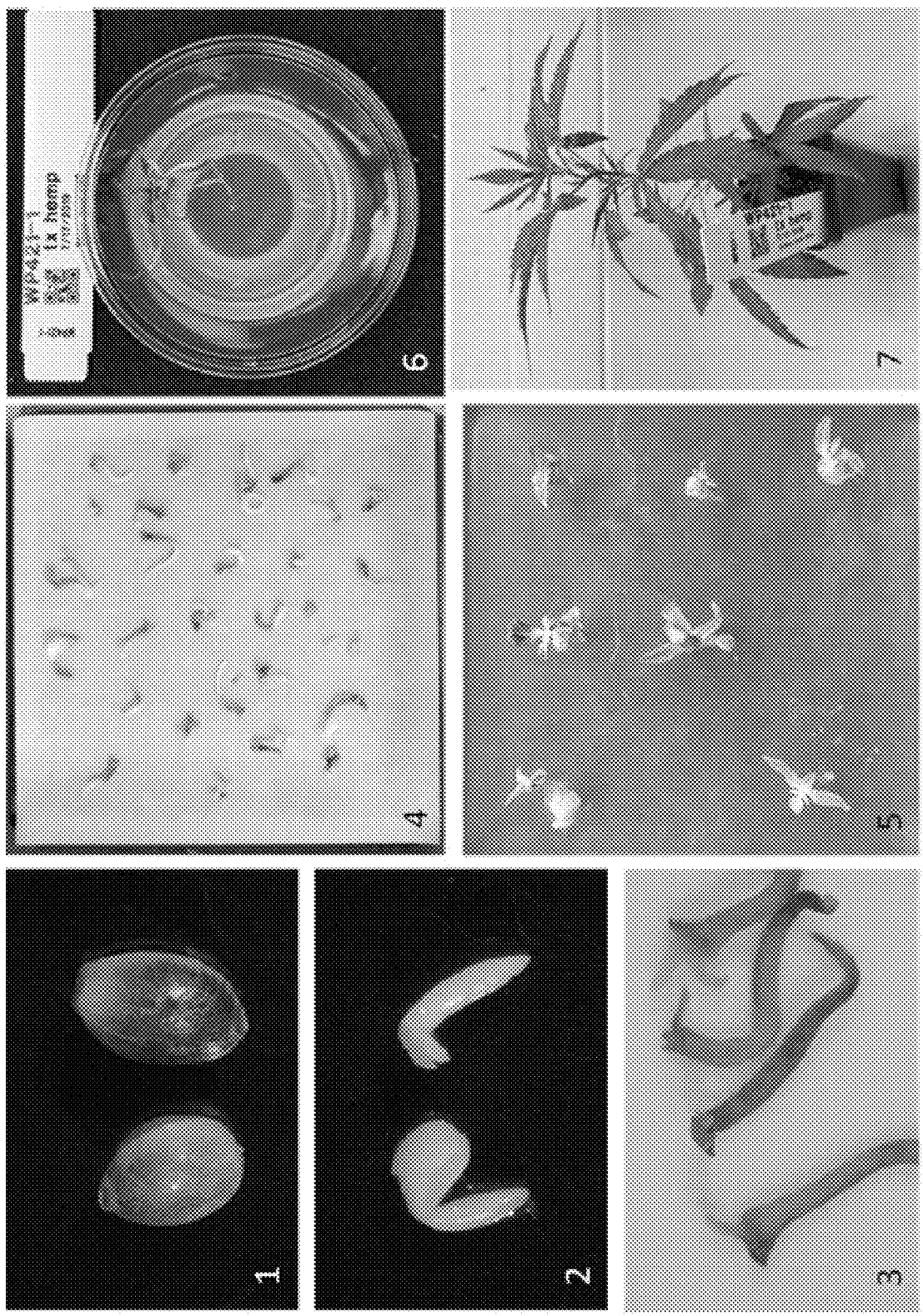
FIG. 79 shows a process diagram timeline for *Cannabis sativa Agrobacterium*-mediated transformation of embodiments described herein. Stage 1 shows *Cannabis* seeds. Stage 2 shows appearance of *Cannabis* meristem explant (mature embryo) derived from imbibed seed, the explant on left has cotyledonary tissue intact; explant on right has cotyledonary tissue removed. Stage 3 shows transient GUS activity in Honey Gold 3WS *Cannabis* explants after co-culture with *Agrobacterium*. Stage 4 shows appearance of *Cannabis* meristem explants after 4 day co-culture. Stage 5 shows phenotypes of *Cannabis* meristem explants after ~3 weeks on 50 mg/L spectinomycin; note incomplete bleaching. Stage 6 shows *Cannabis* T0 event after second selection on 50 mg/L streptomycin prior to handoff to greenhouse. Finally, Stage 7 shows *Cannabis* T0 event prior to transplant in greenhouse.
Figure 80:
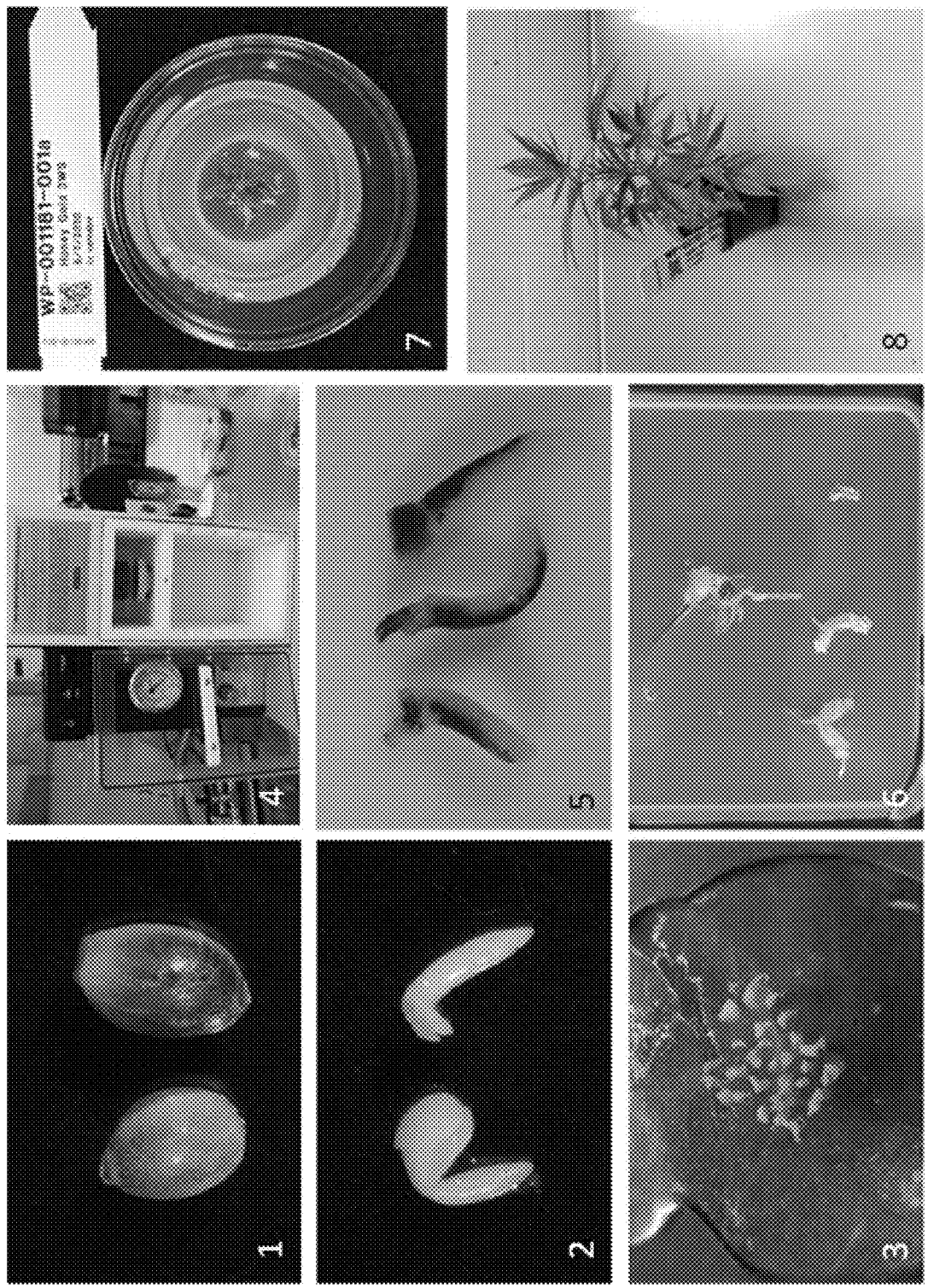
FIG. 80 shows a process diagram timeline for *Cannabis sativa* Particle-mediated transformation. Stage 1 shows *Cannabis* seeds. Stage 2 shows appearance of *Cannabis* meristem explant (mature embryo) derived from imbibed seed, the explant on left has cotyledonary tissue intact; explant on right has cotyledonary tissue removed. Stage 3 shows *Cannabis* embryo target on CMC targeting media. Stage 4 shows PDS-1000 Helium gun. Stage 5 shows transient GUS activity in Honey Gold 3WS *Cannabis* explants 1-day post-bombardment. Stage 6 shows phenotypes of *Cannabis* meristem explants 2 months post-bombardment. Stage 7 shows *Cannabis* T0 event prior to handoff to greenhouse. Finally, Stage 8 shows *Cannabis* T0 event prior to transplant in greenhouse.

Transient transformation and Stable expression of RFP (tdTomato) in Badger variety using *Agrobacterium*-mediated transformation of meristem explants—We have also demonstrated transient expression of GUS in meristem explants of the elite Badger variety using meristem explants inoculated with Ar18r12v/DICOTBINARY-19 (derived from seed imbibed overnight at 23° C. or 37° C.) under a variety of co-culture conditions (FIGS. 76-78).

We claim:

1. A method of transforming a *Cannabis* plant, the method comprising:
   growing a sanitized and imbibed *Cannabis* seed on a non-selective culture medium suitable for supporting the growth and survival of the *Cannabis* seed;
   harvesting an internode, leaf, or petiole tissue to form a *Cannabis* explant;
   inoculating the *Cannabis* explant with a heterologous nucleic acid;
   co-culturing the *Cannabis* explant in a co-culture medium for between about 1 day and about 6 days,
   culturing the *Cannabis* explant on a selection medium comprising meta-topolin to select for transformed *Cannabis* explants.

2. The method of claim 1, wherein the *Cannabis* explant is inoculated using a method selected from the group consisting of particle bombardment, high velocity microprojection, microinjection, electroporation, direct DNA uptake, cell-penetrating peptides, silica carbide fibers, nanoparticles, and bacterially-mediated transformation.

3. The method of claim 1, wherein *Agrobacterium* spp. is used to inoculate the *Cannabis* explant.

4. The method of claim 1, additionally comprising the step of force treating the *Cannabis* explant prior to or following inoculation.

5. The method of claim 4, wherein the force treatment is selected from the group consisting of sonication, vortexing, centrifugation, heat-shock, increased pressure, vacuum infiltration, and addition of chemicals.

6. The method of claim 1, wherein the heterologous nucleic acid modulates the expression or activity of an endogenous *Cannabis* gene selected from the group consisting of tetrahydrocannabinolic acid synthase (THCA synthase), cannabidiolic acid synthase (CBDA synthase), O-methyltransferase (CsOMT21), lipid transfer protein 2 (LTP2), prenyltransferase 3 (CsPT3), and prenyltransferase 1 (CsPT1).

7. The method of claim 1, wherein the *Cannabis* seed is a *Cannabis sativa* seed.

8. The method of claim 1, wherein the heterologous nucleic acid encodes a polypeptide at least 90% identical to SEQ ID NO:28.

9. The method of claim 1, wherein the heterologous nucleic acid encodes a guide RNA that targets *Cannabis sativa* THCA synthase gene, *Cannabis sativa* CBDA synthase gene, or *Cannabis sativa* EPSP synthase gene.

10. The method of claim 1, wherein the tissue harvested is from an internode, leaf, or petiole tissue, and wherein the selection medium further comprises gibberellic acid (GA3).

11. The method of claim 1, wherein culturing is performed under a light/dark photoperiod.

* * * * *

UNITED STATES PATENT AND TRADEMARK OFFICE
CERTIFICATE OF CORRECTION

PATENT NO. : 11,999,958 B2
APPLICATION NO. : 16/930936
DATED : June 4, 2024
INVENTOR(S) : Michael W. Petersen et al.

Page 1 of 1

It is certified that error appears in the above-identified patent and that said Letters Patent is hereby corrected as shown below:

In the Specification

Column 56, Line 34, "Katandin" should be --Katahdin--.

Signed and Sealed this
Twenty-fourth Day of September, 2024

Katherine Kelly Vidal
*Director of the United States Patent and Trademark Office*